(12) United States Patent
Sibley et al.

(10) Patent No.: US 8,993,574 B2
(45) Date of Patent: Mar. 31, 2015

(54) PYRROLE ANTIFUNGAL AGENTS

(75) Inventors: Graham Edward Morris Sibley, Manchester (GB); Robert Downham, Manchester (GB); Lloyd James Payne, Manchester (GB); Derek Law, Manchester (GB); Jason David Oliver, Manchester (GB); Mike Birch, Manchester (GB); Gareth Morse Davies, Manchester (GB); Patricia Suling Davies, legal representative, Macclesfield (GB)

(73) Assignee: F2G Ltd, Manchester (GB)

( * ) Notice: Subject to any disclaimer, the term of this patent is extended or adjusted under 35 U.S.C. 154(b) by 82 days.

(21) Appl. No.: 12/989,410

(22) PCT Filed: Apr. 23, 2009

(86) PCT No.: PCT/GB2009/001058
§ 371 (c)(1),
(2), (4) Date: Mar. 11, 2011

(87) PCT Pub. No.: WO2009/130481
PCT Pub. Date: Oct. 29, 2009

(65) Prior Publication Data
US 2011/0152285 A1  Jun. 23, 2011

(30) Foreign Application Priority Data

Apr. 24, 2008 (GB) .................................. 0807532.7
Oct. 27, 2008 (GB) .................................. 0819696.6

(51) Int. Cl.
| | | |
|---|---|---|
| *C07D 487/04* | (2006.01) | |
| *C07D 498/04* | (2006.01) | |
| *A01N 43/36* | (2006.01) | |
| *A01N 43/60* | (2006.01) | |
| *A01N 43/76* | (2006.01) | |
| *A01N 43/40* | (2006.01) | |
| *A01N 43/42* | (2006.01) | |
| *A01N 43/84* | (2006.01) | |
| *A01N 43/90* | (2006.01) | |

(52) U.S. Cl.
CPC .............. *C07D 487/04* (2013.01); *A01N 43/36* (2013.01); *A01N 43/60* (2013.01); *A01N 43/76* (2013.01); *C07D 498/04* (2013.01); *A01N 43/40* (2013.01); *A01N 43/42* (2013.01); *A01N 43/84* (2013.01); *A01N 43/90* (2013.01)
USPC ....................... 514/253.01; 544/364; 514/427

(58) Field of Classification Search
CPC ....... A01N 43/36; A01N 43/40; A01N 43/42; A01N 43/60; A01N 43/76; A01N 43/84; A01N 43/90; C07D 487/04; C07D 498/04
USPC .............................. 514/253.01, 427; 544/364
See application file for complete search history.

(56) References Cited

U.S. PATENT DOCUMENTS

| | | | |
|---|---|---|---|
| 3,202,654 A | 8/1965 | Perron | |
| 3,252,970 A | 5/1966 | Huebner | |
| 3,256,279 A | 6/1966 | Karmas | |
| 3,458,515 A | 7/1969 | Archibald et al. | |
| 3,573,294 A | 3/1971 | Long et al. | |
| 3,857,857 A | 12/1974 | Bella et al. | |
| 4,148,907 A | 4/1979 | Conti | |
| 4,316,900 A | 2/1982 | Wasley | |
| 4,761,424 A | 8/1988 | Carethers et al. | |
| 4,794,120 A | 12/1988 | Manoury et al. | |
| 5,750,540 A * | 5/1998 | Tsuchiya et al. | 514/318 |
| 6,645,976 B1 | 11/2003 | Dillard et al. | |
| 8,524,705 B2 * | 9/2013 | Payne et al. | 514/218 |
| 2005/0090541 A1 | 4/2005 | Arnaiz et al. | |
| 2006/0058286 A1 | 3/2006 | Krystal et al. | |

FOREIGN PATENT DOCUMENTS

| | | |
|---|---|---|
| DE | 2 253 150 A1 | 5/1973 |
| DE | 2 429 923 A1 | 1/1975 |
| DE | 2 751 571 A1 | 5/1978 |
| EP | 0 252 809 A2 | 1/1988 |

(Continued)

OTHER PUBLICATIONS

Yavari et al. (Tetrahedron (2001), 57(27), 5873-5878).*
Dumoulin et al. (European Journal of Medicinal Chemistry (1998), 33(3), 201-207).*
McDonnell et al. Clinical Microbiology Reviews, Jan. 1999, p. 147-179; vol. 12, Issue 1.*
http://www.merckmillipore.com/chemicals/diethyl-ether/MDA_CHEM-100926/p_NgGb.s1Lay4AAAEW8uEfVhTI—(2012).*
Schoichet Laboratory at UCSF (through ZINC database of commercially available small molecules-entered to CHEMCATS Feb. and Mar. 2008; p. 1-64).*

(Continued)

*Primary Examiner* — Kristin Vajda
*Assistant Examiner* — Valerie Rodriguez-Garcia
(74) *Attorney, Agent, or Firm* — Morrison & Foerster LLP

(57) ABSTRACT

The invention provides compounds of formula (I), and pharmaceutically and agriculturally acceptable salts thereof; wherein: R1, R2, R3, R4, R5, R6, A1, L1 and n are as defined herein. These compounds and their pharmaceutically acceptable salts are useful in prevention or treatment of a fungal disease. Compounds of formula (I), and agriculturally acceptable salts thereof, may also be used as agricultural fungicides.

17 Claims, No Drawings

(56) References Cited

FOREIGN PATENT DOCUMENTS

| EP | 0 747 756 A1 | 12/1996 |
|---|---|---|
| FR | 1 381 256 | 12/1964 |
| FR | 1 556 822 A | 2/1969 |
| GB | 1051723 | 12/1966 |
| GB | 1208014 | 10/1970 |
| GB | 1476503 | 6/1977 |
| JP | 57-142966 A | 9/1982 |
| JP | 57-144255 A | 9/1982 |
| JP | 62-081369 A | 4/1987 |
| JP | 9-249669 A | 9/1997 |
| WO | WO-96/03383 A1 | 2/1996 |
| WO | WO-96/33973 A1 | 10/1996 |
| WO | WO-99/62881 A1 | 12/1999 |
| WO | WO-00/32588 A2 | 6/2000 |
| WO | WO-00/32588 A3 | 6/2000 |
| WO | WO-02/085301 A2 | 10/2002 |
| WO | WO-02/085301 A3 | 10/2002 |
| WO | WO-02/085907 A1 | 10/2002 |
| WO | WO-02/098876 A1 | 12/2002 |
| WO | WO-03/000680 A1 | 1/2003 |
| WO | WO-03/064397 A1 | 8/2003 |
| WO | WO-03/072028 A2 | 9/2003 |
| WO | WO-03/072028 A3 | 9/2003 |
| WO | WO-2004/082606 A2 | 9/2004 |
| WO | WO-2004/082606 A3 | 9/2004 |
| WO | WO-2006/105289 A1 | 10/2006 |
| WO | WO-2006/113875 A2 | 10/2006 |
| WO | WO-2006/113875 A3 | 10/2006 |
| WO | WO-2006/123145 A1 | 11/2006 |
| WO | WO-2007/015866 A2 | 2/2007 |
| WO | WO-2007/015866 A3 | 2/2007 |
| WO | WO-2007/092681 A2 | 8/2007 |
| WO | WO-2007/092681 A3 | 8/2007 |
| WO | WO-2008/046082 A2 | 4/2008 |
| WO | WO-2008/046082 A3 | 4/2008 |
| WO | WO-2008/062182 A1 | 5/2008 |
| WO | WO-2008/106860 A1 | 9/2008 |
| WO | WO-2008/145963 A1 | 12/2008 |

OTHER PUBLICATIONS

Alvarez, M. et al. (1999). "Synthesis of 1,2-Dihydropyrrolo[1,2-c]Pyrimidin-1-Ones," *Journal of Chemical Society* 249-255.

Alves, M.J. et al. (2000). "Novel Aziridine Esters by the Addition of Aromatic Nitrogen Heterocycles to a 2H-Azirine-3-Carboxylic Ester," *Tetrahedron Letters* 41:4991-4995.

Ames, D.E. et al. (1959, e-published Jan. 1, 1959). "The Preparation of Aminoalkylpyrrocolines," *Journal of Chemical Society* 124:620-622.

Archibald, J.L. et al. (Sep. 1967). "New Reactions of Pyrroles. II. Preparation and Reactions of Pyrroleglyoxyloyl Derivatives," *Journal of Heterocyclic Chemistry* 4:335-338.

Archibald, J.L. et al. (1974). "Benzamidopiperidines. 2. Heterocyclic Compounds Related to Indoramin," *Journal of Medicinal Chemistry* 17(7):736-739.

Battersby, A.R. et al. (1992, e-published Jan. 1, 1992). "Synthetic Studies Relevant to Biosynthetic Research on Vitamin B12. Part 10. Construction of the East and West Building Blocks for Synthesis of Isobacteriochlorins," *Journal of Chemical Society* 17:2175-2187.

Bentov, M. et al. (1964). "4-Fluoroindole and Derivatives," *Israel Journal of Chemistry* 2:25-28.

Birchall, G.R. et al. (1971). "The Chlorination of Pyrroles. Part II," *Canadian Journal of Chemistry* 49:919-922.

Black, D.S.C. et al. (1996). "Reaction of Some 4,6-Dimethoxyindoles with Oxalyl Chloride," *Tetrahedron* 52(26):8925-8936.

Black, D.S.C. et al. (1996). "The Indol-2-Ylglyoxylamide Moiety: A New Building Block for the Design and Self-Assembly of Hydrogen Bond Networks," *Journal of American Chemical Society* 118(34):8148-8149.

Black, D.S.C. et al. (2000). "Formation of C-Amido-Calix[3]Indoles from 2'- and 7'-Indolylglyoxylamides," *Tetrahedron* 56:8513-8524.

Bohusch, M. et al. (1991). "Consequences of a Diminution of the Porphyrin π-System: Attempted Syntheses of Bacteriophin and Chlorophin," *Liebigs Annalen der Chemie* 67-70. (Abstract Only).

Borthwick, A.D. et al. (Jan. 3, 2002, e-published Dec. 5, 2001). "Design and synthesis of Pyrrolidine-5,5-*trans*-Lactams (5-Oxohexahdropyrrolo[3,2-*b*]Pyrroles) as Novel Mechanism-Based Inhibitors of Human Cytomegalovirus Protease. 2. Potency and Chirality," *Journal of Medicinal Chemistry* 45(1):1-18.

Cameron, B.D. et al. (1973). "The Synthesis and Metabolic Fate of $^{14}$C-Viminol, a New Analgesic, in the Rat and the Dog," *Arzneimittel-Forshung/Drug Res.* 23(5):708-712.

Cardellini, M. et al. (Feb. 1977). "Indolizine Derivatives with Biological Activity I: N'-Substituted Hydrazides of Indolizine-2-Carboxylic Acid," *Journal of Pharmaceutical Sciences* 66(2):259-262.

Chemcats. (Jan. 25, 2008). "Benzo [b] Thiophene-2-Carboxylic Acid, 3-[2-[[(4-Methoxyphenyl) Amino]Oxoacetyl]-1H-Pyrrol-1-yl]-, Methyl Ester," *Ryan Scientific Screening Library* 5 pages.

Chemcats. (Feb. 13, 2008). "1H-Pyrrole-2-Acetamide, N-(4-Bromophenyl)-1- (2-Chloro-4-Nitrophenyl) -α-Oxo-," *Ambinter Stock Screening Collection* 5 pages.

Chemcats. (Feb. 18, 2008). "1H-Pyrrole-2-Acetamide, N- (2,4-Dichlorophenyl)-1-Methyl-α-Oxo-," *Interchim Intermediates* 5 pages.

Chiarino, D. et al. (1978). "Stereochemistry of Viminol, a Novel Central Analgesic," *Arzneimittel-Forshung/Drug Res.* 28(11):1554-1561.

Cook, A.H. et al. (1949, e-published Jan. 1, 1949). "Studies in the Azole Series. Part XXIV. The Interaction of Carbonyl Compounds and 2-Thio-5-Thiazolidone," *Journal of Chemical Society* 633:3007-3012.

Crowley, K.J. et al. (1957). "Intermediates for the Synthesis of Optically Active Methyl-Substituted Long-Chain Acids. Part II," *Journal of the Chemical Society* 2931-2934.

Dannhardt, G. et al. (1979). "Synthese und Eigenschaften von 2,3-Dihydro-1 *H*-Pyrrolizinen," *Arch. Pharm.* 312:896-907.

Dannhardt, G. et al. (1994). "Nonsteroidal Antiinflammatory Agents, XVIII: C-5 Functionalized 6,7-Diphenyl-2,3-Dihydro-1 *H*-Pyrrolizines as Inhibitors of Bovine Cyclooxygenase and 5-Lipoxygenase," *Arch Pharm* 327:509-514.

Dannhardt, V.G. et al. (1986). "Antiphlogistische 2,3-Dihydro-1H-Pyrrolizine, 11. Mitt. Dihydropyrrolizinyl-Substituierte 2-Aminoethanol- und Glykosäure-Derivate," *Chemiker-Zeitung* 110(3):124-127.

Dumoulin, H. et al. (1998). "2-Oxo-2-(Pehn-2-Ylpyrrol-2-Yl)Acetamides as Potential Anxiolytic Agents: Synthesis and Affinity at the Central Benzodiazepine Receptor," *European Journal of Medicinal Chemistry* 33:201-207.

Dyke, S.F. et al. (1978). "Pavinane and Isopavinane Alkaloids," *Tetrahedron* 34:241-245.

Fryer, R.I. et al. (Dec. 1967). "Quinazolines and 1,4-Benzodiazepines. XXXVII. Synthesis and Rearrangements of a Substituted 5-Phenyl-1 H-1,4-Benzodiazepine," *Journal of Organic Chemistry* 32:3798-3803.

Galbraith, A. et al. (Jan. 20, 1961). "The Formation of Cycl[3,2,2]azine Derivatives via the Reaction of Pyrrocoline with Dimethoxy Acetylenedicarboxylate," *Journal of the American Chemical Society* 83:453-458.

Groll, A.H. et al. (1996). "Trends in the Postmortem Epidemiology of Invasive Fungal Infections at a University Hospital," *Journal of Infection* 33:23-32.

Hagishita, S. et al. (1996). "Potent Inhibitors of Secretory Phospholipase A2: Synthesis and Inhibitory Activities of Indolizine and Indene Derivatives," *Journal of Medicinal Chemistry* 39(19):3636-3658.

Hudack, R.A. et al. (2006, e-published Jan. 14, 2006). "Design, Synthesis, and Biological Activity of Novel Polycyclic Aza-Amide FKBP12 Ligands," *Journal of Medicinal Chemistry* 49(3):1202-1206.

Ignatovich, J. et al. (2008). "Synthesis of Functionalized Benzyl Amines by the Reductive Alkylation of Heterocyclic and

(56) References Cited

OTHER PUBLICATIONS

Heteroaromatic Amines with Arylaldehydes and preparation of the Intermediates for New Synthetic Biomolecules," ARKAT-USA, Inc. (ix):42-51.

Islam, I. et al. (2007, e-published Apr. 27, 2007). "Indolinone Based Phosphoinositide-Dependent Kinase-1 (PDK1) Inhibitors. Part 1: Design, Synthesis and Biological Activity," *Bioorganic & Medicinal Chemistry Letters* 17:3814-3818.

Keawin, T. et al. (2005, e-published Dec. 10, 2004). "Reaction of Some 4,6-Dimethoxyindoles with Nitric Acid: Nitration and Oxidative Dimerisation," *Tetrahedron* 61:853-861.

Mahiout, Z. et al. (2008, e-published Feb. 28, 2008). "Solvent-Dependent Oxidations of 5-and 6-Azaindoles to Trioxopyrrolopyridines and Functionalised Azaindoles," *Organic & Biomolecular Chemistry* 6:1364-1376.

Nourmohammadian, F. et al. (2005, e-published Jan. 21, 2005). "An AB Initio Molecular Orbital Study of Structural Isomers of Diketopyrrolopyrrole," *Dyes and Pigments* 67:15-20.

Pätzel, M. et al. (2005). "Product Class 5: α-Heteroatom-Substituted Alkanamides," *Science of Synthesis* 21:477-535.

Ribaud, P. et al. (1999). "Survival and Prognostic Factors of Invasive Aspergillosis After Allogeneic Bone Marrow Transplantation," *Clinical Infectious Diseases* 28:322-330.

Rowe, F.M. et al. (1935, e-published Jan. 1, 1935). "A Reaction of Certain Diazosulphonates Derived from β-Naphthol-1-Sulphonic Acid. Part XIII. Fission of the Naphthalene Nucleus and Subsequent Closure in Two Directions," *Journal of Chemical Society* 420:1796-1808.

Rowe, F.M. et al. (1936, e-published Jan. 1, 1936). "A Reaction of Certain Diazosulphonates Derived from β-Naphthol-1-Sulphonic Acid. Part XV. Derivatives of 2'-Nitro-4'-Methyl-Benzene-2-Naphthol-1-Diazosulphonate and Synthesis of 2-(2'-Nitro-4'-Methylphenylamino)Isoindolinone-3-Acetic Acid," *Journal of Chemical Society* 232:1098-1108.

Roy, K. et al. (Dec. 2008). "Development of Linear and Nonlinear Predictive QSAR Models and Their External Validation Using Molecular Similarity Principle for Anti-HIV Indolyl Aryl Sulfones," *Journal of Enzyme Inhibition and Medicinal Chemistry* 23(6):980-995.

Savage, S.A. et al. (1998). "Efficient Synthesis of 4-, 5-, and 6-Methyl-2,2'-Bipyridine by a Negishi Cross-Coupling Strategy Followed by High-Yield Conversion to Bromo- and Chloromethyl-2,2'-Bipyridines," *Journal of Organic Chemistry* 63(26):10048-10051.

Scott, M.K. et al. (1995). "Piperazinylalkyl Heterocycles as Potential Antipsychotic Agents," *Journal of Medicinal Chemistry* 38(21):4198-4210.

Si, Z. et al. (Apr. 6, 2004). "Small-Molecule Inhibitors of HIV-1 Entry Block Receptor-Induced Conformational Changes in the Viral Envelope Glycoproteins," *Proceedings of the National Academy of Sciences* 101(14):5036-5041.

Slassi, A. et al. (2000). "5-Alkyltryptamine Derivatives as Highly Selective and Potent 5-HT$_{1D}$ Receptor Agonists," *Bioorganic & Medicinal Chemistry Letters* 10:1707-1709.

Sofan, M.A. et al. (2004). "Studies on 2,3-Dioxopyrrolidines. Synthesis of Piperazine, Pyrrolo[4,5-b]Indole, Pyrazino [5,6-b]Indole and Arylazo Derivatives of Amino Acids," *Polish Journal of Chemistry* 78:837-842.

CAS Registry No. 3758-62-1, created Nov. 16, 1984, last accessed Feb. 2, 2012, 1 page.
CAS Registry No. 3768-71-6, created Nov. 16, 1984, last accessed Feb. 2, 2012, 1 page.
CAS Registry No. 3768-72-7, created Nov. 16, 1984, last accessed Feb. 2, 2012, 1 page.
CAS Registry No. 3768-82-9, created Nov. 16, 1984, last accessed Feb. 2, 2012, 2 pages.
CAS Registry No. 4380-46-5, created Nov. 16, 1984, last accessed Feb. 2, 2012, 1 page.
CAS Registry No. 4595-83-9, created Nov. 16, 1984, last accessed Feb. 2, 2012, 2 pages.
CAS Registry No. 6616-51-9, created Nov. 16, 1984, last accessed Feb. 2, 2012, 1 page.
CAS Registry No. 15940-17-7, created Nov. 16, 1984, last accessed Feb. 2, 2012, 1 page.
CAS Registry No. 15940-18-8, created Nov. 16, 1984, last accessed Feb. 2, 2012, 1 page.
CAS Registry No. 15940-19-9, created Nov. 16, 1984, last accessed Feb. 2, 2012, 1 page.
CAS Registry No. 15940-20-2, created Nov. 16, 1984, last accessed Feb. 2, 2012, 2 pages.
CAS Registry No. 15940-21-3, created Nov. 16, 1984 last accessed Feb. 2, 2012, 1 page.
CAS Registry No. 15940-22-4, created Nov. 16, 1984, last accessed Feb. 2, 2012, 2 pages.
CAS Registry No. 15940-23-5, created Nov. 16, 1984, last accessed Feb. 2, 2012, 1 page.
CAS Registry No. 15940-24-6, created Nov. 16, 1984, last accessed Feb. 2, 2012, 2 pages.
CAS Registry No. 15940-25-7, created Nov. 16, 1984, last accessed Feb. 2, 2012, 1 page.
CAS Registry No. 23502-48-9, created Nov. 16, 1984, last accessed Feb. 2, 2012, 2 pages.
CAS Registry No. 26883-51-2, created Nov. 16, 1984, last accessed Feb. 2, 2012, 1 page.
CAS Registry No. 31709-75-8, created Nov. 16, 1984, last accessed Feb. 2, 2012, 2 pages.
CAS Registry No. 31709-76-9, created Nov. 16, 1984, last accessed Feb. 2, 2012, 1 page.
CAS Registry No. 31709-77-0, created Nov. 16, 1984, last accessed Feb. 2, 2012, 1 page.
CAS Registry No. 31710-23-3, created Nov. 16, 1984, last accessed Feb. 2, 2012, 1 page.
CAS Registry No. 36793-47-2, created Nov. 16, 1984, last accessed Feb. 2, 2012, 2 pages.
CAS Registry No. 41596-37-6, created Nov. 16, 1984, last accessed Feb. 2, 2012, 1 page.
CAS Registry No. 42060-03-7, created Nov. 16, 1984, last accessed Feb. 2, 2012, 2 pages.
CAS Registry No. 42060-05-9, created Nov. 16, 1984, last accessed Feb. 2, 2012, 1 page.
CAS Registry No. 42221-74-9, created Nov. 16, 1984, last accessed Feb. 2, 2012, 2 pages.
CAS Registry No. 43084-49-7, created Nov. 16, 1984, last accessed Feb. 2, 2012, 1 page.
CAS Registry No. 53391-28-9, created Nov. 16, 1984, last accessed Feb. 2, 2012, 2 pages.
CAS Registry No. 53391-29-0, created Nov. 16, 1984, last accessed Feb. 2, 2012, 1 page.
CAS Registry No. 53391-30-3, created Nov. 16, 1984, last accessed Feb. 2, 2012, 2 pages.
CAS Registry No. 53391-52-9, created Nov. 16, 1984, last accessed Feb. 2, 2012, 1 page.
CAS Registry No. 53391-63-2, created Nov. 16, 1984, last accessed Feb. 2, 2012, 2 pages.
CAS Registry No. 65473-58-7, created Nov. 16, 1984, last accessed Feb. 2, 2012, 1 page.
CAS Registry No. 68803-72-5, created Nov. 16, 1984, last accessed Feb. 2, 2012, 2 pages.
CAS Registry No. 81729-69-3, created Nov. 16, 1984, last accessed Feb. 2, 2012, 1 page.
CAS Registry No. 81741-58-4, created Nov. 16, 1984, last accessed Feb. 2, 2012, 1 page.
CAS Registry No. 83996-64-9, created Nov. 16, 1984, last accessed Feb. 2, 2012, 1 page.
CAS Registry No. 130761-64-7, created Nov. 30, 1990, last accessed Feb. 2, 2012, 1 page.
CAS Registry No. 130761-68-1, created Nov. 30, 1990, last accessed Feb. 2, 2012, 2 pages.
CAS Registry No. 145045-69-8, created Dec. 25, 1992, last accessed Feb. 2, 2012, 2 pages.
CAS Registry No. 171854-40-3, created Dec. 29, 1995, last accessed Feb. 2, 2012, 1 page.

(56) References Cited

OTHER PUBLICATIONS

CAS Registry No. 171854-41-4, created Dec. 29, 1995, last accessed Feb. 2, 2012, 2 pages.
CAS Registry No. 171854-42-5, created Dec. 29, 1995, last accessed Feb. 2, 2012, 2 pages.
CAS Registry No. 171854-43-6, created Dec. 29, 1995, last accessed Feb. 2, 2012, 2 pages.
CAS Registry No. 17854-44-7, created Dec. 29, 1995, last accessed Feb. 2, 2012, 1 page.
CAS Registry No. 171845-45-8, created Dec. 29, 1995, last accessed Feb. 2, 2012, 2 pages.
CAS Registry No. 171854-46-9, created Dec. 29, 1995, last accessed Feb. 2, 2012, 1 page.
CAS Registry No. 171854-47-0, created Dec. 29, 1995, last accessed Feb. 2, 2012, 2 pages.
CAS Registry No. 185030-21-1, created Jan. 15, 1997, last accessed Feb. 2, 2012, 1 page.
CAS Registry No. 208765-70-2, created Jul. 22, 1998, last accessed Feb. 2, 2012, 1 page.
CAS Registry No. 208765-71-3, created Jul. 22, 1998, last accessed Feb. 2, 2012, 1 page.
CAS Registry No. 208765-72-4, created Jul. 22, 1998, last accessed Feb. 2, 2012, 2 pages.
CAS Registry No. 208765-73-5, created Jul. 22, 1998, last accessed Feb. 2, 2012, 1 page.
CAS Registry No. 208765-74-6, created Jul. 22, 1998, last accessed Feb. 2, 2012, 1 page.
CAS Registry No. 208765-75-7, created Jul. 22, 1998, last accessed Feb. 2, 2012, 1 page.
CAS Registry No. 208765-76-8, created Jul. 22, 1998, last accessed Feb. 2, 2012, 1 page.
CAS Registry No. 208765-77-9, created Jul. 22, 1998, last accessed Feb. 2, 2012, 2 pages.
CAS Registry No. 208765-78-0, created Jul. 22, 1998, last accessed Feb. 2, 2012, 1 page.
CAS Registry No. 208765-79-1, created Jul. 22, 1998, last accessed Feb. 2, 2012, 2 pages.
CAS Registry No. 208765-80-4, created Jul. 22, 1998, last accessed Feb. 2, 2012, 1 page.
CAS Registry No. 208765-81-5, created Jul. 22, 1998, last accessed Feb. 2, 2012, 2 pages.
CAS Registry No. 208765-82-6, created Jul. 22, 1998, last accessed Feb. 2, 2012, 1 page.
CAS Registry No. 208765-83-7, created Jul. 22, 1998, last accessed Feb. 2, 2012, 2 pages.
CAS Registry No. 208765-84-8, created Jul. 22, 1998, last accessed Feb. 2, 2012, 1 page.
CAS Registry No. 208765-85-9, created Jul. 22, 1998, last accessed Feb. 2, 2012, 2 pages.
CAS Registry No. 208765-86-0, created Jul. 22, 1998, last accessed Feb. 2, 2012, 1 page.
CAS Registry No. 208765-87-1, created Jul. 22, 1998, last accessed Feb. 2, 2012, 2 pages.
CAS Registry No. 208765-88-2, created Jul. 22, 1998, last accessed Feb. 2, 2012, 1 page.
CAS Registry No. 208765-89-3, created Jul. 22, 1998, last accessed Feb. 2, 2012, 2 pages.
CAS Registry No. 208765-90-6, created Jul. 22, 1998, last accessed Feb. 2, 2012, 1 page.
CAS Registry No. 208765-91-7, created Jul. 22, 1998, last accessed Feb. 2, 2012, 1 page.
CAS Registry No. 208765-92-8, created Jul. 22, 1998, last accessed Feb. 2, 2012, 1 page.
CAS Registry No. 208765-93-9, created Jul. 22, 1998, last accessed Feb. 2, 2012, 1 page.
CAS Registry No. 208765-94-0, created Jul. 22, 1998, last accessed Feb. 2, 2012, 2 pages.
CAS Registry No. 208765-95-1, created Jul. 22, 1998, last accessed Feb. 2, 2012, 1 page.
CAS Registry No. 208765-96-2, created Jul. 22, 1998, last accessed Feb. 2, 2012, 2 pages.
CAS Registry No. 208766-03-4, created Jul. 22, 1998, last accessed Feb. 2, 2012, 1 page.
CAS Registry No. 208766-04-5, created Jul. 22, 1998, last accessed Feb. 2, 2012, 2 pages.
CAS Registry No. 208766-05-6, created Jul. 22, 1998, last accessed Feb. 2, 2012, 1 page.
CAS Registry No. 263554-36-5, created May 2, 2000, last accessed Feb. 2, 2012, 1 page.
CAS Registry No. 263554-39-8, created May 2, 2000, last accessed Feb. 2, 2012, 2 pages.
CAS Registry No. 292063-96-8, created Oct. 2, 2000, last accessed Feb. 2, 2012, 1 page.
CAS Registry No. 292064-15-4, created Oct. 2, 2000, last accessed Feb. 2, 2012, 2 pages.
CAS Registry No. 364044-26-8, created Oct. 23, 2001, last accessed Feb. 2, 2012, 1 page.
CAS Registry No. 364044-30-4, created Oct. 23, 2001, last accessed Feb. 2, 2012, 2 pages.
CAS Registry No. 396733-55-4, created Feb. 28, 2002, last accessed Feb. 2, 2012, 1 page.
CAS Registry No. 422507-64-0, created May 29, 2002, last accessed Feb. 2, 2012, 1 page.
CAS Registry No. 422507-66-2, created May 29, 2002, last accessed Feb. 2, 2012, 1 page.
CAS Registry No. 422507-69-5, created May 29, 2002, last accessed Feb. 2, 2012, 1 page.
CAS Registry No. 477709-20-9, created Dec. 27, 2002, last accessed Feb. 2, 2012, 2 pages.
CAS Registry No. 477709-21-0, created Dec. 27, 2002 last accessed Feb. 2, 2012, 2 pages.
CAS Registry No. 477709-22-1, created Dec. 27, 2002, last accessed Feb. 2, 2012, 1 page.
CAS Registry No. 477709-24-3, created Dec. 27, 2002, last accessed Feb. 2, 2012, 2 pages.
CAS Registry No. 477709-25-4, created Dec. 27, 2002, last accessed Feb. 2, 2012, 1 page.
CAS Registry No. 477709-26-5, created Dec. 27, 2002, last accessed Feb. 2, 2012, 2 pages.
CAS Registry No. 477709-27-6, created Dec. 27, 2002, last accessed Feb. 2, 2012, 1 page.
CAS Registry No. 477709-28-7, created Dec. 27, 2002, last accessed Feb. 2, 2012, 2 pages.
CAS Registry No. 477709-29-8, created Dec. 27, 2002, last accessed Feb. 2, 2012, 1 page.
CAS Registry No. 477709-30-1 created Dec. 27, 2002, last accessed Feb. 2, 2012, 2 pages.
CAS Registry No. 477857-72-0, created Dec. 31, 2002, last accessed Feb. 2, 2012, 1 page.
CAS Registry No. 477857-73-1, created Dec. 31, 2002, last accessed Feb. 2, 2012, 2 pages.
CAS Registry No. 477857-74-2, created Dec. 31, 2002, last accessed Feb. 2, 2012, 1 page.
CAS Registry No. 477857-75-3, created Dec. 31, 2002, last accessed Feb. 2, 2012, 2 pages.
CAS Registry No. 477857-76-4, created Dec. 31, 2002, last accessed Feb. 2, 2012, 1 page.
CAS Registry No. 477857-77-5, created Dec. 31, 2002, last accessed Feb. 2, 2012, 2 pages.
CAS Registry No. 477857-78-6, created Dec. 31, 2002, last accessed Feb. 2, 2012, 1 page.
CAS Registry No. 477857-79-7, created Dec. 31, 2002, last accessed Feb. 2, 2012, 2 pages.
CAS Registry No. 477857-80-0, created Dec. 31, 2002, last accessed Feb. 2, 2012, 1 page.
CAS Registry No. 477857-81-1, created Dec. 31, 2002, last accessed Feb. 2, 2012, 2 pages.
CAS Registry No. 477863-31-3, created Dec. 31, 2002, last accessed Feb. 2, 2012, 1 page.
CAS Registry No. 477863-34-6, created Dec. 31, 002, last accessed Feb. 2, 2012, 2 pages.

(56) References Cited

OTHER PUBLICATIONS

CAS Registry No. 477863-37-9, created Dec. 31, 2002, last accessed Feb. 2, 2012, 1 page.
CAS Registry No. 477871-94-6, created Dec. 31, 2002, last accessed Feb. 2, 2012, 2 pages.
CAS Registry No. 477871-95-7, created Dec. 31, 2002, last accessed Feb. 2, 2012, 1 page.
CAS Registry No. 477871-96-8, created Dec. 31, 2002, last accessed Feb. 2, 2012, 1 page.
CAS Registry No. 477871-97-9, created Dec. 31, 2002, last accessed Feb. 2, 2012, 1 page.
CAS Registry No. 477871-98-0, created Dec. 31, 2002, last accessed Feb. 2, 2012, 1 page.
CAS Registry No. 477871-99-,1 created Dec. 31, 2002, last accessed Feb. 2, 2012, 2 pages.
CAS Registry No. 477872-00-7, created Dec. 31, 2002, last accessed Feb. 2, 2012, 1 page.
CAS Registry No. 477872-01-8, created Dec. 31, 2002, last accessed Feb. 2, 2012, 2 pages.
CAS Registry No. 477872-02-9, created Dec. 31, 2002, last accessed Feb. 2, 2012, 1 page.
CAS Registry No. 477872-03-0, created Dec. 31, 2002, last accessed Feb. 2, 2012, 1 page.
CAS Registry No. 477872-04-1, created Dec. 31, 2002, last accessed Feb. 2, 2012, 2 pages.
CAS Registry No. 477872-05-2, created Dec. 31, 2002, last accessed Feb. 2, 2012, 1 page.
CAS Registry No. 477872-69-8, created Dec. 31, 2002, last accessed Feb. 2, 2012, 2 pages.
CAS Registry No. 477872-70-1, created Dec. 31, 2002, last accessed Feb. 2, 2012, 1 page.
CAS Registry No. 477872-71-2, created Dec. 31, 2002, last accessed Feb. 2, 2012, 2 pages.
CAS Registry No. 477872-72-3, created Dec. 31, 2002, last accessed Feb. 2, 2012, 1 page.
CAS Registry No. 477872-73-4 created Dec. 31, 2002, last accessed Feb. 2, 2012, 2 pages.
CAS Registry No. 477872-74-5, created Dec. 31, 2002, last accessed Feb. 2, 2012, 1 page.
CAS Registry No. 477872-75-6, created Dec. 31, 2002, last accessed Feb. 2, 2012, 2 pages.
CAS Registry No. 477872-76-7, created Dec. 31, 2002, last accessed Feb. 2, 2012, 1 page.
CAS Registry No. 477872-77-8, created Dec. 31, 2002, last accessed Feb. 2, 2012, 1 page.
CAS Registry No. 477872-78-9, created Dec. 31, 2002, last accessed Feb. 2, 2012, 2 pages.
CAS Registry No. 477872-79-0, created Dec. 31, 2002, last accessed Feb. 2, 2012, 1 page.
CAS Registry No. 477872-80-3, created Dec. 31, 2002, last accessed Feb. 2, 2012, 2 pages.
Cas Registry No. 485843-91-2, created Feb. 5, 2003, last accessed Feb. 2, 2012, 1 p.
CAS Registry No. 485843-92-3, created Feb. 5, 2003, last accessed Feb. 2, 2012, 1 page.
CAS Registry No. 655223-84-0, created Feb. 27, 2004, last accessed Feb. 2, 2012, 1 page.
CAS Registry No. 655223-85-1, created Feb. 27, 2004 last accessed Feb. 2, 2012, 2 pages.
CAS Registry No. 773098-60-5, created Nov. 1, 2004, last accessed Feb. 2, 2012, 1 page.
CAS Registry No. 773098-61-6, created Nov. 1, 2004, last accessed Feb. 2, 2012, 2 pages.
CAS Registry No. 802313-56-0, created Dec. 25, 2004, last accessed Feb. 2, 2012, 1 page.
CAS Registry No. 860610-36-2, created Aug. 17, 2005, last accessed Feb. 2, 2012, 1 page.
CAS Registry No. 860610-37-3, created Aug. 17, 2005, last accessed Feb. 2, 2012, 1 page.
CAS Registry No. 860649-79-2, created Aug. 17, 2005, last accessed Feb. 2, 2012, 1 page.
CAS Registry No. 860649-80-5, created Aug. 17, 2005, last accessed Feb. 2, 2012, 1 page.
CAS Registry No. 866010-45-9, created Oct. 25, 2005, last accessed Feb. 2, 2012, 1 page.
CAS Registry No. 866010-46-0, created Oct. 25, 2005, last accessed Feb. 2, 2012, 2 pages.
CAS Registry No. 866010-47-1, created Oct. 25, 2005, last accessed Feb. 2, 2012, 1 page.
CAS Registry No. 866010-76-6, created Oct. 25, 2005, last accessed Feb. 2, 2012, 2 pages.
CAS Registry No. 866010-82-4, created Oct. 25, 2005, last accessed Feb. 2, 2012, 1 page.
CAS Registry No. 866010-83-5, created Oct. 25, 2005, last accessed Feb. 2, 2012, 2 pages.
CAS Registry No. 866010-85-7, created Oct. 25, 2005, last accessed Feb. 2, 2012, 1 page.
CAS Registry No. 866042-95-7, created Oct. 25, 2005, last accessed Feb. 2, 2012, 1 page.
CAS Registry No. 866042-98-0, created Oct. 25, 2005, last accessed Feb. 2, 2012, 1 page.
CAS Registry No. 866042-99-1, created Oct. 25, 2005, last accessed Feb. 2, 2012, 1 page.
CAS Registry No. 866043-03-0, created Oct. 25, 2005, last accessed Feb. 2, 2012, 2 pages.
CAS Registry No. 866043-06-3, created Oct. 25, 2005, last accessed Feb. 2, 2012, 1 page.
CAS Registry No. 945220-52-0, created Aug. 21, 2007, last accessed Feb. 2, 2012, 1 page.
CAS Registry No. 1026853-99-5 created Jun. 9, 2008, last accessed Feb. 2, 2012, 1 page.
CAS Registry No. 1027826-94-3, created Jun. 9, 2008, last accessed Feb. 2, 2012, 1 page.
CAS Registry No. 1029775-76-5, created Jun. 22, 2008, last accessed Feb. 2, 2012, 2 pages.
CAS Registry No. 1056748-82-3, created Oct. 3, 2008, last accessed Feb. 2, 2012, 1 page.
Troxler, F. et al. (1968). "Beiträge zur Chemie der Pyrrolo[3,2-c]Azepine und der Pyrrole[3,2-b]Azepine)," *Helvetica Chimica Acta* 51(8):1870-1881, English Summary Only.
Vecchietti, V. et al. (Jan.-Feb. 1974). "Nitro-Pyrrole Derivatives with Antimicrobial Activity," *European Journal of Medicinal Chemistry* 9(1):76-80.
Venturella, V.S. (Oct. 1964). "Arylindolizines III. Methoxyl and Glyoxyl Derivatives of Several Substituted Phenylindolizines," *Journal of Pharmaceutical Sciences* 53(10):1166-1169.
Wahyuningsih, T.D. et al. (2007, e-published May 3, 2007). "Synthesis of Indolo[2,3-c]Quinolines From 3-Arylindole-2-Ketoximes," *Tetrahedron* 63:6713-6719.
Yang, Z. et al. (2002). "A Strategy for the Synthesis of Aryl α-Ketoamides Based Upon the Acylation of Anions Derived from Cyanomethylamines Followed by Oxidative Cleavage," *Organic Letters* 4(7):1103-1105.
Yavari, I. et al. (2001). "Efficient Synthesis of 5,6,7-Trisubstituted 1 H-Pyrrolizines," *Tetrahedron* 57:5873-5878.
Yavari, I. et al. (2002). "A Simple Synthesis of Stable Heterocyclic Phosphorus Ylides Derived from NH-Acids," *Phosphorus, Sulfur and Silicon* 177:545-553.
CAS Registry No. 1002010-45-8, created Feb. 7, 2008, last accessed Oct. 30, 2013, 1 page.
CAS Registry No. 1002010-93-6, created Feb. 7, 2008, last accessed Oct. 30, 2013, 2 pages.
CAS Registry No. 1004172-59-1, created Feb. 18, 2008, last accessed Oct. 30, 2013, 1 page.
CAS Registry No. 1004425-72-2, created Feb. 19, 2008, last accessed Oct. 30, 2013, 1 page.
Anonymous. (Mar. 2006-Nov. 2013). "Anacor Pharmaceuticals Scientific Presentations", 7 pages.

(56) References Cited

OTHER PUBLICATIONS

Mao, W. et al. (Date Unknown) "AN2718 Has Broad Spectrum Antifungal Activity Necessary for the Topical Treatment of Skin and Nail Fungal Infections," P2422, 7 pages, 2014.

Plattner, J.J. et al. (Date Unknown). "Medicinal Chemistry of AN2690, A Novel Broad-Spectrum Antifungal Agent in Development for the Topical Treatment of Onychomycosis," Poster #775, Anacor Pharmaceuticals, 1 page, 2014.

* cited by examiner

PYRROLE ANTIFUNGAL AGENTS

CROSS-REFERENCE TO RELATED APPLICATIONS

This application is a National Phase filing under 35 U.S.C. §371 of International Application No. PCT/GB2009/01058, filed on Apr. 23, 2009, which claims priority to GB Patent Application No. 0807532.7, filed on Apr. 24, 2008 and GB Patent Application No. 0819696.6, filed on Oct. 27, 2008, the contents of which are incorporated herein by reference in their entirety.

FIELD OF THE INVENTION

This invention relates to pyrrole compounds, combinations and compositions comprising the pyrrole compounds and known antifungal agents, and their therapeutic use in prevention or treatment of fungal diseases. It also relates to the use of the compounds, combinations and compositions as agricultural fungicides.

BACKGROUND OF THE INVENTION

Invasive fungal infections are well recognised as diseases of the immunocompromised host. Over the last twenty years there have been significant rises in the number of recorded instances of fungal infection (Groll et al., 1996. *J Infect* 33, 23-32). In part this is due to increased awareness and improved diagnosis of fungal infection. However, the primary cause of this increased incidence is the vast rise in the number of susceptible individuals. This is due to a number of factors including new and aggressive immunosuppressive therapies, increased survival in intensive care, increased numbers of transplant procedures and the greater use of antibiotics worldwide.

In certain patient groups, fungal infection occurs at high frequency; lung transplant recipients have a frequency of up to 20% colonisation and infection with a fungal organism and fungal infection in allogenic haemopoetic stem cell transplant recipients is as high as 15% (Ribaud et al., 1999, *Clin Infect Dis.* 28:322-30).

Currently only four classes of antifungal drug are available to treat systemic fungal infections. These are the polyenes (e.g., amphotericin B), the azoles (e.g., ketoconazole or itraconazole), the echinocandins (e.g., caspofungin) and flucytosine.

The polyenes are the oldest class of antifungal agent being first introduced in the 1950's. The exact mode of action remains unclear but polyenes are only effective against organisms that contain sterols in their outer membranes. It has been proposed that amphotericin B interacts with membrane sterols to produce pores allowing leakage of cytoplasmic components and subsequent cell death.

Azoles work by inhibition of the 14α-demethylase via a cytochrome P450-dependent mechanism. This leads to a depletion of the membrane sterol ergosterol and the accumulation of sterol precursors resulting in a plasma membrane with altered fluidity and structure.

Echinocandins work by the inhibition of the cell wall synthetic enzyme β-glucan synthase. This leads to abnormal cell wall formation, osmotic sensitivity and cell lysis.

Flucytosine is a pyrimidine analogue interfering with cellular pyrimidine metabolism as well DNA, RNA and protein synthesis. However widespread resistance to flucyotosine limits its therapeutic use.

It can be seen that to date the currently available antifungal agents act primarily against only two cellular targets; membrane sterols (polyenes and azoles) and β-glucan synthase (echinocandins).

Resistance to both azoles and polyenes has been widely reported leaving only the recently introduced echinocandins to combat invasive fungal infections. As the use of echinocandins increases, resistance by fungi will inevitably occur.

The identification of new classes of antifungal agent is required to give the promise of positive therapeutic outcomes to patients.

SUMMARY OF THE INVENTION

The present inventors have found that certain pyrrole compounds, and combinations of these pyrrole compounds with known antifungal agents, are antifungal. In particular, the compounds inhibit the growth of human pathogenic fungi such as *Aspergillus* and therefore may be used to treat fungal infection and disease.

Accordingly, the present invention provides a pyrrole derivative of formula (I) or a pharmaceutically acceptable salt thereof for use in the prevention or treatment of a fungal disease:

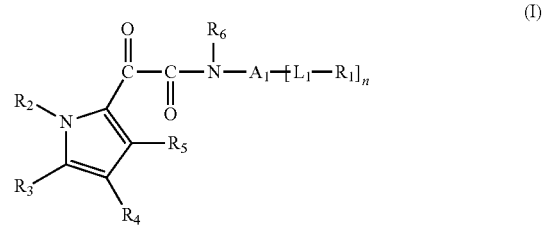

wherein:

R1 represents hydrogen, unsubstituted or substituted C1-C8 alkyl, C2-C8 alkenyl, C2-C8 alkynyl, —COR' or —SO$_2$(C1-C4 alkyl), or a group -A2, -L2-A2, -L3-A2, -A2-L3-A3 or -A4;

A1 represents a bond, a C3-C6 cycloalkyl or an unsubstituted or substituted C6-C10 aryl or 5- to 12-membered heterocyclyl group;

A2 and A3 are the same or different and represent C3-C6 cycloalkyl or an unsubstituted or substituted C6-C10 aryl or 5- to 12-membered heterocyclyl group;

A4 is an unsubstituted or substituted 5- to 12-membered heterocyclyl group wherein 1 or 2 ring carbon atoms are replaced with a group selected from >C(=O), >S(=O)$_2$, >C(=NOR7) where R7 is hydrogen or a C1-C4 alkyl group, >C=CH$_2$ or >C(—OCH$_2$CH$_2$O—);

L1 represents a bond, a C1-C6 alkylene group in which none, one, two or three —CH$_2$— groups are independently replaced by —O—, —S— or —NR'—, or a 5- to 12-membered heterocyclyl group;

L2 represents —NR'—, —O—, —CO—, —OCO—, —OCONR'R"—, —CONR'R"— or —SO$_2$—;

L3 represents a bond or a C1-C4 alkylene group in which none, one or two —CH$_2$— groups are independently replaced by —O—, —S— or —NR'—;

n is 1 or 2;

R6 represents hydrogen or C1-C4 alkyl;

R5 represents an unsubstituted or substituted group selected from C6-C10 aryl, a 5- to 12-membered heterocyclyl group, C1-C8 alkyl and C3-C6 cycloalkyl, hydrogen, halogen or a group of formula —B1-B2 or —B3;

B1 represents an unsubstituted or substituted C6-C10 aryl group;

B2 represents an unsubstituted or substituted C6-C10 aryl or 5- to 12-membered heterocyclyl group;

B3 is an unsubstituted or substituted 5- to 12-membered heterocyclyl group where 1 or 2 ring carbon atoms are replaced with a group selected from >C(=O), >S(=O)$_2$, >C(=NOR11) where R11 is hydrogen or a C1-C4 alkyl group, >C=CH$_2$ or >C(—OCH$_2$CH$_2$O—);

R2 and R3 independently represent C6-C10 aryl, a 5- to 12-membered heterocyclyl group, C3-C6 cycloalkyl, hydrogen, halogen, C1-C8 alkyl, C2-C8 alkenyl, C2-C8 alkynyl, C3-C6 cycloalkyl, —OR', —SR', —SOR', —SO$_2$R', —SO$_2$NR'R", —SO$_3$H, NR'R", —NR'COR', —CO$_2$R', —CONR'R", —COR', —OCOR', —CF$_3$, —NSO$_2$R' or —OCONR'R", or a group (C1-4) alkyl-A5, wherein none, one or two —CH$_2$— groups are independently replaced by —O—, —S— or —NR'— and wherein A5 represents C6-10 aryl or a 5- to 12-membered heterocyclyl group; or R2 and R3 together with the ring atoms to which they are bonded form a 5- to 7-membered, at least partially saturated ring containing a nitrogen atom from the adjacent pyrrole ring, and optionally one or two further heteroatoms selected from N, O and S, with the proviso that R2 and R3 do not form, together with the pyrrole ring to which they are bonded, an indolizine or tetrahydroindolizine ring;

R4 represents hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, —Y—Z, C6-C10 aryl, or 5- to 12-membered heterocyclyl group, or a group of formula -Alk$^6$-L5-A12, where Alk$^6$ is a C1-C4 alkylene group, L5 is a group of formula —C(=O)— or —NR13-C(=O)— and R13 is hydrogen or C1-C4 alkyl, and A12 is an unsubstituted or substituted C6-C10 aryl or 5- to 12-membered heterocyclyl group;

Y represents C1-C8 alkylene, C2-C8 alkenylene or C2-C8 alkynylene;

Z represents halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$, —NSO$_2$R', —OCONR'R" or —CR'=NOR"; and R' and R" independently represent hydrogen, C1-C8 alkyl, C2-C8 alkenyl or C2-C8 alkynyl.

Preferably A1 represents a C3-C6 cycloalkyl or an unsubstituted or substituted C6-C10 aryl or 5- to 12-membered heterocyclyl group.

The present inventors have further found that a number of the compounds of formula (I) have particular activity in inhibiting the growth of a wide variety of fungi such as those of the *Aspergillus* and *Candida* genera. The present invention accordingly also provides a pyrrole derivative of formula (IB) or a pharmaceutically acceptable salt thereof for use in the prevention or treatment of a fungal disease:

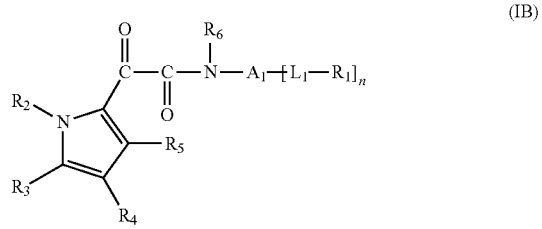

(IB)

wherein A1, L1, n, R1 and R3 to R5 are as defined for formula (I) above, and R2 is a group of formula -Alk$_1$-X—R', wherein Alk$_1$ is an unsubstituted or substituted C1-C6 alkylene group, X is a group —O—, —S—, —NR"—, —CO$_2$—, —CONR"—, —OCO—, —OCONR"— or —SO$_2$—, and R' and R" are independently selected from hydrogen and unsubstituted or substituted C1-C4 alkyl.

The invention also provides the use of a derivative or pharmaceutically acceptable salt of formula (I) or (IB) as defined above for the manufacture of a medicament for the prevention or treatment of a fungal disease. The invention also provides an agent for the treatment of a fungal disease comprising a derivative or pharmaceutically acceptable salt of formula (I) or (IB) as defined above. There is further provided a method of treating a subject suffering from or susceptible to a fungal disease, which method comprises administering to said subject an effective amount of a derivative or pharmaceutically acceptable salt of formula (I) or (IB) as defined above.

The invention also provides a method of controlling a fungal disease in a plant, which method comprises applying to the locus of the plant a derivative of formula (I) or (IB) as defined above or an agriculturally acceptable salt thereof, optionally in combination with a second antifungal agent. The invention also provides the use of a derivative of formula (I) or (IB) as defined above or an agriculturally acceptable salt thereof, optionally in combination with a second antifungal agent, as an agricultural fungicide.

The invention also provides a pharmaceutical combination comprising a combination of a pyrrole derivative of formula (I) or (IB) or a pharmaceutically acceptable salt thereof with a second antifungal agent. Also provided is a pharmaceutical composition comprising a combination of a pyrrole derivative of formula (I) or (IB) or a pharmaceutically acceptable salt thereof with a second antifungal agent.

In the combinations of the invention the pyrrole derivative of formula (I) or (IB) or pharmaceutically acceptable salt thereof has an antifungal effect and is sometimes referred to as the "first antifungal agent", to distinguish it from the second antifungal agent described later. In the combinations, compositions and products of the invention, the first antifungal agent is different from the second antifungal agent.

In the combination therapies of the invention, preferably the pyrrole derivative of formula (I) or (IB) or pharmaceutically acceptable salt thereof and the second antifungal agent are formulated for simultaneous or successive administration. Preferably the combination of the pyrrole derivative of formula (I) or (IB) or pharmaceutically acceptable salt thereof and the second antifungal agent are for use in the treatment or prevention of a fungal disease.

The invention further provides a product comprising a pyrrole derivative of formula (I) or (IB) or a pharmaceutically acceptable salt thereof and a second antifungal agent for separate, simultaneous or sequential use in the prevention or treatment of a fungal disease.

There is also provided a pharmaceutical composition comprising (i) a pyrrole of formula (I) or (IB) or a pharmaceutically acceptable salt thereof, (ii) a second antifungal agent, and (iii) a pharmaceutically acceptable carrier or diluent. Preferably the pharmaceutical composition is for use in the treatment or prevention of a fungal disease.

The invention also provides the use of a pyrrole derivative of formula (I) or (IB) or a pharmaceutically acceptable salt thereof and a second antifungal agent in the manufacture of a medicament for use in the treatment or prevention of fungal disease. The invention also provides the use of a pyrrole derivative of formula (I) or (IB) or a pharmaceutically acceptable salt thereof in the manufacture of a medicament for administration with a second antifungal agent in the treatment or prevention of fungal disease. Alternatively the invention provides the use of an antifungal agent (corresponding to the second antifungal agent mentioned above) in the manufacture of a medicament for administration with a pyrrole derivative of formula (I) or (IB) or a pharmaceutically acceptable salt thereof in the treatment or prevention of fungal disease.

There is also disclosed a method of treating a fungal disease which comprises administering a therapeutically effective amount of a first antifungal agent which is a pyrrole derivative of formula (I) or (IB) or a pharmaceutically acceptable salt thereof and a second antifungal agent. Furthermore, the invention relates to a kit comprising, in admixture or in separate containers, a pyrrole derivative of formula (I) or (IB) or a pharmaceutically acceptable salt thereof and a second antifungal agent.

The invention also provides a compound, which is a pyrrole derivative of formula (I) or a pharmaceutically acceptable salt thereof, for use in a method of treatment of a human or animal body by therapy. In this embodiment, R6 is hydrogen; A1 is a bond, a C3-C6 cycloalkyl or an unsubstituted or substituted C6-C10 aryl, 5- or 6-membered heterocyclyl or 8- to 10-membered bicyclic heterocyclyl group; R2 is as defined above with the exception that when R2 is cycloalkyl it is an unsubstituted cycloalkyl group; R4 represents hydrogen, halogen, C1-C8 alkyl, C2-C8 alkenyl, C2-C8 alkynyl, —OR', —CONR'R", —COR', —CN, —NO$_2$, —NR'R", CF$_3$, —Y—Z, C6-C10 aryl, or 5- to 12-membered heterocyclyl group, or a group of formula -Alk$^6$-L5-A12, where Alk$^6$ is a C1-C4 alkylene group, L5 is a group of formula —O—C(=O)—, —C(=O)— or —NR13-C(=O)— and R13 is hydrogen or C1-C4 alkyl, Alt is an unsubstituted or substituted C6-C10 aryl or 5- to 12-membered heterocyclyl group and R', R", Y and Z are as defined above; with the provisos that (i) when A1 is a bond, -L1-R1 is not hydrogen, (ii) when A1 is a bond, R2 is unsubstituted or substituted phenyl and R3 to R5 are all hydrogen, -L1-R1 is not unsubstituted or substituted benzyl or substituted phenethyl, (iii) when A1 is a bond, R6 is hydrogen and R3 to R5 are all hydrogen or chlorine, then none of L1, L3 and L1-R1 represents an unsubstituted or substituted C1-C4 alkyl group; and (iv) the compound is not:

N-[1-(4-methyl-3-penten-1-yl)-4-piperidinyl]-1H-pyrrole-2-acetamide,
5-Thia-azabicyclo[4.2.0]oct-2-ene-2-carboxylic acid, 3-(hydroxymethyl)-8-oxo-7-[2-(2-pyrrolyl)glyoxylamido]-, acetate ester,
2-Oxo-N-[2-(5-piperidin-1-ylmethyl-1H-pyrrol-2-yl)-ethyl]-2-[5-(1H-pyrrol-2-ylmethyl)-1H-pyrrol-2-yl]-acetamide,
2-oxo-N-[2-(1H-pyrrol-2-yl)-ethyl]-2-[5-(1H-pyrrol-2-ylmethyl)-1H-pyrrol-2-yl]-acetamide,
5-Aminooxalyl-3-(2-methoxycarbonyl-ethyl)-4-methoxycarbonylmethyl-1H-pyrrole-2-carboxylic acid tert-butyl ester,
(2S,5R,6R)-3,3-Dimethyl-6-[2-(1-methyl-1H-pyrrol-2-yl)-2-oxo-acetylamino]-7-oxo-4-thia-1-aza-bicyclo[3.2.0]heptane-2-carboxylic acid,
(2S,5R,6R)-3,3-Dimethyl-7-oxo-6-[2-oxo-2-(1-phenyl-1H-pyrrol-2-yl)-acetylamino]-4-thia-1-aza-bicyclo[3.2.0]heptane-2-carboxylic acid,
(2S,5R,6R)-3,3-Dimethyl-7-oxo-6-[2-oxo-2-(1H-pyrrol-2-yl)-acetylamino]-4-thia-1-aza-bicyclo[3.2.0]heptane-2-carboxylic acid,
Potassium; (2S,5R,6R)-3,3-dimethyl-7-oxo-6-[2-oxo-2-(1-phenyl-1H-pyrrol-2-yl)-acetylamino]-4-thia-1-aza-bicyclo[3.2.0]heptane-2-carboxylate,
Potassium; (2S,5R,6R)-3,3-dimethyl-7-oxo-6-[2-oxo-2-(1H-pyrrol-2-yl)-acetylamino]-4-thia-1-aza-bicyclo[3.2.0]heptane-2-carboxylate, or
Potassium; (2S,5R,6R)-3,3-dimethyl-6-[2-(1-methyl-1H-pyrrol-2-yl)-2-oxo-acetylamino]-7-oxo-4-thia-1-aza-bicyclo[3.2.0]heptane-2-carboxylate.

The invention also provides a compound, which is a pyrrole derivative of formula (I) or a pharmaceutically or agriculturally acceptable salt thereof:

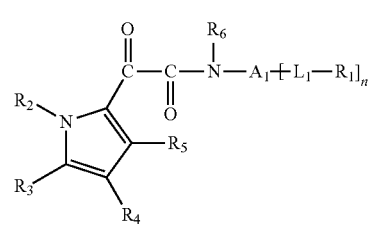

(I)

wherein R1, L1, n, R3 and R5 are as defined above;

A1 is a bond, a C3-C6 cycloalkyl or an unsubstituted or substituted C6-C10 aryl, 5- or 6-membered heterocyclyl or 8- to 10-membered bicyclic heterocyclyl group;

R6 represents hydrogen;

R2 represents C6-C10 aryl, a 5- to 12-membered heterocyclyl group other than benzothiophene, unsubstituted C3-C6 cycloalkyl, hydrogen, halogen, C1-C8 alkyl, C2-C8 alkenyl, C2-C8 alkynyl, C3-C6 cycloalkyl, —OR', —SR', —SOR', —SO$_2$R', —SO$_2$NR'R", —SO$_3$H, —NR'R", —NR'COR', —CO$_2$R', —CONR'R", —COR', —OCOR', —CF$_3$, —NSO$_2$R' or —OCONR'R", or a group (C1-4) alkyl-A5, wherein none, one or two —CH$_2$— groups are independently replaced by —O—, —S— or —NR'— and wherein A5 represents C6-10 aryl or a 5- to 12-membered heterocyclyl group; or R2 together with R3 and the ring atoms to which they are bonded form a 5- to 7-membered, at least partially saturated ring containing a nitrogen atom from the adjacent pyrrole ring, and optionally one or two further heteroatoms selected from N, O and S, with the proviso that R2 and R3 do not form, together with the pyrrole ring to which they are bonded, an indolizine or tetrahydroindolizine ring;

wherein when R2 represents aryl or heterocyclyl it is unsubstituted or substituted with one or more unsubstituted substituents selected from halogen, —NR'R", —CO$_2$R', —CONR'R", —OCONR'R", —OCOR', —COCF$_3$ and hydroxyl, or C1-C6 alkyl or C1-C4 alkoxy which are unsubstituted or substituted with a hydroxyl or unsubstituted C1-C4 alkoxy group; wherein R' and R" are independently selected from hydrogen, unsubstituted C1-C4 alkyl and C1-C4 alkyl substituted with a hydroxyl or unsubstituted C1-C4 alkoxy group;

R4 represents hydrogen, halogen, C1-C8 alkyl, C2-C8 alkenyl, C2-C8 alkynyl, —OR', —CO$_2$R', —CONR'R", —CN, —NO$_2$, —NR'R", CF$_3$, —Y—Z, C6-C10 aryl, or 5- to 12-membered heterocyclyl group, or a group of formula -Alk$^6$-L5-A12, where Alk$^6$ is a C1-C4 alkylene group, L5 is a group of formula —O—C(=O)—, —C(=O)— or —NR13-C(=O)— and R13 is hydrogen or C1-C4 alkyl, and A12 is an unsubstituted or substituted C6-C10 aryl or 5- to 12-membered heterocyclyl group;

wherein Y, Z and, unless otherwise specified, R' and R" are as defined above;

with the provisos that when A1 is a bond, L1-R1 is not hydrogen;

when A1 is a bond, R2 is unsubstituted or substituted phenyl and R3 to R5 are all hydrogen, -L1-R1 is not unsubstituted or substituted benzyl or substituted phenethyl;

when A1 is a bond, R2 is hydrogen and R3 to R5 are all hydrogen or chlorine, then none of L1, L3 and L1-R1 represents an unsubstituted or substituted C1-C4 alkyl group; and the compound is not N-(4-Bromo-phenyl)-2-[1-(2-chloro-4-nitro-phenyl)-1H-pyrrol-2-yl]-2-oxo-acetamide,
2-[1-(2-chloro-4-nitro-phenyl)-1H-pyrrol-2-yl-N-(4-chloro-phenyl)-2-oxo-acetamide,
3-[2-(4-Fluoro-phenylaminooxalyl)-pyrrol-1-yl]-propionic acid,
N-Benzo[1,3]dioxol-5-yl-2-[1-(2-cyano-ethyl)-1H-pyrrol-2-yl]-2-oxo-acetamide,
2-[1-(2-Cyano-ethyl)-1H-pyrrol-2-yl]-N-(4-fluoro-phenyl)-2-oxo-acetamide,
N-(2,4-Difluoro-phenyl)-2-(1-methyl-1H-pyrrol-2-yl)-2-oxo-acetamide,
N-(2,3-Difluoro-phenyl)-2-(1-methyl-1H-pyrrol-2-yl)-2-oxo-acetamide,
2-(1-Methyl-1H-pyrrol-2-yl)-2-oxo-N-(4-phenoxy-phenyl)-acetamide,
N-(2-Methoxy-4-nitro-phenyl)-2-(1-methyl-1H-pyrrol-2-yl)-2-oxo-acetamide,
N-(2,3-Dichloro-phenyl)-2-(1-methyl-1H-pyrrol-2-yl)-2-oxo-acetamide,
4-[2-(1-Methyl-1H-pyrrol-2-yl)-2-oxo-acetylamino]-benzoic acid methyl ester,
2-(1-Methyl-1H-pyrrol-2-yl)-2-oxo-N-(2-trifluoromethyl-phenyl)-acetamide,
2-(1-Methyl-1H-pyrrol-2-yl)-2-oxo-N-(3-trifluoromethyl-phenyl)-acetamide,
N-(3,5-Dichloro-phenyl)-2-(1-methyl-1H-pyrrol-2-yl)-2-oxo-acetamide,
N-(2,4-Dichloro-phenyl)-2-(1-methyl-1H-pyrrol-2-yl)-2-oxo-acetamide,
2-(1-Methyl-1H-pyrrol-2-yl)-2-oxo-N-phenyl-acetamide,
N-(4-Chloro-phenyl)-2-(1-methyl-1H-pyrrol-2-yl)-2-oxo-acetamide,
3-[2-(4-Bromo-phenylaminooxalyl)-pyrrol-1-yl]-thiophene-2-carboxylic acid methyl ester,
3-[2-(4-Chloro-phenylaminooxalyl)-pyrrol-1-yl]-thiophene-2-carboxylic acid methyl ester,
3-[2-(2-trifluoromethyl-phenylaminooxalyl)-pyrrol-1-yl]-thiophene-2-carboxylic acid methyl ester,
3-[2-(4-trifluoromethyl-phenylaminooxalyl)-pyrrol-1-yl]-thiophene-2-carboxylic acid methyl ester,
3-[2-(3-trifluoromethyl-phenylaminooxalyl)-pyrrol-1-yl]-thiophene-2-carboxylic acid methyl ester,
3-[2-(4-Fluoro-phenylaminooxalyl)-pyrrol-1-yl]-thiophene-2-carboxylic acid methyl ester,
N-[1-(4-methyl-3-penten-1-yl)-4-piperidinyl]-1H-pyrrole-2-acetamide,
3-(2-Allylaminooxalyl-pyrrol-1-yl)-thiophene-2-carboxylic acid methyl ester,
3-(2-Propylaminooxalyl-pyrrol-1-yl)-thiophene-2-carboxylic acid methyl ester,
5-Thia-azabicyclo[4.2.0]oct-2-ene-2-carboxylic acid, 3-(hydroxymethyl)-8-oxo-7-[2-(2-pyrrolyl)glyoxylamido]-, acetate ester
3-{2-[2-(3,4-Dimethoxy-phenyl)-ethylaminooxalyl]-pyrrol-1-yl}-propionic acid
2-[1-(2-Cyano-ethyl)-1H-pyrrol-2-yl]-N-furan-2-ylmethyl-2-oxo-acetamide
2-[1-(2-Cyano-ethyl)-1H-pyrrol-2-yl]-N-[2-(3,4-dimethoxy-phenyl)-ethyl]-2-oxo-acetamide
2-Oxo-N-[2-(5-piperidin-1-ylmethyl-1H-pyrrol-2-yl)-ethyl]-2-[5-(1H-pyrrol-2-ylmethyl)-1H-pyrrol-2-yl]-acetamide
2-oxo-N-[2-(1H-pyrrol-2-yl)-ethyl]-2-[5-(1H-pyrrol-2-ylmethyl)-1H-pyrrol-2-yl]-acetamide
5-Aminooxalyl-3-(2-methoxycarbonyl-ethyl)-4-methoxycarbonylmethyl-1H-pyrrole-2-carboxylic acid tert-butyl ester
N-(3-Nitro-biphenyl-4-yl)-2-oxo-2-(1H-pyrrol-2-yl)-acetamide
(2S,5R,6R)-3,3-Dimethyl-6-[2-(1-methyl-1H-pyrrol-2-yl)-2-oxo-acetylamino]-7-oxo-4-thia-1-aza-bicyclo[3.2.0]heptane-2-carboxylic acid
(2S,5R,6R)-3,3-Dimethyl-7-oxo-6-[2-oxo-2-(1-phenyl-1H-pyrrol-2-yl)-acetylamino]-4-thia-1-aza-bicyclo[3.2.0]heptane-2-carboxylic acid
(2S,5R,6R)-3,3-Dimethyl-7-oxo-6-[2-oxo-2-(1H-pyrrol-2-yl)-acetylamino]-4-thia-1-aza-bicyclo[3.2.0]heptane-2-carboxylic acid
Potassium; (2S,5R,6R)-3,3-dimethyl-7-oxo-6-[2-oxo-2-(1-phenyl-1H-pyrrol-2-yl)-acetylamino]-4-thia-1-aza-bicyclo[3.2.0]heptane-2-carboxylate
Potassium; (2S,5R,6R)-3,3-dimethyl-7-oxo-6-[2-oxo-2-(1H-pyrrol-2-yl)-acetylamino]-4-thia-1-aza-bicyclo[3.2.0]heptane-2-carboxylate or
Potassium; (2S,5R,6R)-3,3-dimethyl-6-[2-(1-methyl-1H-pyrrol-2-yl)-2-oxo-acetylamino]-7-oxo-4-thia-1-aza-bicyclo[3.2.0]heptane-2-carboxylate.

The invention also provides a compound of formula (IB) as defined above or a pharmaceutically or agriculturally acceptable salt thereof, provided that the compound is not 3-[2-(4-fluoro-phenylaminooxalyl)-pyrrol-1-yl]-propionic acid or 3-{2-[2-(3,4-Dimethoxy-phenyl)-ethylaminooxalyl]-pyrrol-1-yl}-propionic acid.

Pharmaceutical compositions comprising a compound of the invention and a pharmaceutically acceptable carrier or diluent, optionally together with a second antifungal agent, are also provided. Compositions comprising a compound of the invention and an agriculturally acceptable carrier or diluent, optionally together with a second antifungal agent, are also provided.

DETAILED DESCRIPTION OF THE INVENTION

As used herein, a C1-C8 alkyl group or moiety can be linear, branched or cyclic but is preferably linear. It is preferably a C1-C6 alkyl group, more preferably a C1-C4 alkyl group, most preferably a C1-C3 alkyl group. Suitable such alkyl groups and moieties include methyl, ethyl, n-propyl, i-propyl, n-butyl, sec-butyl and tert-butyl, as well as pentyl, e.g. $CH_2C(CH_3)_3$, hexyl, heptyl and octyl and isomers thereof. As used herein, a C1-C8 alkylene group or moiety is a divalent alkyl group or moiety as defined above, for example a C1-C4 alkylene group or moiety such as methylene, ethylene or propylene.

As used herein, a C2-C8 alkenyl group or moiety can be linear, branched or cyclic but is preferably linear. It contains one or more carbon-carbon double bonds. It is preferably a C2-C6 alkenyl group, more preferably a C2-C4 alkenyl group, most preferably a C2-C3 alkenyl group. Suitable such alkenyl groups and moieties include vinyl, allyl, propenyl, butenyl, e.g. $CH_2C(Me)=CH_2$, pentenyl, hexenyl, heptenyl and octenyl and isomers thereof.

As used herein, a C2-C8 alkynyl group or moiety can be linear or branched but is preferably linear. It contains one or more carbon-carbon triple bonds. It is preferably a C2-C6 alkynyl group, more preferably a C2-C4 alkynyl group, most preferably a C2-C3 alkynyl group. Suitable such alkynyl groups and moieties include ethynyl, propynyl, butynyl, pentynyl, hexynyl, heptynyl and octynyl and isomers thereof.

An alkyl, alkenyl or alkynyl group or moiety can be substituted or unsubstituted. Typically, it carries up to three substituents, e.g. one or two substituents. Suitable substituents are preferably themselves unsubstituted and include halogen such as fluorine, hydroxy, amino, (C1-C4 alkyl)amino, di(C1-C4 alkyl)amino, C1-C4 alkoxy such as methoxy, ethoxy and propoxy, —S(C1-C4 alkyl) such as —SMe, —CO$_2$H, —CO$_2$(C1-C4 alkyl), phenyl, 5- or 6-membered heterocyclyl such as pyridinyl, —CONR'R" and —NR'CO (C1-C4 alkyl) where R' and R" are the same or different and represent hydrogen or unsubstituted C1-C4 alkyl. Preferably R' and R" are the same or different and represent hydrogen or methyl. More preferably R' represents hydrogen and R" represents methyl. Examples of these substituents include unsubstituted substituents such as halogen (for example fluorine), hydroxy, amino, —S(C1-C4 alkyl) (for example —SMe), phenyl, pyridinyl, —COO(C1-C4 alkyl) (for example —COOMe, —COOEt and —COOPr), —CONR'R" (for example —CONHMe), —NR'CO(C1-C4 alkyl) (for example —NHCOMe), (C1-C4 alkyl)amino and di(C1-C4 alkyl)amino, and C1-C4 alkoxy such as methoxy, ethoxy or propoxy which are themselves unsubstituted or further substituted with unsubstituted methoxy or ethoxy. C1-C4 alkoxy, such as methoxy or ethoxy, halogen, such as fluorine, and hydroxy are preferred. Other preferred groups include unsubstituted phenyl or pyridinyl, —NMe$_2$, —COOR' where R' is C1-C3 alkyl, —CONHMe and —NHCOMe.

In a preferred embodiment, suitable substituents on an alkyl, alkenyl or alkynyl group or moiety are preferably themselves unsubstituted and include halogen such as fluorine, hydroxy, amino, (C1-C4 alkyl)amino, di(C1-C4 alkyl)amino, C1-C4 alkoxy such as methoxy or ethoxy, —CO$_2$H and —CO$_2$(C1-C4 alkyl). Preferred examples of these substituents include unsubstituted substituents such as halogen (for example fluorine), hydroxy, amino, (C1-C4 alkyl)amino and di(C1-C4 alkyl)amino, and C1-C4 alkoxy such as methoxy or ethoxy which are themselves unsubstituted or further substituted with unsubstituted methoxy or ethoxy. Most preferred are C1-C4 alkoxy, such as methoxy or ethoxy, halogen, such as fluorine, and hydroxy.

As used herein, a C3-C6 cycloalkyl group is typically a C4, C5 or C6 cycloalkyl group, more preferably a C5 or C6 cycloalkyl group. Typically a cycloalkyl group is unsubstituted or substituted with up to three substituents, e.g. one or two substituents. Suitable substituents include C1-C8 alkyl, C2-C8 alkenyl, C2-C8 alkynyl, Z and —Y—Z wherein Y and Z are as hereinbefore defined. Where present, preferably the substituents are themselves unsubstituted. Typically, a cycloalkyl group is unsubstituted.

When Y is C1-C8 alkylene, it is preferably C1-C4 alkylene, more preferably methylene or ethylene.

When Y is C2-C8 alkenylene, it is preferably C2-C4 alkenylene, more preferably ethenylene.

When Y is C2-C8 alkynylene, it is preferably C2-C4 alkynylene, more preferably ethynylene.

When R' or R" is C1-C8 alkyl, it is preferably C1-C4 alkyl, more preferably methyl or ethyl.

When R' or R" is C2-C8 alkenyl, it is preferably C2-C4 alkenyl, more preferably ethenyl.

When R' or R" is C2-C8 alkynyl, it is preferably C2-C4 alkynyl, more preferably ethynyl.

As used herein, an aryl group or moiety is typically phenyl or naphthyl, more preferably phenyl.

As used herein and unless otherwise stated, a heterocyclyl group or moiety is a saturated or unsaturated, 5- to 12-membered ring system in which the ring contains at least one heteroatom. Typically, the ring contains up to three or four heteroatoms, e.g. one or two heteroatoms, selected from O, S and N. Thus, a heterocyclyl group or moiety is typically a 5- to 12-membered ring containing one, two or three heteroatoms selected from O, S and N. Suitable such heterocyclyl groups and moieties include, for example, monocyclic saturated 5- to 8-membered rings, more preferably 5- to 7-membered rings, such as tetrahydrofuranyl, piperidinyl, oxazolidinyl, morpholinyl, thiomorpholinyl, pyrrolidinyl, dioxolanyl, piperidonyl, azepanyl, piperazinyl, tetrahydropyranyl and 1,4-diazepanyl, more preferably pyrrolidinyl, morpholinyl, piperazinyl, tetrahydropyranyl, piperidinyl, azepanyl and 1,4-diazepanyl, more preferably still more preferably pyrrolidinyl, morpholinyl, piperazinyl, tetrahydropyranyl, piperidinyl, azepanyl and 1,4-diazepanyl; monocyclic at least partially unsaturated 5- to 8-membered rings, more preferably 5- to 6-membered rings, such as furanyl, pyrrolyl, thiophenyl, oxazolyl, isoxazolyl, thiazolyl, pyrazolyl, imidazolyl, triazolyl, tetrazolyl, pyridinyl, pyrimidinyl, pyrazinyl, pyridazinyl and di- and tetrahydropyridinyl, e.g. oxazolyl, isoxazolyl, imidazolyl, furanyl, thiophenyl, pyrimidinyl or pyridinyl; bicyclic 8- to 10-membered ring systems such as indolyl, benzofuranyl, benzothiophenyl, benzimidazolyl, benzoxazolyl, benzopyrazolyl, benzothiazolyl, benzotriazolyl, quinolinyl, quinazolinyl (including isomers thereof, e.g. isoquinolinyl), quinoxalinyl, cinnolinyl, purinyl and cyclopentapyridines which may optionally be partially unsaturated, for example dihydroindolyl; and tricyclic 11- or 12-membered ring systems such as acridinyl, pteridinyl and benzathiazinyl. Particular examples of such heterocyclyl groups and moieties include monocyclic saturated 5- to 8-membered rings, more preferably monocyclic saturated 5- to 7-membered rings such as pyrrolidinyl, morpholinyl, piperazinyl, tetrahydropyranyl, piperidinyl and 1,4-diazepanyl; and monocyclic at least partially unsaturated 5- to 8-membered rings, more preferably monocyclic unsaturated 5- to 6-membered rings such as oxazolyl, isoxazolyl, imidazolyl, furanyl, thiophenyl, pyrimidinyl or pyridinyl. Particular examples of bicyclic 8- to 10-membered ring systems include indolyl, benzofuranyl, quinolinyl and isoquinolinyl, for example benzofuranyl, quinolinyl and isoquinolinyl.

A heterocyclyl or aryl group or moiety may be substituted or unsubstituted. Each ring atom may be unsubstituted or may carry one or two substituents. If desired, a nitrogen atom may be disubstituted and a sulphur atom may be substituted, providing a charged heteroatom. Typically, a heterocyclyl or aryl group or moiety carries up to three substituents, e.g. one or two substituents. The heterocycle may be connected to the remainder of the molecule by a bond to any of its available ring positions.

Suitable substituents include C1-C8 alkyl, C2-C8 alkenyl, C2-C8 alkynyl, Z and —Y—Z wherein Y and Z are as hereinbefore defined. Preferred substituents on an aryl or heterocyclyl group or moiety are unsubstituted substituents selected from halogen, —CO$_2$R', —CONR'R", OCOR', hydroxyl, cyano, —NR'R", —COR', —NSO$_2$R', —O(C2-C4 alkenyl), C2-C4 alkenyl, —SO$_2$R', —OCONR'R" and —CR'=NOR", or C1-C6 alkyl or C1-C6 alkoxy groups which are unsubstituted or substituted with one, two, three or four, for example one, two, or three, for example one, unsubstituted group selected from halogen, hydroxyl, amino, (C1-C4 alkyl)amino, di(C1-C4 alkyl)amino, C1-C4 alkoxy and —O—(C1-

C4 alkyl)-O—(C1-C4 alkyl), preferably hydroxyl, C1-C4 alkoxy and —O—(C1-C4 alkyl)-O—(C1-C2 alkyl). Substituents on A1 when A1 is other than a bond can also include substituents of formula -(C1-C2 alkyl)-O—(C1-C4 alkyl)-NR'R" where R' and R" are the same or different and represent hydrogen or C1-C4 alkyl, or R' and R", together with the nitrogen atom to which they are bonded, form a piperazinyl or morpholinyl group which is unsubstituted or substituted with 1 or 2 C1-C4 alkyl groups. Preferred such substituents which are specific to the A1 group are those of formula —CH$_2$—O—(C2-C3 alkyl)-NR'R" where R' and R" are the same or different and represent hydrogen or methyl, or R' and R", together with the nitrogen atom to which they are bonded, form a piperazinyl or morpholinyl group which is unsubstituted or substituted with one methyl group. Unless otherwise specified, aryl and heterocyclyl groups are not substituted with further aryl or heterocyclyl groups or with substituents containing further aryl or heterocyclyl groups.

Examples of more preferred substituents on an aryl or heterocyclyl group or moiety are unsubstituted substituents selected from halogen, —NR'R", —CO$_2$R', —CONR'R", —OCONR'R", —OCOR', —COCF$_3$, hydroxyl and cyano, or C1-C6 alkyl or C1-C4 alkoxy which are unsubstituted or substituted with a hydroxyl, unsubstituted C1-C4 alkoxy or unsubstituted —O—(C1-C4 alkyl)-O—(C1-C2 alkyl) group; wherein R' and R" are independently selected from hydrogen, unsubstituted C1-C4 alkyl and C1-C4 alkyl substituted with a hydroxyl or unsubstituted C1-C4 alkoxy group. Typically none or one cyano substituent is present.

As used herein, a halogen is typically chlorine, fluorine, bromine or iodine, and is preferably chlorine, fluorine or bromine, more preferably chlorine or fluorine.

A1 preferably represents a bond, a phenyl, naphthyl, a 5- or 6-membered heterocyclyl or 8- to 10-membered bicyclic heterocyclyl group, e.g. an unsaturated 8- to 10-membered bicyclic heterocyclyl group. More preferably A1 represents a bond or a phenyl, naphthyl, pyridyl, piperidinyl, benzofuranyl, indolyl, isoquinolinyl or quinolinyl group. Preferably A1 is other than a bond. A1 is typically other than a penicillin derivative, e.g. other than an oxo-thiaazabicyclo-heptane or -octane group. In a preferred embodiment A1 represents phenyl or a 5- or 6-membered heterocyclyl group, more preferably A1 represents phenyl, pyridyl or piperidinyl. Most preferably A1 represents phenyl.

A1 may be unsubstituted or substituted with one, two or three substituents selected from the unsubstituted groups halogen, —CO$_2$R', —CONR'R", —OCOR', hydroxyl, cyano, —NR'R", —COR', NSO$_2$R', —O(C2-C4 alkenyl), —C2-C4 alkenyl, —SO$_2$R', —OCONR'R" and —CR'=NOR", and from C1-C6 alkyl and C1-C4 alkoxy which are unsubstituted or substituted with a further unsubstituted C1-C4 alkoxy group; wherein R' and R" are independently hydrogen or C1-C4 alkyl. A1 may also be substituted with a group of formula -(C1-C2 alkyl)-O—(C1-C4 alkyl)-NR'R" where R' and R" are the same or different and represent hydrogen or C1-C4 alkyl, or R' and R", together with the nitrogen atom to which they are bonded, form a piperazinyl or morpholinyl group which is unsubstituted or substituted with 1 or 2 C1-C4 alkyl groups. When a substituent of formula -(C1-C2 alkyl)-O—(C1-C4 alkyl)-NR'R" is present, preferably there are no other substituents on the A1 group. Typically only one cyano group is present. Preferred substituents are unsubstituted C1-C4 alkyl, C1-C4 alkyl substituted with an unsubstituted C1-C4 alkoxy group, unsubstituted C1-C4 alkoxy, —CO$_2$H and halogen, and a group of formula -(C1-C2 alkyl)-O—(C1-C4 alkyl)-NR'R". More preferred substituents are unsubstituted C1-C4 alkyl, C1-C4 alkyl substituted with an unsubstituted C1-C4 alkoxy group, unsubstituted C1-C4 alkoxy, —CO$_2$H and halogen. In one embodiment, A1 is unsubstituted.

n is one or two, preferably one. When n is 2, preferably A1 is phenyl, each L1 is the same or different and represents piperazinyl or methylene, and each R1 is the same or different and represents pyridinyl or morpholinyl.

L1 preferably represents a bond, a 5- to 7-membered heterocyclyl group or a C1-C6 alkylene group wherein none, one or two —CH$_2$— groups are independently replaced by —O— or —NR'—, wherein R' is hydrogen, unsubstituted C1-C4 alkyl or C1-C4 alkyl substituted with an unsubstituted C1-C4 alkoxy group.

When L1 represents a 5- to 7-membered heterocyclyl group, it may be linked to A1 and R1 via a carbon atom or a heteroatom. Preferred 5- to 7-membered heterocyclyl groups are saturated groups which contains at least one nitrogen atom, for example one or two nitrogen atoms, wherein the heterocyclyl group is linked to at least one of A1 and R1, preferably both of A1 and R1, via a nitrogen atom. Examples of suitable heterocycles for L1 include piperazinyl, pyrrolidinyl, oxazolyl, morpholinyl, piperidinyl and 1,4-diazepanyl. Preferred examples of suitable heterocycles for L1 include piperazinyl and 1,4-diazepanyl, especially piperazinyl. When L1 represents a 5- to 7-membered heterocyclyl group, it is typically unsubstituted or substituted with an unsubstituted group selected from C1-C4 alkyl, C1-C4 alkoxy, hydroxy and halogen. Hydroxy substituents are preferred. Preferably, when L1 represents a 5- to 7-membered heterocyclyl group, it is unsubstituted.

L1 is most preferably a saturated 5- to 7-membered heterocyclyl group containing one or two nitrogen atoms, or an unsubstituted C1-C6 alkylene group wherein none, one or two —CH$_2$— groups are independently replaced with —O— or —NR'—, wherein R' is hydrogen, unsubstituted C1-C4 alkyl or C1-C4 alkyl substituted with an unsubstituted C1-C4 alkoxy group. In one embodiment, L1 is a saturated 5- to 7-membered heterocyclyl group, preferably a piperazinyl or 1,4-diazepanyl group.

When L1 is an unsubstituted C1-C6 alkylene group wherein none, one or two —CH$_2$— groups are independently replaced with —O— or —NR'—, suitable groups include C4 or C5 alkylene groups where two —CH$_2$— moieties (preferably one or both terminal —CH$_2$-moieties) are replaced by —O— or —NR'— where R' is hydrogen or unsubstituted C1-C2 alkyl. For example, preferred L1 groups in this category include —NMe-CH$_2$—CH$_2$—NMe-, —NH—CH$_2$—CH$_2$—O—, —O—CH$_2$—CH$_2$—NMe-, —O—CH$_2$—CH$_2$—O—, —NMe-CH$_2$—CH$_2$—NH—, —NH—CH$_2$—CH$_2$—NH—, —NH—CH$_2$—CH$_2$—NMe-, —CH$_2$—CH$_2$—CH$_2$—NMe- and —NMe-CH$_2$—CH$_2$—CH$_2$—NMe-. Most preferably L1 is piperazinyl.

R1 preferably represents hydrogen, unsubstituted or substituted C1-C8 alkyl, C2-C8 alkenyl, C2-C8 alkynyl, —COR' or —SO$_2$(C1-C4 alkyl), or a group -A2, -L2-A2, -L3-A2, -A2-L3-A3 or -A4. More preferably R1 represents hydrogen, an unsubstituted group selected from C1-C6 alkyl, C2-C6 alkenyl, C2-C6 alkynyl, —CO(C1-C4 alkyl) and —SO$_2$(C1-C4 alkyl), or a group -A2, -L2-A2, -L3-A2, -A2-L3-A3 or -A4. When L1 is a bond, R1 preferably represents hydrogen or a group -A2, L2-A2, A2-L3-A3 or A4. When L1 is other than a bond, R1 is preferably hydrogen, a C1-C6 alkyl group, a C2-C6 alkenyl group, a C2-C6 alkynyl group, unsubstituted —CO—(C1-C4-alkyl), unsubstituted —SO$_2$(C1-C4 alkyl) or a group -A2, L2-A2, -L3-A2 or -A2-L3-A3. In one embodiment, R1 is preferably a group -A2, -L2-A2, -L3-A2 or -A2-L3-A3, more preferably a group -A2.

In a preferred embodiment R1 represents unsubstituted or substituted C1-C8 alkyl, C2-C8 alkenyl, C2-C8 alkynyl, —COR' or —SO$_2$(C1-C4 alkyl), or a group -A2, -L2-A2, -L3-A2, -A2-L3-A3 or -A4. More preferably R1 represents an unsubstituted group selected from C1-C6 alkyl, C2-C6 alkenyl, C2-C6 alkynyl and —SO$_2$(C1-C4 alkyl), or a group -A2, -L2-A2, -L3-A2, -A2-L3-A3 or -A4. When L1 is a bond, R1 preferably represents A2, L2-A2, A2-L3-A3 or A4. When L1 is other than a bond, R1 is preferably a C1-C6 alkyl group, a C2-C6 alkenyl group, a C2-C6 alkynyl group, unsubstituted —SO$_2$(C1-C4 alkyl) or a group -A2, L2-A2, -L3-A2 or -A2-L3-A3.

When R1 represents an alkyl, alkenyl or alkynyl group it is preferably C1-C6 alkyl, C2-C6 alkenyl or C3-C6 alkynyl, more preferably C1-C6 alkyl (e.g. C3 or C4 alkyl), C3-C6 alkenyl or C3-C6 alkynyl. The alkyl, alkenyl and alkynyl groups are unsubstituted or substituted with 1, 2 or 3 substituents selected from halogen (e.g. fluorine), hydroxyl, amino, C1-C4 alkoxy, CO$_2$H and CO$_2$(C1-C4 alkyl). Halogen, e.g. fluorine, is preferred. The substituents are themselves unsubstituted. Preferably, when R1 represents an alkyl, alkenyl or alkynyl group it is unsubstituted.

A2 preferably represents C3-C6 cycloalkyl, phenyl or a 5- to 12-membered heterocyclyl group. Preferably A2 represents phenyl or a 5- or 6-membered heterocyclyl group. Preferred heterocyclyl groups include monocyclic, saturated or unsaturated, 5- to 6-membered rings, each of which may contain one, two or three, e.g. one or two, heteroatoms selected from N, O and S. Unsaturated 5- or 6-membered rings include oxazolyl, isoxazolyl, imidazolyl, furanyl, thiophenyl, pyrimidinyl and pyridinyl, preferably pyridinyl. Saturated rings are preferably 6-membered rings, for example piperidinyl, morpholinyl and tetrahydropyranyl, e.g. morpholinyl or tetrahydropyranyl. In one embodiment, A2 represents phenyl or pyridinyl, especially pyridinyl.

A2 may be unsubstituted or substituted by one, two or three substituents. Examples of suitable substituents are unsubstituted substituents selected from halogen, —CO$_2$R', —CONR'R", OCOR', hydroxyl, cyano, —NR'R", —COR', —NSO$_2$R', —O(C2-C4 alkenyl), C2-C4 alkenyl, —SO$_2$R', —OCONR'R" and —CR'═NOR", or C1-C6 alkyl or C1-C6 alkoxy groups which are unsubstituted or substituted with one, two, three or four, for example one, two, or three, for example one, unsubstituted group selected from halogen, hydroxyl, amino, (C1-C4 alkyl)amino, di(C1-C4 alkyl)amino, C1-C4 alkoxy and —O—(C1-C4 alkyl)-O—(C1-C4 alkyl), preferably hydroxyl, C1-C4 alkoxy and —O—(C1-C4 alkyl)-O—(C1-C2 alkyl).

Preferred substituents on A2 are unsubstituted substituents selected from halogen, —NR'R", —CO$_2$R', —CONR'R", —OCONR'R", —OCOR', —COCF$_3$, hydroxyl and cyano, or C1-C6 alkyl or C1-C4 alkoxy which are unsubstituted or substituted with a hydroxyl, unsubstituted C1-C4 alkoxy or unsubstituted —O—(C1-C4 alkyl)-O—(C1-C2 alkyl) group; wherein R' and R" are independently selected from hydrogen, unsubstituted C1-C4 alkyl and C1-C4 alkyl substituted with a hydroxyl or unsubstituted C1-C4 alkoxy group. Typically none or one cyano substituent is present.

Particularly preferred substituents on A2 are halogen, —COCF$_3$, —OCONR'R" and —NR'R", and C1-C4 alkyl and C1-C4 alkoxy groups which are unsubstituted or substituted with —OH, —OMe, —OEt or —O(C1-C4 alkyl)-O(C1-C2 alkyl), wherein R' and R" are independently selected from hydrogen, unsubstituted C1-C4 alkyl and C1-C4 alkyl substituted with a hydroxyl or unsubstituted C1-C4 alkoxy group. Most preferred substituents are C1-C2 alkyl and C1-C2 alkoxy, especially methyl.

In one embodiment, L2 represents —SO$_2$—.

In one embodiment, L3 represents a bond or a C1-C4 alkylene group in which none, one or two —CH$_2$— moieties are independently replaced with —O— or —NR'— wherein R' represents hydrogen or unsubstituted C1-C4 alkyl. In another embodiment, L3 represents a bond or an unsubstituted C1-C4 alkylene group. Preferably, L3 represents a bond or unsubstituted methylene, ethylene or propylene, e.g. unsubstituted methylene or ethylene, more preferably unsubstituted methylene. In the group -L3-A2, L3 preferably represents unsubstituted methylene, ethylene or propylene, e.g. unsubstituted methylene or ethylene, more preferably unsubstituted methylene.

In one embodiment, A3 represents phenyl or a 5- to 12-membered heterocyclyl group. Preferred heterocyclyl groups include monocyclic, unsaturated or saturated 5- to 6-membered rings, each of which may contain one, two or three, e.g. one or two, heteroatoms selected from N, O and S. Saturated 5- or 6-membered rings are preferred, e.g. morpholinyl, tetrahydropyranyl, piperidinyl or piperazinyl, in particular morpholinyl and piperazinyl.

A3 may be unsubstituted or substituted by one, two or three unsubstituted groups selected from C1-C4 alkyl, C1-C4 alkoxy, halogen, —CO$_2$R', —CONR'R", —OCOR', hydroxyl, cyano, —NR'R", —COR', —NSO$_2$R', —O(C2-C4 alkenyl), —C2-C4 alkenyl, —SO$_2$R', —OCONR'R" and —CR'═NOR", wherein R' and R" are independently hydrogen or C1-C4 alkyl. Typically only one cyano group is present. Preferred substituents are C1-C4 alkyl, C1-C4 alkoxy and halogen.

A4 is preferably an unsubstituted or substituted 5- to 6-membered heterocyclyl group wherein 1 ring carbon atom has been replaced with a group selected from >C(═O), >S(═O)$_2$, >C(═NOR7) where R7 is hydrogen or a C1-C4 alkyl group, >C═CH$_2$ or >C(—OCH$_2$CH$_2$O—). Preferably A4 is an unsubstituted or substituted 5- to 6-membered heterocyclyl group wherein 1 ring carbon atom has been replaced with >C═CH$_2$. Preferred A4 groups include unsubstituted or substituted dioxothiomorpholinyl, methoxyiminopiperidinyl, methoxyiminopyrrolidinyl, methylenepiperidinyl, dioxoazaspirodecyl and oxadihydropyrazolyl groups. The A9 groups can be unsubstituted or substituted; more preferably they are unsubstituted. Unsubstituted methylenepiperidinyl is preferred.

In one embodiment, R6 is hydrogen or methyl, more preferably R6 is hydrogen.

In one embodiment, R5 is hydrogen, phenyl, a monocyclic 5- to 8-membered heterocyclyl ring, a C3-C6 cycloalkyl group, an unsubstituted C1-C8 alkyl or a C1-C8 alkyl substituted with a C1-C4 alkoxy group. When R5 is C1-C8 alkyl substituted with C1-C4 alkoxy, preferably it is -(C1-C2 alkyl)-O(C1-C2 alkoxy), more preferably —CH$_2$—CH$_2$—OMe. More preferably R5 is hydrogen, phenyl, a monocyclic 5- to 8-membered heterocyclyl ring, a C3-C6 cycloalkyl group or unsubstituted C1-C8 alkyl. The heterocyclyl ring is typically pyridinyl, thiophenyl, furanyl, tetrahydropyranyl or piperidinyl. The cycloalkyl group is typically cyclobutyl, which is itself preferably unsubstituted. The phenyl and heterocyclyl groups are unsubstituted or substituted with one, two or three unsubstituted substituents selected from halogen, C1-C4 alkyl, C1-C4 alkoxy, —CO$_2$R', —CONR'R", —OCOR' or cyano, wherein R' and R" are independently selected from hydrogen and C1-C4 alkyl. Typically only one cyano substituent is present. Most preferably R5 is hydrogen or an unsubstituted phenyl.

In another embodiment, R5 is hydrogen, unsubstituted or substituted phenyl, unsubstituted C3-C6 cycloalkyl, unsubstituted or substituted pyridinyl or piperidinyl, or unsubstituted thiophenyl, furanyl or tetrahydropyranyl, the substituents being selected from halogen, unsubstituted C1-C4 alkyl, unsubstituted C1-C4 alkoxy or cyano, e.g. halogen, unsubstituted C1-C4 alkyl or unsubstituted C1-C4 alkoxy. In this embodiment R5 is, for example, hydrogen, unsubstituted or substituted phenyl or unsubstituted pyridinyl, thiophenyl or furanyl.

Preferably in this embodiment, R5 is hydrogen, unsubstituted or substituted phenyl, unsubstituted C3-C6 cycloalkyl, unsubstituted or substituted pyridinyl or piperidinyl, or unsubstituted thiophenyl, furanyl or tetrahydropyranyl, the substituents being selected from halogen, unsubstituted C1-C4 alkyl, unsubstituted C1-C4 alkoxy or cyano, e.g. halogen, unsubstituted C1-C4 alkyl or unsubstituted C1-C4 alkoxy, or R5 is a C1-C8 alkyl group substituted with a C1-C4 alkoxy group. In this embodiment R5 is, for example, hydrogen, unsubstituted or substituted phenyl or unsubstituted pyridinyl, thiophenyl or furanyl, or is a group —CH$_2$—CH$_2$—OMe.

In another embodiment, R5 is a group —B1-B2 or —B3. When R2 is —B1-B2, B1 is typically an unsubstituted or substituted phenyl group. More preferably B1 is an unsubstituted phenyl group. When R5 is —B1-B2, B2 is typically an unsubstituted or substituted phenyl or 5- to 6-membered heterocyclyl group, more preferably an unsubstituted or substituted phenyl, piperazinyl or morpholinyl group, e.g. an unsubstituted or substituted phenyl or piperazinyl group. When substituted, preferred substituents are 1 or 2 groups selected from halogen atoms and C1-C4 alkyl and C1-C4 alkoxy groups, more preferably halogen atoms or C1-C2 alkyl or C1-C2 alkoxy groups, more preferably C1-C2 alkyl groups such as methyl.

When R5 is B3, typically B3 is a 5- to 6-membered heterocyclyl group where 1 or 2 ring carbon atoms are replaced with >C(=O)—, >S(=O)$_2$—, >C(=NOR11), >C(NR11), >C(=CH$_2$) or >C(—OCH$_2$CH$_2$O—), where R11 is hydrogen or C1-C4 alkyl. Preferably R11 is hydrogen or C1-C2 alkyl, more preferably hydrogen or methyl. When R5 is B3, more preferably B3 is a 5- to 6-membered heterocyclyl group where 1 ring carbon atom is replaced with >C(=O)—, >S(=O)$_2$—, >C(=NOR11), >C(NR11), >C(=CH$_2$) or >C(—OCH$_2$CH$_2$O—), where R11 is hydrogen or C1-C2 alkyl, more preferably 1 ring carbon atom is replaced with >C(=O). A preferred B3 group is oxo-dihydropyridinyl. When R5 is B3, B3 can be unsubstituted or substituted. Preferably it is unsubstituted.

In one embodiment, R2 and R3 independently represent C6-C10 aryl, a 5- to 12-membered heterocyclyl group, C3-C6 cycloalkyl, hydrogen, halogen, C1-C8 alkyl, C2-C8 alkenyl, C2-C8 alkynyl, C3-C6 cycloalkyl, —OR', —SR', —SOR', —SO$_2$R', —SO$_2$NR'R", —SO$_3$H, —NR'R", —NR'COR', —CO$_2$R', —CONR'R", —COR', —OCOR', —CF$_3$, —NSO$_2$R' or —OCONR'R", or a group (C1-4) alkyl-A5, wherein none, one or two —CH$_2$— groups are independently replaced by —O—, —S— or —NR'— and wherein A5 represents C6-10 aryl or a 5- to 12-membered heterocyclyl group;

When R2 and R3 represent or contain C6-C10 aryl or a 5- to 12-membered heterocyclyl group, the aryl or heterocyclyl group is typically phenyl or a 5- or 6-membered, saturated or unsaturated heterocyclyl group. Typically none or one of R2 and R3 represents or contains an aryl or heterocyclyl group. Examples of suitable heterocyclyl groups include saturated rings such as pyrrolidinyl, morpholinyl, piperazinyl, tetrahydropyranyl and piperidinyl, and unsaturated rings such as oxazolyl, furanyl, thiophenyl, pyridinyl and pyrimidinyl, e.g. furanyl, thiphenyl, pyridinyl and pyrimidinyl. Bicyclic 8- to 10-membered rings may also be present at R2 and R3, for example indolyl, benzofuranyl and benzothiophenyl rings.

An aryl or heterocyclyl group or moiety on R2 or R3 may be unsubstituted or substituted on any ring atom. Typically it is unsubstituted or substituted with one, two or three substituents. Examples of suitable substituents are unsubstituted substituents selected from halogen, —CO$_2$R', —CONR'R", OCOR', hydroxyl, cyano, —NR'R", —COR', —NSO$_2$R', —O(C2-C4 alkenyl), C2-C4 alkenyl, —SO$_2$R', —OCONR'R" and —CR'=NOR", or C1-C6 alkyl or C1-C6 alkoxy groups which are unsubstituted or substituted with one, two, three or four, for example one, two, or three, for example one, unsubstituted group selected from halogen, hydroxyl, amino, (C1-C4 alkyl)amino, di(C1-C4 alkyl) amino, C1-C4 alkoxy and —O—(C1-C4 alkyl)-O—(C1-C4 alkyl), preferably hydroxyl, C1-C4 alkoxy and —O—(C1-C4 alkyl)-O—(C1-C2 alkyl).

Preferred substituents are unsubstituted substituents selected from halogen, —NR'R", —CO$_2$R', —CONR'R", —OCONR'R", —OCOR', —COCF$_3$ and hydroxyl, or C1-C6 alkyl or C1-C4 alkoxy which are unsubstituted or substituted with a hydroxyl or unsubstituted C1-C4 alkoxy group; wherein R' and R" are independently selected from hydrogen, unsubstituted C1-C4 alkyl and C1-C4 alkyl substituted with a hydroxyl or unsubstituted C1-C4 alkoxy group. More preferred substituents are halogen, unsubstituted C1-C4 alkyl (e.g. methyl) and unsubstituted C1-C4 alkoxy groups, in particular methyl.

In this embodiment, R2 preferably represents phenyl, hydrogen, —COO(C1-C4 alkyl), halogen, unsubstituted C3-C6 cycloalkyl, or a C1-C4 alkyl, C2-C4 alkenyl or C1-C4 alkoxy group which is unsubstituted or substituted with —SMe, —SEt, hydroxyl, di(C1-C4 alkyl)amino, —COO (C1-C4 alkyl), —CONR'R", —NR'CO(C1-C4 alkyl), unsubstituted C1-C4 alkoxy or C1-C4 alkoxy substituted with —OMe or —OEt, where R' and R" are the same or different and represent hydrogen or unsubstituted C1-C4 alkyl; or R2 represents a group (C1-C4) alkyl-A5, wherein none or one —CH$_2$— groups are independently replaced by —O—, —S— or —NR'— and wherein A5 represents phenyl, pyridinyl or oxazolyl.

More preferably, R2 represents unsubstituted phenyl, hydrogen, halogen, unsubstituted C1-C4 alkoxy, unsubstituted C2-C4 alkenyl, unsubstituted C1-C4 alkyl, or C1-C4 alkyl or C2-C4 alkenyl substituted with —OMe, —OEt, —OPr, —OBu, —OCH$_2$CH$_2$OMe, —SMe, hydroxy, di(C1-C4 alkyl)amino, —COO(C1-C4 alkyl), —CONR'R" or —NR'CO(C1-C4 alkyl) where R' and R" are the same or different and represent hydrogen or unsubstituted C1-C4 alkyl; or R2 represents a group (C1-C4) alkyl-A5, wherein none or one —CH$_2$— groups are independently replaced by —O— and wherein A5 represents phenyl, pyridinyl or oxazolyl, each of which is unsubstituted or substituted with one or two substituents selected from halogen, C1-C4 alkyl and C1-C4 alkoxy.

In this embodiment, more preferably R2 represents phenyl, hydrogen, halogen, unsubstituted C2-C4 alkenyl, unsubstituted C3-C6 cycloalkyl, or a C1-C4 alkyl or C1-C4 alkoxy group which is unsubstituted or substituted with —OMe or —OEt. More preferably, R2 represents unsubstituted phenyl, hydrogen, halogen, unsubstituted C1-C4 alkoxy, unsubstituted C1-C4 alkyl, or C1-C4 alkyl substituted with —OMe or —OEt. Most preferably, R2 represents unsubstituted C1-C4 alkyl, e.g. methyl.

In this embodiment, R3 preferably represents hydrogen, halogen, unsubstituted phenyl, unsubstituted C2-C4 alkenyl, or a C1-C4 alkyl or C1-C4 alkoxy group which is unsubstituted or substituted with —OMe or —OEt. More preferably, R3 represents hydrogen, halogen, unsubstituted phenyl, unsubstituted C1-C4 alkoxy, unsubstituted C1-C4 alkyl, or C1-C4 alkyl substituted with —OMe or —OEt. In this embodiment, still more preferably R3 represents hydrogen, halogen, unsubstituted C2-C4 alkenyl, or a C1-C4 alkyl or C1-C4 alkoxy group which is unsubstituted or substituted with —OMe or —OEt. More preferably, R3 represents hydrogen, halogen, unsubstituted C1-C4 alkoxy, unsubstituted C1-C4 alkyl, or C1-C4 alkyl substituted with —OMe or —OEt. Most preferably R3 represents hydrogen or unsubstituted C1-C4 alkyl, e.g. methyl.

In an alternative embodiment, R2 and R3 together with the ring atoms to which they are bonded form a 5- to 7-membered, at least partially saturated ring containing a nitrogen atom from the adjacent pyrrole ring, and optionally one or two further heteroatoms selected from N, O and S, with the proviso that R2 and R3 do not form, together with the pyrrole ring to which they are bonded, an indolizine or tetrahydroindolizine ring. Preferred heterocyclyl rings are at least partially saturated 5- or 6-membered rings containing a nitrogen atom from the adjacent pyrrole ring and none or one further heteroatom selected from N and O. Examples of preferred rings are piperazinyl, morpholinyl and pyrrolidinyl. Alternative preferred heterocyclyl rings include saturated 5- to 7-membered rings containing a nitrogen atom from the adjacent pyrrole ring and none or one further heteroatom selected from N and O, for example azepanyl.

The heterocyclyl ring formed by R2 and R3 may be unsubstituted or substituted on any ring atom. Typically, none, one or two substituents are present. Examples of suitable substituents on the R2/R3 ring are unsubstituted substituents selected from halogen, —CO₂R', —CONR'R", OCOR', hydroxyl, cyano, —NR'R", —COR', —NSO₂R', —O(C2-C4 alkenyl), C2-C4 alkenyl, —SO₂R', —OCONR'R" and —CR'=NOR", or C1-C6 alkyl or C1-C6 alkoxy groups which are unsubstituted or substituted with one, two, three or four, for example one, two, or three, for example one, unsubstituted group selected from halogen, hydroxyl, amino, (C1-C4 alkyl)amino, di(C1-C4 alkyl)amino, C1-C4 alkoxy and —O—(C1-C4 alkyl)-O—(C1-C4 alkyl), preferably hydroxyl, C1-C4 alkoxy and —O—(C1-C4 alkyl)-O—(C1-C2 alkyl).

Preferred substituents are unsubstituted substituents selected from halogen, —NR'R", —CO₂R', —CONR'R", —OCONR'R", —OCOR', —COCF₃ and hydroxyl, or C1-C6 alkyl or C1-C4 alkoxy which are unsubstituted or substituted with a hydroxyl or unsubstituted C1-C4 alkoxy group; wherein R' and R" are independently selected from hydrogen, unsubstituted C1-C4 alkyl and C1-C4 alkyl substituted with a hydroxyl or unsubstituted C1-C4 alkoxy group. More preferred substituents are halogen, unsubstituted C1-C4 alkyl (e.g. methyl) and unsubstituted C1-C4 alkoxy groups, in particular methyl.

Typically, when R4 is or contains an aryl or heterocyclyl group, the aryl or heterocyclyl group is phenyl, benzyl or pyridyl. The aryl or heterocyclyl group may be unsubstituted or substituted on any ring atom, for example with one, two or three substituents. Preferred substituents are unsubstituted substituents selected from halogen, —NR'R", —CO₂R', —CONR'R", —OCONR'R", —OCOR', —COCF₃ and hydroxyl, or C1-C6 alkyl or C1-C4 alkoxy which are unsubstituted or substituted with a hydroxyl or unsubstituted C1-C4 alkoxy group; wherein R' and R" are independently selected from hydrogen, unsubstituted C1-C4 alkyl and C1-C4 alkyl substituted with a hydroxyl or unsubstituted C1-C4 alkoxy group. More preferred substituents are halogen, unsubstituted C1-C4 alkyl (e.g. methyl) and unsubstituted C1-C4 alkoxy groups, in particular methyl or methoxy. More preferably, the aryl or heterocyclyl ring is unsubstituted.

In one embodiment, R4 represents hydrogen, halogen, phenyl, C1-C4 alkyl, C2-C4 alkenyl, C2-C4 alkynyl, —OR', —CO₂R', CONR'R", —COR', —CN, —NO₂, —NR'R" or —CF₃ wherein R' and R" are independently hydrogen or C1-C4 alkyl, more preferably R4 represents hydrogen, halogen, phenyl, C1-C4 alkyl, C2-C4 alkenyl, C2-C4 alkynyl, —OR', —CO₂R', CONR'R", —COR', —CN, —NO₂, —NR'R" or —CF₃ wherein R' and R" are independently hydrogen or C1-C4 alkyl. In another embodiment R4 represents hydrogen, halogen or C1-C4 alkyl, preferably hydrogen. Where R4 is capable of being substituted, it is typically unsubstituted or substituted with one halogen atom, more preferably it is unsubstituted.

In one embodiment, when R5 is phenyl or thienyl then preferably R4 is hydrogen. In another embodiment when R4 is phenyl preferably R5 is hydrogen.

Typically, Z is halogen, OR', SR', —NR'R', —CO₂R', —CONR'R", —COR', —OCOR' or CN, wherein R' and R" are independently hydrogen or C1-C4 alkyl.

In a preferred embodiment of the invention, R1 represents hydrogen, unsubstituted C1-C8 alkyl, C2-C8 alkenyl, C2-C8 alkynyl, —COR' or —SO₂(C1-C4 alkyl), or a group -A2, -L2-A2, -L3-A2, -A2-L3-A3 or -A4;

A1 represents a bond, phenyl, naphthyl, a 5- or 6-membered monocyclic heterocyclyl group, or an 8- to 10-membered bicyclic heterocyclyl group;

A2 and A3 are the same or different and represent phenyl or a 5- to 12-membered heterocyclyl group;

A4 represents a 5- to 6-membered heterocyclyl group wherein 1 ring carbon atom has been replaced with a group selected from >C(=O), >S(=O)₂, >C(=NOR7) where R7 is hydrogen or a C1-C4 alkyl group, >C=CH₂ or >C(—OCH₂CH₂O—);

L1 represents a bond, a 5- to 7-membered heterocyclyl group which is unsubstituted or substituted with an unsubstituted group selected from C1-C4 alkyl, C1-C4 alkoxy, hydroxy and halogen, or a C1-C6 alkylene group wherein none, one or two —CH₂— groups are independently replaced by —O— or —NR'—, wherein R' is hydrogen, unsubstituted C1-C4 alkyl or C1-C4 alkyl substituted with an unsubstituted C1-C4 alkoxy group;

L2 is as defined above;

L3 represents a bond or a C1-C4 alkylene group in which none, one or two —CH₂— moieties are independently replaced with —O— or —NR'—, wherein R' represents hydrogen or unsubstituted C1-C4 alkyl;

n is as defined above;

R6 represents hydrogen or unsubstituted C1-C4 alkyl;

R5 represents hydrogen, phenyl, a monocyclic 5- to 8-membered heterocyclyl ring, an unsubstituted C3-C6 cycloalkyl group, an unsubstituted C1-C8 alkyl or a C1-C8 alkyl substituted with a C1-C4 alkoxy;

either (i) R2 represents phenyl, hydrogen, —COO(C1-C4 alkyl), halogen, unsubstituted C3-C6 cycloalkyl, or a C1-C4 alkyl, C2-C4 alkenyl or C1-C4 alkoxy group which is unsubstituted or substituted with —SMe, —SEt, hydroxyl, di(C1-C4 alkyl)amino, —COO(C1-C4 alkyl), —CONR'R", —NR'CO(C1-C4 alkyl), unsubstituted C1-C4 alkoxy or C1-C4 alkoxy substituted with —OMe or —OEt, where R' and R" are the same or different and represent hydrogen or unsubstituted C1-C4 alkyl; or R2 represents a group (C1-C4) alkyl-A5, wherein none or one —CH$_2$— groups are independently replaced by —O—, —S— or —NR'— and wherein A5 represents phenyl, pyridinyl or oxazolyl; and R3 represents hydrogen, halogen, unsubstituted C2-C4 alkenyl, or a C1-C4 alkyl or C1-C4 alkoxy group which is unsubstituted or substituted with —OMe or —OEt; or (ii) R2 and R3 together with the ring atoms to which they are bonded form an at least partially saturated 5- or 6-membered ring containing a nitrogen atom from the adjacent pyrrole ring and none or one further heteroatom selected from N and O, with the proviso that R2 and R3 do not form, together with the pyrrole ring to which they are bonded, an indolizine or tetrahydroindolizine ring; and R4 represents hydrogen, halogen, phenyl, or an unsubstituted group selected from C1-C4 alkyl, C2-C4 alkenyl, C2-C4 alkynyl, —OR', —CO$_2$R', CONR'R", —COR', —CN, —NO$_2$, —NR'R" or —CF$_3$, wherein R' and R" are independently hydrogen or C1-C4 alkyl;

wherein the aryl and heterocyclyl rings formed by A1, A2, A3, A4, R5, R2 or R2 and R3 are unsubstituted or substituted with one, two or three substituents selected from the unsubstituted groups halogen, —CO$_2$R', —CONR'R", OCOR', hydroxyl, cyano, —NR'R", —COR', —NSO$_2$R', —O(C2-C4 alkenyl), C2-C4 alkenyl, —SO$_2$R', —OCONR'R" and —CR'=NOR", and from C1-C6 alkyl and C1-C6 alkoxy groups which are unsubstituted or substituted with one, two, three or four unsubstituted groups selected from hydroxyl, C1-C4 alkoxy and —O—(C1-C4 alkyl)-O—(C1-C2 alkyl), and wherein the group A1 can additionally or alternatively be substituted by a group of formula —(C1-C2 alkyl)-O—(C1-C4 alkyl)-NR'R" where R' and R" are the same or different and represent hydrogen or C1-C4 alkyl, or R' and R", together with the nitrogen atom to which they are bonded, form a piperazinyl or morpholinyl group which is unsubstituted or substituted with 1 or 2 C1-C4 alkyl groups.

In this preferred embodiment more preferably R1 represents unsubstituted C1-C8 alkyl, C2-C8 alkenyl, C2-C8 alkynyl, —COR' or —SO$_2$(C1-C4 alkyl), or a group -A2, -L2-A2, -L3-A2, -A2-L3-A3 or -A4. Preferably A1 represents phenyl or a 5- or 6-membered heterocyclyl group. Preferably R5 represents hydrogen, phenyl, a monocyclic 5- to 8-membered heterocyclyl ring, an unsubstituted C3-C6 cycloalkyl group or unsubstituted C1-C8 alkyl. Preferably R4 represents hydrogen, halogen, or an unsubstituted group selected from C1-C4 alkyl, C2-C4 alkenyl, C2-C4 alkynyl, —OR', —CO$_2$R', CONR'R", —COR', —CN, —NO$_2$, —NR'R" or —CF$_3$, wherein R' and R" are independently hydrogen or C1-C4 alkyl. In this preferred embodiment preferably the aryl and heterocyclyl rings formed by A1, A2, A3, A4, R5, R2 or R2 and R3 are unsubstituted or substituted with one, two or three substituents selected from the unsubstituted groups halogen, —CO$_2$R', —CONR'R", OCOR', hydroxyl, cyano, —NR'R", —COR', —NSO$_2$R', —O(C2-C4 alkenyl), C2-C4 alkenyl, —SO$_2$R', —OCONR'R" and —CR'=NOR", and from C1-C6 alkyl and C1-C6 alkoxy groups which are unsubstituted or substituted with one, two, three or four unsubstituted groups selected from hydroxyl, C1-C4 alkoxy and —O—(C1-C4 alkyl)-O—(C1-C2 alkyl).

Particularly preferred compounds for use in the invention are pyrrole derivatives of formula (Ia) and pharmaceutically or agriculturally acceptable salts thereof:

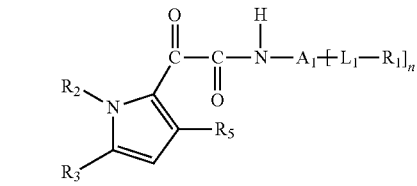

(IA)

wherein:

A1 represents a bond, phenyl, naphthyl, pyridyl, piperidinyl, benzofuranyl, indolyl, isoquinolinyl or quinolinyl, each of which may be unsubstituted or substituted with one or more substituents selected from unsubstituted C1-C4 alkyl, C1-C4 alkyl substituted with an unsubstituted C1-C4 alkoxy group, unsubstituted C1-C4 alkoxy, —CO$_2$H and halogen, or from a group of formula -(C1-C2 alkyl)-O—(C1-C4 alkyl)-NR'R" where R' and R" are the same or different and represent hydrogen or C1-C4 alkyl, or R' and R", together with the nitrogen atom to which they are bonded, form a piperazinyl or morpholinyl group which is unsubstituted or substituted with 1 or 2 C1-C4 alkyl groups;

n represents one or two, preferably one;

L1 represents a bond, a saturated 5- to 7-membered heterocyclyl group containing one or two nitrogen atoms, or an unsubstituted C1-C6 alkylene group wherein none, one or two —CH$_2$— groups are independently replaced with —O— or —NR'—, wherein R' is hydrogen, unsubstituted C1-C4 alkyl or C1-C4 alkyl substituted with an unsubstituted C1-C4 alkoxy group, and wherein the heterocyclyl group is unsubstituted or substituted with an unsubstituted group selected from C1-C4 alkyl, C1-C4 alkoxy, hydroxy and halogen;

when L1 is a bond, R1 represents hydrogen, -A2, —SO$_2$-A2, A2-L3-A3 or A4; and when L1 is other than a bond, R1 represents hydrogen or an unsubstituted group selected from C1-C6 alkyl, C2-C6 alkenyl, C2-C6 alkynyl, —CO(C1-C4 alkyl) and —SO$_2$(C1-C4 alkyl), or a group -A2, —SO$_2$-A2, -L3-A2 or -A2-L3-A3;

A2 and A3 independently represent phenyl or a 5- or 6-membered heterocyclyl group, wherein A2 and A3 are unsubstituted or substituted with one, two or three substituents selected from the unsubstituted substituents halogen, —COCF$_3$, —OCONR'R" and —NR'R", and from C1-C4 alkyl and C1-C4 alkoxy groups which are unsubstituted or substituted with —OH, —OMe, —OEt or —O(C1-C4 alkyl)-O(C1-C2 alkyl), wherein R' and R" are independently selected from hydrogen, unsubstituted C1-C4 alkyl and C1-C4 alkyl substituted with a hydroxyl or unsubstituted C1-C4 alkoxy group;

L3 represents a bond or unsubstituted methylene, ethylene or propylene;

A4 represents unsubstituted dioxothiomorpholinyl, methoxyiminopiperidinyl, methoxyiminopyrrolidinyl, methylenepiperidinyl, dioxoazaspirodecyl or oxadihydropyrazolyl;

R5 represents hydrogen, unsubstituted or substituted phenyl, unsubstituted C3-C6 cycloalkyl, unsubstituted or substituted pyridinyl or piperidinyl, or unsubstituted thiophenyl, furanyl or tetrahydropyranyl, the substituents being selected from halogen, unsubstituted C1-C4 alkyl, unsubstituted C1-C4 alkoxy or R5 is a C1-C8 alkyl group which is unsubstituted or substituted with a C1-C4 alkoxy group; and either (i) R2 represents unsubstituted phenyl, hydrogen, halogen, unsubstituted C1-C4 alkoxy, unsubstituted C2-C4 alkenyl, unsubstituted C1-C4 alkyl, or C1-C4 alkyl or C2-C4 alkenyl substituted with —OMe, —OEt, —OPr, —OBu, —OCH$_2$CH$_2$OMe, —SMe, hydroxy, di(C1-C4 alkyl)amino, —COO(C1-C4 alkyl), —CONR'R" or —NR'CO(C1-C4 alkyl) where R' and R" are the same or different and represent hydrogen or unsubstituted C1-C4 alkyl; or R2 represents a group (C1-C4) alkyl-A5, wherein none or one —CH$_2$— groups are independently replaced by —O— and wherein A5 represents phenyl, pyridinyl or oxazolyl, each of which is unsubstituted or substituted with one or two substituents selected from halogen, C1-C4 alkyl and C1-C4 alkoxy; and R3 represents hydrogen, halogen, unsubstituted phenyl, unsubstituted C1-C4 alkoxy, unsubstituted C1-C4 alkyl, or C1-C4 alkyl substituted with —OMe or —OEt; or (ii) R2 and R3 together with the ring atoms to which they are bonded form a substituted or unsubstituted at least partially saturated 5- or 6-membered ring containing a nitrogen atom from the adjacent pyrrole ring and none or one further heteroatom selected from N and O, the substituents being selected from unsubstituted C1-C4 alkyl and unsubstituted C1-C4 alkoxy groups.

In this more preferred embodiment, preferably A1 is other than a bond. More preferably A1 represents phenyl, pyridyl or piperidinyl, each of which may be unsubstituted or substituted with one or more substituents selected from unsubstituted C1-C4 alkyl, C1-C4 alkyl substituted with an unsubstituted C1-C4 alkoxy group, unsubstituted C1-C4 alkoxy, —CO$_2$H and halogen. Preferably when L1 is a bond, R1 represents -A2, —SO$_2$-A2, A2-L3-A3 or A4; and when L1 is other than a bond, R1 represents an unsubstituted group selected from C1-C6 alkyl, C2-C6 alkenyl, C2-C6 alkynyl and —SO$_2$(C1-C4 alkyl), or a group -A2, —SO$_2$-A2, -L3-A2 or -A2-L3-A3. Preferably R5 represents hydrogen, unsubstituted or substituted phenyl, unsubstituted C3-C6 cycloalkyl, unsubstituted or substituted pyridinyl or piperidinyl, or unsubstituted thiophenyl, furanyl or tetrahydropyranyl, the substituents being selected from halogen, unsubstituted C1-C4 alkyl or unsubstituted C1-C4 alkoxy. Preferably either R2 represents unsubstituted phenyl, hydrogen, halogen, unsubstituted C1-C4 alkoxy, unsubstituted C1-C4 alkyl, or C1-C4 alkyl substituted with —OMe or —OEt, and R3 represents hydrogen, halogen, unsubstituted C1-C4 alkoxy, unsubstituted C1-C4 alkyl, or C1-C4 alkyl substituted with —OMe or —OEt; or R2 and R3 together with the ring atoms to which they are bonded form a substituted or unsubstituted at least partially saturated 5- or 6-membered ring containing a nitrogen atom from the adjacent pyrrole ring and none or one further heteroatom selected from N and O, the substituents being selected from unsubstituted C1-C4 alkyl and unsubstituted C1-C4 alkoxy groups.

A further preferred embodiment provides pyrrole derivatives of formula (Ia) and pharmaceutically or agriculturally acceptable salts thereof, wherein:

A1 represents phenyl, which may be unsubstituted or substituted with one or more substituents selected from unsubstituted C1-C4 alkyl, C1-C4 alkyl substituted with an unsubstituted C1-C4 alkoxy group, unsubstituted C1-C4 alkoxy, —CO$_2$H and halogen, preferably A1 is unsubstituted or substituted with one group selected from F, Cl and methyl, most preferably A1 is unsubstituted;

n represents one;

L1 represents an unsubstituted, saturated 5- to 7-membered heterocyclyl group containing two nitrogen atoms, the heterocycle being attached to A1 and to R1 via a nitrogen atom, preferably L1 represents piperazinyl;

R1 represents unsubstituted C1-C6 alkyl, unsubstituted C2-C6 alkenyl, or a group -A2, —CH$_2$-A2 or -A2-CH$_2$-A3;

A2 and A3 independently represent phenyl or a 5- or 6-membered heterocyclyl group, wherein A2 and A3 are unsubstituted or substituted with one, two or three substituents selected from the unsubstituted substituents halogen, —COCF$_3$, —OCONR'R" and —NR'R", and from C1-C4 alkyl and C1-C4 alkoxy groups which are unsubstituted or substituted with —OH, —OMe, —OEt or —O(C1-C4 alkyl)-O(C1-C2 alkyl), wherein R' and R" are independently selected from hydrogen, unsubstituted C1-C4 alkyl and C1-C4 alkyl substituted with a hydroxyl or unsubstituted C1-C4 alkoxy group;

R5 represents unsubstituted phenyl;

R2 represents hydrogen, or C1-C4 alkyl or C2-C4 alkenyl, each of which may be unsubstituted or substituted with —OMe, —OEt, —OPr, —OBu, —OCH$_2$CH$_2$OMe, —SMe, hydroxy, di(C1-C4 alkyl)amino, —COO(C1-C4 alkyl), —CONR'R" or —NR'CO(C1-C4 alkyl) where W and R" are the same or different and represent hydrogen or unsubstituted C1-C4 alkyl; or R2 represents a group (C1-C4) alkyl-A5, wherein none or one —CH$_2$— groups are independently replaced by —O— and wherein A5 represents phenyl, pyridinyl or oxazolyl, each of which is unsubstituted or substituted with one or two substituents selected from halogen, C1-C4 alkyl and C1-C4 alkoxy; and R3 represents hydrogen or C1-C4 alkyl which is unsubstituted or substituted with —OMe or —OEt.

In a preferred aspect of this embodiment, A1 is a phenyl group which is unsubstituted or substituted with F, Cl or methyl, preferably A1 is unsubstituted phenyl; L1 is piperazinyl and is linked to A1 and R1 via a nitrogen atom; and R1 is unsubstituted C1-C6 alkyl, unsubstituted C2-C6 alkenyl, or piperidinyl, wherein the piperidinyl group is unsubstituted or substituted with one, two or three substituents selected from unsubstituted C1-C4 alkyl groups. More preferably, R1 is piperidinyl which is substituted with two methyl groups.

In a further preferred aspect of this embodiment, R2 and R3 are independently selected from hydrogen and unsubstituted C1-C4 alkyl groups, preferably methyl.

A particular embodiment of the invention relates to pyrrole derivatives of formula (I) and pharmaceutically acceptable salts thereof, for use in a method of treatment of a human or animal body by therapy. In this embodiment, R6 is hydrogen and A1 is a bond, a C3-C6 cycloalkyl or an unsubstituted or substituted C6-C10 aryl, 5- or 6-membered heterocyclyl or 8- to 10-membered bicyclic heterocyclyl group. Preferably, A1 represents a C3-C6 cycloalkyl or an unsubstituted or substituted C6-C10 aryl, 5- or 6-membered heterocyclyl or unsaturated 8- to 10-membered bicyclic heterocyclyl group. More preferably, A1 represents a phenyl, naphthyl, pyridyl, piperidinyl, benzofuranyl, indolyl, isoquinolinyl or quinolinyl group. Possible substituents on A1 are as defined above.

In this embodiment, when A1 is a bond, (i) -L1-R1 is not hydrogen, (ii) when R2 is unsubstituted or substituted phenyl and R3 to R5 are all hydrogen, -L1-R1 is not unsubstituted or substituted benzyl or substituted phenethyl, and (iii) when R6 is hydrogen and R3 to R5 are all hydrogen or chlorine, then none of L1, L3 and L1-R1 represents an unsubstituted or substituted C1-C4 alkyl group. Preferably, when A1 is a bond, -L1-R1 is other than hydrogen, unsubstituted or substituted benzyl, substituted phenethyl or unsubstituted or substituted C2-C4 alkyl. More preferably, A1 is not a bond.

In this embodiment, R4 represents hydrogen, halogen, C1-C8 alkyl, C2-C8 alkenyl, C2-C8 alkynyl, —OR', —CONR'R", —COR', —CN, —NO$_2$, —NR'R", CF$_3$, —Y—Z, C6-C10 aryl, or 5- to 12-membered heterocyclyl group, or a group of formula -Alk$^6$-L5-A12, where Alk$^6$ is a C1-C4 alkylene group, L5 is a group of formula —O—C(=O)—, —C(=O)— or —NR13-C(=O)— and R13 is hydrogen or C1-C4 alkyl, A12 is an unsubstituted or substituted C6-C10 aryl or 5- to 12-membered heterocyclyl group and R', R", Y and Z are as defined above. Where R4 represents an aryl or heterocyclyl group it is typically phenyl, benzyl or pyridyl. The aryl or heterocyclyl group may be unsubstituted or substituted as defined above.

R4 preferably represents hydrogen, halogen, phenyl, C1-C4 alkyl, C2-C4 alkenyl, C2-C4 alkynyl, —OR', CONR'R", —COR', —CN, —NO$_2$, —NR'R" or —CF$_3$ wherein R' and R" are independently hydrogen or C1-C4 alkyl. More preferably R4 represents hydrogen, halogen, phenyl, C1-C4 alkyl, C2-C4 alkenyl, C2-C4 alkynyl, —OR', CONR'R", —COR', —CN, —NO$_2$, —NR'R" or —CF$_3$ wherein R' and R" are independently hydrogen or C1-C4 alkyl. In another embodiment R4 represents hydrogen, halogen or C1-C4 alkyl, preferably hydrogen. Where R4 is capable of being substituted, it is typically unsubstituted or substituted with one halogen atom, more preferably it is unsubstituted.

In this embodiment, when R2 is cycloalkyl it is an unsubstituted cycloalkyl group.

In a further particular embodiment, the present invention provides novel pyrrole derivatives of formula (I) and pharmaceutically or agriculturally acceptable salts thereof. In this embodiment, A1 is a bond, a C3-C6 cycloalkyl or an unsubstituted or substituted C6-C10 aryl, 5- or 6-membered heterocyclyl or 8- to 10-membered bicyclic heterocyclyl group. Preferably, A1 represents a C3-C6 cycloalkyl or an unsubstituted or substituted C6-C10 aryl, 5- or 6-membered heterocyclyl or unsaturated 8- to 10-membered bicyclic heterocyclyl group. More preferably, A1 represents a phenyl, naphthyl, pyridyl, piperidinyl, benzofuranyl, indolyl, isoquinolinyl or quinolinyl group. Possible substituents on A1 are as defined above.

When A1 is a bond, (i) -L1-R1 is not hydrogen, (ii) when R2 is unsubstituted or substituted phenyl and R3 to R5 are all hydrogen, -L1-R1 is not unsubstituted or substituted benzyl or substituted phenethyl, and (iii) when R6 is hydrogen and R3 to R5 are all hydrogen or chlorine, then none of L1, L3 and L1-R1 represents an unsubstituted or substituted C1-C4 alkyl group. Preferably, when A1 is a bond, -L1-R1 is other than hydrogen, unsubstituted or substituted benzyl, substituted phenethyl or unsubstituted or substituted C2-C4 alkyl. More preferably, A1 is not a bond.

In this embodiment, when A1 and L1 are both a bond, R1 preferably represents unsubstituted or substituted C1-C8 alkyl, C2-C8 alkenyl, C2-C8 alkynyl, —COR' or —SO$_2$(C1-C4 alkyl), or a group -A2, -L2-A2, -L3-A2 or -A2-L3-A3. More preferably, R1 represents an unsubstituted group selected from C1-C6 alkyl, C2-C6 alkenyl, C2-C6 alkynyl, —CO(C1-C4 alkyl) and —SO$_2$(C1-C4 alkyl) or a group -A2, -L2-A2, -L3-A2 or -A2-L3-A3. More preferably, R1 represents a group -A2, -L2-A2, -L3-A2 or -A2-L3-A3. Preferred alkyl, alkenyl and alkynyl groups and substituents on these groups are described above. A2, A3, L2 and L3 are as defined above.

In this embodiment, R6 is hydrogen.

In this embodiment, when R2 is heterocyclyl, it is not substituted with an aryl or further heterocyclyl group. Preferred substituents on an R2 heterocyclyl group are defined above. Preferably, when R2 is heterocyclyl it is not thienyl or benzothienyl, more preferably it is not thienyl, benzothienyl or pyrazolyl. More preferably, when R2 is heterocyclyl, it is an unsubstituted 5- or 6-membered heterocyclyl ring other than thienyl. More preferably, R2 is not heterocyclyl. Most preferred R2 groups are defined above.

When R2 is a substituted C1-C8 alkyl group, the substituent(s) do not include —CN or —CO$_2$H. Preferred substituents on an R2 C1-C8 alkyl group are defined above. When R2 is substituted phenyl, the substituent(s) do not include nitro. Preferred substituents on an R2 phenyl group are defined above.

In this embodiment, R4 represents hydrogen, halogen, C1-C8 alkyl, C2-C8 alkenyl, C2-C8 alkynyl, —OR', —CONR'R", —COR', —CN, —NO$_2$, —NR'R", CF$_3$, —Y—Z, C6-C10 aryl, or 5- to 12-membered heterocyclyl group, or a group of formula -Alk$^6$-L5-A12, where Alk$^6$ is a C1-C4 alkylene group, L5 is a group of formula —O—C(=O)—, —C(=O)— or —NR13-C(=O)— and R13 is hydrogen or C1-C4 alkyl, A12 is an unsubstituted or substituted C6-C10 aryl or 5- to 12-membered heterocyclyl group and R', R", Y and Z are as defined above. Where R4 represents an aryl or heterocyclyl group it is typically phenyl, benzyl or pyridyl. The aryl or heterocyclyl group may be unsubstituted or substituted as defined above.

R4 preferably represents hydrogen, halogen, phenyl, C1-C4 alkyl, C2-C4 alkenyl, C2-C4 alkynyl, —OR', CONR'R", —COR', —CN, —NO$_2$, —NR'R" or —CF$_3$ wherein R' and R" are independently hydrogen or C1-C4 alkyl. More preferably R4 represents hydrogen, halogen, phenyl, C1-C4 alkyl, C2-C4 alkenyl, C2-C4 alkynyl, —OR', CONR'R", —COR', —CN, —NO$_2$, —NR'R" or —CF$_3$ wherein R' and R" are independently hydrogen or C1-C4 alkyl. In another embodiment R4 represents hydrogen, halogen or C1-C4 alkyl, preferably hydrogen. Where R4 is capable of being substituted, it is typically unsubstituted or substituted with one halogen atom, more preferably it is unsubstituted.

In a further aspect of this embodiment, when L1 is a bond, R1 preferably represents hydrogen, unsubstituted or substituted C2-C8 alkenyl, C2-C8 alkynyl, —COR' or —SO$_2$(C1-C4 alkyl), or a group -A2, -L2-A2, -L3-A2, -A2-L3-A3 or -A4. More preferably, when L1 is a bond, R1 represents hydrogen, an unsubstituted group selected from C2-C6 alkenyl, C2-C6 alkynyl and —SO$_2$(C1-C4 alkyl), or a group -A2, -L2-A2, -L3-A2, -A2-L3-A3 or -A4. Most preferably, when L1 is a bond, R1 represents hydrogen or a group -A2, -L2-A2, A2-L3-A3 or A4.

In a preferred aspect of this particular embodiment, when L1 is a bond, R1 preferably represents unsubstituted or substituted C2-C8 alkenyl, C2-C8 alkynyl, —COR' or —SO$_2$(C1-C4 alkyl), or a group -A2, -L2-A2, -L3-A2, -A2-L3-A3 or -A4. More preferably, when L1 is a bond, R1 represents an unsubstituted group selected from C2-C6 alkenyl, C2-C6 alkynyl and —SO$_2$(C1-C4 alkyl), or a group -A2, -L2-A2, -L3-A2, -A2-L3-A3 or -A4. Most preferably, when L1 is a bond, R1 represents -A2, -L2-A2, -A2-L3-A3 or A4.

When L1 is other than a bond, R1 represents hydrogen, unsubstituted or substituted C1-C8 alkyl, C2-C8 alkenyl, C2-C8 alkynyl, —COR' or —SO$_2$(C1-C4 alkyl), or a group -A2, -L2-A2, -L3-A2, -A2-L3-A3 or -A4. More preferably, when L1 is other than a bond, R1 represents hydrogen, an unsubstituted group selected from C1-C6 alkyl, C2-C6 alkenyl, C2-C6 alkynyl, —CO(C1-C4 alkyl) and —SO$_2$(C1-C4 alkyl), C1-C6 alkyl substituted with —OMe or —OEt, or a group -A2, -L2-A2, -L3-A2, -A2-L3-A3 or -A4. Most preferably, when L1 is other than a bond, R1 represents hydrogen, a C1-C6 alkyl group, a C2-C6 alkenyl group, a C2-C6 alkynyl group, unsubstituted —CO(C1-C4 alkyl), unsubstituted —SO$_2$(C1-C4 alkyl) or a group -A2, L2-A2, -L3-A2 or -A2-L3-A3.

Alternatively, when L1 is other than a bond, R1 represents an unsubstituted group selected from C1-C6 alkyl, C2-C6 alkenyl, C2-C6 alkynyl and —SO$_2$(C1-C4 alkyl), or a group -A2, -L2-A2, -L3-A2, -A2-L3-A3 or -A4. Most preferably, when L1 is other than a bond, R1 represents a C1-C6 alkyl group, a C2-C6 alkenyl group, a C2-C6 alkynyl group, unsubstituted —SO₂(C1-C4 alkyl) or a group -A2, L2-A2, -L3-A2 or -A2-L3-A3.

In a further preferred aspect of this embodiment, L1 is a bond, —CH₂—, —NR'—, a C2-C6 alkylene group in which none, one, two or three —CH₂— groups are independently replaced by —O—, —S— or —NR'—, or a 5- to 12-membered heterocyclyl group, wherein R' is as defined above. L1 preferably represents a bond, —CH₂—, —NR'—, a 5- to 7-membered heterocyclyl group or a C2-C6 alkylene group wherein none, one or two —CH₂— groups are independently replaced by —O— or —NR'—, wherein R' is hydrogen, unsubstituted C1-C4 alkyl or C1-C4 alkyl substituted with an unsubstituted C1-C4 alkoxy group. When L1 represents a 5- to 7-membered heterocyclyl group, it is preferably as defined above.

In this embodiment, L1 is most preferably —CH₂—, —NR'—, a saturated 5- to 7-membered heterocyclyl group containing one or two nitrogen atoms, or an unsubstituted C2-C6 alkylene group wherein none, one or two —CH₂— groups are independently replaced with —O— or —NR'—, wherein R' is hydrogen, unsubstituted C1-C4 alkyl or C1-C4 alkyl substituted with an unsubstituted C1-C4 alkoxy group.

Preferred compounds of this embodiment are compounds of formula (IA) as defined above, or pharmaceutically or agriculturally acceptable salts thereof, wherein when A1 is a bond, (i) -L1-R1 is not hydrogen, (ii) when R2 is unsubstituted or substituted phenyl and R3 to R5 are all hydrogen, -L1-R1 is not unsubstituted or substituted benzyl or substituted phenethyl, and (iii) when R6 is hydrogen and R3 to R5 are all hydrogen or chlorine, then none of L1, L3 and L1-R1 represents an unsubstituted or substituted C1-C4 alkyl group and (iv) when L1 is a bond, R1 represents an unsubstituted group selected from C1-C6 alkyl, C2-C6 alkenyl, C2-C6 alkynyl, —CO(C1-C4 alkyl) and —SO₂(C1-C4 alkyl) or a group -A2, -L2-A2, -L3-A2 or -A2-L3-A3.

Typically in this embodiment, L1 represents a bond, —CH₂—, —NR'— a saturated 5- to 7-membered heterocyclyl group containing one or two nitrogen atoms, or an unsubstituted C2-C6 alkylene group wherein none, one or two —CH₂— groups are independently replaced with —O— or —NR'—, wherein R' is hydrogen, unsubstituted C1-C4 alkyl or C1-C4 alkyl substituted with an unsubstituted C1-C4 alkoxy group, and wherein the heterocyclyl group is unsubstituted or substituted with an unsubstituted group selected from C1-C4 alkyl, C1-C4 alkoxy, hydroxy and halogen. When L1 represents an unsubstituted C2-C6 alkylene group wherein none, one or two —CH₂— groups are independently replaced with —O— or —NR'—, preferably it is a C4 or C5 alkylene group wherein none, one or two, more preferably one or two, —CH₂— groups are independently replaced with —O— or —NR'— wherein R' is hydrogen or unsubstituted C1-C4 alkyl.

Specific examples of compounds of formula (I) include:
2-(1,5-Dimethyl-3-phenyl-1H-pyrrol-2-yl)-N-{4-[4-(4,6-dimethyl-pyridin-2-yl)-piperazin-1-yl]-phenyl}-2-oxo-acetamide,
N-{4-[4-(4,6-Dimethyl-pyridin-2-yl)-piperazin-1-yl]-phenyl}-2-oxo-2-(1-phenyl-1H-pyrrol-2-yl)-acetamide,
N-{4-[4-(4,6-Dimethyl-pyridin-2-yl)-piperazin-1-yl]-phenyl}-2-(5-methyl-1-phenyl-1H-pyrrol-2-yl)-2-oxo-acetamide,
N-{4-[4-(4,6-Dimethyl-pyridin-2-yl)-piperazin-1-yl]-phenyl}-2-(5-methyl-1H-pyrrol-2-yl)-2-oxo-acetamide,
N-{4-[4-(4,6-Dimethyl-pyridin-2-yl)-piperazin-1-yl]-phenyl}-2-(2-methyl-7-phenyl-1,2,3,4-tetrahydro-pyrrolo[1,2-a]pyrazin-6-yl)-2-oxo-acetamide,
N-{4-[4-(4,6-Dimethyl-pyridin-2-yl)-piperazin-1-yl]-phenyl}-2-oxo-2-(2-phenyl-6,7-dihydro-5H-pyrrolizin-3-yl)-acetamide,
N-{4-[4-(4,6-Dimethyl-pyridin-2-yl)-piperazin-1-yl]-phenyl}-2-oxo-2-(7-phenyl-3,4-dihydro-1H-pyrrolo[2,1-c][1,4]oxazin-6-yl)-acetamide,
N-{4-[4-(4,6-Dimethyl-pyridin-2-yl)-piperazin-1-yl]-phenyl}-2-(1-isopropyl-5-methyl-3-phenyl-1H-pyrrol-2-yl)-2-oxo-acetamide,
N-{4-[4-(4,6-Dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide,
2-(1,5-Dimethyl-3-phenyl-1H-pyrrol-2-yl)-N-[4-[4-(4,6-dimethyl-pyridin-2-yl)-piperazin-1-yl]-3-(3-morpholin-4-yl-propoxymethyl)-phenyl]-2-oxo-acetamide,
N-{3-Chloro-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide,
N-{4-[4-(4,6-Dimethyl-pyridin-2-yl)-piperazin-1-yl]-phenyl}-2-(3-furan-2-yl-1,5-dimethyl-1H-pyrrol-2-yl)-2-oxo-acetamide,
N-{4-[4-(4,6-Dimethyl-pyridin-2-yl)-piperazin-1-yl]-phenyl}-2-(1,5-dimethyl-3-thiophen-2-yl-1H-pyrrol-2-yl)-2-oxo-acetamide,
N-{4-[4-(4,6-Dimethyl-pyridin-2-yl)-piperazin-1-yl]-phenyl}-2-(3-isopropyl-1,5-dimethyl-1H-pyrrol-2-yl)-2-oxo-acetamide,
N-{4-[4-(4,6-Dimethyl-pyridin-2-yl)-piperazin-1-yl]-phenyl}-2-[1,5-dimethyl-3-(tetrahydro-pyran-4-yl)-1H-pyrrol-2-yl]-2-oxo-acetamide,
2-(1,5-Dimethyl-3-phenyl-1H-pyrrol-2-yl)-N-naphthalen-1-yl-2-oxo-acetamide,
N-{3-(2-Dimethylamino-ethoxymethyl)-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide,
2-(1,4-Dimethyl-3-phenyl-1H-pyrrol-2-yl)-N-{4-[4-(4,6-dimethyl-pyridin-2-yl)-piperazin-1-yl]-phenyl}-2-oxo-acetamide,
2-(1,5-Dimethyl-3-phenyl-1H-pyrrol-2-yl)-N-{4-[4-(4,6-dimethyl-pyridin-2-yl)-piperazin-1-yl]-3-[3-(4-methyl-piperazin-1-yl)-propoxymethyl]-phenyl}-2-oxo-acetamide,
N-{4-[4-(4,6-Dimethyl-pyridin-2-yl)-piperazin-1-yl]-phenyl}-2-(5-isopropyl-1-methyl-3-phenyl-1H-pyrrol-2-yl)-2-oxo-acetamide,
N-{2-Chloro-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide,
2-(1,5-Dimethyl-3-phenyl-1H-pyrrol-2-yl)-N-{4-[4-(4,6-dimethyl-pyridin-2-yl)-piperazin-1-yl]-3-hydroxy-phenyl}-2-oxo-acetamide,
N-(2,3-Dihydro-benzofuran-4-yl)-2-(1,5-dimethyl-3-phenyl-1H-pyrrol-2-yl)-2-oxo-acetamide,
N-{3-Chloro-4-[4-(4,6-dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide,
N-{4-[4-(4,6-Dimethyl-pyridin-2-yl)-piperazin-1-yl]-phenyl}-2-[3-isopropyl-1-(2-methoxy-ethyl)-5-methyl-1H-pyrrol-2-yl]-2-oxo-acetamide,
N-{2-Chloro-4-[4-(4,6-dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide, N-{4-[4-(4,6-Dimethyl-pyridin-2-yl)-piperazin-1-yl]-phenyl}-2-[1-(2-ethoxy-ethyl)-5-methyl-3-phenyl-1H-pyrrol-2-yl]-2-oxo-acetamide, 2-(1,5-Dimethyl-3-phenyl-1H-pyrrol-2-yl)-2-oxo-N-[4-(4-pyridin-2-yl-piperazin-1-yl)-phenyl]-acetamide, 2-(1,5-Dimethyl-3-phenyl-1H-pyrrol-2-yl)-N-{4-[4-(4-methyl-pyridin-2-yl)-piperazin-1-yl]-phenyl}-2-oxo-acetamide, 2-(1,5-Dimethyl-3-phenyl-1H-pyrrol-2-yl)-N-{4-[4-(6-methyl-pyridin-2-yl)-piperazin-1-yl]-phenyl}-2-oxo-acetamide, 2-(1,5-Dimethyl-3-phenyl-1H-pyrrol-2-yl)-N-{4-[4-(5-methyl-pyridin-2-yl)-piperazin-1-yl]-phenyl}-2-oxo-acetamide, 2-[1-(2-Methoxy-ethyl)-5-methyl-3-phenyl-1H-pyrrol-2-yl]-2-oxo-N-[4-(4-piperazin-1-yl)-phenyl]-acetamide, 2-[1-(2-Methoxy-ethyl)-5-methyl-3-phenyl-1H-pyrrol-2-yl]-N-{4-[4-(4-methyl-pyridin-2-yl)-piperazin-1-yl]-phenyl}-2-oxo-acetamide, 2-[1-(2-Methoxy-ethyl)-5-methyl-3-phenyl-1H-pyrrol-2-yl]-N-{4-[4-(6-methyl-pyridin-2-yl)-piperazin-1-yl]-phenyl}-2-oxo-acetamide, 2-[1-(2-Methoxy-ethyl)-5-methyl-3-phenyl-1H-pyrrol-2-yl]-N-{4-[4-(5-methyl-pyridin-2-yl)-piperazin-1-yl]-phenyl}-2-oxo-acetamide, 2-Oxo-2-(2-phenyl-6,7-dihydro-5H-pyrrolizin-3-yl)-N-[4-(4-pyridin-2-yl-piperazin-1-yl)-phenyl]-acetamide, N-{4-[4-(4-Methyl-pyridin-2-yl)-piperazin-1-yl]-phenyl}-2-oxo-2-(2-phenyl-6,7-dihydro-5H-pyrrolizin-3-yl)-acetamide, N-{4-[4-(6-Methyl-pyridin-2-yl)-piperazin-1-yl]-phenyl},-2-oxo-2-(2-phenyl-6,7-dihydro-5H-pyrrolizin-3-yl)-acetamide, N-{4-[4-(5-Methyl-pyridin-2-yl)-piperazin-1-yl]-phenyl}-2-oxo-2-(2-phenyl-6,7-dihydro-5H-pyrrolizin-3-yl)-acetamide, N-{3-Chloro-4-[4-(4,6-dimethyl-pyridin-2-yl)-piperazin-1-yl]-phenyl}-2-oxo-2-(2-phenyl-6,7-dihydro-5H-pyrrolizin-3-yl)-acetamide, N-{2-Chloro-4-[4-(4,6-dimethyl-pyridin-2-yl)-piperazin-1-yl]-phenyl}-2-oxo-2-(2-phenyl-6,7-dihydro-5H-pyrrolizin-3-yl)-acetamide, 2-Oxo-2-(7-phenyl-3,4-dihydro-1H-pyrrolo[2,1-c][1,4]oxazin-6-yl)-N-[4-(4-pyridin-2-yl-piperazin-1-yl)-phenyl]-acetamide, N-{4-[4-(4-Methyl-pyridin-2-yl)-piperazin-1-yl]-phenyl}-2-oxo-2-(7-phenyl-3,4-dihydro-1H-pyrrolo[2,1-c][1,4]oxazin-6-yl)-acetamide, N-{4-[4-(6-Methyl-pyridin-2-yl)-piperazin-1-yl]-phenyl}-2-oxo-2-(7-phenyl-3,4-dihydro-1H-pyrrolo[2,1-c][1,4]oxazin-6-yl)-acetamide, N-{4-[4-(5-Methyl-pyridin-2-yl)-piperazin-1-yl]-phenyl}-2-oxo-2-(7-phenyl-3,4-dihydro-1H-pyrrolo[2,1-c][1,4]oxazin-6-yl)-acetamide, N-{3-Chloro-4-[4-(4,6-dimethyl-pyridin-2-yl)-piperazin-1-yl]-phenyl}-2-oxo-2-(7-phenyl-3,4-dihydro-1H-pyrrolo[2,1-c][1,4]oxazin-6-yl)-acetamide, N-{2-Chloro-4-[4-(4,6-dimethyl-pyridin-2-yl)-piperazin-1-yl]-phenyl}-2-oxo-2-(7-phenyl-3,4-dihydro-1H-pyrrolo[2,1-c][1,4]oxazin-6-yl)-acetamide, 2-(1,5-Dimethyl-3-thiophen-2-yl-1H-pyrrol-2-yl)-2-oxo-N-[4-(4-pyridin-2-yl-piperazin-1-yl)-phenyl]-acetamide, 2-(1,5-Dimethyl-3-thiophen-2-yl-1H-pyrrol-2-yl)-N-{4-[4-(4-methyl-pyridin-2-yl)-piperazin-1-yl]-phenyl}-2-oxo-acetamide, 2-(1,5-Dimethyl-3-thiophen-2-yl-1H-pyrrol-2-yl)-N-{4-[4-(5-methyl-pyridin-2-yl)-piperazin-1-yl]-phenyl}-2-oxo-acetamide, 2-(1,5-Dimethyl-3-thiophen-2-yl-1H-pyrrol-2-yl)-N-{4-[4-(6-methyl-pyridin-2-yl)-piperazin-1-yl]-phenyl}-2-oxo-acetamide, N-{3-Chloro-4-[4-(4,6-dimethyl-pyridin-2-yl)-piperazin-1-yl]-phenyl}-2-(1,5-dimethyl-3-thiophen-2-yl-1H-pyrrol-2-yl)-2-oxo-acetamide, N-{2-Chloro-4-[4-(4,6-dimethyl-pyridin-2-yl)-piperazin-1-yl]-phenyl}-2-(1,5-dimethyl-3-thiophen-2-yl-1H-pyrrol-2-yl)-2-oxo-acetamide, 2-(1,5-Dimethyl-3-phenyl-1H-pyrrol-2-yl)-N-[4-({2-[(4,6-dimethyl-pyridin-2-yl)-methyl-amino]-ethyl}-methyl-amino)-phenyl]-2-oxo-acetamide, N-[4-({2-[(4,6-Dimethyl-pyridin-2-yl)-methyl-amino]-ethyl}-methyl-amino)-phenyl]-2-[1-(2-methoxy-ethyl)-5-methyl-3-phenyl-1H-pyrrol-2-yl]-2-oxo-acetamide, N-[4-({2-[(4,6-Dimethyl-pyridin-2-yl)-methyl-amino]-ethyl}-methyl-amino)-phenyl]-2-oxo-2-(7-phenyl-3,4-dihydro-1H-pyrrolo[2,1-c][1,4]oxazin-6-yl)-acetamide, N-[4-({2-[(4,6-Dimethyl-pyridin-2-yl)-methyl-amino]-ethyl}-methyl-amino)-phenyl]-2-oxo-2-(2-phenyl-6,7-dihydro-5H-pyrrolizin-3-yl)-acetamide, N-[4-({2-[(4,6-Dimethyl-pyridin-2-yl)-methyl-amino]-ethyl}-methyl-amino)-phenyl]-2-(1,5-dimethyl-3-thiophen-2-yl-1H-pyrrol-2-yl)-2-oxo-acetamide, 2-(1,5-Dimethyl-3-phenyl-1H-pyrrol-2-yl)-N-{4-[2-(4,6-dimethyl-pyridin-2-yloxy)-ethylamino]-phenyl}-2-oxo-acetamide, N-{4-[2-(4,6-Dimethyl-pyridin-2-yloxy)-ethylamino]-phenyl}-2-[1-(2-methoxy-ethyl)-5-methyl-3-phenyl-1H-pyrrol-2-yl]-2-oxo-acetamide, N-{4-[2-(4,6-Dimethyl-pyridin-2-yloxy)-ethylamino]-phenyl}-2-oxo-2-(7-phenyl-3,4-dihydro-1H-pyrrolo[2,1-c][1,4]oxazin-6-yl)-acetamide, N-{-4-[2-(4,6-Dimethyl-pyridin-2-yloxy)-ethylamino]-phenyl}-2-oxo-2-(2-phenyl-6,7-dihydro-5H-pyrrolizin-3-yl)-acetamide, N-{4-[2-(4,6-Dimethyl-pyridin-2-yloxy)-ethylamino]-phenyl}-2-(1,5-dimethyl-3-thiophen-2-yl-1H-pyrrol-2-yl)-2-oxo-acetamide, 2-(1,5-Dimethyl-3-phenyl-1H-pyrrol-2-yl)-N-(4-{2-[(4,6-dimethyl-pyridin-2-yl)-methyl-amino]-ethoxy}-phenyl)-2-oxo-acetamide, N-(4-{2-[(4,6-Dimethyl-pyridin-2-yl)-methyl-amino]-ethoxy}-phenyl)-2-[1-(2-methoxy-ethyl)-5-methyl-3-phenyl-1H-pyrrol-2-yl]-2-oxo-acetamide, N-(4-{2-[(4,6-Dimethyl-pyridin-2-yl)-methyl-amino]-ethoxy}-phenyl)-2-oxo-2-(7-phenyl-3,4-dihydro-1H-pyrrolo[2,1-c][1,4]oxazin-6-yl)-acetamide, N-(4-{2-[(4,6-Dimethyl-pyridin-2-yl)-methyl-amino]-ethoxy}-phenyl)-2-oxo-2-(2-phenyl-6,7-dihydro-5H-pyrrolizin-3-yl)-acetamide, N-(4-{2-[(4,6-Dimethyl-pyridin-2-yl)-methyl-amino]-ethoxy}-phenyl)-2-(1,5-dimethyl-3-thiophen-2-yl-1H-pyrrol-2-yl)-2-oxo-acetamide, 2-(1,5-Dimethyl-3-phenyl-1H-pyrrol-2-yl)-N-{4-[2-(4,6-dimethyl-pyridin-2-yloxy)-ethoxy]-phenyl}-2-oxo-acetamide, N-{4-[2-(4,6-Dimethyl-pyridin-2-yloxy)-ethoxy]-phenyl}-2-[1-(2-methoxy-ethyl)-5-methyl-3-phenyl-1H-pyrrol-2-yl]-2-oxo-acetamide, N-{4-[2-(4,6-Dimethyl-pyridin-2-yloxy)-ethoxy]-phenyl}-2-oxo-2-(7-phenyl-3,4-dihydro-1H-pyrrolo[2,1-c][1,4]oxazin-6-yl)-acetamide, N-{4-[2-(4,6-Dimethyl-pyridin-2-yloxy)-ethoxy]-phenyl}-2-oxo-2-(2-phenyl-6,7-dihydro-5H-pyrrolizin-3-yl)-acetamide N-{4-[2-(4,6-Dimethyl-pyridin-2-yloxy)-ethoxy]-phenyl}-2-(1,5-dimethyl-3-thiophen-2-yl-1H-pyrrol-2-yl)-2-oxo-acetamide, 2-(1,5-Dimethyl-3-phenyl-1H-pyrrol-2-yl)-N-(4-{[2-(4,6-dimethyl-pyridin-2-ylamino)-ethyl]-methyl-amino}-phenyl)-2-oxo-acetamide, N-(4-{[2-(4,6-Dimethyl-pyridin-2-ylamino)-ethyl]-methyl-amino}-phenyl)-2-[1-(2-methoxy-ethyl)-5-methyl-3-phenyl-1H-pyrrol-2-yl]-2-oxo-acetamide, N-(4-{[2-(4,6-Dimethyl-pyridin-2-ylamino)-ethyl]-methyl-amino}-phenyl)-2-oxo-2-(7-phenyl-3,4-dihydro-1H-pyrrolo[2,1-c][1,4]oxazin-6-yl)-acetamide, N-(4-{[2-(4,6-Dimethyl-pyridin-2-ylamino)-ethyl]-methyl-amino}-phenyl)-2-oxo-2-(2-phenyl-6,7-dihydro-5H-pyrrolizin-3-yl)-acetamide, N-(4-{[2-(4,6-Dimethyl-pyridin-2-ylamino)-ethyl]-methyl-amino}-phenyl)-2-(1,5-dimethyl-3-thiophen-2-yl-1H-pyrrol-2-yl)-2-oxo-acetamide, 2-(1,5-Dimethyl-3-phenyl-1H-pyrrol-2-yl)-N-{4-[2-(4,6-dimethyl-pyridin-2-ylamino)-ethylamino]-phenyl}-2-oxo-acetamide, N-{4-[2-(4,6-Dimethyl-pyridin-2-ylamino)-ethylamino]-phenyl}-2-[1-(2-methoxy-ethyl)-5-methyl-3-phenyl-1H-pyrrol-2-yl]-2-oxo-acetamide, N-{4-[2-(4,6-Dimethyl-pyridin-2-ylamino)-ethylamino]-phenyl}-2-oxo-2-(7-phenyl-3,4-dihydro-1H-pyrrolo[2,1-c][1,4]oxazin-6-yl)-acetamide, N-{4-[2-(4,6-Dimethyl-pyridin-2-ylamino)-ethylamino]-phenyl}-2-oxo-2-(2-phenyl-6,7-dihydro-5H-pyrrolizin-3-yl)-acetamide, N-{4-[2-(4,6-Dimethyl-pyridin-2-ylamino)-ethylamino]-phenyl}-2-(1,5-dimethyl-3-thiophen-2-yl-1H-pyrrol-2-yl)-2-oxo-acetamide, 2-(1,5-Dimethyl-3-phenyl-1H-pyrrol-2-yl)-N-(4-{2-[(4,6-dimethyl-pyridin-2-yl)-methyl-amino]-ethylamino}-phenyl)-2-oxo-acetamide, N-(4-{2-[(4,6-Dimethyl-pyridin-2-yl)-methyl-amino]-ethylamino}-phenyl)-2-[1-(2-methoxy-ethyl)-5-methyl-3-phenyl-1H-pyrrol-2-yl]-2-oxo-acetamide, N-(4-{2-[(4,6-Dimethyl-pyridin-2-yl)-methyl-amino]-ethylamino}-phenyl)-2-oxo-2-(7-phenyl-3,4-dihydro-1H-pyrrolo[2,1-c][1,4]oxazin-6-yl)-acetamide, N-(4-{2-[(4,6-Dimethyl-pyridin-2-yl)-methyl-amino]-ethylamino}-phenyl)-2-oxo-2-(2-phenyl-6,7-dihydro-5H-pyrrolizin-3-yl)-acetamide, N-(4-{2-[(4,6-Dimethyl-pyridin-2-yl)-methyl-amino]ethylamino}-phenyl)-2-(1,5-dimethyl-3-thiophen-2-yl-1H-pyrrol-2-yl)-2-oxo-acetamide, 2-(1,5-Dimethyl-3-phenyl-1H-pyrrol-2-yl)-N-(4-{3-[(4,6-dimethyl-pyridin-2-yl)-methyl-amino]-propyl}-phenyl)-2-oxo-acetamide, N-(4-{3-[(4,6-Dimethyl-pyridin-2-yl)-methyl-amino]-propyl}-phenyl)-2-[1-(2-methoxy-ethyl)-3-phenyl-1H-pyrrol-2-yl]-2-oxo-acetamide, N-(4-{3-[(4,6-Dimethyl-pyridin-2-yl)-methyl-amino]-propyl}-phenyl)-2-oxo-2-(7-phenyl-3,4-dihydro-1H-pyrrolo[2,1-c][1,4]oxazin-6-yl)-acetamide, N-(4-{3-[(4,6-Dimethyl-pyridin-2-yl)-methyl-amino]-propyl}-phenyl)-2-oxo-2-(2-phenyl-6,7-dihydro-5H-pyrrolizin-3-yl)-acetamide, N-(4-{3-[(4,6-Dimethyl-pyridin-2-yl)-methyl-amino]-propyl}-phenyl)-2-(1,5-dimethyl-3-thiophen-2-yl-1H-pyrrol-2-yl)-2-oxo-acetamide, 2-(1,5-Dimethyl-3-phenyl-1H-pyrrol-2-yl)-N-{4-[4-(4,6-dimethyl-pyridin-2-yl)-[1,4]diazepan-1-yl]-phenyl}-2-oxo-acetamide, N-{4-[4-(4,6-Dimethyl-pyridin-2-yl)-[1,4]diazepan-1-yl]-phenyl}-2-[1-(2-methoxy-ethyl)-5-methyl-3-phenyl-1H-pyrrol-2-yl]-2-oxo-acetamide, N-{4-[4-(4,6-Dimethyl-pyridin-2-yl)-[1,4]diazepan-1-yl]-phenyl}-2-oxo-2-(7-phenyl-3,4-dihydro-1H-pyrrolo[2,1-c][1,4]oxazin-6-yl)-acetamide, N-{4-[4-(4,6-Dimethyl-pyridin-2-yl)-[1,4]diazepan-1-yl]-phenyl}-2-oxo-2-(2-phenyl-6,7-dihydro-5H-pyrrolizin-3-yl)-acetamide, N-{4-[4-(4,6-Dimethyl-pyridin-2-yl)-[1,4]diazepan-1-yl]-phenyl}-2-(1,5-dimethyl-3-thiophen-2-yl-1H-pyrrol-2-yl)-2-oxo-acetamide, 2-(1,5-Dimethyl-3-phenyl-1H-pyrrol-2-yl)-N-[4-({3-[(4,6-dimethyl-pyridin-2-yl)-methyl-amino]-propyl}-methyl-amino)-phenyl]-2-oxo-acetamide, N-[4-({3-[(4,6-Dimethyl-pyridin-2-yl)-methyl-amino]-propyl}-methyl-amino)-phenyl]-2-[1-(2-methoxy-ethyl)-5-methyl-3-phenyl-1H-pyrrol-2-yl]-2-oxo-acetamide, N-[4-({3-[(4,6-Dimethyl-pyridin-2-yl)-methyl-amino]-propyl}-methyl-amino)-phenyl]-2-oxo-2-(7-phenyl-3,4-dihydro-1H-pyrrolo[2,1-c][1,4]oxazin-6-yl)-acetamide, N-[4-({3-[(4,6-Dimethyl-pyridin-2-yl)-methyl-amino]-propyl}-methyl-amino)-phenyl]-2-oxo-2-(2-phenyl-6,7-dihydro-5H-pyrrolizin-3-yl)-acetamide, N-[4-({3-[(4,6-Dimethyl-pyridin-2-yl)-methyl-amino]-propyl}-methyl-amino)-phenyl]-2-(1,5-dimethyl-3-thiophen-2-yl-1H-pyrrol-2-yl)-2-oxo-acetamide, 2-(1,5-Dimethyl-3-phenyl-1H-pyrrol-2-yl)-N-{4-[4-(4-ethyl-pyridin-2-yl)-piperazin-1-yl]-phenyl}-2-oxo-acetamide, N-{4-[4-(4-Ethyl-pyridin-2-yl)-piperazin-1-yl]-phenyl}-2-[1-(2-methoxy-ethyl)-5-methyl-3-phenyl-1H-pyrrol-2-yl]-2-oxo-acetamide, N-{4-[4-(4-Ethyl-pridin-2-yl)-piperazin-1-yl]-phenyl}-2-oxo-2-(7-phenyl-3,4-dihydro-1H-pyrrolo[2,1-c][1,4]oxazin-6-yl)-acetamide, N-{4-[4-(4-Ethyl-pyridin-2-yl)-piperazin-1-yl]-phenyl}-2-oxo-2-(2-phenyl-6,7-dihydro-5H-pyrrolizin-3-yl)-acetamide, 2-(1,5-Dimethyl-3-thiophen-2-yl-1H-pyrrol-2-yl)-N-{4-[4-(4-ethyl-pyridin-2-yl)-piperazin-1-yl]-phenyl}-2-oxo-acetamide, 2-(1,5-Dimethyl-3-phenyl-1H-pyrrol-2-yl)-N-{4-[4-(6-ethyl-pyridin-2-yl)-piperazin-1-yl]-phenyl}-2-oxo-acetamide, N-{4-[4-(6-Ethyl-pyridin-2-yl)-piperazin-1-yl]-phenyl}-2-[1-(2-methoxy-ethyl)-5-methyl-3-phenyl-1H-pyrrol-2-yl]-2-oxo-acetamide, N-{4-[4-(6-Ethyl-pyridin-2-yl)-piperazin-1-yl]-phenyl}-2-oxo-2-(7-phenyl-3,4-dihydro-1H-pyrrolo[2,1-c][1,4]oxazin-6-yl)-acetamide, N-{4-[4-(6-Ethyl-pyridin-2-yl)-piperazin-1-yl]-phenyl}-2-oxo-2-(2-phenyl-6,7-dihydro-5H-pyrrolizin-3-yl)-acetamide, and 2-(1,5-Dimethyl-3-thiophen-2-yl-1H-pyrrol-2-yl)-N-{4-[4-(6-ethyl-pyridin-2-yl)-piperazin-1-yl]-phenyl}-2-oxo-acetamide, and pharmaceutically and agriculturally acceptable salts thereof.

Preferred examples of compounds of formula (I) include:

2-(1,5-Dimethyl-3-phenyl-1H-pyrrol-2-yl)-N-{4-[4-(4,6-dimethyl-pyridin-2-yl)-piperazin-1-yl]-phenyl}-2-oxo-acetamide, N-{4-[4-(4,6-Dimethyl-pyridin-2-yl)-piperazin-1-yl]-phenyl}-2-oxo-2-(1-phenyl-1H-pyrrol-2-yl)-acetamide, N-{4-[4-(4,6-Dimethyl-pyridin-2-yl)-piperazin-1-yl]-phenyl}-2-(5-methyl-1-phenyl-1H-pyrrol-2-yl)-2-oxo-acetamide,
N-{4-[4-(4,6-Dimethyl-pyridin-2-yl)-piperazin-1-yl]-phenyl}-2-(5-methyl-1H-pyrrol-2-yl)-2-oxo-acetamide,
N-{4-[4-(4,6-Dimethyl-pyridin-2-yl)-piperazin-1-yl]-phenyl}-2-(2-methyl-7-phenyl-1,2,3,4-tetrahydro-pyrrolo[1,2-a]pyrazin-6-yl)-2-oxo-acetamide,
N-{4-[4-(4,6-Dimethyl-pyridin-2-yl)-piperazin-1-yl]-phenyl}-2-oxo-2-(2-phenyl-6,7-dihydro-5H-pyrrolizin-3-yl)-acetamide,
N-{4-[4-(4,6-Dimethyl-pyridin-2-yl)-piperazin-1-yl]-phenyl}-2-oxo-2-(7-phenyl-3,4-dihydro-1H-pyrrolo[2,1-c][1,4]oxazin-6-yl)-acetamide,
N-{4-[4-(4,6-Dimethyl-pyridin-2-yl)-piperazin-1-yl]-phenyl}-2-(1-isopropyl-5-methyl-3-phenyl-1H-pyrrol-2-yl)-2-oxo-acetamide,
N-{4-[4-(4,6-Dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide,
2-(1,5-Dimethyl-3-phenyl-1H-pyrrol-2-yl)-N-[4-[4-(4,6-dimethyl-pyridin-2-yl)-piperazin-1-yl]-3-(3-morpholin-4-yl-propoxymethyl)-phenyl]-2-oxo-acetamide,
N-{3-Chloro-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide,
N-{4-[4-(4,6-Dimethyl-pyridin-2-yl)-piperazin-1-yl]-phenyl}-2-(3-furan-2-yl-1,5-dimethyl-1H-pyrrol-2-yl)-2-oxo-acetamide,
N-{4-[4-(4,6-Dimethyl-pyridin-2-yl)-piperazin-1-yl]-phenyl}-dimethyl-3-thiophen-2-yl-1H-pyrrol-2-yl)-2-oxo-acetamide,
N-{4-[4-(4,6-Dimethyl-pyridin-2-yl)-piperazin-1-yl]-phenyl}-2-(3-isopropyl-1,5-dimethyl-1H-pyrrol-2-yl)-2-oxo-acetamide,
N-{4-[4-(4,6-Dimethyl-pyridin-2-yl)-piperazin-1-yl]-phenyl}-2-[1,5-dimethyl-3-(tetrahydro-pyran-4-yl)-1H-pyrrol-2-yl]-2-oxo-acetamide,
2-(1,5-Dimethyl-3-phenyl-1H-pyrrol-2-yl)-N-naphthalen-1-yl-2-oxo-acetamide,
N-{3-(2-Dimethylamino-ethoxymethyl)-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide,
2-(1,4-Dimethyl-3-phenyl-1H-pyrrol-2-yl)-N-{4-[4-(4,6-dimethyl-pyridin-2-yl)-piperazin-1-yl]-phenyl}-2-oxo-acetamide,
2-(1,5-Dimethyl-3-phenyl-1H-pyrrol-2-yl)-N-{4-[4-(4,6-dimethyl-pyridin-2-yl)-piperazin-1-yl]-3-[3-(4-methyl-piperazin-1-yl)-propoxymethyl]-phenyl}-2-oxo-acetamide,
N-{4-[4-(4,6-Dimethyl-pyridin-2-yl)-piperazin-1-yl]-phenyl}-2-(5-isopropyl-1-methyl-3-phenyl-1H-pyrrol-2-yl)-2-oxo-acetamide,
N-{2-Chloro-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide,
2-(1,5-Dimethyl-3-phenyl-1H-pyrrol-2-yl)-N-{4-[4-(4,6-dimethyl-pyridin-2-yl)-piperazin-1-yl]-3-hydroxy-phenyl}-2-oxo-acetamide,
N-(2,3-Dihydro-benzofuran-4-yl)-2-(1,5-dimethyl-3-phenyl-1H-pyrrol-2-yl)-2-oxo-acetamide,
N-{3-Chloro-4-[4-(4,6-dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide,
N-{4-[4-(4,6-Dimethyl-pyridin-2-yl)-piperazin-1-yl]-phenyl}-2-[3-isopropyl-1-(2-methoxy-ethyl)-5-methyl-1H-pyrrol-2-yl]-2-oxo-acetamide,
N-{2-Chloro-4-[4-(4,6-dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide, and
N-{4-[4-(4,6-Dimethyl-pyridin-2-yl)-piperazin-1-yl]-phenyl}-2-[1-(2-ethoxy-ethyl)-5-methyl-3-phenyl-1H-pyrrol-2-yl]-2-oxo-acetamide, and pharmaceutically and agriculturally acceptable salts thereof.
Further preferred examples of compounds of formula (I) include:

N-{4-[4-(4,6-Dimethyl-pyridin-2-yl)-piperazin-1-yl]-phenyl}-2-[1-(3-methoxy-propyl)-5-methyl-3-phenyl-1H-pyrrol-2-yl]-2-oxo-acetamide,
2-[1-(2-Methoxy-ethyl)-5-methyl-3-phenyl-1H-pyrrol-2-yl]-2-oxo-N-quinolin-5-yl-acetamide,
N-Isoquinolin-5-yl-2-[1-(2-methoxy-ethyl)-5-methyl-3-phenyl-1H-pyrrol-2-yl]-2-oxo-acetamide,
2-(1,5-Dimethyl-3-phenyl-1H-pyrrol-2-yl)-2-oxo-N-quinolin-8-yl-acetamide,
2-(1,5-Dimethyl-3-phenyl-1H-pyrrol-2-yl)-2-oxo-N-quinolin-5-yl-acetamide,
2-(1,5-Dimethyl-3-phenyl-1H-pyrrol-2-yl)-2-oxo-N-pyridin-4-yl-acetamide,
N-{4-[4-(4,6-Dimethyl-pyridin-2-yl)-piperazin-1-yl]-phenyl}-2-(1-ethyl-5-methyl-3-phenyl-1H-pyrrol-2-yl)-2-oxo-acetamide,
N-{4-[4-(4,6-Dimethyl-pyridin-2-yl)-piperazin-1-yl]-phenyl}-2-(5-methyl-3-phenyl-1-propyl-1H-pyrrol-2-yl)-2-oxo-acetamide,
2-(1-Butyl-5-methyl-3-phenyl-1H-pyrrol-2-yl)-N-{4-[4-(4,6-dimethyl-pyridin-2-yl)-piperazin-1-yl]-phenyl}-2-oxo-acetamide,
2-(1,5-Dimethyl-3-phenyl-1H-pyrrol-2-yl)-2-oxo-N-quinolin-3-yl-acetamide,
2-(1,5-Dimethyl-3-phenyl-1H-pyrrol-2-yl)-2-oxo-N-[4-(4-pyridin-2-yl-piperazin-1-yl)-phenyl]-acetamide,
2-(1,5-Dimethyl-3-phenyl-1H-pyrrol-2-yl)-N-{4-[4-(6-methyl-pyridin-2-yl)-piperazin-1-yl]-phenyl}-2-oxo-acetamide,
2-(1,5-Dimethyl-3-phenyl-1H-pyrrol-2-yl)-N-{4-[4-(4-methyl-pyridin-2-yl)-piperazin-1-yl]-phenyl}-2-oxo-acetamide,
N-{4-[4-(4,6-Dimethyl-pyridin-2-yl)-piperazin-1-yl]-phenyl}-2-oxo-2-(2-phenyl-6,7,8,9-tetrahydro-5H-pyrrolo[1,2-a]azepin-3-yl)-acetamide,
N-{4-[4-(4,6-Dimethyl-pyridin-2-yl)-piperazin-1-yl]-phenyl}-2-oxo-2-(1-phenyl-6,7,8,9-tetrahydro-5H-pyrrolo[1,2-a]azepin-3-yl)-acetamide,
N-Isoquinolin-8-yl-2-[1-(2-methoxy-ethyl)-5-methyl-3-phenyl-1H-pyrrol-2-yl]-2-oxo-acetamide,
2-(1,5-Dimethyl-3-phenyl-1H-pyrrol-2-yl)-N-isoquinolin-8-yl-2-oxo-acetamide,
2-(1,5-Dimethyl-3-phenyl-1H-pyrrol-2-yl)-N-naphthalen-2-yl-2-oxo-acetamide,
N-{4-[4-(4,6-Dimethyl-pyridin-2-yl)-piperazin-1-yl]-phenyl}-2-(1-methyl-3-phenyl-1H-pyrrol-2-yl)-2-oxo-acetamide,
N-{4-[4-(4,6-Dimethyl-pyridin-2-yl)-piperazin-1-yl]-phenyl}-2-(1-methyl-4-phenyl-1H-pyrrol-2-yl)-2-oxo-acetamide,
N-{4-[4-(4,6-Dimethyl-pyridin-2-yl)-piperazin-1-yl]-phenyl}-2-[1-(2-methoxy-ethyl)-3-phenyl-1H-pyrrol-2-yl]-2-oxo-acetamide,
2-(1-Benzyl-5-methyl-3-phenyl-1H-pyrrol-2-yl)-N-{4-[4-(4,6-dimethyl-pyridin-2-yl)-piperazin-1-yl]-phenyl}-2-oxo-acetamide,
2-(1,5-Dimethyl-3-phenyl-1H-pyrrol-2-yl)-N-[5-(4-methyl-piperazin-1-yl)-naphthalen-1-yl]-2-oxo-acetamide, N-{4-[4-(4,6-Dimethyl-pyridin-2-yl)-piperazin-1-yl]-phenyl}-2-(5-methyl-3-phenyl-1H-pyrrol-2-yl)-2-oxo-acetamide,
2-(1,5-Dimethyl-3-phenyl-1H-pyrrol-2-yl)-N-{4-[4-(4,6-dimethyl-pyridin-2-yl)-piperazin-1-yl]-3-methyl-phenyl}-2-oxo-acetamide,
(2-{4-[4-(4,6-Dimethyl-pyridin-2-yl)-piperazin-1-yl]-phenylaminooxalyl}-5-methyl-3-phenyl-pyrrol-1-yl)-acetic acid methyl ester,
N-{4-[4-(4,6-Dimethyl-pyridin-2-yl)-piperazin-1-yl]-phenyl}-2-(5-ethyl-1-methyl-3-phenyl-1H-pyrrol-2-yl)-2-oxo-acetamide,
N-{4-[4-(4,6-Dimethyl-pyridin-2-yl)-piperazin-1-yl]-phenyl}-2-[5-ethyl-1-(2-methoxy-ethyl)-3-phenyl-1H-pyrrol-2-yl]-2-oxo-acetamide,
2-{4-[4-(4,6-Dimethyl-pyridin-2-yl)-piperazin-1-yl]-phenylaminooxalyl}-5-methyl-3-phenyl-pyrrole-1-carboxylic acid ethyl ester,
2-{4-[4-(4,6-Dimethyl-pyridin-2-yl)-piperazin-1-yl]-phenylaminooxalyl}-5-methyl-3-phenyl-pyrrole-1-carboxylic acid methyl ester,
2-[3-(2-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide,
2-[4-(2-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide,
2-[3-(4-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide,
2-[1-(2-Methoxy-ethyl)-5-methyl-3-phenyl-1H-pyrrol-2-yl]-2-oxo-N-phenyl-1-acetamide,
(2-{4-[4-(4,6-dimethyl-pyridin-2-yl)-piperazin-1-yl]-phenylaminooxalyl}-pyrrol-1-yl)-acetic acid methyl ester,
N-{4-[4-(4,6-Dimethyl-pyridin-2-yl)-piperazin-1-yl]-phenyl}-2-(1-methoxymethyl-5-methyl-3-phenyl-1H-pyrrol-2-yl)-2-oxo-acetamide,
N-{4-[4-(4,6-Dimethyl-pyridin-2-yl)-piperazin-1-yl]-phenyl}-2-(1-methoxymethyl-3-phenyl-1H-pyrrol-2-yl)-2-oxo-acetamide,
N-{4-[4-(4,6-Dimethyl-pyridin-2-yl)-piperazin-1-yl]-phenyl}-2-[1-(2-hydroxy-ethyl)-5-methyl-3-phenyl-1H-pyrrol-2-yl]-2-oxo-acetamide,
2-[1-(2-Acetylamino-ethyl)-5-methyl-3-phenyl-1H-pyrrol-2-yl]-N-{4-[4-(4,6-dimethyl-pyridin-2-yl)-piperazin-1-yl]-phenyl}-2-oxo-acetamide,
N-{4-[4-(4,6-Dimethyl-pyridin-2-yl)-piperazin-1-yl]-phenyl}-2-[1-(2-hydroxy-ethyl)-3-phenyl-1H-pyrrol-2-yl]-2-oxo-acetamide,
N-{4-[4-(4,6-Dimethyl-pyridin-2-yl)-piperazine-1-yl]-phenyl}-2[1-(2-methoxy-ethyl)-3-thiophen-2-yl-1H-pyrol-2-yl]-2-oxo-acetamide,
N-{4-[4-(4,6-Dimethyl-pyridin-2-yl)piperazin-1-yl]-phenyl}-2-[3-isobutyl-1-(2-methoxy-ethyl)-1H-pyrrol-2-yl]-2-oxo-acetamide,
2-{4-[4-(4,6-Dimethyl-pyridin-2-yl)-piperazin-1-yl]-phenylaminooxalyl}-5-methyl-3-phenyl-pyrrol-1-yl)-acetic acid ethyl ester,
2-[3-(3-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide,
2-[4-(3-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide,
N-{4-[4-(4,6-Dimethyl-pyridin-2-yl)-piperazine-1-yl]-phenyl}-2[1-(2-methoxy-ethyl)-3-thiophen-3-yl-1H-pyrol-2-yl]-2-oxo-acetamide,
(2-{4-[4-(4,6-Dimethylpyridine-2-yl)-piperazin-1-yl]-phenylaminooxalyl}-3-phenyl pyrrol-1-yl)acetic acid ester,
(2-{4-[4-(4,6-Dimethyl-pyridin-2-yl)-piperazin-1-yl]-phenylaminooxalyl}-3-phenyl-pyrrol-1-yl)-acetic acid methyl ester,
2-(1-Carbamoylmethyl-3-phenyl-1H-pyrrol-2-yl)-N-{4-[4-(4,6-dimethyl-pyridin-2-yl)-piperazin-1-yl]-phenyl}-2-oxo-acetamide,
N-{4-[4-(4,6-Dimethyl-pyridin-2-yl)-piperazin-1-yl]-phenyl}-2-(1-methyl carbamoylmethyl-3-phenyl-1-H-pyrrol-2-yl)-2-oxo-acetamide,
2{4-[4-(4,6-Dimethyl-pyridin-2-yl)-piperazin-1-yl]-phenylaminooxalyl}-5-methyl-3-phenyl-pyrrol-1-yl)acetic acid isopropyl ester,
N-{4-[4-(4,6-Dimethyl-pyridin-2-yl)-piperazin-1-yl]phenyl}-2-[5-isopropyl-1-(2-methoxy-ethyl)-3-phenyl-1H-pyrrol-2-yl]-2-oxo-acetamide,
2-(1,5-Dimethyl-3-phenyl-1H-pyrrol-2-yl)-N-2-oxo-quinolin-5-yl-acetamide,
N-{4-[4-(4,6-Dimethyl-pyridin-2-yl)-piperazin-1-yl]-phenyl}-2-[3-(2-methoxy-ethyl)-5-methyl-1-phenyl-1H-pyrrol-2-yl]-2-oxo-acetamide,
2-[1-(2-Methoxy-ethyl)-3-phenyl-1H-pyrrol-2-yl]-2-oxo-N-phenyl-1-acetamide,
2-[1-(2-Methoxy-ethyl)-3-phenyl-1H-pyrrol-2-yl]-2-oxo-N-propyl-acetamide,
N-{4-[4-(4,6-Dimethyl-pyridin-2-yl)-piperazin-1-yl]-phenyl}-2-[3-iso propyl-1-(2-methoxy-ethyl)-1H-pyrrol-2-yl]-2-oxo acetamide,
2-[1-(2-Dimethylamino-ethyl)-3-phenyl-1H-pyrrol-2-yl]-N-{4-[4-(4,6-dimethyl-pyridin-2-yl)-piperazin-1-yl]-phenyl}-2-oxo-acetamide,
2-[1-(2-Dimethylamino-ethyl)-4-phenyl-1H-pyrrol-2-yl]-N-{4-[4-(4,6-dimethyl-pyridin-2-yl)-piperazin-1-yl]-phenyl}-2-oxo-acetamide,
2-[1-(2-Dimethylamino-ethyl)-5-methyl-3-phenyl-1H-pyrrol-2-yl]-N-{4-[4-(4,6-dimethyl-pyridin-2-yl)-piperazin-1-yl]-phenyl}-2-oxo-acetamide,
(2-{4-[4-(4,6-Dimethyl-pyridin-2-yl)-piperazin-1-yl]-phenylaminooxalyl}-3-thiophen-2-yl-pyrrol-1-yl)-acetic acid methyl ester,
(2-{4-[4-(4,6-Dimethyl-pyridin-2-yl)-piperazin-1-yl]-phenylaminooxalyl}-3-iso propyl-pyrrol-1-yl)-acetic acid methyl ester,
(2-{4-[4-(4,6-Dimethylpyridine-2-yl)piperazine-1-yl]-phenylamino oxalyl}-3-isobutyl-pyrrol-1-yl)-acetic acid methyl ester,
N-{4-[4-(4,6-Dimethyl-pyridin-2-yl)-piperazin-1-yl]-phenyl}-2-(4-fluoro-1,5-dimethyl-3-phenyl-1H-pyrrol-2-yl)-2-oxo-acetamide,
N-{4-[4-(4,6-Dimethyl-pyridin-2-yl)-piperazin-1-yl]-phenyl}-2-(5-methyl-3-phenyl-1pyridin-2-ylmethyl-1H-pyrrol-2-yl)-2-oxo-acetamide,
N-{2-Chloro-4-[4-(4,6-dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide,
N-{4-[4-(4,6-Dimethyl-pyridin-2-yl)-piperazin-1-yl]-phenyl}-2-(5-methyl-3-phenyl-1-pyridin-3-ylmethyl-1H-pyrrol-2-yl)-2-oxo-acetamide,
N-{4-[4-(4,6-Dimethyl-pyridin-2-yl)-piperazin-1-yl]-phenyl}-2,4-fluoro-1-(2-methoxy-ethyl)-5-methyl-3-phenyl-1H-pyrrol-2-yl) -2-oxo-acetamide,
2-(1,5-Dimethyl-3-phenyl-1H-pyrrol-2-yl)-N-[2-fluoro-4-(4-pyridin-2-yl-piperazin-1-yl)-phenyl]-2-oxo-acetamide,
N-[2-Fluoro-4-(4-pyridin-2-yl-piperazin-1-yl)-phenyl]-2-[1-(2-methoxy-ethyl-)-5-methyl-3-phenyl-1H-pyrrol-2-yl]-2-oxo-acetamide, N-{4-[4-(4,6-Dimethyl-pyridin-2-yl)-piperazin-1-yl]-phenyl}-2-[1-(2-isopropoxy-ethyl)-5-methyl-3-phenyl-1H-pyrrol-2-yl]-2-oxo-acetamide, (2-{2-Chloro-4-[4-(4,6-dimethyl-pyridin-2-yl)-piperazin-1-yl]-phenylaminooxalyl}-5-methyl-3-phenyl-pyrrol-1-yl)-acetic acid methyl ester, 2-(1,5-Dimethyl-3-phenyl-1H-pyrrol-2-yl)-2-oxo-N-(6-pyrrolidin-1-yl-pyridin-3-yl)-acetamide, 2-(1,5-Dimethyl-3-phenyl-1H-pyrrol-2-yl)-N-[2-fluoro-4-oxazole-2-yl-phenyl)-2-oxo-acetamide, 2-(1,5-Dimethyl-3-phenyl-1H-pyrrol-2-yl)-N-(2-fluoro-4-morpholin-4-yl-phenyl)-2-oxo-acetamide, N-{4-[4-(4,6-Dimethyl-pyridin-2-yl)-piperazin-1-yl]-phenyl}-2-(5-methyl-3-phenyl-1-pyridin-4-ylmethyl-1H-pyrrol-2-yl)-2-oxo-acetamide, 2-[1-(2-Methoxy-ethyl)-5-methyl-3-phenyl-1H-pyrrol-2-yl]-N-{4-[4-(5-morpholin-4-ylmethyl-pyridin-2-yl)-piperazin-1-yl]-phenyl}-2-oxo-acetamide, 2-[3-Cyclobutyl-1-(2-methoxy-ethyl)-1H-pyrrol-2-yl]-N-{4-[4-(4,6-Dimethyl-pyridin-2-yl)-piperizin-1-yl]-phenyl}-2-oxo-acetamide, 2-(1,5-Dimethyl-3-phenyl-1H-pyrrol-2-yl)-N-[2-fluoro-4-(4-isobutyl-piperazin-1-yl)-phenyl]-2-oxoacetamide, 2-(1,5-Dimethyl-3-phenyl-1H-pyrrol-2-yl)-N-(2-fluoro-4-piperidin-1-yl-phenyl)-2-oxo-acetamide, (3-Cyclobutyl-2-{4-[4-(4,6-dimethyl-pyridin-2-yl)-piperazin-1-yl-]-phenylaminooxalyl}-pyrrol-1-yl)-acetic acid methyl ester, 2-(1,5-Dimethyl-3-phenyl-1H-pyrrol-2-yl)-N-{2-fluoro-4-[4-(2-methyl-allyl)-piperazin-1-yl]-phenyl}-2-oxo-acetamide, N-{2-Fluoro-4-[4-(2-methyl-allyl)-piperazin-1-yl]-phenyl}-2-[1-(2-methoxy-ethyl)-5-methyl-3-phenyl-1H-pyrrol-2-yl]-2-oxo-acetamide, N-[2-Fluoro-5-(4-isobutyl-piperazine-1-yl)-phenyl]-2-[1-(2-methoxy-ethyl)-5-methyl-3-phenyl-1H-pyrrol-2-yl]-2-oxo-acetamide, (2-{4-[4-(4,6-Dimethyl-pyridin-2-yl)-piperazin-1-yl]-2-fluoro-phenylaminooxylyl}-5-methyl-3-phenyl-pyrrol-1-yl)-acetic acid methyl ester, 2-(1,5-Dimethyl-3-phenyl-1H-pyrrol-2-yl)-N-{4-[4-(2,2-dimethyl-propyl)-piperazin-1-yl]-2-fluoro-phenyl}-2-oxo-acetamide, N-{4-[4-(2,2-Dimethyl-propyl)-piperazin-1-yl]-2-fluoro-phenyl}-2-[1-(2-methoxy-ethyl)-5-methyl-3-phenyl-1H-pyrrol-2-yl]-2-oxo-acetamide, N-(2-Fluoro-4-piperidin-1-yl-phenyl)-2-[1-(2-methoxy-ethyl)-5-methyl-3-phenyl-1H-pyrrol-2-yl]-2-oxo-acetamide, 2-(1,5-Dimethyl-3-phenyl-1H-pyrrol-2-yl)-N-(3-fluoro-4-piperidin-1-yl-phenyl)-2-oxo-acetamide, 2-(1,5-Dimethyl-3-phenyl-1H-pyrrol-2-yl)-N-[3-fluoro-4-(4-pyridin-2-yl-piperazin-1-yl)-phenyl]-2-oxo-acetamide, N-(2-Fluoro-4-morpholin-4-yl-phenyl)-2-[1-(2-methoxy-ethyl)-5-methyl-3-phenyl-1H-pyrrol-2-yl]-2-oxo-acetamide, 2-(1,5-Dimethyl-3-phenyl-1H-pyrrol-2-yl)-N-[3-fluoro-4(4-isobutyl-piperazin-1-yl)-phenyl]-2-oxo-acetamide, N-(3-Fluoro-4-piperidin-1-yl-phenyl)-2-[1-(2-methoxy-ethyl)-5-methyl-3-phenyl-1H-pyrrol-2-yl]-2-oxo-acetamide, 2-(1,5-Dimethyl-3-phenyl-1H-pyrrol-2-yl)-N-{4-[4-(5-morpholin-4-ylmethyl-pyridin-2-yl)-piperazin-1-yl]-phenyl}-2-oxo-acetamide, 2-[1-(2-Methoxy-ethyl)-4-phenyl-1H-pyrrol-2-yl]-2-oxo-N-propyl-acetamide, (2-{4-[4-(4,6-Dimethyl-pyridin-2-yl)-piperazin-1-yl]-phenylaminooxalyl}-4-phenyl-pyrrol-1-yl)-acetic acid methyl ester, N-{4-[4-(4,6-Dimethyl-pyridin-2-yl)-piperazin-1-yl]-2-fluoro-phenyl}-2-[1-(2-methoxy-ethyl)-5-methyl-3-phenyl-1H-pyrrol-2-yl]-2-oxo-acetamide, N-{4-[4-(4,6-Dimethyl-pyridin-2-yl)-piperizin-1-yl]-phenyl}-2-[1-methyl-3-phenyl-5-propyl-1H-pyrrol-2-yl)-2-oxo-acetamide, N-{4-[4-(4,6-Dimethyl-pyridin-2-yl)-piperazin-1-yl]-phenyl}-2-(5-ethyl-1-methoxymethyl-3-phenyl-1H-pyrrol-2-yl)-2-oxo-acetamide, N-(3-Fluoro-4-morpholin-4-yl-phenyl)-2-[1-(2-methoxy-ethyl)-5-methyl-3-phenyl-1H-pyrrol-2-yl]-2-oxo-acetamide, 2-(1,5-Dimethyl-3-phenyl-1H-pyrrol-2-yl)-N-(5-fluoro-naphthalen-1-yl)-2-oxo-acetamide, 2-(1,5-Dimethyl-3-phenyl-1H-pyrrol-2-yl)-N-(1-ethyl-4-fluoro-1H-indol-5-yl)-2-oxo-acetamide, N-{4-[4-(4,6-Dimethyl-pyridin-2-yl)-piperazin-1-yl]-phenyl}-2-[5-(2-methoxy-ethyl)-1-methyl-3-phenyl-1H-pyrrol-2-yl]-2-oxo-acetamide, N-{4-[4-(4,6-Dimethyl-pyridin-2-yl)-piperazin-1-yl]-phenyl}-2-(5-methoxymethyl-1-methyl-3-phenyl-1H-pyrrol-2-yl)-2-oxo-acetamide, 2-(1,5-Bis-methoxymethyl-3-phenyl-1H-pyrrol-2-yl)-N-{4-[4-(4,6-dimethyl-pyridin-2-yl)-piperazine-1-yl]-phenyl}-2-oxo-acetamide, N-{4-[4-(4,6-Dimethyl-pyridin-2-yl)-piperazin-1-yl]-phenyl}-2-(1-ethoxymethyl-5-methyl-3-phenyl-1H-pyrrol-2-yl)-2-oxo-acetamide, N-{4-[4-(4,6-Dimethyl-pyridin-2-yl)-piperazin-1-yl]-phenyl}-2-[5-methyl-1-(2-methylsulfanyl-ethyl)-3-phenyl-1H-pyrrol-2-yl]-2-oxo-acetamide, N-{4-[4-(4,6-Dimethyl-pyridin-2-yl)-piperazin-1-yl]-phenyl}-2-[5-methyl-1-(2-phenoxy-ethyl)-3-phenyl-1H-pyrrol-2-yl]-2-oxo-acetamide, 2-(1-Butoxymethyl-5-methyl-3-phenyl-1H-pyrrol-2-yl)-N-{4-[4-(4,6-dimethyl-pyridin-2-yl)-piperazin-1-yl]-phenyl}-2-oxo-acetamide, N-{4-[4-(4,6-Dimethyl-pyridin-2-yl)-piperazin-1-yl]-phenyl}-2-[1-(3-ethoxy-propyl)-5-methyl-3-phenyl-1H-pyrrol-2-yl]-2-oxo-acetamide, N-{4-[4-(4,6-Dimethyl-pyridin-2-yl)-piperazin-1-yl]-phenyl}-2-(5-methyl-1-methylsulfanylmethyl-3-phenyl-1H-pyrrol-2-yl)-2-oxo-acetamide, N-{4-[4-(4,6-Dimethyl-pyridin-2-yl)-piperazin-1-yl]-phenyl}-2-[1-(2-methoxy-ethoxymethyl)-5-methyl-3-phenyl-1H-pyrrol-2-yl]-2-oxo-acetamide, N-{4-[4-(4,6-Dimethyl-pyridin-2-yl)-piperazin-1-yl]-phenyl}-2-(5-methyl-3-phenyl-1-propoxymethyl-1H-pyrrol-2-yl)-2-oxo-acetamide, N-{4-[4-(4,6-Dimethyl-pyridin-2-yl)-piperazin-1-yl]-phenyl}-2-[5-methyl-3-phenyl-1-(2-propoxy-ethyl)-1H-pyrrol-2-yl]-2-oxo-acetamide, N-{4-[4-(4,6-Dimethyl-pyridin-2-yl)-piperazin-1-yl]-phenyl}-2-[1-(4-methoxy-but-2-enyl)-5-methyl-3-phenyl-1H-pyrrol-2-yl]-2-oxo-acetamide, N-{4-[4-(4,6-Dimethyl-pyridin-2-yl)-piperazin-1-yl]-phenyl}-2-[1-(4-methoxy-butyl)-5-methyl-3-phenyl-1H-pyrrol-2-yl]-2-oxo-acetamide, 2-(1,5-Dimethyl-3-phenyl-1H-pyrrol-2-yl)-2-oxo-N-(4-piperidin-1-yl-phenyl)-acetamide, N-[4-(4-Benzyl-piperazin-1-yl)-phenyl]-2-(1,5-dimethyl-3-phenyl-1H-pyrrol-2-yl)-2-oxo-acetamide, 2-(1,5-Dimethyl-3-phenyl-1H-pyrrol-2-yl)-N-[4-(4-isobutyryl-piperazin-1-yl)-phenyl]-2-oxo-acetamide, N-{4-[4-(4,6-Dimethyl-pyridin-2-yl)-piperazin-1-yl]-phenyl}-2-[5-methyl-1-(2-methyl-oxazol-4-ylmethyl)-3-phenyl-1H-pyrrol-2-yl]-2-oxo-acetamide
2-(1,5-Dimethyl-3-phenyl-1H-pyrrol-2-yl)-N-(4-oxazol-2-yl-phenyl)-2-oxo-acetamide,
2-(1,5-Dimethyl-3-phenyl-1H-pyrrol-2-yl)-N-(3-fluoro-4-oxazole-2-yl-phenyl)-2-oxo-acetamide,
2-[1-(2-Methoxy-ethyl)-5-methyl-3-phenyl-1H-pyrrol-2-yl]-N-(4-oxazol-2-yl-phenyl)-2-oxo-acetamide,
2-(1,5-Dimethyl-3-phenyl-1H-pyrrol-2-yl)-N-{4-[4-(1,2-dimethyl-propyl)-piperazin-1-yl]-phenyl}-2-oxo-acetamide,
2-(1,5-Dimethyl-3-phenyl-1H-pyrrol-2-yl)-N-{4-[4-(2-methoxy-1-methyl-ethyl)-piperazin-1-yl]-phenyl}-2-oxo-acetamide,
2-(1,5-Dimethyl-3-phenyl-1H-pyrrol-2-yl)-N-{4-[4-(2-furan-2-yl-1-methyl-ethyl)-piperazin-1-yl]-phenyl}-2-oxo-acetamide,
2-(1,5-Dimethyl-3-phenyl-1H-pyrrol-2-yl)-2-oxo-N-[4-(5-piperidin-1-ylmethyl-oxazol-2-yl)-phenyl]-acetamide, and
2-(1,5-Dimethyl-3-phenyl-1H-pyrrol-2-yl)-N-(4-morpholin-4-yl-phenyl)-2-oxo-acetamide,
and pharmaceutically or agriculturally acceptable salts thereof.

Particularly preferred compounds of the invention are
2-(1,5-Dimethyl-3-phenyl-1H-pyrrol-2-yl)-N-{4-[4-(4,6-dimethyl-pyridin-2-yl)-piperazin-1-yl]-phenyl}-2-oxo-acetamide,
N-{4-[4-(4,6-Dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide,
N-{3-Chloro-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide,
N-{2-Chloro-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide,
N-{3-Chloro-4-[4-(4,6-dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide,
N-{4-[4-(4,6-Dimethyl-pyridin-2-yl)-piperazin-1-yl]-phenyl}-2-(1-ethyl-5-methyl-3-phenyl-1H-pyrrol-2-yl)-2-oxo-acetamide,
N-{4-[4-(4,6-Dimethyl-pyridin-2-yl)-piperazin-1-yl]-phenyl}-2-(5-methyl-3-phenyl-1-propyl-1H-pyrrol-2-yl)-2-oxo-acetamide,
2-(1-Butyl-5-methyl-3-phenyl-1H-pyrrol-2-yl)-N-{4-[4-(4,6-dimethyl-pyridin-2-yl)-piperazin-1-yl]-phenyl}-2-oxo-acetamide,
2-(1,5-Dimethyl-3-phenyl-1H-pyrrol-2-yl)-2-oxo-N-[4-(4-pyridin-2-yl-piperazin-1-yl)-phenyl]-acetamide,
2-(1,5-Dimethyl-3-phenyl-1H-pyrrol-2-yl)-N-{4-[4-(6-methyl-pyridin-2-yl)-piperazin-1-yl]-phenyl}-2-oxo-acetamide,
2-(1,5-Dimethyl-3-phenyl-1H-pyrrol-2-yl)-N-{4-[4-(4-methyl-pyridin-2-yl)-piperazin-1-yl]-phenyl}-2-oxo-acetamide,
N-{4-[4-(4,6-Dimethyl-pyridin-2-yl)-piperazin-1-yl]-phenyl}-2-(1-methyl-3-phenyl-1H-pyrrol-2-yl)-2-oxo-acetamide,
N-{4-[4-(4,6-Dimethyl-pyridin-2-yl)-piperazin-1-yl]-phenyl}-2-(5-methyl-3-phenyl-1H-pyrrol-2-yl)-2-oxo-acetamide,
2-(1,5-Dimethyl-3-phenyl-1H-pyrrol-2-yl)-N-{4-[4-(4,6-dimethyl-pyridin-2-yl)-piperazin-1-yl]-3-methyl-phenyl}-2-oxo-acetamide,
N-{4-[4-(4,6-Dimethyl-pyridin-2-yl)-piperazin-1-yl]-phenyl}-2-(5-ethyl-1-methyl-3-phenyl-1H-pyrrol-2-yl)-2-oxo-acetamide,
N-{4-[4-(4,6-Dimethyl-pyridin-2-yl)-piperazin-1-yl]-phenyl}-2-(1-methoxymethyl-5-methyl-3-phenyl-1H-pyrrol-2-yl)-2-oxo-acetamide,
2-(1,5-Dimethyl-3-phenyl-1H-pyrrol-2-yl)-N-[2-fluoro-4-(4-pyridin-2-yl-piperazin-1-yl)-phenyl]-2-oxo-acetamide,
(2-{2-Chloro-4-[4-(4,6-dimethyl-pyridin-2-yl)-piperazin-1-yl]-phenylaminooxalyl}-5-methyl-3-phenyl-pyrrol-1-yl)-acetic acid methyl ester,
2-(1,5-Dimethyl-3-phenyl-1H-pyrrol-2-yl)-N-[2-fluoro-4-(4-isobutyl-piperazin-1-yl)-phenyl]-2-oxoacetamide,
2-(1,5-Dimethyl-3-phenyl-1H-pyrrol-2-yl)-N-{2-fluoro-4-[4-(2-methyl-allyl)-piperazin-1-yl]-phenyl}-2-oxo-acetamide,
2-(1,5-Dimethyl-3-phenyl-1H-pyrrol-2-yl)-N-{4-[4-(2,2-dimethyl-propyl)-piperazin-1-yl]-2-fluoro-phenyl}-2-oxo-acetamide,
2-(1,5-Dimethyl-3-phenyl-1H-pyrrol-2-yl)-N-[3-fluoro-4-(4-pyridin-2-yl-piperazin-1-yl)-phenyl]-2-oxo-acetamide,
2-(1,5-Dimethyl-3-phenyl-1H-pyrrol-2-yl)-N-[3-fluoro-4-(4-isobutyl-piperazin-1-yl)-phenyl]-2-oxo-acetamide,
2-(1,5-Dimethyl-3-phenyl-1H-pyrrol-2-yl)-N-{4-[4-(5-morpholin-4-ylmethyl-pyridin-2-yl)-piperazin-1-yl]-phenyl}-2-oxo-acetamide,
N-{4-[4-(4,6-Dimethyl-pyridin-2-yl)-piperazin-1-yl]-2-fluoro-phenyl}-2-[1-(2-methoxy-ethyl)-5-methyl-3-phenyl-1H-pyrrol-2-yl]-2-oxo-acetamide,
N-{4-[4-(4,6-Dimethyl-pyridin-2-yl)-piperazin-1-yl]-phenyl}-2-(1-ethoxymethyl-5-methyl-3-phenyl-1H-pyrrol-2-yl)-2-oxo-acetamide, and
pharmaceutically and agriculturally acceptable salts thereof.

2-(1,5-Dimethyl-3-phenyl-1H-pyrrol-2-yl)-N-{4-[4-(4,6-dimethyl-pyridin-2-yl)-piperazin-1-yl]-phenyl}-2-oxo-acetamide, and its pharmaceutically and agriculturally acceptable salts, is particularly preferred.

One embodiment of the invention relates to pyrrole derivatives of formula (IB), which are particularly active against fungi from both the *Aspergillus* and *Candida* genera and may therefore find use as broad spectrum anti-fungal agents. The pyrrole derivatives of this embodiment are of formula (IB):

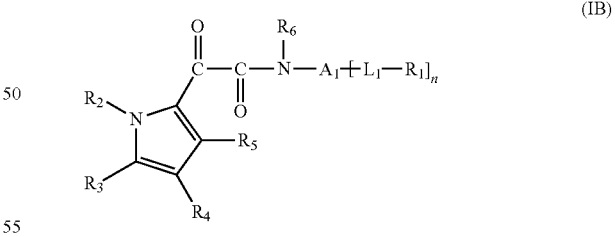

wherein A1, L1, n, R1 and R3 to R5 are as defined for formula (I) or (IA) above, and R2 is a group of formula wherein $Alk_1$ is an unsubstituted or substituted C1-C6 alkylene group, X is a group —O—, —S—, —NR"—, —CO$_2$—, —CONR"—, —OCO—, —OCONR"— or —SO$_2$—, and R' and R" are independently selected from hydrogen and unsubstituted or substituted C1-C4 alkyl, for example unsubstituted or substituted C1-C4 alkyl.

$Alk_1$ is typically an unsubstituted or substituted C1-C4 alkylene group, for example methylene or ethylene. Where $Alk_1$ is substituted, it typically carries one or two, preferably one, substituent selected from halogen and further groups of formula —XR' as defined herein. Preferably $Alk_1$ is unsubstituted.

X is typically selected from —O—, —NR"—, —$CO_2$— and —CONR"—. When X is —$CO_2$—, R' is typically a C1-C4 alkyl group.

R' and R" typically represent hydrogen or unsubstituted or substituted methyl or ethyl. R' is typically a methyl or ethyl group. R' and R" are independently unsubstituted or substituted, typically with one or two, preferably one, substituent. Suitable substituents are selected from unsubstituted substituents such as halogen (for example fluorine), hydroxyl, amino, (C1-C4 alkylamino, di(C1-C4 alkyl)amino, —$CO_2H$ and —$CO_2$(C1-C4 alkyl) and from C1-C4 alkoxy such as methoxy or ethoxy which are themselves unsubstituted or further substituted with unsubstituted methoxy or ethoxy. Preferred substituents are hydroxyl, amino, (C1-C4 alkyl) amino, di(C1-C4 alkyl)amino and unsubstituted C1-C4 alkoxy. Preferably R' and R" are unsubstituted.

Specific examples of compounds of formula (IB) include:
N-{4-[4-(4,6-Dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide,
N-{4-[4-(4,6-Dimethyl-pyridin-2-yl)-piperazin-1-yl]-phenyl}-2-(1,5-dimethyl-3-thiophen-2-yl-1H-pyrrol-2-yl)-2-oxo-acetamide,
N-{4-[4-(4,6-Dimethyl-pyridin-2-yl)-piperazin-1-yl]-phenyl}-2-[1-(2-methoxy-ethyl)-3-phenyl-1H-pyrrol-2-yl]-2-oxo-acetamide,
(2-{4-[4-(4,6-Dimethyl-pyridin-2-yl)-piperazin-1-yl]-phenylaminooxalyl}-5-methyl-3-phenyl-pyrrol-1-yl)-acetic acid methyl ester,
2-[3-(2-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide,
2-[3-(4-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide,
2-[1-(2-Methoxy-ethyl)-5-methyl-3-phenyl-1H-pyrrol-2-yl]-2-oxo-N-phenyl-1-acetamide,
N-{4-[4-(4,6-Dimethyl-pyridin-2-yl)-piperazin-1-yl]-phenyl}-2-(1-methoxymethyl-3-phenyl-1H-pyrrol-2-yl)-2-oxo-acetamide,
N-{4-[4-(4,6-Dimethyl-pyridin-2-yl)piperazin-1-yl]-phenyl}-2-[3-isobutyl-1-(2-methoxy-ethyl)-1H-pyrrol-2-yl]-2-oxo-acetamide,
2-{4-[4-(4,6-Dimethyl-pyridin-2-yl)-piperazin-1-yl]-phenylaminooxalyl}-5-methyl-3-phenyl-pyrrol-1-yl)-acetic acid ethyl ester,
2-[3-(3-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide,
N-{4-[4-(4,6-Dimethyl-pyridin-2-yl)-piperazine-1-yl]-phenyl}-2[1-(2-methoxy-ethyl)-3-thiophen-3-yl-1H-pyrol-2-yl]-2-oxo-acetamide,
(2-{4-[4-(4,6-Dimethylpyridine-2-yl)-piperazin-1-yl]-phenylaminooxalyl}-3-phenyl pyrrol-1-yl)acetic acid ester,
(2-{4-[4-(4,6-Dimethyl-pyridin-2-yl)-piperazin-1-yl]-phenylaminooxalyl}-3-phenyl-pyrrol-1-yl)-acetic acid methyl ester,
N-{4-[4-(4,6-Dimethyl-pyridin-2-yl)-piperazin-1-yl]-phenyl}-2-(1-methyl carbamoylmethyl-3-phenyl-1-H-pyrrol-2-yl)-2-oxo-acetamide,
2-[1-(2-Methoxy-ethyl)-3-phenyl-1H-pyrrol-2-yl]-2-oxo-N-phenyl-1-acetamide,
2-[1-(2-Dimethylamino-ethyl)-3-phenyl-1H-pyrrol-2-yl]-N-{4-[4-(4,6-dimethyl-pyridin-2-yl)-piperazin-1-yl]-phenyl}-2-oxo-acetamide,
2-[1-(2-Dimethylamino-ethyl)-4-phenyl-1H-pyrrol-2-yl]-N-{4-[4-(4,6-dimethyl-pyridin-2-yl)-piperazin-1-yl]-phenyl}-2-oxo-acetamide,
2-[1-(2-Dimethylamino-ethyl)-5-methyl-3-phenyl-1H-pyrrol-2-yl]-N-{4-[4-(4,6-dimethyl-pyridin-2-yl)-piperazin-1-yl]-phenyl}-2-oxo-acetamide,
(2-{4-[4-(4,6-Dimethyl-pyridin-2-yl)-piperazin-1-yl]-phenylaminooxalyl}-3-thiophen-2-yl-pyrrol-1-yl)-acetic acid methyl ester,
(2-{4-[4-(4,6-Dimethyl-pyridin-2-yl)-piperazin-1-yl]-phenylaminooxalyl}-3-iso propyl-pyrrol-1-yl)-acetic acid methyl ester,
(2-{4-[4-(4,6-Dimethylpyridine-2-yl)piperazine-1-yl]-phenylamino oxalyl}-3-isobutyl-pyrrol-1-yl)-acetic acid methyl ester,
2-[1-(2-Methoxy-ethyl)-5-methyl-3-phenyl-1H-pyrrol-2-yl]-N-{4-[-(5-morpholin-4-ylmethyl-pyridin-2-yl)-piperazin-1-yl]-phenyl}-2-oxo-acetamide,
2-[3-Cyclobutyl-1-(2-methoxy-ethyl)-1H-pyrrol-2-yl]-N-{4-[4-(4,6-Dimethyl-pyridin-2-yl)-piperizin-1-yl]-phenyl}-2-oxo-acetamide,
N-{2-Fluoro-4-[4-(2-methyl-allyl)-piperazin-1-yl]-phenyl}-2-[1-(2-methoxy-ethyl)-5-methyl-3-phenyl-1H-pyrrol-2-yl]-2-oxo-acetamide,
N-{4-[4-(2,2-Dimethyl-propyl)-piperazin-1-yl]-2-fluoro-phenyl}-2-[1-(2-methoxy-ethyl)-5-methyl-3-phenyl-1H-pyrrol-2-yl]-2-oxo-acetamide, and
N-(2-Fluoro-4-piperidin-1-yl-phenyl)-2-[1-(2-methoxy-ethyl)-5-methyl-3-phenyl-1H-pyrrol-2-yl]-2-oxo-acetamide, and
pharmaceutically and agriculturally acceptable salts thereof.

Compounds of the invention containing one or more chiral centre may be used in enantiomerically or diastereoisomerically pure form, or in the form of a mixture of isomers. For the avoidance of doubt, the compounds of the invention can, if desired, be used in the form of solvates. Further, for the avoidance of doubt, the compounds of the invention may be used in any tautomeric form.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic, hydroiodic or nitric acid and organic acids such as citric, fumaric, maleic, malic, ascorbic, succinic, tartaric, benzoic, acetic, methanesulphonic, ethanesulphonic, benzenesulphonic, p-toluenesulphonic acid, formic, acetic, propionic, glycolic, lactic, pyruvic, oxalic, salicylic, trichloroacetic, picric, trifluoroacetic, cinnamic, pamoic, malonic, mandelic, bismethylene salicylic, ethanedisulfonic, gluconic, citraconic, aspartic, stearic, palmitic, EDTA, p-aminobenzoic or glutamic acid, sulfates, nitrates, phosphates, perchlorates, borates, acetates, benzoates, hydroxynaphthoates, glycerophosphates or ketoglutarates. Further examples of pharmaceutically acceptable inorganic or organic acid addition salts include the pharmaceutically acceptable salts listed in Journal of Pharmaceutical Science, 66, 2 (1977) which are known to the skilled artisan. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines, lysine, guanidine, diethanolamine and choline.

Also intended as pharmaceutically acceptable acid addition salts are the hydrates which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of this invention may form solvates with standard low molecular weight solvents using methods known to the skilled artisan.

The present invention also provides prodrugs of the compounds of the invention. A prodrug is an analogue of a compound of the invention which will be converted in vivo to the desired active compound. Examples of suitable prodrugs include compounds of formula (I) which have been modified at a carboxylic acid group to form an ester, or at hydroxyl group to form an ester or carbamate. Other suitable methods will be known to those skilled in the art. Further suitable prodrugs include those in which a nitrogen atom of a compound of formula (I) is quaternised by addition of an ester or alkyl ester group. For example, the nitrogen atom of an amine group or heterocyclyl ring on a substituent R1 or R5 may be quaternised by addition of a —CH$_2$—O—COR group, wherein R is typically methyl or tert-butyl.

Suitable salts of the compounds of the invention include those mentioned herein as examples of pharmaceutically and agriculturally acceptable salts.

The compounds of the invention may be synthesised by reacting a compound of formula (II), wherein R2, R3, R4 and R5 are as hereinbefore defined, with a compound of formula (III), wherein R6, A1, n, L1 and R1 are as hereinbefore defined. Typically the reaction takes place in the presence of an organic solvent and a base. Preferably the solvent is dichloromethane or tetrahydrofuran and the base is triethylamine or pyridine. Typically the reaction is carried out at 0° C. initially while the reagents are added and then stirred at room temperature until the reaction is complete. Compounds of formula (III) are typically available from commercial sources or can be prepared by known methods. Details of the synthesis of certain compounds of formula (III) are provided hereinafter.

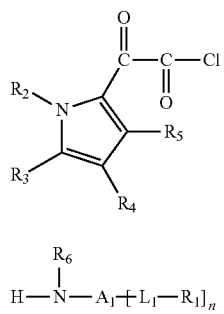

(II)

(III)

A compound of formula (II) may be prepared by reacting a compound of formula (IV), wherein R2, R3, R4 and R5 are as hereinbefore defined, with preferably oxalyl chloride. Typically the reaction takes place in an organic solvent. Preferably, the solvent is dichloromethane. Typically, the reaction is carried out at 0° C. initially while the reagents are added and then stirred at room temperature until the reaction is complete.

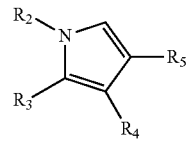

(IV)

The experimental section provides specific synthetic examples, and other compounds of the invention can be prepared by analogy with these specific synthetic examples and with reference to the general synthetic methodology discussed above. Some further general synthetic schemes and specific aniline-intermediate preparation summaries are as follows:

Preparation of β-Ketoesters:

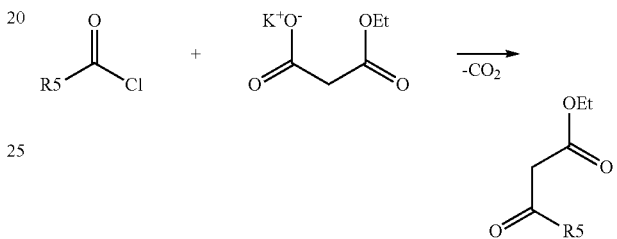

Solvent: acetonitrile
Base: triethylamine
Additional reagent: magnesium chloride Preparation of Oximes:

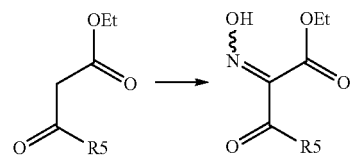

Reagent: sodium nitrite
Solvent: acetic acid

Preparation of Pyrrole Diesters:

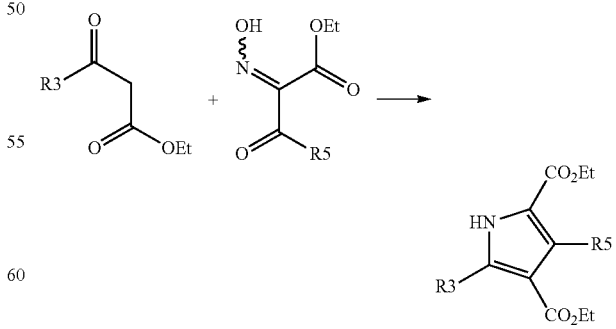

Reagents: zinc powder, sodium acetate
Solvent: acetic acid
Temperature: 60-75° C.

Pyrrole N-alkylation:

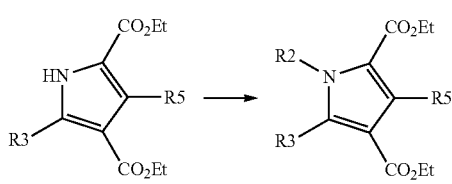

Reagents/solvents: sodium hydride, THF, 0° C. to room temperature; sodium hydride, DMF, 0° C. to 90° C.; potassium carbonate, acetonitrile, reflux.

Ester Hydrolysis:

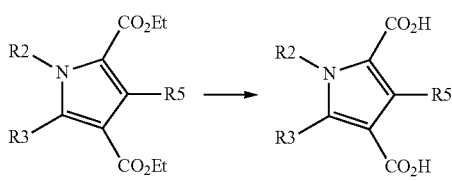

Reagents: sodium or potassium hydroxide, water/ethanol or water/methanol mixtures, reflux temperature.

Decarboxylation:

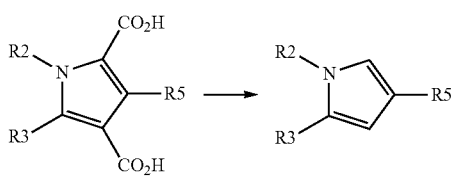

Solvent: ethanolamine
Temperature: 175-180° C.

Primary Amines:

There are a large number of ways of preparing primary alkyl amines and many examples are commercially available. Two of the most common examples of primary amine synthesis are:

1. The catalytic reduction of commercially available nitriles and nitro compounds to the corresponding amine:

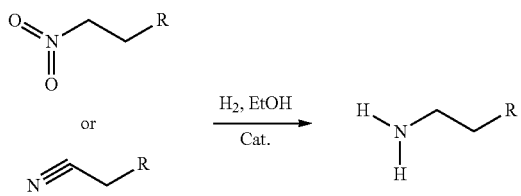

2. Gabriel synthesis

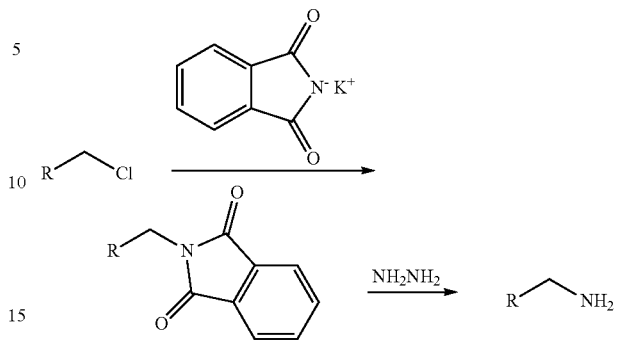

Exemplary anilines required for preparation of a number of preferred compounds of the invention could be prepared according to the following sequences of reactions:

4-(4-Pyridin-2-yl-piperazin-1-yl)-phenylamine

From 1-(4-nitro-phenyl)-piperazine and 2-chloropyridine, by heating in DMSO to give 1-(4-nitro-phenyl)-4-pyridin-2-yl-piperazine then catalytic hydrogenation over Raney nickel in methanol.

4-[4-(4-Methyl-pyridin-2-yl)-piperazin-1-yl]-phenylamine

From 1-(4-nitro-phenyl)-piperazine and 2-chloro-4-methylpyridine, by heating in diglyme to give 1-(4-methyl-pyridin-2-yl)-4-(4-nitro-phenyl)-piperazine then catalytic hydrogenation over Raney nickel in methanol.

4-[4-(6-Methyl-pyridin-2-yl)-piperazin-1-yl]-phenylamine

From 1-(4-nitro-phenyl)-piperazine and 2-chloro-6-methylpyridine, by heating in the presence of palladium (II) acetate, 2-dicyclohexylphospino-2-(N,N'-dimethyl amino) biphenyl and caesium carbonate in a mixture of toluene and THF to give 1-(6-methyl-pyridin-2-yl)-4-(4-nitro-phenyl)-piperazine then catalytic hydrogenation over Raney nickel in methanol.

4-[4-(5-Methyl-pyridin-2-yl)-piperazin-1-yl]-phenylamine

From 1-(4-nitro-phenyl)-piperazine and 2-chloro-5-methylpyridine, in the same manner as the preparation of 4-[4-(6-methyl-pyridin-2-yl)-piperazin-1-yl]-phenylamine.

4-[4-(4-Ethyl-pyridin-2-yl)-piperazin-1-yl]-phenylamine

From 2-amino-4-ethylpyridine by treatment with sodium nitrite in hydrochloric acid in the presence of sodium chloride to afford 2-chloro-4-ethylpyridine, then in the same manner as 4-[4-(6-methyl-pyridin-2-yl)-piperazin-1-yl]-phenylamine.

4-[4-(6-Ethyl-pyridin-2-yl)-piperazin-1-yl]-phenylamine

From 2-amino-6-ethylpyridine, in the same manner as 4-[4-(4-ethyl-pyridin-2-yl)-piperazin-1-yl]-phenylamine.

N-{2-[(4,6-Dimethyl-pyridin-2-yl)-methyl-amino]-ethyl}-N-methyl-benzene-1,4-diamine From 1-chloro-4-nitrobenzene by heating in neat ethylene diamine to give N*1*-(4-nitro-phenyl)-ethane-1,2-diamine, followed by treatment with trifluoro-methanesulfonic acid 4,6-dimethyl-pyridin-2-yl ester (itself prepared according to J. Org. Chem., 63, 10048-51 (1998) using pyridine as base) in diglyme at reflux to afford N-(4,6-dimethyl-pyridin-2-yl)-N'-(4-nitro-phenyl)-ethane-1,2-diamine. Dimethylation with methyl iodide in THF in the presence of sodium hydride followed by catalytic hydrogenation over Raney nickel in methanol gives the required aniline.

N-[2-(4,6-Dimethyl-pyridin-2-yloxy)-ethyl]-benzene-1,4-diamine

From 2-chloro-4,6-dimethylpyridine by treatment with ethanolamine and sodium hydroxide in a mixture of water and dioxane to afford 2-(4,6-dimethyl-pyridin-2-yloxy)-ethylamine, followed by heating with 1-fluoro-4-nitrobenzene in ethanol to give [2-(4,6-dimethyl-pyridin-2-yloxy)-ethyl]-(4-nitro-phenyl)-amine. The free amine is protected as a trifluoroacetamide by treatment with trifluoroacetic anhydride and sodium hydride in THF then the nitro group is reduced with zinc powder in the presence of ammonium chloride in ethanol. Following coupling with the appropriately-selected acid chloride, a final treatment with lithium hydroxide in methanol removes the trifluoroacetamide to give the final compound described.

[2-(4-Amino-phenoxy)-ethyl]-(4,6-dimethyl-pyridin-2-yl)-methyl-amine

From 4-nitrophenol by etherification with bromoacetic acid in the presence of sodium hydride in THF, acid chloride formation with thionyl chloride and catalytic DMF and amide formation with 2-amino-4,6-dimethylpyridine in triethylamine and chloroform to give N-(4,6-dimethyl-pyridin-2-yl)-2-(4-nitro-phenoxy)-acetamide. The amide is the reduced with borane-dimethylsulfide in THF at reflux, the resulting amine methylated with methyl iodide in the presence of sodium hydride in THF, and finally catalytic hydrogenation over Raney nickel in methanol gives the required aniline.

4-[2-(4,6-Dimethyl-pyridin-2-yloxy)-ethoxy]-phenylamine

From 4-nitrophenol by etherification with 1,2-dibromoethane, with potassium carbonate as the base in 2-butanone to give 1-(2-bromo-ethoxy)-4-nitro-benzene, followed by O-alkylation of 2-hydroxy-4,6-dimethylpyridine using potassium carbonate in DMF to give 2,4-Dimethyl-6-[2-(4-nitro-phenoxy)-ethoxy]-pyridine. Reduction of the nitro group with tin (II) chloride in a mixture of ethanol and ethyl acetate gives the required aniline.

N-[2-(4,6-Dimethyl-pyridin-2-ylamino)-ethyl]-N-methyl-benzene-1,4-diamine

From 1-fluoro-4-nitrobenzene by heating with glycine at reflux in a mixture of aqueous sodium bicarbonate and dioxane to give (4-nitro-phenylamino)-acetic acid, followed by treatment with formaldehyde and formic acid at reflux to give [methyl-(4-nitro-phenyl)-amino]-acetic acid. Treatment with thionyl chloride and catalytic DMF to give the acid chloride followed by amide formation with 2-amino-4,6-dimethylpyridine in triethylamine and chloroform gives N-(4,6-dimethyl-pyridin-2-yl)-2-(4-nitro-phenylamino)-acetamide. The amide is the reduced with borane-dimethylsulfide in THF at reflux then catalytic hydrogenation over Raney nickel in methanol gives the required aniline.

N-[2-(4,6-Dimethyl-pyridin-2-ylamino)-ethyl]-benzene-1,4-diamine

From 4-nitroaniline by treatment with ethyl oxalyl chloride in triethylamine and THF to give N-(4-nitro-phenyl)-oxalamic acid ethyl ester, followed by aminolysis with 2-amino-4,6-dimethylpyridine in triethylamine at reflux to afford N-(4,6-dimethyl-pyridin-2-yl)-N-(4-nitro-phenyl)-oxalamide. The amides are then reduced with borane-dimethylsulfide in THF at reflux, the free amine is protected as a trifluoroacetamide by treatment with trifluoroacetic anhydride and sodium hydride in THF then the nitro group is reduced with zinc powder in the presence of ammonium chloride in ethanol. Following coupling with the appropriately-selected acid chloride, a final treatment with lithium hydroxide in methanol removes the trifluoroacetamide to give the final compound described.

N-{2-[(4,6-Dimethyl-pyridin-2-yl)-methyl-amino]-ethyl}-benzene-1,4-diamine

From (4-nitro-phenylamino)-acetic acid (prepared as described above) by treatment with trifluoroacetic anhydride and sodium hydride in THF to give [(4-nitro-phenyl)-(2,2,2-trifluoro-acetyl)-amino]-acetic acid followed by acid chloride formation with thionyl chloride in chloroform and coupling with (4,6-dimethyl-pyridin-2-yl)-methyl-amine to yield N-{[(4,6-dimethyl-pyridin-2-yl)-methyl-carbamoyl]-methyl}-2,2,2-trifluoro-N-(4-nitro-phenyl)-acetamide. Treatment with lithium hydroxide in methanol removes the trifluoroacetamide, then the amide is reduced with borane-dimethylsulfide in THF at reflux to give N-(4,6-Dimethyl-pyridin-2-yl)-N-methyl-N'-(4-nitro-phenyl)-ethane-1,2-diamine. Catalytic hydrogenation over Raney nickel in methanol gives the required aniline.

[3-(4-Amino-phenyl)-propyl]-(4,6-dimethyl-pyridin-2-yl)-methyl-amine

Alkylation of diethyl malonate with 4-nitrobenzyl bromide using sodium hydride in THF, followed by ester hydrolysis with sodium hydroxide in water and ethanol, then heating the resulting diacid to its melting point causing decarboxylation gives 3-(4-nitro-phenyl)-propionic acid. Conversion to the acid chloride with thionyl chloride in DCM and coupling with 2-amino-4,6-dimethylpyridine affords N-(4,6-dimethyl-pyridin-2-yl)-3-(4-nitro-phenyl)-propionamide. Amide reduction with borane-dimethylsulfide in THF at reflux, methylation of the resulting amine with methyl iodide and sodium hydride in THF and finally catalytic hydrogenation over Raney nickel in methanol gives the required aniline.

4-[4-(4,6-Dimethyl-pyridin-2-yl)-[1,4]diazepan-1-yl]-phenylamine

From 1-chloro-4-nitrobenzene and [1,4]diazepane (homopiperazine) by heating in n-butanol at reflux to give 1-(4-nitro-phenyl)-[1,4]diazepane, followed by reaction with 2-chloro-4,6-dimethylpyridine by heating in the presence of palladium (II) acetate, 2-dicyclohexylphospino-2-(N,N'-dimethyl amino)biphenyl and caesium carbonate in a mixture of toluene and THF to give 1-(4,6-dimethyl-pyridin-2-yl)-4-(4-nitro-phenyl)-[1,4]diazepane, and finally reduction with tin (II) chloride in a mixture of ethanol and ethyl acetate gives the required aniline.

N-{3-[(4,6-Dimethyl-pyridin-2-yl)-methyl-amino]-propyl}-N-methyl-benzene-1,4-diamine From methyl-(4-nitro-phenyl)-amine and acrylic acid by heating with catalytic sulfuric acid to give 3-[methyl-(4-nitro-phenyl)-amino]-propionic acid, acid chloride formation with thionyl chloride in DCM and coupling with (4,6-dimethyl-pyridin-2-yl)-methyl-amine to afford N-(4,6-dimethyl-pyridin-2-yl)-N-methyl-3-[methyl-(4-nitro-phenyl)-amino]-propionamide. Amide reduction with borane-dimethylsulfide in THF at reflux and catalytic hydrogenation over Raney nickel in methanol gives the required aniline.

All of the starting materials referred to in the reactions described above are available from commercial sources or can be prepared by analogy with known methods.

In one embodiment, the present invention provides combinations of the pyrrole derivative of formula (I), (IA) or (IB) or a pharmaceutically acceptable salt thereof, with a further antifungal agent. Thus, the pyrrole derivative of formula (I), (IA), (IB) or pharmaceutically acceptable salt thereof (also referred to herein as the first antifungal agent) is present in the combinations, compositions and products of the invention with a second antifungal agent. The second antifungal agent used in the invention can be any suitable antifungal agent that the skilled person would judge to be useful in the circumstances. Particularly suitable classes of antifungal agents include azoles, polyenes, purine nucleotide inhibitors, pyrimidine nucleotide inhibitors, mannan inhibitors, protein elongation factor inhibitors, chitin synthase inhibitors, Beta-glucan synthase inhibitors, echinocandins, allylamines, anti-HSP90 antibodies, bactericidal/permeability inducing protein products and polyoxins. Other suitable antifungal agents which do not fall within the classes above include the compounds AN2690, AN2718 and icofungipen.

Preferred azoles are clotrimazole, econazole, bifonazole, butoconazole, fenticonazole, fluconazole, isoconazole, itraconazole, ketoconazole, miconazole, oxiconazole, sertaconazole, sulconazole, tioconazole, isavuconazole, ravuconazole, posaconazole, terconazole and voriconazole. Preferred echinocandins are anidulafungin, caspofungin and micafungin. Preferred allylamines are terbinafine, butenafine, amorolfine and naftifine. Preferred polyenes are amphotericin B and nystatin. A preferred example of a purine or pyrimidine nucleotide inhibitor is flucytosine. A preferred mannan inhibitor is pradamicin. A preferred protein elongation factor inhibitor is sordarin and analogues thereof. A preferred polyoxin is nikkomycin Z.

Particularly preferred second antifungal agents are caspofungin, micafungin, amphotericin B, voriconazole, posaconazole, fluconazole and itraconazole.

Examples of preferred combinations of the invention are compounds of formula (IA) and their pharmaceutically acceptable salts as defined above with a second antifungal agent selected from caspofungin, micafungin, amphotericin B, voriconazole, posaconazole, fluconazole and itraconazole. Further preferred combinations of the invention are combinations of (i) compounds of formula (Ia) and pharmaceutically acceptable salts thereof wherein:

A1 represents phenyl, which may be unsubstituted or substituted with one or more substituents selected from unsubstituted C1-C4 alkyl, C1-C4 alkyl substituted with an unsubstituted C1-C4 alkoxy group, unsubstituted C1-C4 alkoxy, —$CO_2H$ and halogen, preferably A1 is unsubstituted or substituted with one group selected from F, Cl and methyl, most preferably A1 is unsubstituted;

n represents one;

L1 represents an unsubstituted, saturated 5- to 7-membered heterocyclyl group containing two nitrogen atoms, the heterocycle being attached to A1 and to R1 via a nitrogen atom, preferably L1 represents piperazinyl;

R1 represents unsubstituted C1-C6 alkyl, unsubstituted C2-C6 alkenyl, or a group -A2, —$CH_2$-A2 or -A2-$CH_2$-A3;

A2 and A3 independently represent phenyl or a 5- or 6-membered heterocyclyl group, wherein A2 and A3 are unsubstituted or substituted with one, two or three substituents selected from the unsubstituted substituents halogen, —$COCF_3$, —OCONR'R" and —NR'R", and from C1-C4 alkyl and C1-C4 alkoxy groups which are unsubstituted or substituted with —OH, —OMe, —OEt or —O(C1-C4 alkyl)-O(C1-C2 alkyl), wherein R' and R" are independently selected from hydrogen, unsubstituted C1-C4 alkyl and C1-C4 alkyl substituted with a hydroxyl or unsubstituted C1-C4 alkoxy group;

R5 represents unsubstituted phenyl;

R2 represents hydrogen, or C1-C4 alkyl or C2-C4 alkenyl, each of which may be unsubstituted or substituted with —OMe, —OEt, —OPr, —OBu, —$OCH_2CH_2OMe$, —SMe, hydroxy, di(C1-C4 alkyl)amino, —COO(C1-C4 alkyl), —CONR'R" or —NR'CO(C1-C4 alkyl) where R' and R" are the same or different and represent hydrogen or unsubstituted C1-C4 alkyl; or R2 represents a group (C1-C4) alkyl-A5, wherein none or one —$CH_2$— groups are independently replaced by —O— and wherein A5 represents phenyl, pyridinyl or oxazolyl, each of which is unsubstituted or substituted with one or two substituents selected from halogen, C1-C4 alkyl and C1-C4 alkoxy; and R3 represents hydrogen or C1-C4 alkyl which is unsubstituted or substituted with —OMe or —OEt;

with (ii) a second antifungal agent selected from caspofungin, micafungin, amphotericin B, voriconazole, posaconazole, fluconazole and itraconazole.

In a preferred aspect of this embodiment, in the compounds of formula (IA), A1 is a phenyl group which is unsubstituted or substituted with F, Cl or methyl, preferably A1 is unsubstituted phenyl; L1 is piperazinyl and is linked to A1 and R1 via a nitrogen atom; and R1 is unsubstituted C1-C6 alkyl, unsubstituted C2-C6 alkenyl, or piperidinyl, wherein the piperidinyl group is unsubstituted or substituted with one, two or three substituents selected from unsubstituted C1-C4 alkyl groups. More preferably, R1 is piperidinyl which is substituted with two methyl groups.

In a further preferred aspect of this embodiment, in the compounds of formula (IA), R2 and R3 are independently selected from hydrogen and unsubstituted C1-C4 alkyl groups, preferably methyl.

In a further preferred aspect of this embodiment, the compound of formula (IA) is 2-(1,5-Dimethyl-3-phenyl-1H-pyrrol-2-yl)-N-{4-[4-(4,6-dimethyl-pyridin-2-yl)-piperazin-1-yl]-phenyl}-2-oxo-acetamide, N-{4-[4-(4,6-Dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide, N-{3-Chloro-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide, N-{2-Chloro-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide, N-{3-Chloro-4-[4-(4,6-dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide, N-{4-[4-(4,6-Dimethyl-pyridin-2-yl)-piperazin-1-yl]-phenyl}-2-(1-ethyl-5-methyl-3-phenyl-1H-pyrrol-2-yl)-2-oxo-acetamide, N-{4-[4-(4,6-Dimethyl-pyridin-2-yl)-piperazin-1-yl]-phenyl}-2-(5-methyl-3-phenyl-1-propyl-1H-pyrrol-2-yl)-2-oxo-acetamide, 2-(1-Butyl-5-methyl-3-phenyl-1H-pyrrol-2-yl)-N-{4-[4-(4,6-dimethyl-pyridin-2-yl)-piperazin-1-yl]-phenyl}-2-oxo-acetamide, 2-(1,5-Dimethyl-3-phenyl-1H-pyrrol-2-yl)-2-oxo-N-[4-(4-pyridin-2-yl-piperazin-1-yl)-phenyl]-acetamide, 2-(1,5-Dimethyl-3-phenyl-1H-pyrrol-2-yl)-N-{4-[4-(6-methyl-pyridin-2-yl)-piperazin-1-yl]-phenyl}-2-oxo-acetamide, 2-(1,5-Dimethyl-3-phenyl-1H-pyrrol-2-yl)-N-{4-[4-(4-methyl-pyridin-2-yl)-piperazin-1-yl]-phenyl}-2-oxo-acetamide, N-{4-[4-(4,6-Dimethyl-pyridin-2-yl)-piperazin-1-yl]-phenyl}-2-(1-methyl-3-phenyl-1H-pyrrol-2-yl)-2-oxo-acetamide, N-{4-[4-(4,6-Dimethyl-pyridin-2-yl)-piperazin-1-yl]-phenyl}-2-(5-methyl-3-phenyl-1H-pyrrol-2-yl)-2-oxo-acetamide, 2-(1,5-Dimethyl-3-phenyl-1H-pyrrol-2-yl)-N-{4-[4-(4,6-dimethyl-pyridin-2-yl)-piperazin-1-yl]-3-methyl-phenyl}-2-oxo-acetamide, N-{4-[4-(4,6-Dimethyl-pyridin-2-yl)-piperazin-1-yl]-phenyl}-2-(5-ethyl-1-methyl-3-phenyl-1H-pyrrol-2-yl)-2-oxo-acetamide, N-{4-[4-(4,6-Dimethyl-pyridin-2-yl)-piperazin-1-yl]-phenyl}-2-(1-methoxymethyl-5-methyl-3-phenyl-1H-pyrrol-2-yl)-2-oxo-acetamide, 2-(1,5-Dimethyl-3-phenyl-1H-pyrrol-2-yl)-N-[2-fluoro-4-(4-pyridin-2-yl-piperazin-1-yl)-phenyl]-2-oxo-acetamide, (2-{2-Chloro-4-[4-(4,6-dimethyl-pyridin-2-yl)-piperazin-1-yl]-phenylaminooxalyl}-5-methyl-3-phenyl-pyrrol-1-yl)-acetic acid methyl ester, 2-(1,5-Dimethyl-3-phenyl-1H-pyrrol-2-yl)-N-[2-fluoro-4-(4-isobutyl-piperazin-1-yl)-phenyl]-2-oxoacetamide, 2-(1,5-Dimethyl-3-phenyl-1H-pyrrol-2-yl)-N-{2-fluoro-4-[4-(2-methyl-allyl)-piperazin-1-yl]-phenyl}-2-oxo-acetamide, 2-(1,5-Dimethyl-3-phenyl-1H-pyrrol-2-yl)-N-{4-[4-(2,2-dimethyl-propyl)-piperazin-1-yl]-2-fluoro-phenyl}-2-oxo-acetamide, 2-(1,5-Dimethyl-3-phenyl-1H-pyrrol-2-yl)-N-[3-fluoro-4-(4-pyridin-2-yl-piperazin-1-yl)-phenyl]-2-oxo-acetamide, 2-(1,5-Dimethyl-3-phenyl-1H-pyrrol-2-yl)-N-[3-fluoro-4(4-isobutyl-piperazin-1-yl)-phenyl]-2-oxo-acetamide, 2-(1,5-Dimethyl-3-phenyl-1H-pyrrol-2-yl)-N-{4-[4-(5-morpholin-4-ylmethyl-pyridin-2-yl)-piperazin-1-yl]-phenyl}-2-oxo-acetamide, N-{4-[4-(4,6-Dimethyl-pyridin-2-yl)-piperazin-1-yl]-2-fluoro-phenyl}-2-[1-(2-methoxy-ethyl)-5-methyl-3-phenyl-1H-pyrrol-2-yl]-2-oxo-acetamide, or N-{4-[4-(4,6-Dimethyl-pyridin-2-yl)-piperazin-1-yl]-phenyl}-2-(1-ethoxymethyl-5-methyl-3-phenyl-1H-pyrrol-2-yl)-2-oxo-acetamide, or a pharmaceutically acceptable salt thereof.

The most preferred combinations of the invention include combinations of 2-(1,5-Dimethyl-3-phenyl-1H-pyrrol-2-yl)-N-{4-[4-(4,6-dimethyl-pyridin-2-yl)-piperazin-1-yl]-phenyl}-2-oxo-acetamide or a pharmaceutically acceptable salt thereof, with a second antifungal agent selected from caspofungin, micafungin, amphotericin B, voriconazole, posaconazole, fluconazole and itraconazole.

The compounds of the invention have antifungal activity. Accordingly, they may be used in a method of treating a subject suffering from or susceptible to a fungal disease, which method comprises administering to said subject an effective amount of a pyrrole derivative of formula (I), (IA) or (IB) or a pharmaceutically acceptable salt thereof. The compounds may be used in combination with a second antifungal agent, as desired.

Preferably, the fungal disease comprises an infection by a fungus, for example an Ascomycete. Preferably, the fungal disease comprises an infection by an organism selected from the genera *Absidia; Acremonium; Alternaria; Aspergillus; Bipolaris; Blastomyces; Blumeria; Candida; Cladosporium; Coccidioides; Colletotrichium; Cryptococcus; Curvularia; Encephalitozoon; Epicoccum; Epidermophyton; Exophiala; Exserohilum; Fusarium; Histoplasma; Leptosphaeria; Microsporum; Mycosphaerella; Neurospora, Paecilomyces; Penicillium; Phytophthora; Plasmopara; Pneumocystis; Pyricularia; Pythium; Puccinia; Rhizoctonia; Rhizomucor; Scedosporium; Scopulariopsis; Trichophyton; Trichosporon*; and *Ustilago*.

Preferably, the fungal disease comprises an infection by an organism of the genus *Aspergillus* or *Candida*.

Preferably, the fungal disease comprises an infection by an organism selected from the species *Absidia corymbifera; Acremonium* spp; *Alternaria alternata; Aspergillus flavus; Aspergillus fumigatus; Aspergillus nidulans; Aspergillus niger; Aspergillus parasiticus; Aspergillus terreus; Bipolaris* spp; *Blastomyces dermatitidis; Blumeria graminis; Candida albicans; Candida glabrata; Candida krusei; Candida parapsilosis; Candida tropicalis; Cladosporium cladosporoides; Cladosporium herbarium; Coccidioides immitis; Coccidioides posadasii; Curvularia lunata; Colletotrichium trifolii; Cryptococcus neoformans; Encephalitozoon cuniculi; Epicoccum nigrum; Epidermophyton fioccosum; Exophiala* spp; *Exserohilum rostratum; Fusarium graminarium; Fusarium solani; Fusarium sporotrichoides; Histoplasma capsulatum; Leptosphaeria nodorum; Microsporum canis; Mycosphaerella graminicola; Paecilomyces lilanicus; Paecilomyces varioti; Penicillium chrysogenum; Phytophthora capsici; Phytophthora infestans; Plasmopara viticola; Pneumocystis firoveci; Puccinia coronata; Puccinia graminis; Pyricularia oryzae; Pythium ultimum; Rhizoctonia solani; Rhizomucor* spp; *Rhizopus* spp; *Scedosporium apiospermum; Scedosporium prolificans; Scopulariopsis brevicaulis; Trichophyton mentagrophytes; Trichophyton interdigitale; Trichophyton rubrum; Trichosporon asahii; Trichosporon beigelii*; and *Ustilago maydis*.

Preferably, the fungal disease comprises an infection by *Aspergillus fumigatus*.

Examples of fungal diseases, which can be prevented or treated using the compounds of the invention, include both systemic and superficial infections. The fungal diseases include invasive fungal diseases caused by *Aspergillus* and *Candida* species such as aspergillosis or candidiasis, but also local forms of these infections. The compounds of the invention are particularly useful against diseases caused by *Aspergillus* species, for which a fungicidal drug is required which has lower toxicity than amphotericin. The invention also provides for the treatment of dermatological infections.

In one embodiment, the compounds of the invention are for use in the prevention or treatment of a disease caused by *Aspergillus* species. In a further embodiment of the invention, the compounds of the invention are pyrrole derivatives of formula (IB) or pharmaceutically acceptable salts thereof, these compounds being for use in preventing or treating diseases caused by *Candida* species. The compounds of formula (IB) or pharmaceutically acceptable salts thereof are therefore particularly useful in the prevention or treatment of diseases caused by *Aspergillus* species and diseases caused by *Candida* species.

The diseases caused by *Aspergillus* species include diseases caused by *A. fumigatus, A. flavus, A. terreus* and *A. niger*.

The diseases cause by *Candida* species include diseases caused by *C. albicans, C. glabrata, C. krusei, C. tropicalis* and *C. parapsillosis*.

Examples of systemic infections which might be prevented or treated using the compounds of the invention include: systemic candidiasis; pulmonary aspergillosis, e.g. in immunosuppressed patients such as bone marrow recipients or AIDS patients; systemic aspergillosis; cryptococcal meningitis; rhinocerebral mucomycosis; blastomycosis; histoplasmosis; coccidiomycosis; paracoccidiomycosis; lobomycosis; sporotrichosis; chromoblastomycosis; phaeohyphomycosis; zygomycosis; cryptococcosis and disseminated sporotrichosis.

Examples of superficial infections, which can be prevented or treated using the compounds of the invention, include: ring worm; athlete's foot; tinea unguium (nail infection); candidiasis of skin, mouth or vagina; and chronic mucocutaneous candidiasis.

Examples of diseases or conditions which are caused by fungi or where fungi exacerbate an allergic response, and which can be prevented or treated using the compounds of the invention, include allergic bronchopulmonary asthma (ABPA); asthma, rhinosinusitis and sinusitis.

The present invention includes a pharmaceutical composition comprising a compound according to the invention and a pharmaceutically acceptable carrier or diluent. Said pharmaceutical composition typically contains up to 85 wt % of a compound of the invention. More typically, it contains up to 50 wt % of a compound of the invention. Preferred pharmaceutical compositions are sterile and pyrogen free. Where a compound of the invention can exist as optical isomers, the pharmaceutical compositions provided by the invention typically contain a substantially pure optical isomer.

In one embodiment, the composition additionally comprises a second antifungal agent. In this embodiment, the pyrrole and second antifungal agent need not be present in admixture in a single composition. However, the pyrrole and second antifungal agent are preferably formulated for simultaneous or successive administration.

The compounds, combinations, compositions and products of the invention may be administered in a variety of dosage forms. Thus, they can be administered orally, for example as tablets, troches, lozenges, aqueous or oily suspensions, dispersible powders or granules. The compounds, combinations, compositions and products of the invention may also be administered parenterally, either subcutaneously, intravenously, intramuscularly, intrasternally, transdermally or by infusion techniques. The compounds, combinations, compositions and products may also be administered as suppositories. The compounds, combinations, compositions and products may be administered by inhalation in the form of an aerosol via an inhaler or nebuliser.

A compound of the invention, and optionally a second antifungal agent, is typically formulated for administration with a pharmaceutically acceptable carrier or diluent. For example, solid oral forms may contain, together with the active compound, solubilising agents, e.g. cyclodextrins or modified cyclodextrins; diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be solutions, syrups, emulsions and suspensions. The solutions may contain solubilising agents e.g. cyclodextrins or modified cyclodextrins. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol; solubilising agents, e.g. cyclodextrins or modified cyclodextrins, and if desired, a suitable amount of lidocaine hydrochloride.

Solutions for intravenous or infusions may contain as carrier, for example, sterile water and solubilising agents, e.g. cyclodextrins or modified cyclodextrins or preferably they may be in the form of sterile, aqueous, isotonic saline solutions.

Nanoformulations are also envisaged.

A therapeutically effective amount of a compound of the invention is administered to a patient. A typical daily dose is up to 200 mg, e.g. up to 100 mg or up to 50 mg per kg of body weight, for example from 0.001 to 200 or 0.001 to 50 mg per kg of body weight, according to the activity of the specific compound or combination of specific antifungal agents used, the age, weight and conditions of the subject to be treated, the type and severity of the disease and the frequency and route of administration. Preferably, daily dosage levels are up to 200 mg, e.g. up to 150 mg, up to 100 mg, up to 50 mg or up to 40 mg per kg of body weight. Daily dosage levels are for example at least 1 mg, at least 2 mg or at least 5 mg per kg of body weight. In one embodiment the daily dosage level is from 0.05 mg to 2 g, preferably from 0.1 mg to 10 mg. Where a combination is administered, the compound of the invention is typically administered in an amount of at least 0.05 mg, preferably at least 0.1 mg, 2 mg or at least 5 mg. A preferred upper limit on the amount of compound of the invention administered is typically 200 mg, e.g. 100 mg, 50 mg or 25 mg. The second antifungal agent is typically administered at or below the standard dose used for that drug. An advantage of the combinations of the present invention is that known antifungal agents may be administered in lower doses than are currently used, resulting in a reduction in toxic effects. The compound, combination or composition of the invention is typically administered to the patient in a non-toxic amount.

The present invention also provides a method of controlling a fungal disease of a plant, which comprises applying to the locus of the plant a pyrrole derivative of formula (I), (IA) or (IB) or an agriculturally acceptable salt thereof, and optionally a second antifungal agent.

The compounds, combinations, compositions and products of the invention may, for example, be applied to the seeds of the plants, to the medium (e.g. soil or water) in which the plants are grown, or to the foliage of the plants.

The compounds, combinations, compositions and products of the invention are preferably used in the treatment or prevention of fungal diseases. Examples of fungal diseases of plants which can be controlled using the compounds of the invention include fungal diseases caused by the following plant pathogens: *Blumeria graminis; Colletotrichium Fusarium graminearium; Fusarium solani; Fusarium sporotrichoides; Leptosphaeria nodoruin; Magnaporthe grisea; Mycosphaerella graminicola; Neurospora crassa; Phytophthora capsici; Phytophthora infestans; Plasmopara viticola; Puccinia coronata; Puccinia graminis; Pyricularia oryzae; Pythium ultimum; Rhizoctonia solani; Trichophyton rubrum*; and *Ustilago maydis*.

The present invention includes a composition comprising a compound of the invention, or an agriculturally acceptable salt thereof, and an agriculturally acceptable carrier or diluent. In one embodiment of the invention, the composition further comprises a second antifungal agent. Said agricultural composition typically contains up to 85 wt % of a compound of the invention. More typically, it contains up to 50 wt % of a compound of the invention. When used in an agricultural composition, the skilled person will readily be able to determine suitable levels of administration. As examples, the antifungal agent(s) can be used at a level of from 5 g to 10 kg per hectare, for example from 10 g to 5 kg per hectare, for example from 100 g to 2 kg per hectare.

Suitable agriculturally acceptable salts include salts with agriculturally acceptable acids, both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Salts may also be formed with agriculturally acceptable bases such as alkali metal (e.g. sodium or potassium) and alkaline earth metal (e.g. calcium or magnesium) hydroxides and organic bases such as alkyl amines, aralkyl amines or heterocyclic amines. A preferred agriculturally acceptable salt is the hydrochloride salt.

The compounds of the invention, and optional second antifungal agents, may be applied in combination with inert carriers or diluents, as in aqueous sprays, granules and dust formulations in accordance with established practice in the art. An aqueous spray is usually prepared by mixing a wettable powder or emulsifiable concentrate formulation of a compound of the invention with a relatively large amount of water to form a dispersion.

Wettable powders may comprise an intimate, finely divided mixture of a compound of the invention, an inert solid carrier and a surface-active agent. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates may comprise a solution of a compound of the invention in a liquid carrier which is a mixture of a water-immiscible solvent and a surfactant, including an emulsifier. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

The fungicide formulations desirably contain from 0.1 percent to 95 percent by weight of the compound of the invention, or in the case of a combination of antifungal agents the total weight of antifungal agent, and from 0.1 to 75 percent of an inert carrier or surfactant. The direct application to plant seeds prior to planting may be accomplished in some instances by mixing either a powdered solid compound of the invention or a dust formulation with seed to obtain a substantially uniform coating which is very thin and represents only one or two percent by weight or less, based on the weight of the seed. In some instances, however, a non-phytotoxic solvent such as methanol is conveniently employed as a carrier to facilitate the uniform distribution of the compound of the invention on the surface of the seed.

When a compound of the invention, or in the case of a combination of antifungal agents one of the antifungal agents used, is to be applied to the soil, as for pre-emergence protection, granular formulations or dusts are sometimes more convenient than sprays. A typical granular formulation comprises a compound of the invention dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound is sprayed on the granules while they are being agitated in a suitable mixing apparatus, after which the granules are dried with a current of air during continued agitation. Dust formulations customarily employ essentially the same inert diluents as wettable powders and granules, but are well-mixed in powder form and do not usually contain emulsifiers. Dusts may contain some surface active agents to facilitate uniform distribution of the active ingredient in the formulation and to improve the uniformity and adhesion of the dust coating on seeds and plants. The colloidal dispersion of dust formulations in the air is usually prevented by incorporation of a minor amount of an oily or waxy material in the formulation to cause agglomeration of colloidal size particles. In this way the dust may be applied to seeds or plants without generation of an air-polluting aerosol.

The following examples illustrate the invention but are not intended to limit the scope of the invention. In this regard, it is important to understand that the particular assays used in the Examples section are designed only to provide an indication of anti-fungal activity. There are many assays available to determine such activity, and a negative result in any one particular assay is therefore not determinative.

EXAMPLES

Reference Example 1

3-Methoxypropionyl chloride

Thionyl chloride (7.48 g, 64.46 mmol) was added to a solution of 2-methoxy-propionic acid (6.0 g, 57.69 mmol) in chloroform (50 mL) and refluxed for 2 h. Chloroform was then added and excess thionyl chloride removed in vacuo to afford (6.0 g, 82%) of 3-methoxypropionyl chloride as a colourless liquid.

Reference Example 2

Ethyl 3-(2-furyl)-3-oxo-propanoate

Triethylamine (11.7 mL, 84.3 mmol) was added dropwise to a suspension of potassium ethyl malonate (13.4 g, 78.5 mmol) in acetonitrile (80 mL) at 10° C., followed by portionwise addition of anhydrous magnesium chloride (9.12 g, 95.8 mmol). The reaction mixture was warmed to room temperature and stirred for 2.5 h. The resulting white slurry was cooled to 0° C. and furan-2-carbonyl chloride (5.0 g, 38.3 mmol) in acetonitrile (20 mL) was added dropwise over a period of 20 min. The mixture was allowed to stir at ambient temperature overnight. The solvent was evaporated in vacuo and the residue was azeotroped with toluene (10 mL) then dissolved in toluene, cooled to between 0 and 5° C. and acidified with 13% aqueous hydrochloric acid (50 mL). After stirring for 15 min the aqueous phase was separated and the organic phase was washed with 13% aqueous hydrochloric acid (2×50 mL) followed by water (2×25 mL) and concentrated in vacuo to afford the crude compound. Purification by flash column chromatography over silica gel (100-200 mesh) using 5% ethyl acetate in petroleum ether as eluent afforded ethyl 3-(2-furyl)-3-oxo-propanoate (5.01 g, 72%) as a pale yellow liquid.

Reference Examples 3 to 8

The compounds set out below were prepared in a manner analogous to Reference Example 2:

| Reference Example | Compound |
|---|---|
| 3 | Ethyl 3-oxo-3-(2-thienyl)propanoate |
| 4 | Ethyl 4-methyl-3-oxo-pentanoate |
| 5 | Ethyl 3-oxo-3-tetrahydropyran-4-yl-propanoate |
| 6 | Ethyl 3-oxopentanoate |
| 7 | Ethyl 3-oxohexanoate |
| 8 | Ethyl 5-methoxy-3-oxo-pentanoate |

Reference Example 9

Ethyl-2-hydroxyimino-3-oxo-3-phenyl-propanoate

A solution of sodium nitrite (56.5 g, 0.815 mol) in water (400 mL) was added to a solution of ethyl benzoyl acetate (120 g, 0.625 mol) in glacial acetic acid (300 mL) at 0-10° C. over a period of 2 h. The product started precipitating during the course of addition and the reaction mixture was warmed to room temperature and stirred for 30 min. Water (2.5 L) was added and the mixture was stirred for a further 30 min and then filtered under suction. The solid was washed with water (20 mL), petroleum ether (200 mL) and then dissolved in chloroform (700 mL). The filtrate was extracted with chloroform (2×100 mL) and the combined organic phase was washed with water (2×200 mL), brine solution (2×250 mL), dried over anhydrous sodium sulfate and concentrated in vacuo to afford ethyl-2-hydroxyimino-3-oxo-3-phenyl-propanoate (122.5 g, 88%).

Reference Example 10 to 14

The compounds set out below were prepared in a manner analogous to Reference Example 9:

| Reference Example | Compound |
|---|---|
| 10 | Ethyl 3-(2-furyl)-2-hydroxyimino-3-oxo-propanoate |
| 11 | Ethyl 2-hydroxyimino-3-oxo-3-(2-thienyl)propanoate |
| 12 | Ethyl 2-hydroxyimino-4-methyl-3-oxo-pentanoate |
| 13 | Ethyl 2-hydroxyimino-3-oxo-3-tetrahydropyran-4-yl-propanoate |
| 14 | Ethyl 2-hydroxyimino-5-methoxy-3-oxo-pentanoate |

Reference Example 15

Diethyl 5-methyl-3-phenyl-1H-pyrrole-2,4-dicarboxylate

A mixture of ethyl acetoacetate (72.5 g, 0.56 mol), zinc dust (98 g, 1.51 mol) and anhydrous sodium acetate (102 g, 1.21 mol) in glacial acetic acid (110 mL) was heated to 60° C. Ethyl-2-hydroxyimino-3-oxo-3-phenyl-propanoate (110 g, 0.5 mol) was added as a solution (some precipitation on standing) in glacial acetic acid (550 mL) in 3 portions with vigorous stirring over a period of 1 h. The temperature increased to 90° C. during the addition and the reaction was then maintained at 60-75° C. for 3 h. Additional zinc dust (49 g, 0.75 mol) was added over 15 min, again causing a temperature rise, and then the reaction mixture was then stirred at 60 to 75° C. for 1 h. After cooling to room temperature the mixture was filtered and the filtrate was evaporated in vacuo to give a residue which was azeotroped with toluene (2×200 mL) to remove residual acetic acid. Water (2 L) and ethyl acetate (300 mL) were added to the residue and the mixture was stirred until two clear phases were obtained. The organic phase was separated and the aqueous phase extracted with ethyl acetate (2×200 mL). The combined organic phases were washed successively with water (2×250 mL), saturated bicarbonate solution (2×250 mL), water (2×100 mL), brine (2×100 mL), dried over anhydrous sodium sulfate and then concentrated to give a gummy residue. A mixture of dichloromethane and petroleum ether (175 mL; 1:6) was added to the solid and it was stirred for 15 min. The resulting free-flowing solid was filtered off and washed with chilled petroleum ether (100 mL) to afford diethyl 5-methyl-3-phenyl-1H-pyrrole-2,4-dicarboxylate (85 g, 57%) as an off-white solid.

Reference Examples 16 to 24

The compounds set out below were prepared in a manner analogous to Reference Example 15:

| Reference Example | Compound |
|---|---|
| 16 | 2-Ethyl 4-methyl 3-(2-furyl)-5-methyl-1H-pyrrole-2,4-dicarboxylate |
| 17 | Diethyl 5-methyl-3-(2-thienyl)-1H-pyrrole-2,4-dicarboxylate |
| 18 | 2-Ethyl 4-methyl 3-isopropyl-5-methyl-1H-pyrrole-2,4-dicarboxylate |
| 19 | 2-Ethyl 4-methyl 5-methyl-3-tetrahydropyran-4-yl-1H-pyrrole-2,4-dicarboxylate |
| 20 | Diethyl 5-isopropyl-3-phenyl-1H-pyrrole-2,4-dicarboxylate |
| 21 | Diethyl 5-ethyl-3-phenyl-1H-pyrrole-2,4-dicarboxylate |
| 22 | Diethyl 3-(2-methoxyethyl)-5-methyl-1H-pyrrole-2,4-dicarboxylate |
| 23 | Diethyl 3-phenyl-5-propyl-1H-pyrrole-2,4-dicarboxylate |
| 24 | Diethyl 5-(2-methoxyethyl)-3-phenyl-1H-pyrrole-2,4-dicarboxylate |

Reference Example 25

Ethyl 4-methyl-3-phenyl-1H-pyrrole-2-carboxylate 1,8-Diazabicyclo[5.4.0]undec-7-ene (3.70 g, 24.6 mmol) was added dropwise to a stirred solution of ethyl isocyanoacetate (1.50 g, 13.3 mmol) and 2-nitro-3-phenyl-2-propene (2.0 g, 12.3 mmol) in a mixture of tetrahydrofuran (15 mL) and iso-propanol (5 mL) at between 10 and 20° C. The reaction mixture was stirred at room temperature for 4 h. Excess tetrahydrofuran was removed in vacuo, water (15 mL) was added to the residue and the mixture was extracted with diethyl ether (3×25 mL). The combined organic phases were washed with brine (2×15 mL), dried over anhydrous sodium sulfate and concentrated under reduced pressure to afford ethyl 4-methyl-3-phenyl-1H-pyrrole-2-carboxylate (2.5 g, 90%) as an oil.

Reference Example 26

Diethyl-1,5-dimethyl-3-phenyl-pyrrole-2,4-dicarboxylate

A solution of diethyl 5-methyl-3-phenyl-1H-pyrrole-2,4-dicarboxylate (85 g, 0.28 mol) in dry tetrahydrofuran (240 mL) was added to a suspension of sodium hydride (60% w/w; 17 g, 0.425 mol) in dry tetrahydrofuran (200 mL) at 0° C. over 45 min. The mixture was warmed to room temperature and stirred for 1 h before cooling back to 0 C. Methyl iodide (71 mL, 1.13 mol) was added dropwise over 30 min and the reaction mixture and then stirred at room temperature for 18 h. The mixture was quenched with ice-water (100 mL) and concentrated in vacuo to remove volatile organics. The aqueous phase was decanted off and the residual solid was extracted with dichloromethane (350 mL). The aqueous phase was extracted with dichloromethane (2×100 mL) and the combined extracts were washed successively with water (2×200 mL), brine (2×100 mL), dried over anhydrous sodium sulfate and concentrated to afford diethyl 1,5-dimethyl-3-phenyl-pyrrole-2,4-dicarboxylate (80 g, 90%) as a yellow solid.

Reference Examples 27 to 34

The compounds set out below were prepared in a manner analogous to Reference Example 26:

| Reference Example | Compound |
| --- | --- |
| 27 | 2-Ethyl 4-methyl 3-(2-furyl)-1,5-dimethyl-pyrrole-2,4-dicarboxylate |
| 28 | Diethyl 1,5-dimethyl-3-(2-thienyl)pyrrole-2,4-dicarboxylate |
| 29 | 2-Ethyl 4-methyl 3-isopropyl-1,5-dimethyl-pyrrole-2,4-dicarboxylate |
| 30 | 2-Ethyl 4-methyl 1,5-dimethyl-3-tetrahydropyran-4-yl-pyrrole-2,4-dicarboxylate |
| 31 | Ethyl 1,4-dimethyl-3-phenyl-pyrrole-2-carboxylate |
| 32 | Diethyl 5-isopropyl-1-methyl-3-phenyl-pyrrole-2,4-dicarboxylate |
| 33 | Diethyl 1-methyl-3-phenyl-5-propyl-pyrrole-2,4-dicarboxylate |
| 34 | 2-(Methoxymethyl)-1-methyl-4-phenyl-pyrrole |

Reference Example 35

Diethyl 3-isopropyl-1-(2-methoxyethyl)-5-methyl-pyrrole-2,4-dicarboxylate

Sodium hydride (55%; 555 mg, 12.7 mmol) was added to a solution of 2-ethyl 4-methyl 3-isopropyl-5-methyl-1H-pyrrole-2,4-dicarboxylate (1.8 g, 6.74 mmol) in dry dimethylformamide (10 mL) at 0-5° C. and stirred for 30 min. 1-Bromo-2-methoxy-ethane (1.0 mL, 10.1 mmol) was added dropwise to the mixture which was stirred at 90° C. for 2 h. Additional sodium hydride (55%; 275 mg, 6.37 mmol) was added followed by 1-bromo-2-methoxy-ethane (1.0 mL, 10.1 mmol) and stirring continued at 90° C. for 5 h. The reaction mixture was cooled to room temperature, quenched with ice water and extracted with ethyl acetate (2×30 mL). The combined organic phases were washed with water (2×50 mL), brine (50 mL), dried over anhydrous sodium sulfate and concentrated in vacuo to afford diethyl 3-isopropyl-1-(2-methoxyethyl)-5-methyl-pyrrole-2,4-dicarboxylate (2.2 g, 100%).

Reference Examples 36 to 43

The compounds set out below were prepared in a manner analogous to Reference Example 35:

| Reference Example | Compound |
| --- | --- |
| 36 | Diethyl 1-ethyl-5-methyl-3-phenyl-pyrrole-2,4-dicarboxylate |
| 37 | Diethyl 5-methyl-3-phenyl-1-propyl-pyrrole-2,4-dicarboxylate |
| 38 | Diethyl 1-butyl-5-methyl-3-phenyl-pyrrole-2,4-dicarboxylate |
| 39 | Ethyl 1-methyl-4-phenyl-pyrrole-2-carboxylate |
| 40 | Diethyl 1-benzyl-5-methyl-3-phenyl-pyrrole-2,4-dicarboxylate |
| 41 | Methyl 2-(2-methyl-4-phenyl-pyrrol-1-yl)acetate |
| 42 | Diethyl 1-(2-methoxyethyl)-5-methyl-3-phenyl-pyrrole-2,4-dicarboxylate |
| 43 | Diethyl 5-methyl-1-(2-phenoxyethyl)-3-phenyl-pyrrole-2,4-dicarboxylate |

Reference Example 44

1-Ethoxy-2-iodo-ethane

Toluene-4-sulfonic acid 2-ethoxy-ethyl ester (prepared according to Crowley et. al., J. Chem. Soc., 1957, 2931-2934; 3.5 g, 14.3 mmol) was added to a solution of sodium iodide (4.30 g, 28.7 mmol) in acetone (30 mL) and heated at reflux overnight. Acetone was evaporated from the reaction mixture and ether was added. The mixture was filtered and the filtrate was concentrated in vacuo to afford 1-ethoxy-2-iodo-ethane (1.5 g, 52%).

Reference Example 45

Diethyl 1-(2-ethoxyethyl)-5-methyl-3-phenyl-pyrrole-2,4-dicarboxylate

Potassium carbonate (1.82 g, 13.3 mmol) was added to a solution of diethyl 5-methyl-3-phenyl-1H-pyrrole-2,4-dicarboxylate (1.0 g, 3.32 mmol) and 1-ethoxy-2-iodo-ethane (1.98 g, 9.96 mmol) in acetonitrile (20 mL) and the mixture heated at reflux for 72 h. The inorganic salts were filtered off and the filtrate was concentrated in vacuo to afford diethyl 1-(2-ethoxyethyl)-5-methyl-3-phenyl-pyrrole-2,4-dicarboxylate (1.25 g, quantitative).

Reference Examples 46 to 49

The compounds set out below were prepared in a manner analogous to Reference Example 45:

| Reference Example | Compound |
|---|---|
| 46 | Diethyl 1-(3-chloropropyl)-5-methyl-3-phenyl-pyrrole-2,4-dicarboxylate |
| 47 | Diethyl 5-isopropyl-1-(2-methoxyethyl)-3-phenyl-pyrrole-2,4-dicarboxylate |
| 48 | 1-Benzyl-4-isobutyl-piperazine |
| 49 | tert-Butyl 4-(2-methylallyl)piperazine-1-carboxylate |

Reference Example 50

Ethyl 2-cyano-4-methyl-pent-2-enoate

A solution of piperidine (0.3 mL, 3.04 mmol) in acetic acid (3 mL) was added to a solution of ethyl cyano acetate (10 g, 88.50 mmol) and isobutyraldehyde (9.35 g, 0.13 mol) in acetic acid at room temperature. The reaction mixture was allowed to stand for 24 h at room temperature, then diluted with water (50 mL) and extracted with ether (3×50 mL). The combined ether layers were washed with saturated bicarbonate solution, water, and brine and the organics were dried over anhydrous sodium sulfate and concentrated under reduced pressure to give the crude compound. Purification by vacuum distillation (95° C. at 0.1 mm Hg) afforded ethyl 2-cyano-4-methyl-pent-2-enoate (6.5 g, 30%) as a liquid.

Reference Example 51

2-Isopropylbutanedinitrile

A solution of potassium cyanide (5.81 g, 89.52 mmol) in water (12 mL) was added to a solution of ethyl 2-cyano-4-methyl-pent-2-enoate (6.5 g, 38.92 mmol) in ethanol (20 mL) at room temperature and the reaction mixture was stirred overnight. The resulting mixture was refluxed for 2 h and then cooled to room temperature. The ethanol was evaporated and the residue dissolved in dichloromethane. The dichloromethane layer was washed with water and brine, dried over anhydrous sodium sulfate and concentrated under reduced pressure to give 2-isopropylbutanedinitrile (3.5 g, 74%) as a liquid.

Reference Example 52

3-Isopropyl-1H-pyrrole

20% Diisobutyl aluminium hydride in toluene (62 mL, 74.59 mmol) was added to a solution of 2-isopropylbutanedinitrile (3.5 g, 28.69 mmol) in benzene (25 mL) at 0° C. The reaction mixture was warmed to room temperature and stirred for 3 h. The reaction mixture was quenched with 2M sodium dihydrogen phosphate solution (200 mL), refluxed for 1 h then cooled to room temperature. Ether (50 mL) was added and the un-dissolved salts were filtered and 15% aq sodium chloride solution was added to the filtrate. The ether layer was separated, washed with water, brine solution and dried over anhydrous sodium sulfate. The organics were concentrated under reduced pressure to give the crude compound which was purified by vacuum distillation (100° C. at 0.15 mm Hg) to afford 3-isopropyl-1H-pyrrole (350 mg, 11%) as a liquid.

Reference Example 53

Ethyl 1-(2-methoxyethyl)-4-phenyl-pyrrole-2-carboxylate

Potassium tert-butoxide (780 mg, 6.96 mmol) was added in three portions over a period of 10 min to a stirred solution of ethyl 4-phenyl-1H-pyrrole-2-carboxylate (1.0 g, 4.63 mmol) in dimethylsulfoxide (10 mL) at 10° C. and maintained at this temperature for 30 min. A solution of 1-bromo-2-methoxyethane (770 mg, 5.50 mmol) in dimethylsulfoxide (2 mL) was added dropwise to the reaction mixture at 10° C. and then stirred for 2 h at room temperature. The reaction mixture was poured into ice water (25 mL) and the aqueous layer extracted with diethyl ether (3×20 mL). The combined organic layer was washed with water, brine (2×20 mL), dried over anhydrous sodium sulphate and concentrated under reduced pressure to afford ethyl 1-(2-methoxyethyl)-4-phenyl-pyrrole-2-carboxylate (1.15 g, 91%) as an oil.

Reference Examples 54 to 77

The compounds set out below were prepared in a manner analogous to Reference Example 53:

| Reference Example | Compound |
|---|---|
| 54 | Diethyl 5-ethyl-1-methyl-3-phenyl-pyrrole-2,4-dicarboxylate |
| 55 | Diethyl 5-ethyl-1-(2-methoxyethyl)-3-phenyl-pyrrole-2,4-dicarboxylate |
| 56 | Ethyl 4-(2-chlorophenyl)-1-(2-methoxyethyl)pyrrole-2-carboxylate |
| 57 | 4-(4-Chlorophenyl)-1-(2-methoxyethyl)pyrrole-2-carboxylic acid |
| 58 | Methyl 2-pyrrol-1-ylacetate |
| 59 | 1-(2-Methoxyethyl)-3-(2-thienyl)pyrrole |
| 60 | Ethyl 4-isobutyl-1-(2-methoxyethyl)pyrrole-3-carboxylate |
| 61 | 5-(3-Phenylpyrrol-1-yl)pentanenitrile |
| 62 | tert-Butyl 2-(2-methyl-4-phenyl-pyrrol-1-yl)acetate |
| 63 | Ethyl 4-(3-chlorophenyl)-1-(2-methoxyethyl)pyrrole-2-carboxylate |
| 64 | 1-(2-Methoxyethyl)-3-(3-thienyl)pyrrole |
| 65 | tert-Butyl 2-(3-phenylpyrrol-1-yl)acetate |
| 66 | 3-Isopropyl-1-(2-methoxyethyl)pyrrole |
| 67 | N,N-dimethyl-2-(3-phenylpyrrol-1-yl)ethanamine |
| 68 | N,N-dimethyl-2-(2-methyl-4-phenyl-pyrrol-1-yl)ethanamine |
| 69 | tert-Butyl 2-[3-(2-thienyl)pyrrol-1-yl]acetate |
| 70 | tert-Butyl 2-(3-isobutylpyrrol-1-yl)acetate |
| 71 | Diethyl 5-methyl-3-phenyl-1-(2-pyridylmethyl)pyrrole-2,4-dicarboxylate |
| 72 | 3-[(2-Methyl-4-phenyl-pyrrol-1-yl)methyl]pyridine |
| 73 | 3-Bromo-1-(2-methoxyethyl)-2-methyl-4-phenyl-pyrrole |
| 74 | 1-(2-Isopropoxyethyl)-2-methyl-4-phenyl-pyrrole |
| 75 | Diethyl 5-methyl-3-phenyl-1-(4-pyridylmethyl)pyrrole-2,4-dicarboxylate |
| 76 | 3-Cyclobutyl-1-(2-methoxyethyl)pyrrole |
| 77 | tert-Butyl 2-(3-cyclobutylpyrrol-1-yl)acetate |

Reference Example 78

Diethyl 5-methyl-1-(2-methylsulfanylethyl)-3-phenyl-pyrrole-2,4-dicarboxylate

Potassium t-butoxide (224 mg, 2.00 mmol) was added to a solution of diethyl 5-methyl-3-phenyl-1H-pyrrole-2,4-dicarboxylate (500 mg, 1.66 mmol) in dry dimethylsulfoxide (10 mL) at 10° C. over 5 min. The reaction mixture was allowed to warm to ambient temperature and stirred for 30 min before cooling again to 10° C. 1-Chloro-2-methylsulfanyl-ethane (200 mg, 1.81 mmol) was added slowly and the reaction mixture then stirred at ambient temperature for 72 h. Saturated aqueous ammonium chloride was added and the mixture extracted with diethyl ether. The combined organic layers were washed with brine, dried over anhydrous sodium sulfate and concentrated in vacuo to afford the crude product. Purification by flash column chromatography over 100-200 mesh silica gel by eluting with 5%-7% ethyl acetate in petroleum ether afforded diethyl 5-methyl-1-(2-methylsulfanylethyl)-3-phenyl-pyrrole-2,4-dicarboxylate (420 mg, 68%) as a liquid.

Reference Example 79

The compound set out below was prepared in a manner analogous to Reference Example 78:

| Reference Example | Compound |
|---|---|
| 79 | Diethyl 5-methyl-1-(methylsulfanylmethyl)-3-phenyl-pyrrole-2,4-dicarboxylate |

Reference Example 80

Diethyl 5-ethyl-1-(methoxymethyl)-3-phenyl-pyrrole-2,4-dicarboxylate

Sodium hydride (50% in mineral oil; 220 mg, 4.76 mmol) was added to a solution of diethyl 5-methyl-3-phenyl-1H-pyrrole-2,4-dicarboxylate (1 g, 3.18 mmol) in dimethylformamide (15 mL) at 0° C. and then the mixture stirred for 30 min at ambient temperature. The mixture was cooled to 0° C. and chloro-methoxy-methane (0.3 ml, 3.8 mmol) was added and the whole refluxed for 6 h. The reaction mixture was cooled, washed with water (2×25 ml) and extracted with ethyl acetate (4×25 ml). The combined ethyl acetate extracts were washed with water (2×25 ml), brine (25 ml), dried over anhydrous sodium sulphate and concentrated to afford diethyl 5-ethyl-1-(methoxymethyl)-3-phenyl-pyrrole-2,4-dicarboxylate (1 g, 88%) as a pale yellow liquid.

Reference Examples 81

The compound set out below was prepared in a manner analogous to Reference Example 80:

| Reference Example | Compound |
|---|---|
| 81 | Methyl 1-(methoxymethyl)-4-phenyl-pyrrole-2-carboxylate |

Reference Example 82

Diethyl 5-(2-methoxyethyl)-1-methyl-3-phenyl-pyrrole-2,4-dicarboxylate

Potassium t-butoxide (0.51 g, 4.62 mmol) was added to a solution of diethyl 5-(2-methoxyethyl)-3-phenyl-1H-pyrrol-2,4-dicarboxylate (0.8 g, 2.31 mmol) in dry dimethylsulfoxide (15 mL) and stirred for 30 min at ambient temperature. To the reaction mixture was added methyl iodide (0.49 g, 3.47 mmol) and the reaction was stirred for a further 1 h. Saturated aqueous ammonium chloride was added and the mixture extracted with ethyl acetate. The organic layer was washed with brine, dried over anhydrous sodium sulfate and concentrated in vacuo to afford diethyl 542-methoxyethyl)-1-methyl-3-phenyl-pyrrole-2,4-dicarboxylate (0.6 g, 72%) as a solid.

Reference Example 83

1,2-Bis(methoxymethyl)-4-phenyl-pyrrole

Sodium hydride (400 mg 1.83 mmol, 60%) was added to a solution of (1-methoxymethyl-4-phenyl-1H-pyrrol-2-yl)-methanol (420 mg, 2.08 mmol) in tetrahydrofuran (15 mL) at 0° C. and stirred for a further 15 min. Methyl iodide (517 mg, 3.66 mmol) was added and the reaction mixture stirred for 12 h. The mixture was poured into saturated aqueous ammonium chloride and extracted with ethyl acetate (2×50 mL). The combined organic layers were washed with brine, dried over anhydrous sodium sulfate and concentrated in vacuo to afford 1,2-bis(methoxymethyl)-4-phenyl-pyrrole (300 mg, 72%) as a brown liquid.

Reference Examples 84 to 85

The compounds set out below were prepared in a manner analogous to Reference Example 83:

| Reference Example | Compound |
|---|---|
| 84 | 1-(3-Ethoxypropyl)-2-methyl-4-phenyl-pyrrole |
| 85 | 2-Methyl-4-phenyl-1-(2-propoxyethyl)pyrrole |

Reference Example 86

3-(2-Thienyl)prop-2-enoic acid

Piperidine (2.45 g, 0.056 mol) was added drop wise over a period of 10 min to a stirred solution of thiophene-2-carbaldehyde (4.00 g, 0.036 mol) and malonic acid (1.00 g, 0.18 mol) in pyridine (40 mL) at 0° C. and the resulting reaction mixture was refluxed for 2 h. The reaction mixture was poured into 2N HCl (100 mL) and the precipitated solid filtered. The aqueous layer was extracted with ethyl acetate and the organic layer was washed with brine solution, dried over anhydrous sodium sulphate and concentrated under reduced pressure to afford 3-(2-thienyl)prop-2-enoic acid (5.00 g, 92%) as a solid.

Reference Examples 87 to 89

The compounds set out below were prepared in a manner analogous to Reference Example 86:

| Reference Example | Compound |
|---|---|
| 87 | 5-Methylhex-2-enoic acid |
| 88 | 3-(3-Thienyl)prop-2-enoic acid |
| 89 | 4-Methylpent-2-enoic acid |

Reference Example 90

Ethyl (3-(2-thienyl)prop-2-enoate

A mixture of 3-(2-thienyl)prop-2-enoic acid (4.00 g, 25.94 mmol), thionyl chloride (6.20 mL, 77.90 mmol) and ethanol (45 mL) were refluxed for 3 h. Excess ethanol was removed in vacuo, then chloroform was added to the residue. The organic phase was washed with saturated sodium bicarbonate solution, water, brine and dried over anhydrous sodium sulfate. The organics were concentrated under reduced pressure to give the crude compound which was purified by column chromatography over silica gel (100-200 mesh) using 5% ethyl acetate in pet ether as eluent to afford ethyl (3-(2-thienyl)prop-2-enoate (2.70 g, 57%) as an oil.

Reference Examples 91 to 96

The compounds set out below were prepared in a manner analogous to Reference Example 90:

| Reference Example | Compound |
| --- | --- |
| 91 | Ethyl 5-methylhex-2-enoate |
| 92 | Ethyl 2-(2-methyl-4-phenyl-pyrrol-1-yl)acetate |
| 93 | Ethyl 3-(3-thienyl)prop-2-enoate |
| 94 | Methyl 2-(3-phenylpyrrol-1-yl)acetate |
| 95 | Methyl 2-[3-(2-thienyl)pyrrol-1-yl]acetate |
| 96 | Methyl 4-methylpent-2-enoate |

Reference Example 97

Ethyl 4-(2-thienyl)-1H-pyrrole-3-carboxylate

A solution of ethyl (3-(2-thienyl)prop-2-enoate (2.50 g, 13.70 mmol) and toluenesulfonylmethyl isocyanide (2.90 g, 14.90 mmol) in dimethylsulfoxide:diethyl ether (12.50 mL:20 mL) was added drop wise over a period of 15 min to a stirred solution of 60% sodium hydride in mineral oil (760 mg, 18.30 mmol) in diethyl ether (20 mL) at 10° C. Stirring was continued for 3 h at room temperature and the reaction mixture was quenched with saturated ammonium chloride solution and extracted with diethyl ether. The organic layer was washed with brine, dried over anhydrous sodium sulfate and concentrated under reduced pressure to give crude compound which was purified by column chromatography over silica gel (100-200 mesh) using 18% ethyl acetate in pet ether as eluent to afford 4-thiophene-2-yl-1H-pyrrole-3-carboxylic acid ethyl ester (100 mg, 42%) as a solid.

Reference Examples 98 to 100

The compounds set out below were prepared in a manner analogous to Reference Example 97:

| Reference Example | Compound |
| --- | --- |
| 98 | Ethyl 4-isobutyl-1H-pyrrole-3-carboxylate |
| 99 | Ethyl 4-(3-thienyl)-1H-pyrrole-3-carboxylate |
| 100 | Ethyl 4-isopropyl-1H-pyrrole-3-carboxylate |

Reference Example 101

Diethyl 3-(2-methoxyethyl)-5-methyl-1-phenyl-pyrrole-2,4-dicarboxylate

A mixture of diethyl 3-(2-methoxyethyl)-5-methyl-1H-pyrrole-2,4-dicarboxylate (100 mg, 0.35 mmol), phenyl boronic acid (130 mg, 1.06 mmol), copper acetate (130 mg, 0.71 mmol), dry pyridine (110 mg, 1.40 mmol), molecular sieves (400 mg) and dichloromethane (10 mL) was purged with argon gas for 30 min and stirred overnight. The mixture was filtered through a celite bed, washed with dichloromethane (15 mL) and concentrated under reduced pressure. The crude compound was purified by column chromatography over silica gel (100-200 mesh) using 20% ethyl acetate/pet ether as eluent to afford diethyl 3-(2-methoxyethyl)-5-methyl-1-phenyl-pyrrole-2,4-dicarboxylate (50 mg, 40%) as a colourless oil.

Reference Example 102

Ethyl 3-cyclobutylprop-2-enoate

A mixture of cyclobutyl-methanol (8.00 g, 93.02 mmol), ethoxycarbonylmethylene triphenylphosphorane (19.42 g, 55.81 mmol) and pyridine (3 mL) were dissolved in dry chloroform (100 mL) and heated at 70° C. Manganese dioxide (97.11 g, 1.12 mol) was added portion wise over a period of 5 h (with 1 h gap between each addition) and refluxing was continued for 20 h. The reaction mixture was cooled to room temperature, filtered over celite and washed with chloroform. The filtrate was concentrated and the residue subjected to column chromatography over silica gel (60-120 mesh) using 0% to 15% of ethyl acetate in pet ether as eluent to afford ethyl 3-cyclobutylprop-2-enoate (2.10 g, 15%) as a liquid.

Reference Example 103

Ethyl 4-cyclobutyl-1H-pyrrole-3-carboxylate

Toluenesulfonylmethyl isocyanide (3.04 g, 15.59 mmol) was added to the stirred solution of ethyl 3-cyclobutylprop-2-enoate (2.00 g, 12.99 mmol) in a mixture of dimethylsulfoxide (2 mL) and diethyl ether (30 mL) and stirred for 45 min. The resulting mixture was added to a slurry of sodium hydride (675 mg, 38.14 mmol, 60% in mineral oil) in diethyl ether (10 mL) over a period of 30 min then stirred for a further 1 h. The reaction mixture was quenched with saturated ammonium chloride solution, the organics were separated and the aqueous layer was extracted with diethyl ether (4×10 mL). The combined organic layer was washed with water, brine, dried over anhydrous sodium sulphate, filtered and concentrated. The residue was subjected to column chromatography over silica gel (100-200 mesh) using 0% to 15% of ethyl acetate in pet-ether as eluent, concentrated and dried under reduced pressure to afford ethyl 4-cyclobutyl-1H-pyrrole-3-carboxylate (1.70 g, 67%) as a liquid.

Reference Example 104

1,5-Dimethyl-3-phenyl-pyrrole-2,4-dicarboxylic acid

A solution of sodium hydroxide (101 g, 2.53 mol) in water (340 mL) was added to a solution of diethyl 1,5-dimethyl-3-phenyl-pyrrole-2,4-dicarboxylate (80 g, 0.25 mol) in ethanol (340 mL) and heated at reflux for 15 h. Ethanol was removed under reduced pressure and the residue diluted with water (200 mL) and chilled to 0° C. Concentrated hydrochloric acid (~150 mL) was slowly added to adjust pH to ~2, while maintaining temperature below 10° C. and the mixture was stirred for 30 min. The precipitated solid was filtered, washed with water (100 mL) and petroleum ether (200 mL) and dried under vacuum at 60° C. to afford 1,5-dimethyl-3-phenyl-pyrrole-2,4-dicarboxylic acid (60 g, 91%) as a white solid.

Reference Examples 105 to 145

The compounds set out below were prepared in a manner analogous to Reference Example 104:

| Reference Example | Compound |
| --- | --- |
| 105 | 3-(2-Furyl)-1,5-dimethyl-pyrrole-2,4-dicarboxylic acid |
| 106 | 1,5-Dimethyl-3-(2-thienyl)pyrrole-2,4-dicarboxylic acid |

-continued

| Reference Example | Compound |
|---|---|
| 107 | 3-Isopropyl-1,5-dimethyl-pyrrole-2,4-dicarboxylic acid |
| 108 | 1,5-Dimethyl-3-tetrahydropyran-4-yl-pyrrole-2,4-dicarboxylic acid |
| 109 | 1,4-Dimethyl-3-phenyl-pyrrole-2-carboxylic acid |
| 110 | 5-Isopropyl-1-methyl-3-phenyl-pyrrole-2,4-dicarboxylic acid |
| 111 | 3-Isopropyl-1-(2-methoxyethyl)-5-methyl-pyrrole-2,4-dicarboxylic acid |
| 112 | 1-(2-Ethoxyethyl)-5-methyl-3-phenyl-pyrrole-2,4-dicarboxylic acid |
| 113 | 1-(3-Methoxypropyl)-5-methyl-3-phenyl-pyrrole-2,4-dicarboxylic acid |
| 114 | 1-Ethyl-5-methyl-3-phenyl-pyrrole-2,4-dicarboxylic acid |
| 115 | 5-Methyl-3-phenyl-1-propyl-pyrrole-2,4-dicarboxylic acid |
| 116 | 1-Butyl-5-methyl-3-phenyl-pyrrole-2,4-dicarboxylic acid |
| 117 | 1-Methyl-4-phenyl-pyrrole-2-carboxylic acid |
| 118 | 1-Benzyl-5-methyl-3-phenyl-pyrrole-2,4-dicarboxylic acid |
| 119 | 5-Methyl-3-phenyl-1H-pyrrole-2,4-dicarboxylic acid |
| 120 | 5-Ethyl-1-methyl-3-phenyl-pyrrole-2,4-dicarboxylic acid |
| 121 | 5-Ethyl-1-(2-methoxyethyl)-3-phenyl-pyrrole-2,4-dicarboxylic acid |
| 122 | 4-(2-Chlorophenyl)-1-(2-methoxyethyl)pyrrole-2-carboxylic acid |
| 123 | 4-Isobutyl-1-(2-methoxyethyl)pyrrole-3-carboxylic acid |
| 124 | 4-(3-Chlorophenyl)-1-(2-methoxyethyl)pyrrole-2-carboxylic acid |
| 125 | 5-Isopropyl-1-(2-methoxyethyl)-3-phenyl-pyrrole-2,4-dicarboxylic acid |
| 126 | 3-(2-Methoxyethyl)-5-methyl-1-phenyl-pyrrole-2,4-dicarboxylic acid |
| 127 | 4-Isopropyl-1H-pyrrole-3-carboxylic acid |
| 128 | 4-Isobutyl-1H-pyrrole-3-carboxylic acid |
| 129 | 5-methyl-3-phenyl-1-(2-pyridylmethyl)pyrrole-2,4-dicarboxylic acid |
| 130 | 5-Methyl-3-phenyl-1-(4-pyridylmethyl)pyrrole-2,4-dicarboxylic acid |
| 131 | 4-Cyclobutyl-1H-pyrrole-3-carboxylic acid |
| 132 | 1-Methyl-3-phenyl-5-propyl-pyrrole-2,4-dicarboxylic acid |
| 133 | 5-Ethyl-1-(methoxymethyl)-3-phenyl-pyrrole-2,4-dicarboxylic acid |
| 134 | 5-(2-methoxyethyl)-1-methyl-3-phenyl-pyrrole-2,4-dicarboxylic acid |
| 135 | 1-(Ethoxymethyl)-5-methyl-3-phenyl-pyrrole-2,4-dicarboxylic acid |
| 136 | 5-Methyl-1-(2-methylsulfanylethyl)-3-phenyl-pyrrole-2,4-dicarboxylic acid |
| 137 | 1-(3-Hydroxypropyl)-5-methyl-3-phenyl-pyrrole-2,4-dicarboxylic acid |
| 138 | 5-Methyl-1-(methylsulfanylmethyl)-3-phenyl-pyrrole-2,4-dicarboxylic acid |
| 139 | 1-(2-Methoxyethoxymethyl)-5-methyl-3-phenyl-pyrrole-2,4-dicarboxylic acid |
| 140 | 5-Methyl-3-phenyl-1-(propoxymethyl)pyrrole-2,4-dicarboxylic acid |
| 141 | 1-(2-Methoxyethyl)-5-methyl-3-phenyl-pyrrole-2,4-dicarboxylic acid |
| 142 | 5-Methyl-1-(2-phenoxyethyl)-3-phenyl-pyrrole-2,4-dicarboxylic acid |
| 143 | 1-(4-methoxybut-2-enyl)-5-methyl-3-phenyl-pyrrole-2,4-dicarboxylic acid |
| 144 | 5-Methyl-1-[(2-methyloxazol-4-yl)methyl]-3-phenyl-pyrrole-2,4-dicarboxylic acid |
| 145 | 1-(Butoxymethyl)-5-methyl-3-phenyl-pyrrole-2,4-dicarboxylic acid |

Reference Example 146

4-Phenyl-1H-pyrrole-2-carboxylic acid

A mixture of ethyl 4-phenyl-1H-pyrrole-2-carboxylate (700 mg, 3.25 mmol), aqueous sodium hydroxide (10% w/v, 10 mL) and ethanol (10 mL) were stirred at room temperature over night. The ethanol was evaporated in vacuo, then water (20 mL) was added and the organics were extracted with ethyl acetate (3×20 mL). The aqueous layer was acidified with 2N HCl (to pH 3) and extracted with ethyl acetate (3×20 mL). The combined organic layer was washed with water, brine (20 mL), dried over anhydrous sodium sulphate and concentrated under reduced pressure to afford 4-phenyl-1H-pyrrole-2-carboxylic acid (400 mg, 66%) as a solid.

Reference Examples 147 to 150

The compounds set out below were prepared in a manner analogous to Reference Example 146:

| Reference Example | Compound |
|---|---|
| 147 | 1-(2-Methoxyethyl)-4-phenyl-pyrrole-2-carboxylic acid |
| 148 | 1-(Methoxymethyl)-4-phenyl-pyrrole-2-carboxylic acid |
| 149 | 4-(2-Thienyl)-1H-pyrrole-3-carboxylic acid |
| 150 | 4-(3-Thienyl)-1H-pyrrole-3-carboxylic acid |

Reference Example 151 & 152

Dimethyl 1-(3-methoxypropyl)-5-methyl-3-phenyl-pyrrole-2,4-dicarboxylate (151) & 4-methoxycarbonyl-1-(3-methoxypropyl)-5-methyl-3-phenyl-pyrrole-2-carboxylic acid (152)

Sodium methoxide (190 mg, 3.50 mmol) was added to a solution of diethyl 1-(3-chloropropyl)-5-methyl-3-phenyl-pyrrole-2,4-dicarboxylate (1.1 g, 2.91 mmol) in methanol (10 mL) and stirred at reflux for 28 h. The reaction mixture was cooled to room temperature and concentrated to dryness. The residue was dissolved in water and the aqueous layer was extracted with dichloromethane. The organic layer was washed with water, brine, dried over anhydrous sodium sulphate and concentrated in vacuo to afford dimethyl 1-(3-methoxypropyl)-5-methyl-3-phenyl-pyrrole-2,4-dicarboxylate (330 mg, 33%) as a yellow oil. The aqueous layer was acidified with 2N hydrochloric acid to pH 2 and extracted with ethyl acetate. The combined organic layer was washed with water, brine, dried over anhydrous sodium sulphate and concentrated to afford 4-methoxycarbonyl-1-(3-methoxypropyl)-5-methyl-3-phenyl-pyrrole-2-carboxylic acid (170 mg, 18%) as a pink oil.

Reference Example 153

The compound set out below was prepared in a manner analogous to Reference Example 151 & 152:

| Reference Example | Compound |
|---|---|
| 153 | Diethyl 1-(4-methoxybut-2-enyl)-5-methyl-3-phenyl-pyrrole-2,4-dicarboxylate |

Reference Example 154

Ethyl 4-bromo-5-methyl-3-phenyl-1H-pyrrole-2-carboxylate

N-Bromo succinimide (1.40 g, 7.87 mmol) was added to a solution of ethyl 5-methyl-3-phenyl-1H-pyrrole-2-carboxylate (1.5 g, 6.55 mmol) in a mixture of dioxane (10 mL) and acetic acid (20 mL) at 0° C. The reaction mixture was stirred at 0° C. for 15 min. The reaction mixture was warmed to room temperature and stirred for another 15 min. The mixture was quenched with 2N NaOH solution and the organic layer was separated, washed with water, brine solution, dried over anhydrous sodium sulfate and concentrated under reduced pressure to give ethyl 4-bromo-5-methyl-3-phenyl-1H-pyrrole-2-carboxylate (1.68 g, 84%) as a solid.

Reference Example 155

Ethyl 4-bromo-1,5-dimethyl-3-phenyl-pyrrole-2-carboxylate

60% Sodium hydride (320 mg, 8.03 mmol) in mineral oil was added to a solution of 4-bromo-5-methyl-3-phenyl-1H-pyrrole-2-carboxylate (1.65 g, 5.36 mmol) in tetrahydrofuran (20 mL) at 0° C. The reaction mixture was stirred at 0° C. for 15 min and then the methyl iodide (0.66 mL, 10.72 mmol) was added at 0° C. and then the reaction mixture was allowed to warm to room temperature overnight. The reaction mixture was quenched with ice and the solvent was evaporated. The organics were extracted with ethyl acetate and the organic layer was washed with water, brine and dried over anhydrous sodium sulfate. The ethyl acetate layer was concentrated under reduced pressure to afford ethyl 4-bromo-1,5-dimethyl-3-phenyl-pyrrole-2-carboxylate (1.68 g, 98%) as a liquid.

Reference Example 156

4-Bromo-1,5-dimethyl-3-phenyl-pyrrole-2-carboxylic acid

A solution of potassium hydroxide (1.40 g, 25.0 mmol) in water (3 mL) was added to a solution of ethyl 4-bromo-1,5-dimethyl-3-phenyl-pyrrole-2-carboxylate (1.60 g, 4.97 mmol) in ethanol (5 mL) and the reaction mixture was refluxed overnight. The solvent was evaporated and the residue was washed with diethyl ether. The resultant filter cake was acidified with diluted HCl and extracted with ether. The organic layer was washed with water, brine, dried over anhydrous sodium sulfate and concentrated under reduced pressure to give 4-bromo-1,5-dimethyl-3-phenyl-pyrrole-2-carboxylic acid (1.0 g, 69%) as a solid.

Reference Examples 157

The compound set out below was prepared in a manner analogous to Reference Example 156:

| Reference Example | Compound |
|---|---|
| 157 | 4-Bromo-5-methyl-3-phenyl-1H-pyrrole-2-carboxylic acid |

Reference Example 158

1,2-Dimethyl-4-phenyl-pyrrole

A suspension of 1,5-dimethyl-3-phenyl-pyrrole-2,4-dicarboxylic acid (60 g, 0.23 mol) and 2-aminoethanol (300 mL) was heated to 175° C. under a nitrogen atmosphere for 30 min. The mixture was allowed to cool to room temperature, diluted with water (100 mL) and extracted with ethyl acetate (2×100 mL). The combined organic layers were washed successively with water (3×100 mL) and brine (2×100 mL), dried over anhydrous sodium sulfate and concentrated in vacuo at a temperature below 40° C. to afford the crude product. Flash column chromatography over neutral alumina using 5% ethyl acetate in petroleum ether as eluent afforded 1,2-dimethyl-4-phenyl-pyrrole (30.5 g, 78%) as a white solid.

Reference Examples 159 to 207

The compounds set out below were prepared in a manner analogous to Reference Example 158:

| Reference Example | Compound |
|---|---|
| 159 | 4-(2-Furyl)-1,2-dimethyl-pyrrole |
| 160 | 1,2-Dimethyl-4-(2-thienyl)pyrrole |
| 161 | 4-Isopropyl-1,2-dimethyl-pyrrole |
| 162 | 1,2-Dimethyl-4-tetrahydropyran-4-yl-pyrrole |
| 163 | 1,3-Dimethyl-4-phenyl-pyrrole |
| 164 | 2-Isopropyl-1-methyl-4-phenyl-pyrrole |
| 165 | 4-Isopropyl-1-(2-methoxyethyl)-2-methyl-pyrrole |
| 166 | 1-(2-Ethoxyethyl)-2-methyl-4-phenyl-pyrrole |
| 167 | 1-(3-Methoxypropyl)-2-methyl-4-phenyl-pyrrole |
| 168 | 1-Ethyl-2-methyl-4-phenyl-pyrrole |
| 169 | 2-Methyl-4-phenyl-1-propyl-pyrrole |
| 170 | 1-Butyl-2-methyl-4-phenyl-pyrrole |
| 171 | 3-Phenyl-1H-pyrrole |
| 172 | 1-Methyl-3-phenyl-pyrrole |
| 173 | 1-(2-Methoxyethyl)-3-phenyl-pyrrole |
| 174 | 1-Benzyl-2-methyl-4-phenyl-pyrrole |
| 175 | 2-Methyl-4-phenyl-1H-pyrrole |
| 176 | 2-Ethyl-1-methyl-4-phenyl-pyrrole |
| 177 | 2-Ethyl-1-(2-methoxyethyl)-4-phenyl-pyrrole |
| 178 | 3-(2-Chlorophenyl)-1-(2-methoxyethyl)pyrrole |
| 179 | 3-(4-Chlorophenyl)-1-(2-methoxyethyl)pyrrole |
| 180 | 1-(Methoxymethyl)-3-phenyl-pyrrole |
| 181 | 3-(2-Thienyl)-1H-pyrrole |
| 182 | 3-Isobutyl-1-(2-methoxyethyl)pyrrole |
| 183 | 3-(3-Chlorophenyl)-1-(2-methoxyethyl)pyrrole |
| 184 | 3-(3-Thienyl)-1H-pyrrole |
| 185 | 2-Isopropyl-1-(2-methoxyethyl)-4-phenyl-pyrrole |
| 186 | 4-(2-Methoxyethyl)-2-methyl-1-phenyl-pyrrole |
| 187 | 3-Isopropyl-1H-pyrrole |
| 188 | 3-Isobutyl-1H-pyrrole |
| 189 | 3-Bromo-1,2-dimethyl-4-phenyl-pyrrole |
| 190 | 2-[(2-Methyl-4-phenyl-pyrrol-1-yl)methyl]pyridine |
| 191 | 3-Bromo-2-methyl-4-phenyl-1H-pyrrole |
| 192 | 4-[(2-Methyl-4-phenyl-pyrrol-1-yl)methyl]pyridine |
| 193 | 3-Cyclobutyl-1H-pyrrole |
| 194 | 1-Methyl-4-phenyl-2-propyl-pyrrole |
| 195 | 2-Ethyl-1-(methoxymethyl)-4-phenyl-pyrrole |
| 196 | 2-(2-Methoxyethyl)-1-methyl-4-phenyl-pyrrole |
| 197 | 1-(Ethoxymethyl)-2-methyl-4-phenyl-pyrrole |
| 198 | 2-Methyl-1-(2-methylsulfanylethyl)-4-phenyl-pyrrole |
| 199 | 3-(2-Methyl-4-phenyl-pyrrol-1-yl)-propan-1-ol |
| 200 | 2-Methyl-1-(methylsulfanylmethyl)-4-phenyl-pyrrole |
| 201 | 1-(2-Methoxyethoxymethyl)-2-Methyl)-4-phenyl-pyrrole |
| 202 | 2-Methyl-4-phenyl-1-(propoxymethyl)pyrrole |
| 203 | 1-(2-Methoxyethyl)-2-methyl-4-phenyl-pyrrole |
| 204 | 2-Methyl-1-(2-phenoxyethyl)-4-phenyl-pyrrole |
| 205 | 1-(4-Methoxybut-2-enyl)-2-methyl-4-phenyl-pyrrole |
| 206 | 2-Methyl-4-[(2-methyl-4-phenyl-pyrrol-1-yl)methyl]oxazole |
| 207 | 1-(Butoxymethyl)-2-methyl-4-phenyl-pyrrole |

Reference Examples 208 and 209

2-Phenyl-5,6,7,8-tetrahydropyrrolo[1,2-a]azepin-9-one (208) & 1-Phenyl-5,6,7,8-tetrahydropyrrolo[1,2-a]azepin-9-one (209)

Dry hydrogen chloride gas was bubbled into a stirred solution of 5-(3-phenyl-pyrrol-1-yl)pentanenitrile (1.45 g, 6.47 mmol) in dry diethyl ether (50 mL) and boron trifluoride etherate (2 mL) at −5 to 0° C. When the mixture became saturated with the hydrogen chloride gas, it was allowed to stand for 24 h. Excess diethyl ether was removed in vacuo and the residue hydrolyzed by adding dilute ammonium hydroxide (20 mL) and chloroform (30 mL). The reaction mixture was refluxed for 12 h and the chloroform layer separated. The chloroform layer was dried over anhydrous sodium sulphate and concentrated under reduced pressure to afford a mixture of 2-phenyl-5,6,7,8-tetrahydro-pyrrolo[1,2-a]azepin-9-one & 1-phenyl-5,6,7,8-tetrahydro-pyrrolo[1,2-a]azepin-9-one (1.50 g, 99%) as a gummy solid.

Reference Example 210 and 211

2-Phenyl-6,7,8,9-tetrahydro-5H-pyrrololo[1,2-a]azepine (210) & 1-phenyl-6,7,8,9-tetrahydro-5H-pyrrolo[1,2-a]azepine (211)

80% Hydrazine hydrate (0.56 mL, 9.0 mmol) was added in one portion to a stirred solution of 2-phenyl-5,6,7,8-tetrahydro-pyrrolo[1,2-a]azepin-9-one & 1-phenyl-5,6,7,8-tetrahydro-pyrrolo[1,2-a]azepin-9-one (50 mg, 2.22 mmol) and potassium hydroxide (500 mg, 8.90 mmol) in diethylene glycol (6 mL) and heated at 160-165° C. for 16 h. The reaction mixture was cooled, poured into ice-water (20 mL) and extracted with diethyl ether (3×20 mL). The combined organic layer was washed with brine (20 mL), dried over anhydrous sodium sulphate, concentrated under reduced pressure to give the crude compound which was purified by column chromatography over neutral alumina using 20% ethyl acetate in petroleum ether as eluent to afford a mixture of 2-phenyl-6,7,8,9-tetrahydro-5H-pyrrolo[1,2-a]azepine & 1-phenyl-6,7,8,9-tetrahydro-5H-pyrrolo[1,2-a]azepine (170 mg, 36%) as an oil.

Reference Example 212

(3-Dimethylamino-2-phenyl-prop-2-enylidene)-dimethyl-ammonium perchlorate

Phosphorus oxychloride (6.8 g, 44.4 mmol) was added to anhydrous dimethylformamide (16 g, 220 mmol) over a period of 15 min at 0-5° C., then warmed to room temperature and stirred for 1 h. Phenylacetic acid (2.0 g, 14.7 mmol) was added and the reaction mixture stirred at 90-100° C. for 16 h. The reaction mixture was quenched by pouring into ice water with vigorous stirring. A solution of 70% perchloric acid (1.88 mL, 2.2 g, 22.0 mmol) in water (5 mL) was added drop-wise with vigorous stirring. A solid precipitated which was filtered, washed with ice cold water and dried in vacuo to afford (3-dimethylamino-2-phenyl-prop-2-enylidene)-dimethyl-ammonium perchlorate (2.0 g, 66%) as a brown solid.

Reference Examples 213 to 215

The compounds set out below were prepared in a manner analogous to Reference Example 212:

| Reference Example | Compound |
| --- | --- |
| 213 | [2-(2-Chlorophenyl)-3-dimethylamino-prop-2-enylidene]-dimethyl-ammonium perchlorate |
| 214 | [2-(4-Chlorophenyl)-3-dimethylamino-prop-2-enylidene]-dimethyl-ammonium perchlorate |
| 215 | [2-(3-Chlorophenyl)-3-dimethylamino-prop-2-enylidene]-dimethyl-ammonium; oxalate |

Reference Example 216

Ethyl 4-phenyl-1H-pyrrole-2-carboxylate

Sodium metal (900 mg, 41.0 mmol) was added to dry ethanol (150 mL) and allowed to dissolve over 30 min. Glycine methyl ester hydrochloride (3.2 g, 25.0 mmol) and (3-dimethylamino-2-phenyl-prop-2-enylidene)-dimethyl-ammonium perchlorate (5.0 g, 16.0 mmol) were added successively and the reaction mixture heated at reflux for 16 h. Ethanol was evaporated in vacuo, the residue diluted with water and extracted with chloroform. The organic layer was washed with water, brine, dried over anhydrous sodium sulfate, filtered and concentrated in vacuo. The crude product obtained was purified by column chromatography over neutral alumina using 10% ethyl acetate in petroleum ether as eluent to afford ethyl 4-phenyl-1H-pyrrole-2-carboxylate (2.0 g, 57%) as a solid.

Reference Examples 217 to 219

The compounds set out below were prepared in a manner analogous to Reference Example 219:

| Reference Example | Compound |
| --- | --- |
| 217 | Ethyl 4-(2-chlorophenyl)-1H-pyrrole-2-carboxylate |
| 218 | Ethyl 4-(4-chlorophenyl)-1H-pyrrole-2-carboxylate |
| 219 | Ethyl 4-(3-chlorophenyl)-1H-pyrrole-2-carboxylate |

Reference Example 220

Ethyl 1-(3-ethoxy-3-oxo-propyl)-4-phenyl-pyrrole-2-carboxylate

Potassium tert-butoxide (100 mg, 0.90 mmol), ethyl 4-phenyl-1H-pyrrole-2-carboxylate (1.0 g, 4.65 mmol) and ethyl acrylate (50 mL) were heated at reflux for 90 min. The reaction mixture was allowed to cool to room temperature and neutralized with acetic acid (1 mL). Excess ethyl acrylate was evaporated in vacuo, the residue diluted with water and extracted with chloroform. The organic layer was dried over anhydrous sodium sulfate, filtered and concentrated in vacuo to give the crude compound. Purification by column chromatography over neutral alumina using 5% ethyl acetate in petroleum ether as eluent gave ethyl 1-(3-ethoxy-3-oxo-propyl)-4-phenyl-pyrrole-2-carboxylate (1.0 g, 69%) as an oil.

Reference Example 221

Diethyl 1-(ethoxymethyl)-5-methyl-3-phenyl-pyrrole-2,4-dicarboxylate

Potassium tert-butoxide (557 mg, 4.97 mmol) was added to a stirred solution of diethyl 5-methyl-3-phenyl-1H-pyrrole-2,4-dicarboxylate (600 mg, 1.99 mmol) in dimethylsulfoxide (15 mL) at 10° C. and stirred at ambient temperature for 1 h. Upon cooling to 10° C., chloromethyl ethyl ether (377 mg, 3.99 mmol) was added and stirred at ambient temperature for 12 h. The mixture was poured onto ice-water and extracted with diethyl ether (5×10 mL). The combined organic layers were washed with water, brine, dried over anhydrous sodium sulphate and filtered. The filtrate was concentrated in vacuo and subjected to column chromatography over silica gel (100-200 mesh) using 8% ethyl acetate in petroleum ether as eluent to afford diethyl 1-(ethoxymethyl)-5-methyl-3-phenyl-pyrrole-2,4-dicarboxylate (400 mg, 56%) as a liquid.

Reference Examples 222 to 227

The compounds set out below were prepared in a manner analogous to Reference Example 221:

| Reference Example | Compound |
|---|---|
| 222 | Diethyl 1-(2-methoxyethoxymethyl)-5-methyl-3-phenyl-pyrrole-2,4-dicarboxylate |
| 223 | Diethyl 5-methyl-3-phenyl-1-(propoxymethyl)pyrrole-2,4-dicarboxylate |
| 224 | Diethyl 1-(4-chlorobut-2-enyl)-5-methyl-3-phenyl-pyrrole-2,4-dicarboxylate |
| 225 | 1-(4-Methoxybutyl)-2-methyl-4-phenyl-pyrrole |
| 226 | Diethyl 5-methyl-1-[(2-methyloxazol-4-yl)methyl]-3-phenyl-1H-pyrrole-2,4-dicarboxylate |
| 227 | Diethyl 1-(butoxymethyl)-5-methyl-3-phenyl-pyrrole-2,4-dicarboxylate |

Reference Example 228

Diethyl 1-(3-hydroxypropyl)-5-methyl-3-phenyl-pyrrole-2,4-dicarboxylate

Potassium tert-butoxide (744 mg, 6.64 mmol) was added to a stirred solution of diethyl 5-methyl-3-phenyl-1H-pyrrole-2,4 dicarboxylate (1.00 g, 1.99 mmol) in dimethylsulfoxide (15 mL) at 10° C. and stirred at ambient temperature for 1 h. The mixture was cooled to 10° C., 3-bromo-1-propanol (738 mg, 5.31 mmol) added and stirring continued at ambient temperature for 12 h. The mixture was poured onto ice-water and extracted with diethyl ether (5×10 mL). The combined organic layers were washed with water, brine, dried over anhydrous sodium sulphate and filtered. The filtrate was concentrated in vacuo and subjected to column chromatography over silica gel (100-200 mesh) using 40% of ethyl acetate in petroleum ether as eluent to afford of diethyl 1-(3-hydroxypropyl)-5-methyl-3-phenyl-pyrrole-2,4-dicarboxylate (600 mg, 50%) as a liquid.

Reference Example 229

1-(2-Carboxyethyl)-4-phenyl-pyrrole-2-carboxylic acid

10% Aqueous sodium hydroxide solution (20 mL) was added to a stirred solution of ethyl 1-(3-ethoxy-3-oxo-propyl)-4-phenyl-pyrrole-2-carboxylate (2.0 g, 6.35 mmol) in ethanol (20 mL). The reaction mixture was stirred for 2 h at 50-60° C. The ethanol was evaporated in vacuo and then water added to the residue and acidified with 5N HCl to pH 4-5. The precipitated solid was filtered, washed with water and dried in vacuo to afford 1-(2-carboxyethyl)-4-phenyl-pyrrole-2-carboxylic acid (900 mg, 56%) as a solid.

Reference Example 230

6-Phenyl-2,3-dihydropyrrolizin-1-one

Anhydrous sodium acetate (200 mg, 2.5 mmol) was added to a stirred solution of 1-(2-carboxyethyl)-4-phenyl-pyrrole-2-carboxylic acid (1.0 g, 3.90 mmol) in acetic anhydride (10 mL) and heated at reflux for 16 h. Excess acetic anhydride was evaporated in vacuo and water was added. The mixture was extracted with ethyl acetate and the separated organic layer was washed with water, brine, dried over anhydrous sodium sulfate, filtered and concentrated in vacuo to afford the crude product. Purification by column chromatography over neutral alumina using 25% ethyl acetate in petroleum ether as eluent afforded 6-phenyl-2,3-dihydropyrrolizin-1-one (200 mg, 27%) as a brown solid.

Reference Example 231

(4-Phenyl-M-pyrrol-2-yl)methanol

A solution of ethyl 4-phenyl-1H-pyrrole-2-carboxylate (1 g, 5.58 mmol) in tetrahydrofuran (10 mL) was added to a suspension of lithium aluminum hydride (300 mg, 8.10 mmol) in tetrahydrofuran (20 mL) at 0° C. The reaction mixture was slowly warmed to ambient temperature and stirred for 5 h. The mixture was slowly added to saturated sodium sulphate followed by extraction with ethyl acetate (2×25 mL). The combined organic layers were washed with water, brine, dried over anhydrous sodium sulfate and concentrated in vacuo to afford (4-phenyl-1H-pyrrol-2-yl)methanol (800 mg, 84%) as a solid.

Reference Example 232

2-Methyl-1H-pyrrole

Lithium aluminium hydride (899 mg, 23.6 mmol) was added to the solution of 1H-pyrrole-2-carbaldehyde (750 mg, 7.9 mmol) in tetrahydrofuran (10 mL) at 0° C. then the mixture was heated at reflux for 16 h. The mixture was quenched into ice water and extracted with ethyl acetate. The combined organic phases were washed with water, brine, dried over anhydrous sodium sulfate, filtered and concentrated under reduced pressure to obtain a residue which was purified by washing with n-pentane. Drying afforded 2-methyl-1H-pyrrole (500 mg, 77%).

Reference Example 233

4-Iodo-1H-pyrrole-2-carbaldehyde

A solution of 1H-pyrrole-2-carbaldehyde (7.0 g, 73.6 mmol) in tetrahydrofuran (45 mL) was cooled to −75° C. N-iodosuccinimide (19.8 g, 88.3 mmol) was added portion-wise over 20 min and the reaction mixture was then stirred for 2 h at −75° C. Water and petroleum ether were added and the reaction mixture warmed to ambient temperature. The organic layer was separated and the aqueous phase extracted with petroleum ether. The combined organic layers were washed with water, brine, dried over anhydrous sodium sulfate, filtered and concentrated in vacuo to afford 4-iodo-1H-pyrrole-2-carbaldehyde (13.2 g, 81%) as a black solid.

Reference Example 234

Chloro(methoxy)methane

Dry HCl gas was passed through a suspension of paraformaldehyde (30.0 g, 1 mol) in methanol (32.0 g, 1 mol) at 0-5° C. for 6 h. The reaction mixture was filtered and the organic layer in the filtrate was separated and dried over anhydrous calcium chloride for 16 h. The organic layer was distilled using a Vigreux column to afford chloro(methoxy)methane (20 g, 25%) of 90% purity (by Gas Chromatography).

Reference Example 235

Isopropyl 2-chloroacetate

Chloro acetyl chloride (5 g, 0.045 mmol) was added drop wise to isopropanol (2.7 g, 0.045 mmol) at 0° C. The mixture was heated to 80° C. under a nitrogen atmosphere and maintained at this temperature for 3 h. The compound was purified by fractional distillation in vacuo to afford isopropyl 2-chloroacetate (5 g, 84%) as a liquid.

Reference Example 236

Ethyl 2-(2-formyl-4-iodo-pyrrol-1-yl)acetate

Sodium hydride (1.62 g, 60% w/w dispersion in mineral oil, 67.9 mmol) was added to a solution of 4-iodo-1H-pyrrole-2-carbaldehyde (5.0 g, 22.6 mmol) in tetrahydrofuran (30 mL) over 10 min. The reaction mixture was stirred for 15 min, then ethyl bromoacetate (7.56 g, 45.2 mmol) was added and the mixture stirred for 2 h at ambient temperature. The reaction was quenched with methanol and concentrated in vacuo. The crude compound was then extracted into ethyl acetate. The organic layer washed with water, brine, dried over anhydrous sodium sulfate, filtered and concentrated under in vacuo to afford the crude compound. Purification by column chromatography over silica gel (100-200 mesh) using 2% ethyl acetate in petroleum ether afforded ethyl 2-(2-formyl-4-iodo-pyrrol-1-yl)acetate (3.4 g, 49%).

Reference Examples 237 to 240

The compounds set out below were prepared in a manner analogous to Reference Example 236:

| Reference Example | Compound |
|---|---|
| 237 | 1-(Methoxymethyl)-2-methyl-4-phenyl-pyrrole |
| 238 | Methyl 1-(methoxymethyl)-4-phenyl-pyrrole-2-carboxylate |
| 239 | Isopropyl 2-(2-methyl-4-phenyl-pyrrol-1-yl)acetate |
| 240 | tert-Butyl 2-(3-isopropylpyrrol-1-yl)acetate |

Reference Example 241

Ethyl 2-(2-formyl-4-phenyl-pyrrol-1-yl)acetate

A solution of ethyl 2-(2-formyl-4-iodo-pyrrol-1-yl)acetate (3.0 g, 9.77 mmol) in dimethylformamide (25 mL) was purged with argon gas for 10 min. Bis-(triphenylphosphine)-palladium(II) chloride (0.48 g, 0.68 mmol) was added and the mixture was purged with argon gas for 5 min. Anhydrous potassium phosphate (6.18 g, 29.3 mmol) and phenylboronic acid (1.43 g, 11.7 mmol) were added successively and the reaction mixture purged with argon gas for 10 min, then heated to 110° C. and maintained at that temperature for 4 h. The resulting mixture was allowed to cool to ambient temperature and diethyl ether added. The reaction mixture was filtered, the filtrate being washed with water and the separated aqueous phase being further extracted with diethyl ether. The combined organic layers were washed with brine, dried over anhydrous sodium sulfate, filtered and concentrated in vacuo to afford the crude product. Purification by column chromatography over silica gel (100-200 mesh) using 8% ethyl acetate in petroleum ether as eluent afforded ethyl 2-(2-formyl-4-phenyl-pyrrol-1-yl)acetate (680 mg, 27%).

Reference Example 242

2-Methyl-7-phenyl-1,2-dihydropyrrolo[1,2-a]pyrazin-3-one

Acetic acid was added to a solution of methylamine (0.45 mL, 5.30 mmol, 40% in water) in tetrahydrofuran (8 mL) to adjust the pH to 6. A solution of (2-formyl-4-phenyl-pyrrol-1-yl)-acetic acid ethyl ester (680 mg, 2.65 mmol) in tetrahydrofuran (4 mL) was added and the reaction mixture stirred at ambient temperature for 45 min. Sodium cyanoborohydride (0.33 g, 5.30 mmol) was added and the reaction mixture heated at 75 C for 18 h. Concentration in vacuo yielded a residue which was partitioned between water and ethyl acetate. The organic layer was washed with brine, dried over anhydrous sodium sulfate, filtered and concentrated in vacuo to afford the crude product. Purification by column chromatography over silica gel (100-200 mesh) using 30% ethyl acetate in petroleum ether afforded 2-methyl-7-phenyl-1,2-dihydropyrrolo[1,2-a]pyrazin-3-one (180 mg, 30%) as a solid.

Reference Example 243

2-methyl-7-phenyl-3,4-dihydro-1H-pyrrolo[1,2-a]pyrazine

Borane-dimethyl sulfide complex (0.25 mL, 2.6 mmol) was added to cold tetrahydrofuran (6 mL) and stirred for 10 min. 2-Methyl-7-phenyl-1,2-dihydropyrrolo[1,2-a]pyrazin-3-one (180 mg, 0.8 mmol) was added, and the reaction mixture allowed to warm to room temperature and stirred for 3 h. The mixture was poured slowly into saturated ammonium chloride solution and extracted with ethyl acetate. The organic layer was washed with water then brine, dried over anhydrous sodium sulfate, filtered and concentrated in vacuo to give the crude compound. Purification by column chromatography over silica gel (100-200 mesh) using 8% ethyl acetate in petroleum ether afforded 2-methyl-7-phenyl-3,4-dihydro-1H-pyrrolo[1,2-a]pyrazine (110 mg, 64%) as a solid.

Reference Example 244

4-Iodo-1-isopropyl-pyrrole-2-carbaldehyde

Sodium hydride (860 mg, 55% in mineral oil, 19.7 mmol) was added to a solution of 4-iodo-pyrrole-2-carbaldehyde (3.0 g, 13.2 mmol) in dry dimethylformamide at ambient temperature under a nitrogen atmosphere. After stirring for 15 min 2-bromopropane (3.87 mL, 40.9 mmol) was added and the reaction mixture heated at reflux for 16 h. The mixture was allowed to cool to ambient temperature, quenched with water and extracted with diethyl ether. The combined organic layers were washed with water, brine, dried over anhydrous sodium sulfate and concentrated in vacuo to give a crude residue. Purification by column chromatography over silica gel (60-120 mesh) using 2% ethyl acetate in petroleum ether afforded 4-iodo-1-isopropyl-pyrrole-2-carbaldehyde (1.5 g, 43%) as a brown liquid.

Reference Example 245

The compound set out below was prepared in a manner analogous to Reference Example 245.

| Reference Example | Compound |
|---|---|
| 245 | 4-Iodo-1-(2-methoxyethyl-pyrrole-2-carbaldehyde |

Reference Example 246

1-(2-Hydroxyethyl)-4-iodo-pyrrole-2-carbaldehyde

Potassium hydroxide (3.1 g, 54.3 mmol) was added to a stirred solution of 4-iodo-1H-pyrrole-2-carbaldehyde (4.0 g, 18.1 mmol) in dioxane (20 mL). 2-Bromo-ethanol (2.56 mL, 36.2 mmol) was added to the reaction mixture and heated at 60° C. for 16 h. The reaction mixture was cooled to room temperature and the pH was adjusted to ~6 by the addition of acetic acid. The reaction mixture was then concentrated in vacuo to give a residue which was partitioned between water and ethyl acetate. The organic phase was washed with water, brine, dried over anhydrous sodium sulfate and concentrated in vacuo to give a residue which was purified by column chromatography over silica gel (100-200 mesh) using 10% ethyl acetate in petroleum ether as eluent to afford 1-(2-hydroxyethyl)-4-iodo-pyrrole-2-carbaldehyde (2.4 g, 50%) as a colourless solid.

Reference Example 247

2-(2-Formyl-4-iodo-pyrrol-1-yl)ethyl 4-methylbenzenesulfonate

Triethylamine (3.3 mL, 23.8 mmol) was added to a stirred solution of 1-(2-hydroxyethyl)-4-iodo-pyrrole-2-carbaldehyde (2.1 g, 7.92 mmol) in dichloromethane (15 mL). The reaction mixture was chilled to 0° C. and 4-methyl-benzenesulfonyl chloride (1.82 g, 9.51 mmol) was added over 15 min. The reaction mixture was allowed to warm to ambient temperature and stirred overnight. Water was added, the organic phase separated and the aqueous phase extracted with dichloromethane. The combined organic layers were washed with saturated sodium bicarbonate solution, brine, dried over anhydrous sodium sulfate and concentrated in vacuo to give a residue which was purified by washing with petroleum ether to afford 2-(2-formyl-4-iodo-pyrrol-1-yl)ethyl 4-methylbenzenesulfonate (2.4 g, 72%) as a grey solid.

Reference Example 248

2-[2-(Hydroxymethyl)-4-iodo-pyrrol-1-yl]ethyl 4-methylbenzenesulfonate 2-(2-Formyl-4-iodo-pyrrol-1-yl)ethyl 4-methylbenzenesulfonate (2.1 g, 5.01 mmol) in ethanol (25 mL) was cooled to 0° C. and sodium borohydride (95 mg, 2.50 mmol) was added. After 30 min, the reaction mixture was allowed to warm to ambient temperature and stirred for a further 1 h, after which time acetic acid was added and the mixture was concentrated in vacuo. The residue was partitioned between water and dichloromethane and the organic phase was washed with water, brine, dried over anhydrous sodium sulfate and concentrated in vacuo to give 2-[2-(hydroxymethyl)-4-iodo-pyrrol-1-yl]ethyl 4-methylbenzenesulfonate (2.0 g, 95%) as a brownish crystalline solid.

Reference Example 249

7-Iodo-3,4-dihydro-4H-pyrrolo[2,1-c][1,4]oxazine

A solution of 2-[2-(hydroxymethyl)-4-iodo-pyrrol-1-yl] ethyl 4-methylbenzenesulfonate (2.0 g, 4.79 mmol) in tetrahydrofuran (15 mL) was slowly added to a suspension of sodium hydride (120 mg, 60% dispersion in mineral oil; 4.75 mmol) in tetrahydrofuran (5 mL) and stirred at room temperature for 36 h. The reaction was quenched with water and extracted with diethyl ether. The combined organic phases were washed with water, brine, dried over anhydrous sodium sulfate and concentrated under reduced pressure to give a residue which was purified by column chromatography over silica gel using 2% ethyl acetate in petroleum ether to afford 7-iodo-3,4-dihydro-1H-pyrrolo[2,1-c][1,4]oxazine (800 mg, 66%) as a colorless crystalline solid.

Reference Example 250

7-Phenyl-3,4-dihydro-1H-pyrrolo[2,1-c][1,4]oxazine

A solution of 7-iodo-3,4-dihydro-1H-pyrrolo[2,1-c][1,4] oxazine (800 mg, 3.21 mmol) in dimethylformamide (8 mL) was purged with argon gas for 5 min. Caesium carbonate (3.14 g, 9.64 mmol) and phenylboronic acid (590 mg, 4.82 mmol) were added and the vessel was again purged with argon gas for 5 min. Tetrakis(triphenylphosphine)palladium (0) (185 mg, 0.16 mmol) was added, the vessel was purged for a final time with argon gas for 5 min and then the mixture was heated at 75° C. for 3 h. The reaction mixture was allowed to cool to ambient temperature, filtered and then water was added and mixture extracted with diethyl ether. The organic phase was washed with water, brine, dried over anhydrous sodium sulfate and concentrated in vacuo. The crude compound was purified by column chromatography over silica gel (100-200 mesh) using 4% ethyl acetate in petroleum ether to afford 7-phenyl-3,4-dihydro-1H-pyrrolo[2,1-e][1,4]oxazine (90 mg, 14%) as a pale yellow solid.

Reference Examples 251 and 252

The compounds set out below were prepared in a manner analogous to Reference Example 250:

| Reference Example | Compound |
|---|---|
| 251 | 1-Isopropyl-4-phenyl-1H-pyrrole-2-carbaldehyde |
| 252 | 1-(2-Methoxyethyl)-4-phenyl-pyrrole-2-carbaldehyde |

Reference Example 253

1-Phenylpyrrole-2-carbaldehyde

Phosphorus oxychloride (0.7 mL, 7.68 mmol) was added slowly to ice-cold dimethylformamide (0.6 mL, 7.68 mmol). The mixture was warmed to room temperature and stirred for 15 min. A solution of 1-phenylpyrrole (1.0 g, 6.98 mmol) in ethylene dichloride (5 mL) was added and the reaction mixture heated at reflux for 1 h. The mixture was cooled to 10° C. and quenched into 10% sodium acetate solution (20 mL). The organic layer was separated and the aqueous phase was extracted with ether. The combined organic layers were washed with water, brine, dried over anhydrous sodium sulfate, filtered and concentrated under in vacuo to give a crude residue. Purification by column chromatography over silica gel (60-120 mesh) using 2% ethyl acetate in petroleum ether as eluent gave 1-phenylpyrrole-2-carbaldehyde (700 mg, 59%) as a colourless oil.

Reference Example 254

2-Methyl-1-phenyl-pyrrole

A mixture of 1-phenylpyrrole-2-carbaldehyde (700 mg, 4.1 mmol), potassium hydroxide (490 mg, 12.3 mmol) and hydrazine hydrate (0.8 mL, 12.3 mmol) in ethylene glycol (15 mL) was stirred at ambient temperature for 30 min and then slowly heated to 150° C. and maintained for 2 h. The reaction mixture was allowed to cool to ambient temperature, poured into ice-water and extracted with diethyl ether. The organic layer was washed with water, brine, dried over anhydrous sodium sulfate, filtered and concentrated in vacuo to give the crude compound. Purification by column chromatography over silica gel (60-120 mesh) using petroleum ether as eluent to afford 2-methyl-1-phenyl-pyrrole (430 mg, 66%) as a yellow oil.

Reference Examples 255 to 256

The compounds set out below were prepared in a manner analogous to Reference Example 254.

| Reference Example | Compound |
|---|---|
| 255 | 6-Phenyl-2,3-dihydro-1H-pyrrolizine |
| 256 | 1-Isopropyl-2-methyl-4-phenyl-pyrrole |

Reference Example 257

Ethyl 2-methyl-4-phenyl-pyrrole-1-carboxylate n-Butyllithium (0.87 mL, 1.6M solution, 1.40 mmol) was added to a cold (below 0° C.) solution of 2-methyl-4-phenyl-1H-pyrrole (200 mg, 1.27 mmol) in tetrahydrofuran (6 mL) and stirred at below 0° C. for 20 min. Ethyl chloroformate (0.1 mL, 1.02 mmol) was added slowly to the reaction mixture and stirred at 0 to 10° C. for 90 min. The reaction mixture was quenched into saturated ammonium chloride solution and the aqueous layer was extracted with ethyl acetate. The organic layer was washed with saturated sodium bicarbonate solution, brine, dried over anhydrous sodium sulphate and concentrated in vacuo to afford ethyl 2-methyl-4-phenyl-pyrrole-1-carboxylate (250 mg, 86%) as a brown solid.

Reference Examples 258

The compound set out below was prepared in a manner analogous to Reference Example 257.

| Reference Example | Compound |
|---|---|
| 258 | Methyl 2-methyl-4-phenyl-pyrrole-1-carboxylate |

Reference Example 259

3-Fluoro-1,2-dimethyl-4-phenyl-pyrrole n-Butyllithium (2.06 mL, 1.6M solution, 3.30 mmol) was added to a solution of 3-bromo-1,2-dimethyl-4-phenyl-pyrrole (550 mg, 2.20 mmol) in tetrahydrofuran (10 mL) at −78° C. and the reaction mixture was stirred at −78° C. for 30 min. A solution of n-fluorodibenzene sulfonamide (901 mg, 2.86 mmol) in tetrahydrofuran (8 mL) was added to the reaction mixture at −78° C. and the reaction mixture was stirred at this temperature for another 1 h. The reaction mixture was allowed to warm to ambient temperature and stirred for 16 h after which time the reaction mixture was quenched with dilute HCl and evaporated to dryness. The residue was diluted with water and extracted with ethyl acetate. The ethyl acetate layer was washed with water, brine, dried over anhydrous sodium sulfate and concentrated under reduced pressure to give the crude product. Purification by preparative HPLC afforded 3-fluoro-1,2-dimethyl-4-phenyl-pyrrole (160 mg, 39%) as a solid.

Reference Example 260

The compound set out below was prepared in a manner analogous to Reference Example 259.

| Reference Example | Compound |
|---|---|
| 260 | 3-Fluoro-1-(2-methoxyethyl)-2-methyl-4-phenyl-pyrrole |

Reference Example 261

2-(2-Methyl-4-phenyl-pyrrol-1-yl)ethanol

Boron tribromide (0.3 mL, 3.07 mmol) was added drop wise to a solution of 1-(2-methoxyethyl)-2-methyl-4-phenyl-pyrrole (330 mg, 1.53 mmol) in dry dichloromethane (20 mL) at 0 to 5° C. and stirred for 1 h. The reaction mixture was quenched with a 10% sodium bicarbonate solution (20 mL) at 0 to 5° C. and extracted with ethyl acetate (2×25 mL). The organic layer was washed successively with water (2×25 mL), brine (2×25 mL), dried over anhydrous sodium sulphate and concentrated in vacuo to yield 2-(2-methyl-4-phenyl-pyrrol-1-yl)-ethanol (270 mg, 88%) as a brown solid.

Reference Examples 262

The compound set out below was prepared in a manner analogous to Reference Example 261.

| Reference Example | Compound |
|---|---|
| 262 | 2-(3-Phenylpyrrol-1-yl)ethanol |

Reference Example 263

2-(2-methyl-4-phenyl-pyrrol-1-yl)ethyl 4-methylbenzenesulfonate

Triethylamine (2.1 mL, 15.22 mmol) was added to a solution of 2-(2-methyl-4-phenylpyrrol-1-yl)ethanol (1.53 g, 7.61 mmol) in dry dichloromethane (20 mL) at room temperature followed by the addition of p-toluene sulfonyl chloride (1.88 g, 9.89 mmol). The resulting reaction mixture was stirred for 16 h and then diluted with water (30 mL) and extracted with ethyl acetate (2×25 mL). The combined organic layers were washed with water (2×25 mL), brine (2×25 mL), dried over anhydrous sodium sulphate and concentrated in vacuo to yield the crude compound. Purification by column chromatography over silica gel (100-200 mesh) with gradient elution with 10-12% ethyl acetate in petroleum ether as eluent afforded 2-(2-methyl-4-phenyl-pyrrol-1-yl) ethyl 4-methylbenzenesulfonate (1.2 g, 44%) as a brownish white crystalline solid.

Reference Example 264

The compound set out below was prepared in a manner analogous to Reference Example 263

| Reference Example | Compound |
|---|---|
| 264 | 2-Isopropoxyethyl 4-methylbenzenesulfonate |

Reference Example 265

1-(2-Azidoethyl)-2-methyl-4-phenyl-pyrrole

Sodium azide (327 mg, 5.02 mmol) was added to a solution of 2-(2-methyl-4-phenyl-pyrrol-1-yl)ethyl 4-methylbenzenesulfonate (1.19 g, 3.35 mmol) in dry dimethylformamide (10 mL) and heated to 90° C. and stirred for 1 h. The reaction mixture was allowed to cool to ambient temperature and partitioned between water (20 mL) and ethyl acetate (25 mL). After stirring for 5 min, the organic layer was separated and washed successively with water (2×30 mL), brine (2×30 mL), dried over anhydrous sodium sulphate and concentrated in vacuo to yield 1-(2-azidoethyl)-2-methyl-4-phenyl-pyrrole (650 mg, 86%) as a brown liquid.

Reference Example 266

2-(2-Methyl-4-phenyl-pyrrol-1-yl)ethanamine

10% Palladium-carbon (100 mg) was added to a solution of 1-(2-azidoethyl)-2-methyl-4-phenyl-pyrrole (640 mg, 2.96 mmol) in methanol (20 mL) at room temperature and hydrogenated at atmospheric pressure for 27 h. The catalyst was filtered and washed with methanol (20 mL). The combined filtrate and washings were concentrated in vacuo to afford 2-(2-methyl-4-phenyl-pyrrol-1-yl)ethanamine (490 mg, 83%) as a brown syrup.

Reference Example 267

The compound set out below was prepared in a manner analogous to Reference Example 266:

| Reference Example | Compound |
|---|---|
| 267 | 1-Isobutyl-piperazine |

Reference Example 268

2-(2-Methyl-4-phenyl-pyrrol-1-yl)ethyl acetate

Triethylamine (0.5 mL, 3.59 mmol) was added dropwise to a solution of 2-(2-methyl-4-phenyl-pyrrol-1-yl)ethanol (260 mg, 1.29 mmol) in dry dichloromethane (20 mL) at 0 to 5° C. followed by the addition of acetyl chloride (0.2 mL, 2.81 mmol). The reaction mixture was stirred for 30 min and then quenched into ice water (30 mL) and ethyl acetate (20 mL) and stirred for 15 min. The organic layer was separated and washed with water (2×25 mL), brine (2×25 mL), dried over anhydrous sodium sulphate and concentrated in vacuo to afford 2-(2-methyl-4-phenyl-pyrrol-1-yl)ethyl acetate (300 mg, 96%) as a brown liquid.

Reference Examples 269 to 270

The compounds set out below were prepared in a manner analogous to Reference Example 268:

| Reference Example | Compound |
|---|---|
| 269 | N-[2-(2-Methyl-4-phenyl-pyrrol-1-yl)-ethyl]acetamide |
| 270 | 2-(3-Phenyl-pyrrol-1-yl)-ethyl acetate |

Reference Example 271

Ethyl 2-(3-Phenylpyrrol-1-yl)acetate

Glycine ethyl ester hydrochloride (0.44 g, 3.17 mmol), sodium acetate (0.47 g, 5.76 mmol) were dissolved in minimum amount of water (5 mL) and added to glacial acetic acid (5 mL). The mixture was heated to 80° C. and then added to a solution of 2,5-dimethoxy-3-phenyl-tetrahydrofuran (0.6 g, 2.88 mmol) in glacial acetic acid (5 mL). The reaction was stirred at 80° C. for 2 h and then diluted with water and extracted with ethyl acetate. The combined organic layers were washed with copious amount of water, dried over anhydrous sodium sulfate and concentrated in vacuo to afford ethyl 2-(3-phenylpyrrol-1-yl)acetate (0.55 g, 83%).

Reference Example 272

2-(3-Isopropylpyrrol-1-yl)acetic acid

Trifluoroacetic acid (1.20 mL, 15.70 mmol) was added to a solution of tert-butyl 2-(3-isopropyl-pyrrol-1-yl)acetate (350 mg, 1.57 mmol) in dichloromethane at 0° C. and the reaction mixture was stirred at ambient temperature for 16 h. The solvent was evaporated in vacuo and the residue was basified with saturated sodium bicarbonate solution. The solution was washed with diethyl ether and the alkaline solution was then acidified with concentrated aqueous HCl and extracted with diethyl ether. The organic layer was washed with water, brine solution, dried over anhydrous sodium sulfate and concentrated in vacuo to give 2-(3-isopropylpyrrol-1-yl)acetic acid (180 mg, 69%) as a semi-solid.

Reference Examples 273 to 275

The compounds set out below were prepared in a manner analogous to Reference Example 272:

| Reference Example | Compound |
| --- | --- |
| 273 | 2-(3-Isobutyl-pyrrole-1-yl)acetic acid |
| 274 | 2-(3-Cyclobutylpyrrol-1-yl)acetic acid |
| 275 | 1-(2-Methylallyl)piperazine |

Reference Example 276

Methyl 2-(3-Isopropylpyrrol-1-yl)acetate

Potassium carbonate (298 mg, 2.15 mmol) was added to a solution of 2-(3-isopropylpyrrol-1-yl)acetic acid (180 mg, 1.07 mmol) in acetone at 0° C. and the reaction was stirred at 0° C. for 15 min. Methyl iodide (0.13 mL, 2.15 mmol) was added at 0° C. and the mixture refluxed for 16 h. The reaction mixture was concentrated in vacuo and the residue was diluted with water and extracted with diethyl ether. The organic layer was washed with water, brine solution, dried over anhydrous sodium sulphate, filtered and concentrated in vacuo to give the crude compound. Purification by column chromatography over neutral alumina by using 1-2% ethyl acetate in petroleum ether as eluent afforded methyl 2-(3-Isopropylpyrrol-1-yl)acetate (135 mg, 69%) as a liquid.

Reference Examples 277 to 278

The compounds set out below were prepared in a manner analogous to Reference Example 276:

| Reference Example | Compound |
| --- | --- |
| 277 | Methyl 2-(3-Isobutylpyrrol-1-yl)acetate |
| 278 | Methyl 2-(3-Cyclobutyl-pyrrol-1-yl)acetate |

Reference Example 279

Ethyl 2-[5-(methoxymethyl)-1-methyl-3-phenyl-pyrrol-2-yl]-2-oxo-acetate

Ethyl chloro oxoacetate (760 mg, 5.59 mmol) was added to a solution of 2-methoxymethyl-1-methyl-4-phenyl-pyrrole (750 mg 3.73 mmol) and triethylamine (490 mg 4.85 mmol) in dichloromethane (10 mL) at 0° C. The mixture was stirred for 4 h then concentrated in vacuo. The resulting residue was dissolved in dichloromethane and washed with saturated sodium bicarbonate solution, brine, dried over anhydrous sodium sulfate and concentrated in vacuo to afford the crude product. Purification by column chromatography over neutral alumina using 5-10% ethyl acetate in petroleum ether as eluent afforded ethyl 2-[5-(methoxymethyl)-1-methyl-3-phenyl-pyrrol-2-yl]-2-oxo-acetate (600 mg, 53%) as a liquid.

Reference Example 280

The compound set out below was prepared in a manner analogous to Reference Example 279:

| Reference Example | Compound |
| --- | --- |
| 280 | Ethyl 2-[1,5-bis(methoxymethyl)-3-phenyl-pyrrol-2-yl]-2-oxo-acetate |

Reference Example 281

2-[5-(methoxymethyl)-1-methyl-3-phenyl-pyrrol-2-yl]-2-oxo-acetic acid

Lithium hydroxide (170 mg, 4.04 mmol) was added to a solution of ethyl 2-[5-(methoxymethyl)-1-methyl-3-phenyl-pyrrol-2-yl]-2-oxo-acetate (600 mg, 1.90 mmol) in methanol (20 mL) and stirred for 3 h at ambient temperature. The mixture was concentrated in vacuo and the residue dissolved in water and acidified with acetic acid. The mixture was extracted with ethyl acetate, the organic layer washed with brine, dried over anhydrous sodium sulphate and concentrated in vacuo to afford 2-[5-(methoxymethyl)-1-methyl-3-phenyl-pyrrol-2-yl]-2-oxo-acetic acid (350 mg, 64%) as a solid.

Reference Examples 282 to 283

The compounds set out below were prepared in a manner analogous to Reference Example 281:

| Reference Example | Compound |
| --- | --- |
| 282 | 2-[1,5-Bis(methoxymethyl)-3-phenyl-pyrrol-2-yl]-2-oxo-acetic acid |
| 283 | 2-[1-(2-Methoxyethyl)-3-(3-thienyl)pyrrol-2-yl]-2-oxo-acetic acid |

Reference Example 284

2-(1,5-Dimethyl-3-phenyl-pyrrol-2-yl)-2-oxo-acetyl chloride

Oxalyl chloride (19.5 mL, 0.21 mol) was added slowly to a 0° C. solution of 1,2-dimethyl-4-phenyl-pyrrole (30.5 g, 0.178 mol) in dry dichloromethane (150 mL). The reaction mixture was warmed to room temperature and stirred for 1 h. The solvent was removed in vacuo to afford 2-(1,5-dimethyl-3-phenyl-pyrrol-2-yl)-2-oxo-acetyl chloride (46 g, 99%) as a brown oil.

Reference Examples 285 to 348

The compounds set out below were prepared in a manner analogous to Reference Example 284:

| Reference Example | Compound |
| --- | --- |
| 285 | 2-Oxo-(1-phenylpyrrol-2-yl)acetyl chloride |
| 286 | 2-(5-Methyl-1-phenylpyrrol-2-yl)-2-oxo-acetyl chloride |
| 287 | 2-(5-Methyl-1H-pyrrol-2-yl)-2-oxo-acetyl chloride |
| 288 | 2-(2-Methyl-7-phenyl-3,4-dihydro-1H-pyrrolo[1,2-a]pyrazin-6-yl)-2-oxo-acetyl chloride |
| 289 | 2-Oxo-2-(2-phenyl-6,7-dihydro-5H-pyrrolizin-3-yl)acetyl chloride |
| 290 | 2-Oxo-2-(7-phenyl-3,4-dihydro-1H-pyrrolo[2,1-c][1,4]oxazin-6-yl)acetyl chloride |
| 291 | 2-(1-Isopropyl-5-methyl-3-phenyl-pyrrol-2-yl)-2-oxo-acetyl chloride |
| 292 | 2-[1-(2-Methoxyethyl)-5-methyl-3-phenyl-pyrrol-2-yl]-2-oxo-acetyl chloride |
| 293 | 2-[3-(2-Furyl)-1,5-dimethyl-pyrrol-2-yl]-2-oxo-acetyl chloride |
| 294 | 2-[1,5-Dimethyl-3-(2-thienyl)pyrrol-2-yl]-2-oxo-acetyl chloride |

-continued

| Reference Example | Compound |
|---|---|
| 295 | 2-(3-Isopropyl-1,5-dimethyl-pyrrol-2-yl)-2-oxo-acetyl chloride |
| 296 | 2-(1,5-Dimethyl-3-tetrahydropyran-4-yl-pyrrol-2-yl)-2-oxo-acetyl chloride |
| 297 | 2-(1,4-Dimethyl-3-phenyl-pyrrol-2-yl)-2-oxo-acetyl chloride (obtained as a mixture with the regioisomer 2-(1,3-dimethyl-4-phenyl-1H-pyrrol-2-yl)-2-oxo-acetyl chloride) |
| 298 | 2-(5-Isopropyl-1-methyl-3-phenyl-pyrrol-2-yl)-oxo-acetyl chloride |
| 299 | 2-[3-Isopropyl-1-(2-methoxyethyl)-5-methyl-pyrrol-2-yl]-2-oxo-acetyl chloride |
| 300 | 2-[1-(2-Ethoxyethyl)-5-methyl-3-phenyl-pyrrol-2-yl]-2-oxo-acetyl chloride |
| 301 | 2-[1-(3-Methoxypropyl)-5-methyl-3-phenyl-pyrrol-2-yl]-2-oxo-acetyl chloride |
| 302 | 2-(5-Ethyl-1-methyl-3-phenyl-pyrrol-2-yl)-2-oxo-acetyl chloride |
| 303 | 2-[5-Ethyl-1-(2-methoxyethyl)-3-phenyl-pyrrol-2-yl]-2-oxo-acetyl chloride |
| 304 | Ethyl 2-(2-chloro-2-oxo-acetyl)-5-methyl-3-phenyl-pyrrole-1-carboxylate |
| 305 | Methyl 2-(2-chloro-2-oxo-acetyl)-5-methyl-3-phenyl-pyrrole-1-carboxylate |
| 306 | 2-[3-(2-Chlorophenyl)-1-(2-methoxyethyl)pyrrol-2-yl]-2-oxo-acetyl chloride |
| 307 | 2-[4-(2-Chlorophenyl)-1-(2-methoxyethyl)pyrrol-2-yl]-2-oxo-acetyl chloride |
| 308 | 2-[3-(4-Chlorophenyl)-1-(2-methoxyethyl)pyrrol-2-yl]-2-oxo-acetyl chloride |
| 309 | Methyl 2-[2-(2-chloro-2-oxo-acetyl)pyrrol-1-yl]acetate |
| 310 | 2-[1-(Methoxymethyl)-3-phenyl-pyrrol-2-yl]-2-oxo-acetyl chloride & 2-[l-(Methoxymethyl)-4-phenyl-1H-pyrrol-2-yl]-2-oxo-acetyl chloride |
| 311 | 2-[2-(2-Chloro-2-oxo-acetyl)-5-methyl-3-phenyl-pyrrol-1-yl]acetate |
| 312 | 2-[1-(2-Acetamidoethyl)-5-methyl-3-phenyl-pyrrol-2-yl]-2-oxo-acetyl chloride |
| 313 | 2-[1-(2-Methoxyethyl)-3-(2-thienyl)pyrrol-2-yl]-2-oxo-acetyl chloride |
| 314 | 2-[3-Isobutyl-1-(2-methoxyethyl)pyrrol-2-yl]-2-oxo-acetyl chloride |
| 315 | 2-[3-(3-Chlorophenyl)-1-(2-methoxyethyl)pyrrol-2-yl]-2-oxo-acetyl chloride & 2-[4-(3-Chlorophenyl)-1-(2-methoxyethyl)pyrrol-2-yl]-2-oxo-acetyl chloride |
| 316 | Ethyl 2-[2-(2-chloro-2-oxo-acetyl)-3-phenyl-pyrrol-1-yl]acetate |
| 317 | Methyl 2-[2-(2-chloro-2-oxo-acetyl)-3-phenyl-pyrrol-1-yl] acetate & methyl 2-[2-(2-chloro-2-oxo-acetyl)-4-phenyl-pyrrol-1-yl]acetate |
| 318 | Isopropyl 2-[2-(2-chloro-2-oxo-acetyl)-5-methyl-3-phenyl-pyrrol-1-yl]acetate |
| 319 | 2-[5-Isopropyl-1-(2-methoxyethyl)-3-phenyl-pyrrol-2-yl]-2-oxo-acetyl chloride |
| 320 | 2-[3-(2-Methoxyethyl)-5-methyl-1-phenyl-pyrrol-2-yl]-2-oxo-acetyl chloride |
| 321 | 2-[1-(2-Methoxyethyl)-3-phenyl-pyrrol-2-yl]-2-oxo-acetyl chloride |
| 322 | 2-[3-Isopropyl-1-(2-methoxyethyl)pyrrol-2-yl]-2-oxo-acetyl chloride |
| 323 | 2-[1-(2-Dimethylaminoethyl)-3-phenyl-pyrrol-2-yl]-2-oxo-acetyl chloride |
| 324 | 2-[1-(2-Dimethylaminoethyl)-4-phenyl-pyrrol-2-yl]-2-oxo-acetyl chloride |
| 325 | 2-[1-(2-Dimethylaminoethyl)-5-methyl-3-phenyl-pyrrol-2-yl]-2-oxo-acetyl chloride |
| 326 | Methyl 2-[2-(2-chloro-2-oxo-acetyl)-3-(2-thienyl)pyrrol-1-yl] acetate |
| 327 | Methyl 2-[2-(2-chloro-2-oxo-acetyl)-3-isopropyl-pyrrol-1-yl]acetate |
| 328 | Methyl 2-[2-(2-chloro-2-oxo-acetyl)-3-isobutyl-pyrrol-1-yl]acetate |
| 329 | 2-(4-Fluoro-1,5-dimethyl-3-phenyl-pyrrol-2-yl)-2-oxo-acetyl chloride |
| 330 | 2-[5-Methyl-3-phenyl-1-(2-pyridylmethyl)pyrrol-2-yl]-2-oxo-acetyl chloride |
| 331 | 2-[5-Methyl-3-phenyl-1-(3-pyridylmethyl)pyrrol-2-yl]-2-oxo-acetyl chloride |
| 332 | 2-[4-Fluoro-1-(2-methoxyethyl)-5-methyl-3-phenyl-pyrrol-2-yl]-2-oxo-acetyl chloride |
| 333 | 2-[1-(2-Isopropoxyethyl)-5-methyl-3-phenyl-pyrrol-2-yl]-2-oxo-acetyl chloride |
| 334 | 2-[5-Methyl-3-phenyl-1-(4-pyridylmethyl)pyrrol-2-yl]-2-oxo-acetyl chloride |
| 335 | 2-[3-Cyclobutyl-1-(2-methoxyethyl)pyrrol-2-yl]-2-oxo-acetyl chloride |
| 336 | Methyl 2-[2-(2-chloro-2-oxo-acetyl)-3-cyclobutyl-pyrrol-1-yl]acetate |
| 337 | 2-(1-Methyl-3-phenyl-5-propyl-pyrrol-2-yl)-2-oxo-acetyl chloride |
| 338 | 2-[5-Ethyl-1-(methoxymethyl)-3-phenyl-pyrrol-2-yl]-2-oxo-acetyl chloride |
| 339 | 2-[1-(Ethoxymethyl)-5-methyl-3-phenyl-pyrrol-2-yl]-2-oxo-acetyl chloride |
| 340 | 2-[5-Methyl-1-(2-methylsulfanylethyl)-3-phenyl-pyrrol-2-yl]-2-oxo-acetyl chloride |
| 341 | 2-[1-(3-Ethoxypropyl)-5-methyl-3-phenyl-pyrrol-2-yl]-2-oxo-acetyl chloride |
| 342 | 2-[1-(2-Methoxyethoxymethyl)-5-methyl-3-phenyl-pyrrol-2-yl]-2-oxo-acetyl chloride |
| 343 | 2-[5-Methyl-3-phenyl-1-(propoxymethyl)pyrrol-2-yl]-2-oxo-acetyl chloride |
| 344 | 2-[5-Methyl-1-(2-phenoxyethyl)-3-phenyl-pyrrol-2-yl]-2-oxo-acetyl chloride |
| 345 | 2-[5-Methyl-3-phenyl-1-(2-propoxyethyl)pyrrol-2-yl]-2-oxo-acetyl chloride |
| 346 | 2-[1-(4-Methoxybut-2-enyl)-5-methyl-3-phenyl-pyrrol-2-yl]-2-oxo-acetyl chloride |
| 347 | 2-[1-(4-Methoxybutyl)-5-methyl-3-phenyl-pyrrol-2-yl]-2-oxo-acetyl chloride |
| 348 | 2-[1-(Butoxymethyl)-5-methyl-3-phenyl-pyrrol-2-yl]-2-oxo-acetyl chloride |

Reference Example 349

Ethyl 2-[1-(2-methoxyethyl)-3-(3-thienyl)pyrrol-2-yl]-2-oxo-acetate

Chloroethyl oxalate (0.13 mL, 1.18 mmol) was added slowly to a cooled solution of 1-(2-methoxy-ethyl)-3-thiophen-2-yl-1H-pyrrole (300 mg, 1.55 mmol) and triethylamine (0.28 mL) in dry dichloromethane (15 mL) at 0° C. The reaction mixture was allowed to warm to ambient temperature and stirred for 16 h. The solvent was removed in vacuo to afford ethyl 2-[1-(2-methoxyethyl)-3-(3-thienyl)pyrrol-2-yl]-2-oxo-acetate (250 mg, 85%) as a brown oily liquid.

Reference Example 350

2-Chloro-4,6-dimethyl-pyridine

A mixture of 2-amino-4,6-dimethylpyridine (90 g, 0.736 mol) and sodium chloride (216 g, 3.69 mol) in concentrated hydrochloric acid (720 mL) was cooled to between −15 and −20° C. A solution of sodium nitrite (71.2 g, 1.03 mol) in water (135 mL) was added over 30 min. More sodium chloride (216 g, 3.69 mol) was added and the reaction mixture was allowed to warm to ambient temperature and stirred for 1 h. The reaction mixture was basified with solid bicarbonate (700 g) and extracted with dichloromethane (1 L), filtered and the two phases separated. The organic layer was concentrated in vacuo and the crude purified by flash column chromatography over silica gel (100-200 mesh) with 20% dichloromethane in petroleum ether as eluent to afford 2-chloro-4,6-dimethylpyridine (40 g, 38%) as a solid.

Reference Example 351

1-(4,6-dimethyl-2-pyridyl)piperazine

A solution of piperazine (195 g, 2.26 mol) in diglyme (250 mL) was heated to 160° C. and a solution of 2-chloro-4,6-dimethylpyridine (40 g, 0.283 mol) in diglyme (150 mL) was added over a period of 30 min. The mixture was maintained at this temperature for 36 h and then the reaction mixture was allowed to cool to ambient temperature, diluted with brine and extracted with ethyl acetate (3×500 mL). The combined organic layers were washed with brine (2×100 mL), dried over anhydrous sodium sulfate and concentrated in vacuo to give the crude compound. Vacuum distillation to remove diglyme afforded 1-(4,6-dimethyl-2-pyridyl)piperazine (50 g, 92%) as an oil.

Reference Examples 352 to 354

The compounds set out below were prepared in a manner analogous to Reference Example 351:

| Reference Example | Compound |
|---|---|
| 352 | 1-(2-Pyridyl)piperazine |
| 353 | 1-(6-Methyl-2-pyridyl)piperazine |
| 354 | 1-(4-Methyl-2-pyridyl)piperazine |

Reference Example 355

1-(4,6-dimethyl-2-pyridyl)-4-(4-nitrophenyl)piperazine

A solution of 1-(4,6-dimethyl-2-pyridyl)piperazine (52 g, equivalent to 50.0 g after correcting for residual diglyme determined by GC analysis, 265 mmol) and potassium carbonate (72.4 g, 523 mmol) in diglyme (150 mL) was stirred at room temperature for 15 min and then heated to 150° C. A solution of 1-chloro-4-nitro-benzene (62 g, 392 mmol) in diglyme (150 mL) was added over 15 min and the mixture heated at reflux for 46 h. The reaction mixture was allowed to cool to ambient temperature and filtered to remove insoluble salts and the filter cake was washed with ethyl acetate (2×250 mL). The filtrate was concentrated in vacuo to give a viscous oil, to which was added 3N hydrochloric acid (650 mL). After stirring for 1 h the precipitated solid was filtered off and washed with water (100 mL). This solid was stirred in ethyl acetate (500 mL) for 30 min and filtered. The process was repeated once more yielding the crude product as its hydrochloride salt (85 g). The salt was suspended in water (1.0 L), basified to pH ~9 with ammonium hydroxide (100 mL) and extracted with dichloromethane (2×750 mL). The combined organic layers were washed with brine (2×250 mL), dried and evaporated to dryness to afford 1-(4,6-dimethyl-2-pyridyl)-4-(4-nitrophenyl)piperazine (49 g, 60%) as a solid.

Reference Examples 356 to 360

The compounds set out below were prepared in a manner analogous to Reference Example 355:

| Reference Example | Compound |
|---|---|
| 356 | [2-[4-(4,6-Dimethyl-2-pyridyl)piperazin-1-yl]-5-nitro-phenyl]methanol |
| 357 | 1-(2-Chloro-4-nitro-phenyl)-4-(4,6-dimethyl-2-pyridyl)piperazine |
| 358 | 5-[4-(4,6-Dimethyl-2-pyridyl)piperazin-1-yl]-2-nitro-aniline |
| 359 | 1-Methyl-4-(5-nitro-1-naphthyl)piperazine |
| 360 | 1-(4,6-Dimethyl-2-pyridyl)-4-(2-methyl-4-nitro-phenyl)piperazine |

Reference Example 361

2-Chloro-5-nitro-phenol

A saturated solution of sodium nitrite (1.8 g, 26.0 mmol) in water (12 mL) was added dropwise to a suspension of 2-amino-5-nitro-phenol (2.0 g, 13.0 mmol) in concentrated hydrochloric acid (10 mL) at 0° C. and stirred for 30 min. A solution of Copper (I) chloride (5.15 g, 52.0 mmol) and concentrated hydrochloric acid (20 mL) heated to between 60 and 70° C. was added dropwise over a period of 30 min. The resultant reaction mixture was heated to 80° C. and stirred for 15 min and then allowed to cool to ambient temperature. Ethyl acetate (50 mL) was added and after stirring for 5 min the organic phase was separated and the aqueous phase was re-extracted with ethyl acetate (2×50 mL). The combined organic phases were washed with water (4×50 mL), brine, dried over anhydrous sodium sulfate and concentrated in vacuo to give a residue which was purified by column chromatography over silica gel (100-200 mesh) using 5% ethyl acetate in petroleum ether as eluent to afford 2-chloro-5-nitro-phenol (2.08 g, 92%) as a crystalline yellow solid.

Reference Example 362

1-Fluoro-5-nitro-naphthalene

Sodium nitrite (660 mg, 9.57 mmol) was added portionwise to a suspension of 5-nitronaphthalen-1-amine (1.2 g, 6.38 mmol) in a 1:1 mixture of water/concentrated hydrochloric acid (10 mL) at −5° C. The mixture was stirred for 15 min at −5° C. and a 60% w/w hexafluoro phosphoric acid solution (6 mL) was added. The brown precipitate was filtered and washed with cold water and diethyl ether and then allowed to dry in vacuo. The resulting solid was suspended in toluene and heated to 110° C. for 2 h before the mixture was then allowed to cool to ambient temperature and the solvent removed in vacuo to afford the crude product. Purification by column chromatography over silica gel (100-200 mesh) using petroleum ether as eluent afforded 1-fluoro-5-nitro-naphthalene (450 mg, 37%) as a yellow solid.

Reference Example 363

2-Benzyloxy-1-chloro-4-nitro-benzene

Benzyl bromide (0.6 mL, 5.04 mmol) was added dropwise to a mixture of 2-chloro-5-nitro-phenol (800 mg, 4.61 mmol) and potassium carbonate (1.27 g, 9.22 mmol) in acetone (20 mL) at ambient temperature and then heated at reflux for 2 h. The inorganic residue was filtered off and washed with acetone (20 mL). The combined filtrate and washings were concentrated in vacuo and the resulting residue was then dissolved in ethyl acetate (25 mL) and washed successively with water (2×20 mL), brine (20 mL), dried over anhydrous sodium sulfate and concentrated in vacuo to yield 2-benzyloxy-1-chloro-4-nitro-benzene (1.20 g, 99%) as a cream solid.

Reference Example 364

1-(2-Benzyloxy-4-nitro-phenyl)-4-(4,6-dimethyl-2-pyridyl)piperazine

A mixture of 2-benzyloxy-1-chloro-4-nitro-benzene (700 mg, 2.66 mmol), 1-(4,6-dimethyl-pyridin-2-yl)-piperazine (457 mg, 2.39 mmol) and caesium carbonate (2.58 g, 7.97 mmol) in toluene (30 mL) was purged with argon gas. Palladium acetate (24 mg, 0.106 mmol) and 2-(dicyclohexylphosphino)-2'-N,N-dimethylamino)-biphenyl (42 mg, 0.106 mmol) were added. After purging again with argon gas the reaction mixture was heated at reflux for 20 h. The reaction mixture was cooled, filtered and the filter cake was washed with ethyl acetate (30 mL). The combined filtrate and washings were washed successively with water (2×50 mL), brine (2×50 mL), dried over anhydrous sodium sulfate and concentrated in vacuo to yield a residue which was purified by flash column chromatography over silica gel (100-200 mesh) using 8-10% ethyl acetate in petroleum ether as eluent to afford 1-(2-benzyloxy-4-nitro-phenyl)-4-(4,6-dimethyl-2-pyridyl)piperazine (510 mg, 46%) as a pale yellow solid.

Reference Example 365

4-[3-[[2-[4-(4,6-Dimethyl-2-pyridyl)piperazin-1-yl]-5-nitro-phenyl]methoxy]propyl]morpholine Aqueous sodium hydroxide (50% w/w, 10 g, 125 mmol) and tetrabutylammonium hydrogen sulfate (0.20 g) were added successively to a solution of [2-[4-(4,6-dimethyl-2-pyridyl)piperazin-1-yl]-5-nitro-phenyl]methanol (0.50 g, 1.46 mmol) in toluene (5 mL). The mixture was heated to reflux with vigorous stirring for 45 min then 4-(3-chloropropyl)-morpholine (0.50 g, 3.00 mmol) was added and reflux continued for 28 h. The reaction mixture was cooled and the organic phase separated. The aqueous phase was extracted with ethyl acetate (3×5 mL). The organic phases were combined, washed with water and brine, dried over anhydrous sodium sulfate, filtered and concentrated under vacuum to give a residue which was purified by preparative TLC eluting with 2% methanol in chloroform to afford 4-[3-[[2-[4-(4,6-dimethyl-2-pyridyl)piperazin-1-yl]-5-nitro-phenyl]methoxy]propyl]morpholine (550 mg, 80%) as a solid.

Reference Examples 366 and 367

The compounds set out below were prepared in a manner analogous to Reference Example 365.

| Reference Example | Compound |
|---|---|
| 366 | 2-[[2-[4-(4,6-Dimethyl-2-pyridyl)piperazin-1-yl]-5-nitro-phenyl]methoxy]-N,N-dimethyl-ethanamine |
| 367 | 1-(4,6-Dimethyl-2-pyridyl)-4-[2-[3-(4-methylpiperazin-1-yl)propoxymethyl]-4-nitro-phenyl]piperazine |

Reference Example 368

1-(3-chloro-4-nitro-phenyl)-4-(4,6-dimethyl-2-pyridyl)piperazine

50% Aqueous hydrochloric acid (30 mL) was cooled to −20° C., 5-[4-(4,6-dimethyl-2-pyridyl)piperazin-1-yl]-2-nitro-aniline (1.4 g, 4.28 mmol) was added and the reaction mixture stirred for 15 min. A solution of sodium nitrite (350 mg, 5.14 mmol) in water (8 mL) was added and the reaction mixture stirred for 15 min. This solution was added dropwise to a cooled solution of copper (I) chloride (635 mg, 6.42 mmol) in 50% hydrochloric acid (20 mL) over a period of 20 min and stirred for a further 10 min before basifying with saturated sodium carbonate solution. The mixture was extracted with ethyl acetate and the organic phase was washed with water, brine, dried over anhydrous sodium sulfate and concentrated under vacuum to give a crude residue. Purification by column chromatography over silica gel (100-200 mesh) using 8% ethyl acetate in petroleum ether as eluent afforded 1-(3-chloro-4-nitro-phenyl)-4-(4,6-dimethyl-pyridin-2-yl)-piperazine 1-(3-chloro-4-nitro-phenyl)-4-(4,6-dimethyl-2-pyridyl)piperazine (800 mg, 54%) as a yellow solid.

Reference Example 369

2-[4-(4,6-dimethyl-2-pyridyl)piperazin-1-yl]-5-nitrophenol

Trifluoroacetic acid (5 mL) was added to 1-(2-benzyloxy-4-nitro-phenyl)-4-(4,6-dimethyl-2-pyridyl)piperazine (720 mg, 1.72 mmol) at between 0 and 5° C. followed by concentrated hydrochloric acid (2 mL). The mixture was heated at reflux for 16 h then cooled to between 0 and 5° C. and quenched with saturated sodium bicarbonate solution (30 mL). Chloroform (30 mL) was added and the mixture was stirred for 15 min. The organic phase was separated and the aqueous phase was extracted with chloroform (30 mL). The combined organic phases were washed with water (2×30 mL), brine (30 mL), dried over anhydrous sodium sulfate and concentrated in vacuo to give a crude residue. Trituration with petroleum ether afforded 2-[4-(4,6-dimethyl-2-pyridyl)piperazin-1-yl]-5-nitro-phenol (510 mg, 90%) as a brownish-yellow solid.

Reference Example 370

[2-[4-(4,6-dimethyl-2-pyridyl)piperazin-1-yl]-5-nitro-phenyl]acetate

Triethylamine (1.0 mL, 7.17 mmol) was added to a solution of 2-[4-(4,6-dimethyl-pyridin-2-yl)-piperazin-1-yl]-5-nitro-phenol (500 mg, 1.52 mmol) in dry dichloromethane (20 mL) followed by the dropwise addition of acetyl chloride (0.2 mL, 2.80 mmol). After stirring for 15 min, water was added and the mixture warmed to room temperature. The organic phase was separated and the aqueous phase was extracted with dichloromethane (2×30 mL). The combined organic phases were washed with water (2×30 mL), brine (2×30 mL), dried over anhydrous sodium sulfate and concentrated in vacuo. The residue was triturated with 5% dichloromethane in petroleum ether (2×20 mL) to afford [2-[4-(4,6-dimethyl-2-pyridyl)piperazin-1-yl]-5-nitro-phenyl]acetate (365 mg, 65%) as a pale brownish-yellow solid.

Reference Example 371

The compound set out below was prepared in a manner analogous to Reference Example 370.

| Reference Example | Compound |
|---|---|
| 371 | N-[2-(2-Methyl-4-phenyl-pyrrol-1-yl)ethyl]acetamide |

Reference Example 372

2-(Bromomethyl)-1-methoxy-3-nitro-benzene

N-bromosuccinimide (590 mg, 3.30 mmol) was added to a solution of 1-methoxy-2-methyl-3-nitro-benzene (500 mg, 3.0 mmol) in carbon tetrachloride (5 mL) followed by a catalytic amount of dibenzoyl peroxide (25 mg). The reaction mixture was heated at reflux for 3 h then cooled to room temperature and poured into water. The organic phase was separated, washed with water (2×20 mL), dried over the anhydrous sodium sulfate and concentrated in vacuo to afford 2-(bromomethyl)-1-methoxy-3-nitro-benzene (640 mg, 86%) as a solid.

Reference Example 373

2-(2-Methoxy-6-nitro-phenyl)acetonitrile

Sodium cyanide (165 mg, 3.36 mmol) was added to a solution of 2-(bromomethyl)-1-methoxy-3-nitro-benzene (680 mg, 2.56 mmol) in ethanol (5 mL) and the mixture was heated at reflux for 16 h. The solvent was removed in vacuo, water (30 mL) was added and the mixture was extracted with dichloromethane (25 mL). The organic phase was washed with water (2×20 mL), brine (20 mL), dried over anhydrous sodium sulfate and concentrated in vacuo. The crude compound was purified by column chromatography over silica gel (100-200 mesh) using 8% ethyl acetate in petroleum ether to afford 2-(2-methoxy-6-nitro-phenyl)acetonitrile (300 mg, 61%).

Reference Example 374

Ethyl 2-(2-methoxy-6-nitro-phenyl)acetate

Concentrated sulfuric acid (1 mL) was slowly added to a solution of 2-(2-methoxy-6-nitro-phenyl)acetonitrile (200 mg, 1.04 mmol) in 95% ethanol (2 mL). The mixture was heated at reflux overnight then quenched into ice cold water and extracted with diethyl ether (10 mL). The organic phase was washed with water (2×10 mL), dried over anhydrous sodium sulfate and concentrated in vacuo to afford ethyl 2-(2-methoxy-6-nitro-phenyl)acetate (180 mg, 72%).

Reference Example 375

2-(2-Methoxy-6-nitro-phenyl)ethanol

Diisobutylaluminium hydride (20 wt %; 2.38 g, 16.8 mmol) in toluene was added to a solution of 2-(2-methoxy-6-nitro-phenyl)acetate (1.0 g, 4.18 mmol) in tetrahydrofuran (8 mL) at −5° C. The reaction mixture was stirred at 0° C. for 1 h and then poured into 1N hydrochloric acid. The mixture was extracted with ethyl acetate (30 mL) and the separated organic phase was washed with water (2×30 mL), brine (25 mL), dried over anhydrous sodium sulfate and concentrated in vacuo to afford 2-(2-methoxy-6-nitro-phenyl)ethanol (780 mg, 94%).

Reference Example 376

[1-(methoxymethyl)-4-phenyl-pyrrol-2-yl]methanol

Lithium aluminum hydride (113 mg, 3.06 mmol) was added portionwise to a stirred solution of methyl 1-(methoxymethyl)-4-phenyl-pyrrole-2-carboxylate (500 mg, 2.04 mmol) in tetrahydrofuran (10 mL) over a period of 15 min at 0° C. The resulting mixture stirred for 12 h and then quenched with ice and the mixture extracted with ethyl acetate. The combined organic layers were washed with brine, dried over anhydrous sodium sulfate and concentrated in vacuo to yield [1-(methoxymethyl)-4-phenyl-pyrrol-2-yl]methanol (400 mg, 91%) as a brown liquid.

Reference Example 377

4-Nitro-2,3-dihydrobenzofuran 2-(2-Methoxy-6-nitro-phenyl)ethanol (700 mg, 3.55 mmol) was dissolved in polyphosphoric acid (3 mL) and heated at 120° C. for 1 h. After cooling to ambient temperature, ice-water water was added and the mixture was extracted with ethyl acetate. The organic phase was washed with water (2×20 mL), dried over anhydrous sodium sulfate and concentrated in vacuo to afford 4-nitro-2,3-dihydrobenzofuran (400 mg, 68%).

Reference Example 378

1-(4-nitrophenyl)-4-(2-pyridyl)piperazine

A mixture of 1-chloro-4-nitro-benzene (4.34 g, 27.6 mmol) and anhydrous potassium carbonate (5.08 g, 36.8 mmol) was added to a solution of 1-(2-pyridyl)piperazine (3.0 g, 18.4 mmol) in diglyme (10 mL) and heated at reflux for 24 h. The reaction mixture was cooled to ambient temperature, filtered and the filtrate was concentrated in vacuo. The residue was diluted with chloroform and the organic layer was washed with water (5×40 mL), brine (3×30 mL), dried over anhydrous sodium sulphate and concentrated to yield a crude compound. This was purified by washing with hexane (5×5 mL) and then pentane (2×5 mL) to afford 1-(4-nitrophenyl)-4-(2-pyridyl)piperazine (4.0 g, 77%) as a yellow solid.

Reference Examples 379 to 381

The compounds set out below were prepared in a manner analogous to Reference Example 378:

| Reference Example | Compound |
|---|---|
| 379 | 1-(6-Methyl-2-pyridyl)-4-(4-nitrophenyl)piperazine |
| 380 | 1-(4-Methyl-2-pyridyl)-4-(4-nitrophenyl)piperazine |
| 381 | 6-[4-(4-Nitrophenyl)piperazin-1-yl]pyridine-3-carbaldehyde |

Reference Example 382

4-[[6-[4-(4-nitrophenyl)piperazin-1-yl]-3-pyridyl]methyl]morpholine

Morpholine (250 mg, 2.87 mmol) was added to a suspension of 6-[4-(4-nitrophenyl)piperazin-1-yl]pyridine-3-carbaldehyde (750 mg, 2.41 mmol) and sodium cyanoborohydride (454 mg, 7.23 mmol) in a mixture of tetrahydrofuran (10 mL) and acetic acid (0.5 mL) at ambient temperature then heated at reflux for 3 h. The mixture was then concentrated in vacuo to give a gummy solid which was dissolved in chloroform (40 mL), washed with water (2×20 mL), brine (2×15 mL), dried over anhydrous sodium sulfate and concentrated in vacuo to give the crude compound. Purification by column chromatography over neutral alumina using 20-30% of ethyl acetate in petroleum ether afforded 4-[[6-[4-(4-nitrophenyl)piperazin-1-yl]-3-pyridyl]methyl]morpholine (550 mg, 59%).

Reference Example 383

1-(2-fluoro-4-nitro-phenyl)piperidine

Piperidine (0.80 g, 9.42 mmol) was added to a solution of 3,4-difluoro-nitro benzene (1.0 g, 6.28 mmol) in acetonitrile (15 mL) and diisopropyl ethylamine (1.62 g, 12.57 mmol) and the mixture was refluxed for 3 h. The acetonitrile was removed in vacuo and the residue was diluted with water and extracted with ethyl acetate. The combined organic extracts were washed with brine, dried over anhydrous sodium sulphate and concentrated in vacuo to afford 1-(2-fluoro-4-nitro-phenyl)piperidine (1.3 g, 92%) as a yellow liquid.

Reference Examples 384 to 388

The compounds set out below were prepared in a manner analogous to Reference Example 383:

| Reference Example | Compound |
|---|---|
| 384 | 1-(2-Fluoro-4-nitro-phenyl)-4-(2-pyridyl)piperazine |
| 385 | 1-(2-Fluoro-4-nitro-phenyl)-4-isobutyl-piperazine |
| 386 | 4-(2-Fluoro-4-nitro-phenyl)morpholine |
| 387 | 1-(4-Nitrophenyl)piperidine |
| 388 | 4-(4-Nitrophenyl)morpholine |

Reference Example 389

1-Benzyl-4-(4-nitrophenyl)piperazine

Benzyl bromide (1.42 mL, 11.6 mmol) was added to a solution of 1-(4-nitrophenyl)piperazine (2.0 g, 11.6 mmol) in acetonitrile (30 mL) with triethylamine (2.68 mL, 19.32 mmol) and refluxed for 12 h. The mixture was concentrated in vacuo and the residue partitioned between water and ethyl acetate. The organic layer was separated, washed with brine, dried over anhydrous sodium sulfate and concentrated in vacuo to afford 1-benzyl-4-(4-nitrophenyl)piperazine (2.2 g, 77%).

Reference Example 390

1-(1,2-Dimethylpropyl)-4-(4-nitrophenyl)piperazine

3-Methyl-2-butanone (0.76 mL, 7.24 mmol) was added to a solution of 1-(4-nitrophenyl)piperazine (1.0 g, 4.83 mmol) in methanol (10 mL) and acetic acid (1 mL) and stirred for 30 min at ambient temperature. Sodium cyanoborohydride (1.81 g, 28.98 mmol) was added and the mixture refluxed for 12 h, cooled and then poured into water and extracted with ethyl acetate. The combined organic layers were washed with water, brine, dried over anhydrous sodium sulfate and concentrated in vacuo to afford the crude product. Purification by column chromatography over silica gel (100-200 mesh) using 5-10% ethyl acetate/petroleum ether as eluent afforded 1-(1,2-Dimethylpropyl)-4-(4-nitrophenyl)piperazine (0.46 g, 34%).

Reference Examples 391 to 392

The compounds set out below were prepared in a manner analogous to Reference Example 390:

| Reference Example | Compound |
|---|---|
| 391 | 1-(2-Methoxy-1-methyl-ethyl)-4-(4-nitrophenyl)piperazine |
| 392 | 1-[2-(2-Furyl)-1-methyl-ethyl]-4-(4-nitrophenyl)piperazine |

Reference Example 393

2-(4-Nitrophenyl)-5-(1-piperidylmethyl)oxazole 5-(Bromomethyl)-2-(4-nitrophenyl)oxazole (800 mg, 2.82 mmol) was heated with piperidine (10 mL) in a sealed tube at 100-110° C. for 12 h. The resulting mixture was allowed to cool ambient temperature and then poured into water (30 0 mL) and stirred for 30 min. The resultant solid was filtered and washed with water to remove excess piperidine. The residue was dried to give 2-(4-nitrophenyl)-5-(1-piperidylmethyl)oxazole (700 mg, 86%) as light orange colour solid.

Reference Example 394

4-Nitro-N-prop-2-ynyl-benzamide

To a stirred solution of propargylamine hydrochloride (5.0 g, 54.6 mmol) and pyridine (7.8 g, 99.1 mmol) in tetrahydrofuran (30 mL) was added 4-nitro-benzoylchloride (9.2 g, 49.6 mmol) in tetrahydrofuran (20 mL) and the mixture was heated at reflux for 16 h. The mixture was allowed to cool to ambient temperature and concentrated in vacuo. The crude residue was dissolved in ethyl acetate and washed with saturated aqueous sodium bicarbonate solution, water, brine, dried over anhydrous sodium sulphate, filtered and concentrated in vacuo to afford 4-nitro-N-prop-2-ynyl-benzamide (7.74 g, 77%) as a solid.

Reference Example 395

5-Methyl-2-(4-nitrophenyl)oxazole

To a stirred solution of 4-nitro-N-prop-2-ynyl-benzamide (7.5 g, 36.7 mmol) in ethanol (150 mL) was added a solution of potassium hydroxide (4.1 g, 73.4 mmol) in ethanol (100 mL) and the mixture was stirred at 50-55° C. for 12 h. The mixture was acidified with acetic acid and concentrated to dryness in vacuo at 45-50° C. The resultant residue was extracted into ethyl acetate and the separated organic phase was washed with water; aqueous sodium bicarbonate, brine, dried over anhydrous sodium sulphate and concentrated in vacuo to afford 5-methyl-2-(4-nitrophenyl)oxazole (3.47 g, 46%) as an oil.

Reference Example 396

Preparation of 5-(Bromomethyl)-2-(4-nitrophenyl)oxazole

To a stirred solution of 5-methyl-2-(4-nitrophenyl)oxazole (3.2 g, 15.68 mmol) and benzoyl peroxide (10 mg, catalytic)

in carbon tetrachloride (20 mL), was added N-bromo succinamide (2.77 g, 15.68 mmol). The mixture was heated to reflux for 9 h, filtered and the residue was washed with carbon tetrachloride. The combined filtrates were washed with water, sodium bicarbonate solution, brine, dried over anhydrous sodium sulphate and concentrated in vacuo. The crude product was purified over silica gel (60-120 mesh) with 30% ethyl acetate/hexane as eluent to afford 5-(bromomethyl)-2-(4-nitro-phenyl)-oxazole (2.9 g, 65%) as a solid.

Reference Example 397

2-Methyl-1-[4-(4-nitrophenyl)piperazin-1-yl]propan-1-one

Triethylamine (976 mg, 9.66 mmol) was added to a solution of 1-(4-nitrophenyl)piperazine (1.00 g, 4.83 mmol) in dichloromethane (20 mL) at 0° C. and stirred for 30 min. Isobutyryl chloride (617 mg, 5.79 mmol) was then added and the mixture was warmed to ambient temperature and stirred for 4 h. the reaction mixture was quenched with ice-water and the organic layer separated. The aqueous layer was extracted with dichloromethane (5×5 mL) and the combined organic layers were washed water, saturated sodium bicarbonate solution, brine, dried over anhydrous sodium sulphate and concentrated in vacuo to afford 2-methyl-1-[4-(4-nitrophenyl)piperazin-1-yl]propan-1-one (1.20 g, 90%) as a yellow solid.

Reference Example 398

4-[4-(4,6-dimethyl-2-pyridyl)piperazin-1-yl]aniline

A solution of 1-(4,6-dimethyl-2-pyridyl)-4-(4-nitrophenyl)piperazine (49 g, 157 mmol) in methanol was hydrogenated over Raney Nickel (15 g) at 90 psi pressure for 36 h. The mixture was filtered through Celite and the filtrate was concentrated in vacuo giving a crude product which was washed with petroleum ether (100 mL) to afford 4-[4-(4,6-dimethyl-2-pyridyl)piperazin-1-yl]aniline (43.5 g, 98%).

Reference Examples 399 to 417

The compounds set out below were prepared in a manner analogous to Reference Example 398 at a suitable pressure:

| Reference Example | Compound |
| --- | --- |
| 399 | 4-[4-(4,6-Dimethyl-2-pyridyl)piperazin-1-yl]-3-(3-morpholinopropoxymethyl)aniline |
| 400 | 3-Chloro-4-[4-(4,6-dimethyl-2-pyridyl)piperazin-1-yl]aniline |
| 401 | 3-(2-Dimethylaminoethoxymethyl)-4-[4-(4,6-dimethyl-2-pyridyl)piperazin-1-yl]aniline |
| 402 | 4-[4-(4,6-Dimethyl-2-pyridyl)piperazin-1-yl]-3-[3-(4-methylpiperazin-1-yl)propoxymethyl]aniline |
| 403 | 5-Amino-2-[4-(4,6-dimethyl-2-pyridyl)piperazin-1-yl]phenol |
| 404 | 2,3-Dihydrobenzofuran-4-amine |
| 405 | 4-[4-(2-Pyridyl)piperazin-1-yl]aniline |
| 406 | 4-[4-(6-Methyl-2-pyridyl)piperazin-1-yl]aniline |
| 407 | 4-[4-(4-Methyl-2-pyridyl)piperazin-1-yl]aniline |
| 408 | 5-(4-Methylpiperazin-1-yl)naphthalen-1-amine |
| 409 | 4-[4-(4,6-Dimethyl-2-pyridyl)piperazin-1-yl]-3-methyl-aniline |
| 410 | 4-[4-[5-(Morpholinomethyl)-2-pyridyl]piperazin-1-yl]aniline |
| 411 | 3-Fluoro-4-(1-piperidyl)aniline |
| 412 | 3-Fluoro-4-(4-isobutylpiperazin-1-yl)aniline |
| 413 | 3-Fluoro-4-morpholino-aniline |
| 414 | 5-Fluoro-naphthalen-1-amine |
| 415 | 4-(1-Piperidyl)aniline |
| 416 | 4-Morpholinoaniline |
| 417 | 4-[4-(2-Methoxy-1-methyl-ethyl)piperazin-1-yl]aniline |

Reference Example 418

5-Nitro-2-pyrrolidin-1-yl-pyridine

A mixture of 2-bromo-5-nitro pyridine (300 mg, 1.48 mmol) and pyrrolidine (313 mg, 4.41 mmol) in toluene (5 mL) was heated at 110° C. for 2 h. The reaction mixture was allowed to cool to ambient temperature, poured onto ice-water, and the organic layer was separated. The aqueous layer was extracted with ethyl acetate (3×5 mL). The combined organic layers were washed with water, brine, dried over anhydrous sodium sulphate, filtered and concentrated in vacuo to afford 5-nitro-2-pyrrolidin-1-yl-pyridine (250 mg, 88%) as a solid.

Reference Example 419

2-Chloro-4-[4-(4,6-dimethyl-2-pyridyl)piperazin-1-yl]aniline

Stannous chloride dihydrate (2.6 g, 11.5 mmol) was added to a solution of 1-(3-chloro-4-nitro-phenyl)-4-(4,6-dimethyl-pyridin-2-yl)-piperazine (800 mg, 2.31 mmol) in a mixture of ethyl acetate (20 mL) and ethanol (5 mL). The reaction mixture was heated at reflux for 2 h, allowed to cool to ambient temperature and basified with triethylamine. The reaction mixture was filtered and the filtrate was concentrated in vacuo. The residue was purified by column chromatography over neutral alumina with 10% ethyl acetate in petroleum ether as eluent to afford 2-chloro-4-[4-(4,6-dimethyl-2-pyridyl)piperazin-1-yl]aniline (470 mg, 64%) as a viscous light brown oil.

Reference Examples 420 to 428

The compounds set out below were prepared in a manner analogous to Reference Example 419:

| Example | Compound |
| --- | --- |
| 420 | 6-Pyrrolidin-1-yl-pyridin-3-amine |
| 421 | 1-Ethyl-4-fluoro-indol-5-amine |
| 422 | 4-(4-Benzylpiperazin-1-yl)aniline |
| 423 | 4-Oxazol-2-ylaniline |
| 424 | 3-Fluoro-4-oxazol-2-yl-aniline |
| 425 | 4-[4-(1,2-Dimethylpropyl)piperazin-1-yl]aniline |
| 426 | 1-[4-(4-Aminophenyl)piperazin-1-yl]-2-methyl-propan-1-one |
| 427 | 4-[4-[2-(2-Furyl)-1-methyl-ethyl]piperazin-1-yl]aniline |
| 428 | 4-[(5-Piperidylmethyl)oxazol-2-yl]aniline |

Reference Example 429

5-Nitronaphthalen-1-amine

A 70° C. solution of sodium sulfide (3.17 g, 32.97 mmol) and sodium bicarbonate in water (7 mL) was added dropwise to suspension of 1,5-dinitro naphthalene (2.0 g, 9.16 mmol) in methanol (30 mL) at reflux and the resultant mixture was stirred for 5 min. The mixture was cooled to 0° C., quenched with ice and stirred for a further 10 min followed by acidification with concentrated hydrochloric acid. The resulting mixture was stirred for 30 min then washed with ethyl acetate (2×50 mL). The aqueous layer was basified with aqueous ammonia and extracted with ethyl acetate (2×100 mL). The combined organic layers were washed with water (2×50 mL), brine (2×50 mL), dried over anhydrous sodium sulphate, filtrated and concentration in vacuo afforded of 5-nitronaphthalen-1-amine (710 mg, 42%) as a brown solid.

Reference Example 430

5-Bromoisoquinoline

A solution of sodium nitrite (2.15 g, 31.21 mmol) in water (2 mL) was added to a solution of isoquinolin-5-ylamine (3.0 g, 20.80 mmol) in aqueous 46% hydrogen bromide (9.98 g, 124.84 mmol) at 0° C. The mixture was stirred at 0° C. for 30 min then a solution of cuprous bromide (3.58 g, 24.96 mmol) in aqueous 46% hydrogen bromide (9.98 g, 124.84 mmol) was added and the reaction was allowed to warm to ambient temperature and stirred for 2 h. The resulting mixture was basified with aqueous ammonium and extracted with ethyl acetate. The combined organic layers were washed with brine, dried over anhydrous sodium sulphate and concentrated to afford the crude compound. Purification by column chromatography over silica gel (100-200 mesh) with 20% ethyl acetate in petroleum ether as eluent afforded 5-bromoisoquinoline (2.3 g, 53%) as a pale yellow solid.

Reference Example 431

5-Bromo-8-nitro-isoquinoline

Potassium nitrate (1.17 g, 11.59 mmol) was added portionwise to a solution of 5-bromo-isoquinoline (2.0 g, 9.66 mmol) in concentrated sulphuric acid (10 mL) and stirred at ambient temperature for 1 h. The reaction mixture was quenched with water and basified with aqueous ammonia. The aqueous layer was washed with water, brine, dried over anhydrous sodium sulphate and concentrated in vacuo to afford 5-bromo-8-nitro-isoquinoline (2.0 g, 82%) as a yellow solid.

Reference Example 432

3-Phenylfuran

Furan-3-boronic acid (1.0 g, 8.93 mmol), bromo benzene (1.26 g, 8.04 mmol) and sodium carbonate (1.89 g, 17.86 mmol) were dissolved in a mixture of toluene (15 mL) and methanol (5 mL) and purged with argon for 15 min. Tetrakis palladium (0) (20 mg) was added and the mixture again degassed for 15 min. The reaction was heated at 80° C. for 4 h and the resultant solids which formed were filtered and the filtrate was concentrated in vacuo to give a crude residue. Purification by flash chromatography over silica gel (100-200 mesh) using 2% ethyl acetate/petroleum ether as eluent afforded 3-phenylfuran (0.9 g, 70%).

Reference Example 433

2,5-Dimethoxy-3-phenyl-2,5-dihydrofuran

Bromine (0.83 g, 5.31 mmol) dissolved in methanol (5 mL) was added drop wise to a solution of 3-phenylfuran (0.85 g, 5.90 mmol) in methanol (5 mL) and diethyl ether (3 mL) at −40° C. The resultant mixture was allowed to warm to −25° C. and stirred for a further 2 h. The reaction the mixture was quenched with ice cold water and extracted with diethyl ether. The combined organic extracts were washed with saturated bicarbonate solution, dried over anhydrous sodium sulfate and concentrated in vacuo to give the crude compound. Purification by flash chromatography over silica gel (100-200 mesh) with 2% ethyl acetate/petroleum ether as eluent afforded 2,5-dimethoxy-3-phenyl-2,5-dihydrofuran (0.65 g, 54%).

Reference Example 434

Isoquinolin-8-amine

A suspension of 5-bromo-8-nitro-isoquinoline (2.0 g, 7.93 mmol), triethylamine (1.2 g, 11.90 mmol) and Pd/C (10%; 200 mg) in dimethylformamide (10 mL) was hydrogenated at atmospheric pressure for 2 h. The reaction mixture was filtered through Celite and washed with ethyl acetate. The filtrate was concentrated in vacuo to afford isoquinolin-8-amine (700 mg, 66%) as a pale yellow solid.

Reference Examples 435 and 436

The compounds set out below were prepared in a manner analogous to Reference Example 434:

| Example | Compound |
| --- | --- |
| 435 | 2,5-Dimethoxy-3-phenyl-tetrahydrofuran |
| 436 | 3-Fluoro-4-[4-(2-pyridyl)piperazin-1-yl]aniline |

Reference Example 437

Naphthalen-2-amine

Polyphosphoric acid (7.5 g) was added to a mixture of 2-naphthoic acid (600 mg, 3.48 mmol) and hydroxylamine hydrochloride (254 mg, 3.66 mmol) at room temperature and heated slowly to 160° C. The reaction mixture was stirred for 90 min and then allowed to cool to ambient temperature and quenched with crushed ice (50 g). The resultant solid was filtered and washed with water (2×20 mL). The combined filtrate and washings were basified with 10% potassium hydroxide solution (100 mL). The precipitated solid was filtered, washed with water (2×25 mL), petroleum ether (2×20 mL), diethyl ether (2×20 mL) and dried in vacuo to afford naphthalen-2-amine (165 mg, 34%) as a light pink solid.

Reference Example 438

2-Fluoro-4-[4-(2-pyridyl)piperazin-1-yl]aniline

2-Fluoro-4-iodoaniline (750 mg, 3.16 mmol) was added to a suspension of 2-pyridyl-piperazine (568 mg, 3.48 mmol), 8-hydroxyquinoline (68 mg, 0.47 mmol) and potassium carbonate (660 mg, 4.74 mmol) in dimethylsulfoxide (5 mL) under an inert atmosphere. Cuprous iodide (94 mg, 0.47 mmol) was added and the reaction mixture was heated at 140-145° C. for 16 h. The reaction mixture was allowed to cool to ambient temperature and poured into a mixture of ammonium hydroxide, ethyl acetate and charcoal and stirred for 30 min. The organic layer was separated and the aqueous layer extracted with ethyl acetate (2×75 mL). The combined organic layers were washed with brine (100 mL), dried over sodium sulphate and concentrated to dryness in vacuo. The crude product was purified by column chromatography with silica gel (100-200 mesh) using 13% ethyl acetate in petroleum ether as eluent to afford 2-fluoro-4-[4-(2-pyridyl)piperazin-1-yl]aniline (220 mg, 26%) as an orange semi-solid.

Examples 439 to 444

The compounds set out below were prepared in a manner analogous to Reference Example 438:

| Reference Example | Compound |
| --- | --- |
| 439 | 2-Fluoro-4-morpholino-aniline |
| 440 | 2-Fluoro-4-(4-isobutylpiperazin-1-yl)aniline |
| 441 | 2-Fluoro-4-(1-piperidyl)aniline |
| 442 | 2-Fluoro-4-[4-(2-methylallyl)piperazin-1-yl]aniline |
| 443 | 4-[4-(2,2-Dimethylpropyl)piperazin-1-yl]-2-fluoro-aniline |
| 444 | 4-[4-(4,6-Dimethyl-2-pyridyl)piperazin-1-yl]-2-fluoro-aniline |

Reference Example 445

3-Fluoro-4-nitro-benzoic acid

2-Fluoro-4-methyl-1-nitro-benzene (1.0 g, 12.9 mmol) was added portion-wise to a suspension of potassium dichromate (5.04 g, 17.16 mmol) in glacial acetic acid (8 mL) follow by concentrated sulfuric acid (3.6 mL). The reaction mixture was heated to 120° C. for 2 h and then allowed to cool to ambient temperature. The reaction was quenched with crushed ice and extracted with ethyl acetate. The organic layer was washed with brine, dried over anhydrous sodium sulfate and concentrated in vacuo to afford 3-fluoro-4-nitro-benzoic acid (1.9 g, 83%) as a white solid.

Reference Example 446

3-Fluoro-4-nitro-benzoyl chloride

A stirred solution of 3-fluoro-4-nitro-benzoic acid (1.65 g, 8.91 mmol) in thionyl chloride (10 mL) was heated at reflux for 2 h. Excess thionyl chloride was evaporated in vacuo and the residue azeotroped with toluene to afford 3-fluoro-4-nitro-benzoyl chloride (1.7 g, 99%) as a brown oil.

Reference Example 447

The compound set out below was prepared in a manner analogous to Reference Example 446:

| Reference Example | Compound |
| --- | --- |
| 447 | 2-Fluoro-4-nitro-benzoyl chloride |

Reference Example 448

N-(2,2-Dimethoxyethyl)-3-fluoro-4-nitro-benzamide

To a cooled solution of amino acetaldehyde dimethyl acetal (0.91 mL, 8.30 mmol) in dry tetrahydrofuran (15 mL) was added sodium bicarbonate (769 mg, 9.16 mmol) and then a solution of 3-fluoro-4-nitro-benzoyl chloride (1.7 g, 8.30 mmol) in dry tetrahydrofuran (15 mL) was added dropwise at 0° C. over a period of 30 min. The reaction mixture was stirred overnight at ambient temperature, the solvent was removed in vacuo, and the residue was diluted with water and extracted with ethyl acetate. The organic layer was washed with water, brine, dried over anhydrous sodium sulfate and concentrated to yield N-(2,2-dimethoxyethyl)-3-fluoro-4-nitro-benzamide (2.0 g, 90%) as a brown liquid.

Reference Example 449 to 450

The compounds set out below were prepared in a manner analogous to Reference Example 448:

| Reference Example | Compound |
| --- | --- |
| 449 | N-(2,2-Dimethoxyethyl)-4-nitro-benzamide |
| 450 | N-(2,2-Dimethoxyethyl)-2-fluoro-4-nitro-benzamide |

Reference Example 451

2-(3-Fluoro-4-nitrophenyl)oxazole

Phosphorous pentoxide (4.14 g, 29.41 mmol) was added portion-wise to a solution of N-(2,2-dimethoxyethyl)-3-fluoro-4-nitro-benzamide (2.0 g, 7.35 mmol) in methane sulphonic acid (3 mL) at 0° C. over a period of 30 min. The mixture was heated to 145° C. for 5 h. The reaction mixture was allowed to cool to ambient temperature and quenched with crushed ice and then extracted with ethyl acetate. The combined organic layers were washed with water, brine, dried over anhydrous sodium sulfate and concentrated to afford the crude residue. Purification by flash chromatography with silica (60-120 mesh) using 15% ethyl acetate-petroleum ether as eluent to afforded 2-(3-fluoro-4-nitrophenyl)oxazole (500 mg, 33%) as a white solid.

Examples 452 to 453

The compounds set out below were prepared in a manner analogous to Reference Example 451:

| Reference Example | Compound |
| --- | --- |
| 452 | 2-(4-Nitrophenyl)oxazole |
| 453 | 2-(2-Fluoro-4-nitrophenyl)oxazole |

Reference Example 454

1-Ethyl-4-fluoro-5-nitro-indole 2,3-Dichloro-5,6-dicyanohydroquinone (1.02 g, 4.50 mmol) was added to the solution of 4-fluoro-5-nitro-2,3-dihydro-indole (0.47 g, 2.25 mmol) in benzene (30 mL) and the mixture was refluxed for 7 h. The solvent was removed in vacuo and the residue partitioned between ethyl acetate (100 mL) and water (100 mL). The organic phase was washed with water (3×10 mL), brine (3×10 mL), dried over anhydrous sodium sulphate and concentration in vacuo afforded the crude product. Purification by column chromatography over neutral alumina using 5% ethyl acetate in hexane as eluent afforded 1-ethyl-4-fluoro-5-nitro-indole (0.33 g, 72%) as yellow solid.

Reference Example 455

1-ethyl-4-fluoro-5-nitro-indoline

Anhydrous potassium carbonate (0.83 g, 6 mmol) was added to a solution of 4-fluoro-5-nitro-indoline (0.54 g, 3 mmol) in acetone (20 mL). The mixture was stirred at 60° C. for 10 min and ethyl bromide (0.33 mL, 4.50 mmol) added dropwise and the mixture was refluxed for a further 12 h. The mixture was concentrated in vacuo and the residue partitioned between ethyl acetate (50 mL) and water (50 mL). The organic layer was separated and the aqueous layer extracted with ethyl acetate (5×10 mL). The combined organic layers were washed with water (3×10 mL), brine (3×10 mL) and then dried over anhydrous sodium sulphate. Concentration of the organic layer afforded the crude product which was purified by column chromatography over silica gel neutral alumina mesh using 5-8% ethyl acetate in hexane as eluent to afford 1-ethyl-4-fluoro-5-nitro-indoline (0.47 g, 75%) as a yellow solid.

Reference Example 456

4-Fluoro-5-nitro-indoline

A mixture of 1-(4-fluoro-5-nitro-indolin-1-yl)ethanone (0.56 g, 2.51 mmol) and concentrated hydrochloric acid (10 mL) was refluxed for 16 h. The reaction mixture was cooled to ambient temperature and partitioned between chlorofolin (100 mL) and water (100 mL). The organic layer was separated and the aqueous layer extracted with chloroform (5×30 mL). The combined organic layers were washed with water (3×20 mL), brine (3×20 mL) and dried over anhydrous sodium sulphate. Concentration in vacuo afforded 4-fluoro-5-nitro-indoline (0.35 g, 76%) as a yellow solid.

Reference Example 457

1-(4-Fluoro-5-nitro-indolin-1-yl)ethanone

Fuming nitric acid (0.22 mL) was added dropwise to a solution of 1-(4-fluoro-indolin-1-yl)ethanone (1 g, 5.58 mmol) in concentrated sulfuric acid (10 mL) at −15° C. to 0° C. The reaction mixture was stirred at 0° C. for 2 h and then the resulting mixture was basified with sodium bicarbonate solution (100 mL). The reaction mixture was partitioned between chloroform (100 mL) and water (100 mL). The organic layer was separated and the aqueous layer was extracted with chloroform (5×30 mL). The combined organic layers were washed with water (3×20 mL), brine (3×20 mL), dried over anhydrous sodium sulphate and concentrated in vacuo to give the crude product. Purification by column chromatography over neutral alumina using 10-12% ethyl acetate in hexane as eluent afforded 1-(4-fluoro-5-nitro-indolin-1-yl) ethanone (0.56 g, 45%) as a yellow solid.

Reference Example 458

1-(4-Fluoro-indolin-1-yl)ethanone

A mixture of 4-fluoro-indoline (1 g, 7.30 mmol) and acetic anhydride (10 mL) was stirred at ambient temperature for 1 h. The resulting mixture was partitioned between ethyl acetate (100 mL) and water (100 mL). The organic layer was separated and the aqueous layer was extracted with ethyl acetate (5×30 mL). The combined organic layers were washed with water (3×20 mL), sodium bicarbonate solution (3×20 mL), brine (3×20 mL), dried over anhydrous sodium sulphate and concentrated in vacuo to afford 1-(4-fluoro-indolin-1-yl) ethanone (1 g, 77%) as a white solid.

Reference Example 459

4-Fluoroindoline

Sodium cyanoborohydride (1.86 g, 29.62 mmol) was added portion wise to a solution of 4-fluoro-1H-indole (2 g, 14.81 mmol) in acetic acid (20 mL) at 0° C. and stirred at ambient temperature for 2 h. The resulting mixture was concentrated in vacuo and partitioned between ethyl acetate (100 mL) and water (100 mL). The organic layer was separated and the aqueous layer was extracted with ethyl acetate (5×30 mL). The combined organic layers were then washed with water (5×20 mL), sodium bicarbonate solution (3×30 mL), brine (3×20 mL), dried over anhydrous sodium sulphate and concentrated in vacuo to give the crude product. Purification by column chromatography over neutral alumina using 5% ethyl acetate in hexane as eluent to afforded 4-fluoroindoline (1 g, 45%) as a brown liquid.

Reference Example 460

4-Fluoro-1H-indole

Raney Nickel (500 mg) was added to a suspension of 1-[2-(2-fluoro-6-nitro-phenyl)vinyl]pyrrolidine (6 g, 25.42 mmol) in methanol (50 mL) and hydrogenated under atmospheric pressure at ambient temperature for 20 h. The mixture was filtered through a pad of Celite and the filtrate was concentrated in vacuo to afford 4-fluoro-1H-indole (2.05 g, 60%) as a brown liquid.

Reference Example 461

1-[2-(2-Fluoro-6-nitro-phenyl)vinyl]pyrrolidine

Pyrrolidine (0.26 mL, 3.22 mmol) was added to a solution of 2-fluoro-6-nitrotoluene (5 g, 32.23 mmol) in N,N-dimethyl formamide dimethyl acetal (50 mL) and refluxed for 48 h. The resulting mixture was cooled to ambient temperature and partitioned between ethyl acetate (150 mL) and water (150 mL). The organic layer was separated and the aqueous layer extracted with ethyl acetate (5×30 mL). The combined organic layers were washed with water (3×30 mL), brine (3×20 mL), dried over anhydrous sodium sulphate and concentrated in vacuo to give 1-[2-(2-fluoro-6-nitro-phenyl)vinyl]pyrrolidine (6.08 g, 80%) as brown liquid.

Reference Example 462

2-Fluoro-4-oxazol-2-yl-aniline

A stirred solution of 2-(3-fluoro-4-nitro-phenyl)oxazole (500 mg, 2.40 mmol) in methanol (10 mL) was added to stannous chloride (2.7 g, 12.01 mmol) under nitrogen atmosphere and stirred for 16 h. The reaction mixture was diluted with water and filtered through Celite. The filtrate was basified with bicarbonate solution and extracted with ethyl acetate. The organic layer was washed with water, brine, dried over anhydrous sodium sulfate and concentrated in vacuo to afford 2-fluoro-4-oxazol-2-yl aniline (350 mg, 83%) as a yellow colour solid.

Reference Example 463

1-(Chloromethoxy)butane

Hydrogen chloride was continuously passed through a suspension of n-butanol (10 g, 135.13 mmol) and paraformaldehyde (4.06 g, 135.33 mmol) until the mixture appeared transparent with two separate layers. The upper layer was separated and fractionally distilled to afford 1-Chloromethoxy-butane (8 g, 48%).

Reference Example 464

4-Methoxybutyl-4-methylbenzenesulfonate

Triethylamine (2.91 g, 28.86 mmol) was added to the stirred solution of 4-methoxy-1-butanol (1.00 g, 9.62 mmol) in dichloromethane (15 mL) at 0° C. and stirred for 15 min. p-Toluene sulfonyl chloride (1.83 g, 9.62 mmol) was added and the mixture was warmed to ambient temperature and stirred for 2 h. The reaction mixture was quenched with ice-water and the organic layer was separated. The aqueous layer was extracted with dichloromethane (3×5 mL) and the combined organic layers were washed with saturated sodium bicarbonate, water, and brine; dried over anhydrous sodium sulphate and concentrated in vacuo. The crude product was purified by column chromatography over silica gel (60-120 mesh) with 0% to 20% ethyl acetate in petroleum ether as eluent to afford 4-methoxybutyl-4-methylbenzenesulfonate (800 mg, 32%) as a liquid.

Reference Example 465

4-(Bromomethyl)-2-methyl-oxazole

Carbon tetrabromide (1.58 g 4.77 mmol) and triphenylphosphine (1.25 g 4.77 mmol) were added to a solution of (2-methyloxazol-4-yl)methanol (450 mg 3.98 mmol) in dry acetonitrile (8 mL) and the mixture was stirred for 12 h at ambient temperature. The volatiles were removed in vacuo to afford the crude product which was used without further purification.

Reference Example 466

(2-Methyloxazol-4-yl)methanol

1M Diisobutyl aluminum hydride (23.23 mL; 23.23 mmol) was added to a solution of methyl 2-methyloxazol-4-carboxylate (1.1 g, 7.80 mmol) in dry tetrahydrofuran (25 mL) at −60° C. The resulting mixture was allowed to warm to ambient temperature and was stirred for 3 h. Saturated aqueous ammonium chloride was added and the resultant suspension was filtered and the organic layer separated. The aqueous layer was extracted with ethyl acetate (2×25 mL) and the combined organic layers washed with brine, dried over anhydrous sodium sulfate and concentrated in vacuo to afford (2-methyloxazol-4-yl)methanol (450 mg, 51%) as a semisolid.

Reference Example 467

Methyl 2-methyloxazol-4-carboxylate

Hexamethylenetetramine (11.7 g, 5.00 mmol) and 1,8-diazabicyclo(5,4,0)undec-7-ene were added to a stirred suspension of copper bromide (18.7 g, 83.85 mmol) in dichloromethane (50 mL) at 0° C. and purged with argon gas for 20 min. To the mixture was added methyl 2-methyl-4,5-dihydrooxazole-4-carboxylate (3 g, 20.97 mmol) at 0° C. The mixture was allowed to warm to ambient temperature and stirred for a further 12 h. The solvent was removed in vacuo and the resulting residue partitioned between ethyl acetate and 1:1 saturated aqueous ammonium chloride and ammonium hydroxide. The organic layer was separated and the aqueous layer extracted with ethyl acetate (2×20 mL). The combined organic layers were washed with 1:1 saturated aqueous ammonium chloride and ammonium hydroxide, 10% aqueous citric acid, saturated sodium bicarbonate solution, brine, dried over anhydrous sodium sulfate and concentrated in vacuo to afford methyl 2-methyloxazol-4-carboxylate (1.1 g, 34%) as a solid.

Reference Example 468

Methyl 2-methyl-4,5-dihydrooxazole-4-carboxylate

Triethylamine (5.86 g, 58.01 mmol) was added to a suspension of L-serine methyl hydrochloride (4.5 g, 29.03 mmol) and ethylacetimidate hydrochloride (4.3 g, 34.95 mmol) in dichloromethane (40 mL) at 0° C. over a period of 20 min. The mixture was then stirred at ambient temperature for 18 h. The suspension was filtered and washed with diethyl ether. The solid which precipitated from the filtrate was again filtered and washed with diethyl ether. The resulting filtrate was dried over anhydrous sodium sulfate and concentrated in vacuo to afford methyl 2-methyl-4,5-dihydrooxazole-4-carboxylate (3 g, 72%) as a liquid.

Example 1

2-(1,5-Dimethyl-3-phenyl-1H-pyrrol-2-yl)-N-{4-[4-(4,6-dimethyl-pyridin-2-yl)-piperazin-1-yl]-phenyl}-2-oxo-acetamide A solution of (1,5-dimethyl-3-phenyl-1H-pyrrol-2-yl)-oxo-acetyl chloride (46 g, 0.176 mol) in dry dichloromethane (300 mL) was added to a solution of 4-[4-(4,6-dimethyl-pyridin-2-yl)-piperazin-1-yl]-phenylamine (40 g, 0.140 mol) and triethylamine (14.2 g, 0.140 mol) in dry dichloromethane (300 mL) over 15 min. After stirring for 1 h the reaction mixture was quenched into water (200 mL) and the organic phase separated. The aqueous layer was extracted with dichloromethane (2×50 mL) and the combined organic layers were washed successively with water (2×200 mL), brine (2×100 mL), dried over anhydrous sodium sulfate and concentrated to give a solid. This was dissolved in acetone (580 mL) and silica gel was added (72.5 g, 100-200 mesh). The mixture was stirred at room temperature for 1 h, filtered and the solids washed with acetone (75 mL). The silica treatment was repeated a second time. The filtrate was concentrated to ~300 mL (~4 vols), activated carbon (8 g) was added and heated at reflux for 15 min. The mixture was cooled to 45-50° C. and filtered over celite, washing with acetone (75 mL). The solution was again concentrated to ~300 mL and petroleum ether (725 mL, 10 vols) was added, slowly, at reflux. The resulting suspension was cooled to room temperature, stirred for 15 min, then cooled to 0° C. and stirred for 1 h. The solid was filtered off, washed with petroleum ether (150 mL) and dried under vacuum to afford 2-(1,5-dimethyl-3-phenyl-1H-pyrrol-2-yl)-N-{4-[4-(4,6-dimethyl-pyridin-2-yl)-piperazin-1-yl]-phenyl}-2-oxo-acetamide (53.5 g, 74%) as a yellow solid.

The compounds set out below were prepared in a manner analogous to Example 1:

| Example | Compound |
|---|---|
| 2 | N-{4-[4-(4,6-Dimethyl-pyridin-2-yl)-piperazin-1-yl]-phenyl}-2-oxo-2-(1-phenyl-1H-pyrrol-2-yl)-acetamide |
| 3 | N-{4-[4-(4,6-Dimethyl-pyridin-2-yl)-piperazin-1-yl]-phenyl}-2-(5-methyl-1-phenyl-1H-pyrrol-2-yl)-2-oxo-acetamide |
| 4 | N-{4-[4-(4,6-Dimethyl-pyridin-2-yl)-piperazin-1-yl]-phenyl}-2-(5-methyl-1H-pyrrol-2-yl)-2-oxo-acetamide |
| 5 | N-{4-[4-(4,6-Dimethyl-pyridin-2-yl)-piperazin-1-yl]-phenyl}-2-(2-methyl-7-phenyl-1,2,3,4-tetrahydro-pyrrolo[1,2-a]pyrazin-6-yl)-2-oxo-acetamide |
| 6 | N-{4-[4-(4,6-Dimethyl-pyridin-2-yl)-piperazin-1-yl]-phenyl}-2-oxo-2-(2-phenyl-6,7-dihydro-5H-pyrrolizin-3-yl)-acetamide |
| 7 | N-{4-[4-(4,6-Dimethyl-pyridin-2-yl)-piperazin-1-yl]-phenyl}-2-oxo-2-(7-phenyl-3,4-dihydro-1H-pyrrolo[2,1-c][1,4]oxazin-6-yl)-acetamide |
| 8 | N-{4-[4-(4,6-Dimethyl-pyridin-2-yl)-piperazin-1-yl]-phenyl}-2-(1-isopropyl-5-methyl-3-phenyl-1H-pyrrol-2-yl)-2-oxo-acetamide |
| 9 | N-{4-[4-(4,6-Dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide |
| 10 | 2-(1,5-Dimethyl-3-phenyl-1H-pyrrol-2-yl)-N-[4-[4-(4,6-dimethyl-pyridin-2-yl)-piperazin-1-yl]-3-(3-morpholin-4-yl-propoxymethyl)-phenyl]-2-oxo-acetamide |
| 11 | N-{3-Chloro-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide |
| 12 | N-{4-[4-(4,6-Dimethyl-pyridin-2-yl)-piperazin-1-yl]-phenyl}-2-(3-furan-2-yl-1,5-dimethyl-1H-pyrrol-2-yl)-2-oxo-acetamide |
| 13 | N-{4-[4-(4,6-Dimethyl-pyridin-2-yl)-piperazin-1-yl]-phenyl}-2-(1,5-dimethyl-3-thiophen-2-yl-1H-pyrrol-2-yl)-2-oxo-acetamide |
| 14 | N-{4-[4-(4,6-Dimethyl-pyridin-2-yl)-piperazin-1-yl]-phenyl}-2-(3-isopropyl-1,5-dimethyl-1H-pyrrol-2-yl)-2-oxo-acetamide |
| 15 | N-{4-[4-(4,6-Dimethyl-pyridin-2-yl)-piperazin-1-yl]-phenyl}-2-[1,5-dimethyl-3-(tetrahydro-pyran-4-yl)-1H-pyrrol-2-yl]-2-oxo-acetamide |
| 16 | 2-(1,5-Dimethyl-3-phenyl-1H-pyrrol-2-yl)-N-naphthalen-1-yl-2-oxo-acetamide |
| 17 | N-{3-(2-Dimethylamino-ethoxymethyl)-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide |
| 18 | 2-(1,4-Dimethyl-3-phenyl-1H-pyrrol-2-yl)-N-{4-[4-(4,6-dimethyl-pyridin-2-yl)-piperazin-1-yl]-phenyl}-2-oxo-acetamide |
| 19 | 2-(1,5-Dimethyl-3-phenyl-1H-pyrrol-2-yl)-N-{4-[4-(4,6-dimethyl-pyridin-2-yl)-piperazin-1-yl]-3-[3-(4-methyl-piperazin-1-yl)-propoxymethyl]-phenyl}-2-oxo-acetamide |
| 20 | N-{4-[4-(4,6-Dimethyl-pyridin-2-yl)-piperazin-1-yl]-phenyl}-2-(5-isopropyl-1-methyl-3-phenyl-1H-pyrrol-2-yl)-2-oxo-acetamide |
| 21 | N-{2-Chloro-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide |
| 22 | 2-(1,5-Dimethyl-3-phenyl-1H-pyrrol-2-yl)-N-{4-[4-(4,6-dimethyl-pyridin-2-yl)-piperazin-1-yl]-3-hydroxy-phenyl}-2-oxo-acetamide |
| 23 | N-(2,3-Dihydro-benzofuran-4-yl)-2-(1,5-dimethyl-3-phenyl-1H-pyrrol-2-yl)-2-oxo-acetamide |
| 24 | N-{3-Chloro-4-[4-(4,6-dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide |
| 25 | N-{4-[4-(4,6-Dimethyl-pyridin-2-yl)-piperazin-1-yl]-phenyl}-2-[3-isopropyl-1-(2-methoxy-ethyl)-5-methyl-1H-pyrrol-2-yl]-2-oxo-acetamide |
| 26 | N-{2-Chloro-4-[4-(4,6-dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide |
| 27 | N-{4-[4-(4,6-Dimethyl-pyridin-2-yl)-piperazin-1-yl]-phenyl}-2-[1-(2-ethoxy-ethyl)-5-methyl-3-phenyl-1H-pyrrol-2-yl]-2-oxo-acetamide |
| 28 | N-{4-[4-(4,6-Dimethyl-pyridin-2-yl)-piperazin-1-yl]-phenyl}-2-[1-(3-methoxy-propyl)-5-methyl-3-phenyl-1H-pyrrol-2-yl]-2-oxo-acetamide |
| 29 | 2-[1-(2-Methoxy-ethyl)-5-methyl-3-phenyl-1H-pyrrol-2-yl]-2-oxo-N-quinolin-5-yl-acetamide |
| 30 | N-Isoquinolin-5-yl-2-[1-(2-methoxy-ethyl)-5-methyl-3-phenyl-1H-pyrrol-2-yl]-2-oxo-acetamide |
| 31 | 2-(1,5-Dimethyl-3-phenyl-1H-pyrrol-2-yl)-2-oxo-N-quinolin-8-yl-acetamide |
| 32 | 2-(1,5-Dimethyl-3-phenyl-1H-pyrrol-2-yl)-2-oxo-N-quinolin-5-yl-acetamide |
| 33 | 2-(1,5-Dimethyl-3-phenyl-1H-pyrrol-2-yl)-2-oxo-N-pyridin-4-yl-acetamide |
| 34 | N-{4-[4-(4,6-Dimethyl-pyridin-2-yl)-piperazin-1-yl]-phenyl}-2-(1-ethyl-5-methyl-3-phenyl-1H-pyrrol-2-yl)-2-oxo-acetamide |
| 35 | N-{4-[4-(4,6-Dimethyl-pyridin-2-yl)-piperazin-1-yl]-phenyl}-2-(5-methyl-3-phenyl-1-propyl-1H-pyrrol-2-yl)-2-oxo-acetamide |
| 36 | 2-(1-Butyl-5-methyl-3-phenyl-1H-pyrrol-2-yl)-N-{4-[4-(4,6-dimethyl-pyridin-2-yl)-piperazin-1-yl]-phenyl}-2-oxo-acetamide |
| 37 | 2-(1,5-Dimethyl-3-phenyl-1H-pyrrol-2-yl)-2-oxo-N-quinolin-3-yl-acetamide |
| 38 | 2-(1,5-Dimethyl-3-phenyl-1H-pyrrol-2-yl)-2-oxo-N-[4-(4-pyridin-2-yl-piperazin-1-yl)-phenyl]-acetamide |
| 39 | 2-(1,5-Dimethyl-3-phenyl-1H-pyrrol-2-yl)-N-{4-[4-(6-methyl-pyridin-2-yl)-piperazin-1-yl]-phenyl}-2-oxo-acetamide |
| 40 | 2-(1,5-Dimethyl-3-phenyl-1H-pyrrol-2-yl)-N-{4-[4-(4-methyl-pyridin-2-yl)-piperazin-1-yl]-phenyl}-2-oxo-acetamide |
| 41a | N-{4-[4-(4,6-Dimethyl-pyridin-2-yl)-piperazin-1-yl]-phenyl}-2-oxo-2-(2-phenyl-6,7,8,9-tetrahydro-5H-pyrrolo[1,2-a]azepin-3-yl)-acetamide |

| Example | Compound |
|---|---|
| 41b | N-{4-[4-(4,6-Dimethyl-pyridin-2-yl)-piperazin-1-yl]-phenyl}-2-oxo-2-(1-phenyl-6,7,8,9-tetrahydro-5H-pyrrolo[1,2-a]azepin-3-yl)-acetamide |
| 42 | N-Isoquinolin-8-yl-2-[1-(2-methoxy-ethyl)-5-methyl-3-phenyl-1H-pyrrol-2-yl]-2-oxo-acetamide |
| 43 | 2-(1,5-Dimethyl-3-phenyl-1H-pyrrol-2-yl)-N-isoquinolin-8-yl-2-oxo-acetamide |
| 44 | 2-(1,5-Dimethyl-3-phenyl-1H-pyrrol-2-yl)-N-naphthalen-2-yl-2-oxo-acetamide |
| 45 | N-{4-[4-(4,6-Dimethyl-pyridin-2-yl)-piperazin-1-yl]-phenyl}-2-(1-methyl-3-phenyl-1H-pyrrol-2-yl)-2-oxo-acetamide |
| 46 | N-{4-[4-(4,6-Dimethyl-pyridin-2-yl)-piperazin-1-yl]-phenyl}-2-(1-methyl-4-phenyl-1H-pyrrol-2-yl)-2-oxo-acetamide |
| 47 | N-{4-[4-(4,6-Dimethyl-pyridin-2-yl)-piperazin-1-yl]-phenyl}-2-[1-(2-methoxy-ethyl)-3-phenyl-1H-pyrrol-2-yl]-2-oxo-acetamide |
| 48 | 2-(1-Benzyl-5-methyl-3-phenyl-1H-pyrrol-2-yl)-N-{4-[4-(4,6-dimethyl-pyridin-2-yl)-piperazin-1-yl]-phenyl}-2-oxo-acetamide |
| 49 | 2-(1,5-Dimethyl-3-phenyl-1H-pyrrol-2-yl)-N-[5-(4-methyl-piperazin-1-yl)-naphthalen-1-yl]-2-oxo-acetamide |
| 50 | N-{4-[4-(4,6-Dimethyl-pyridin-2-yl)-piperazin-1-yl]-phenyl}-2-(5-methyl-3-phenyl-1H-pyrrol-2-yl)-2-oxo-acetamide |
| 51 | 2-(1,5-Dimethyl-3-phenyl-1H-pyrrol-2-yl)-N-{4-[4-(4,6-dimethyl-pyridin-2-yl)-piperazin-1-yl]-3-methyl-phenyl}-2-oxo-acetamide |
| 52 | (2-{4-[4-(4,6-Dimethyl-pyridin-2-yl)-piperazin-1-yl]-phenylaminooxalyl}-5-methyl-3-phenyl-pyrrol-1-yl)-acetic acid methyl ester |
| 53 | N-{4-[4-(4,6-Dimethyl-pyridin-2-yl)-piperazin-1-yl]-phenyl}-2-(5-ethyl-1-methyl-3-phenyl-1H-pyrrol-2-yl)-2-oxo-acetamide |
| 54 | N-{4-[4-(4,6-Dimethyl-pyridin-2-yl)-piperazin-1-yl]-phenyl}-2-[5-ethyl-1-(2-methoxy-ethyl)-3-phenyl-1H-pyrrol-2-yl]-2-oxo-acetamide |
| 55 | 2-{4-[4-(4,6-Dimethyl-pyridin-2-yl)-piperazin-1-yl]-phenylaminooxalyl}-5-methyl-3-phenyl-pyrrole-1-carboxylic acid ethyl ester |
| 56 | 2-{4-[4-(4,6-Dimethyl-pyridin-2-yl)-piperazin-1-yl]-phenylaminooxalyl}-5-methyl-3-phenyl-pyrrole-1-carboxylic acid methyl ester |
| 57 | 2-[3-(2-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide |
| 58 | 2-[4-(2-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide |
| 59 | 2-[3-(4-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide |
| 60 | 2-[1-(2-Methoxy-ethyl)-5-methyl-3-phenyl-1H-pyrrol-2-yl]-2-oxo-N-phenyl-1-acetamide |
| 61 | (2-{4-[4-(4,6-Dimethyl-pyridin-2-yl)-piperazin-1-yl]-phenylaminooxalyl}-pyrrol-1-yl)-acetic acid methyl ester |
| 62 | N-{4-[4-(4,6-Dimethyl-pyridin-2-yl)-piperazin-1-yl]-phenyl}-2-(1-methoxymethyl-5-methyl-3-phenyl-1H-pyrrol-2-yl)-2-oxo-acetamide |
| 63 | N-{4-[4-(4,6-Dimethyl-pyridin-2-yl)-piperazin-1-yl]-phenyl}-2-(1-methoxymethyl-3-phenyl-1H-pyrrol-2-yl)-2-oxo-acetamide |
| 65 | 2-[1-(2-Acetylamino-ethyl)-5-methyl-3-phenyl-1H-pyrrol-2-yl]-N-{4-[4-(4,6-dimethyl-pyridin-2-yl)-piperazin-1-yl]-phenyl}-2-oxo-acetamide |
| 66 | N-{4-[4-(4,6-Dimethyl-pyridin-2-yl)-piperazin-1-yl]-phenyl}-2-[1-(2-hydroxy-ethyl)-3-phenyl-1H-pyrrol-2-yl]-2-oxo-acetamide |
| 67 | N-{4-[4-(4,6-Dimethyl-pyridin-2-yl)-piperazin-1-yl]-phenyl}-2-[1-(2-methoxy-ethyl)-3-thiophen-2-yl-1H-pyrrol-2-yl]-2-oxo-acetamide |
| 68 | N-{4-[4-(4,6-Dimethyl-pyridin-2-yl)-piperazin-1-yl]-phenyl}-2-[3-isobutyl-1-(2-methoxy-ethyl)-1H-pyrrol-2-yl]-2-oxo-acetamide |
| 69 | (2-{4-[4-(4,6-Dimethyl-pyridin-2-yl)-piperazin-1-yl]-phenylaminooxalyl}-5-methyl-3-phenyl-pyrrol-1-yl)-acetic acid ethyl ester |
| 70 | 2-[3-(3-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide |
| 71 | 2-[4-(3-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide |
| 73 | (2-{4-[4-(4,6-Dimethyl-pyridin-2-yl)-piperazin-1-yl]-phenylaminooxalyl}-3-phenyl-pyrrol-1-yl)-acetic acid ethyl ester |
| 74 | (2-{4-[4-(4,6-Dimethyl-pyridin-2-yl)-piperazin-1-yl]-phenylaminooxalyl}-3-phenylpyrrol-1-yl)-acetic acid methyl ester |
| 77 | (2-{4-[4-(4,6-Dimethyl-pyridin-2-yl)-piperazin-1-yl]-phenylaminooxalyl}-5-methyl-3-phenyl-pyrrol-1-yl)-acetic acid isopropyl ester |
| 78 | N-{4-[4-(4,6-Dimethyl-pyridin-2-yl)-piperizin-1-yl]-phenyl}-2-[5-isopropyl-1-(2-methoxy-ethyl)-3-phenyl-1H-pyrrol-2-yl]-2-oxo-acetamide |
| 79 | 2-(1,5-Dimethyl-3-phenyl-1H-pyrrol-2-yl)-2-oxo-N-quinolin-5-yl-acetamide |

-continued

| Example | Compound |
|---|---|
| 80 | N-{4-[4-(4,6-Dimethyl-pyridin-2-yl)-piperazin-1-yl]-phenyl}-2-[3-(2-methoxy-ethyl)-5-methyl-1-phenyl-1H-pyrrol-2-yl]-2-oxo-acetamide |
| 81 | 2-[1-(2-Methoxy-ethyl)-3-phenyl-1H-pyrrol-2-yl]-2-oxo-N-phenyl-acetamide |
| 82 | 2-[1-(2-Methoxy-ethyl)-3-phenyl-1H-pyrrol-2-yl]-2-oxo-N-propyl-acetamide |
| 83 | N-{4-[4-(4,6-Dimethyl-pyridin-2-yl)-piperazin-1-yl]-phenyl}-2-[3-isopropyl-1-(2-methoxy-ethyl)-1H-pyrrol-2-yl]-2-oxo-acetamide |
| 84 | 2-[1-(2-Dimethylamino-ethyl)-3-phenyl-1H-pyrrol-2-yl]-N-{4-[4-(4,6-dimethyl-pyridin-2-yl)-piperazin-1-yl]-phenyl}-2-oxo-acetamide |
| 85 | 2-[1-(2-Dimethylamino-ethyl)-4-phenyl-1H-pyrrol-2-yl]-N-{4-[4-(4,6-dimethyl-pyridin-2-yl)-piperazin-1-yl]-phenyl}-2-oxo-acetamide |
| 86 | 2-[1-(2-Dimethylamino-ethyl)-5-methyl-3-phenyl-1H-pyrrol-2-yl]-N-{4-[4-(4,6-dimethyl-pyridin-2-yl)-piperazin-1-yl]-phenyl}-2-oxo-acetamide |
| 87 | (2-{4-[4-(4,6-Dimethyl-pyridin-2-yl)-piperazin-1-yl]-phenylaminooxalyl}-3-thiophen-2-yl-pyrrol-1-yl)-acetic acid methyl ester |
| 88 | (2-{4-[4-(4,6-Dimethyl-pyridin-2-yl)-piperazin-1-yl]-phenylaminooxalyl}-[3-isopropyl-pyrrol-1-yl)-acetic acid methyl ester |
| 89 | (2-{4-[4-(4,6-Dimethyl-pyridin-2-yl)-piperazin-1-yl]-phenylaminooxalyl}-3-isobutyl-pyrrol-1-yl)-acetic acid methyl ester |
| 90 | N-{4-[4-(4,6-Dimethyl-pyridin-2-yl)-piperazin-1-yl]-phenyl}-2-(4-fluoro-1,5-dimethyl-3-phenyl-1H-pyrrol-2-yl)-2-oxo-acetamide |
| 91 | N-{4-[4-(4,6-Dimethyl-pyridin-2-yl)-piperazin-1-yl]-phenyl}-2-(5-methyl-3-phenyl-1-pyridin-2-ylmethyl-1H-pyrrol-2-yl)-2-oxo-acetamide |
| 92 | N-{2-Chloro-4-[4-(4,6-dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide |
| 93 | N-{4-[4-(4,6-Dimethyl-pyridin-2-yl)-piperazin-1-yl]-phenyl}-2-(5-methyl-3-phenyl-1-pyridin-3-ylmethyl-1H-pyrrol-2-yl)-2-oxo-acetamide |
| 94 | N-{4-[4-(4,6-Dimethyl-pyridin-2-yl)-piperazin-1-yl]-phenyl}-2-[4-fluoro-1-(2-methoxy-ethyl)-5-methyl-3-phenyl-1H-pyrrol-2-yl]-2-oxo-acetamide |
| 95 | 2-(1,5-Dimethyl-3-phenyl-1H-pyrrol-2-yl)-N-[2-fluoro-4-(4-pyridin-2-yl-piperazin-1-yl)-phenyl]-2-oxo-acetamide |
| 96 | N-[2-Fluoro-4-(4-pyridin-2-yl-piperazin-1-yl)-phenyl]-2-[1-(2-methoxy-ethyl)-5-methyl-3-phenyl-1H-pyrrol-2-yl]-2-oxo-acetamide |
| 97 | N-{4-[4-(4,6-Dimethyl-pyridin-2-yl)-piperazin-1-yl]-phenyl}-2-[1-(2-isopropoxy-ethyl)-5-methyl-3-phenyl-1H-pyrrol-2-yl]-2-oxo-acetamide |
| 98 | (2-{2-Chloro-4-[4-(4,6-dimethyl-pyridin-2-yl)-piperazin-1-yl]-phenylaminooxalyl}-5-methyl-3-phenyl-pyrrol-1-yl)-acetic acid methyl ester |
| 99 | 2-(1,5-Dimethyl-3-phenyl-1H-pyrrol-2-yl)-2-oxo-N-(6-pyrrolidin-1-yl-pyridin-3-yl)-acetamide |
| 100 | 2-(1,5-Dimethyl-3-phenyl-1H-pyrrol-2-yl)-N-[2-fluoro-4-oxazol-2-yl-phenyl)-2-oxo-acetamide |
| 101 | 2-(1,5-Dimethyl-3-phenyl-1H-pyrrol-2-yl)-N-(2-fluoro-4-morpholin-4-yl-phenyl)-2-oxo-acetamide |
| 102 | N-{4-[4-(4,6-Dimethyl-pyridin-2-yl)-piperazin-1-yl]-phenyl}-2-(5-methyl-3-phenyl-1-pyridin-4-ylmethyl-1H-pyrrol-2-yl)-2-oxo-acetamide |
| 103 | 2-[1-(2-Methoxy-ethyl)-5-methyl-3-pheny-1H-pyrrol-2-yl]-N-{4-[4-(5-morpholin-4-ylmethyl-pyridin-2-yl)-piperazin-1-yl]-phenyl}-2-oxo-acetamide |
| 104 | 2-[3-Cyclobutyl-1-(2-methoxy-ethyl)-1H-pyrrol-2-yl]-N-{4-[4-(4,6-dimethyl-pyridin-2-yl)-piperizin-1-yl]-phenyl}-2-oxo-acetamide |
| 105 | 2-(1,5-Dimethyl-3-phenyl-1H-pyrrol-2-yl)-N-[2-fluoro-4-(4-isobutyl-piperazin-1-yl)-phenyl]-2-oxo-acetamide |
| 106 | 2-(1,5-Dimethyl-3-phenyl-1H-pyrrol-2-yl)-N-(2-fluoro-4-piperidin-1-yl-phenyl)-2-oxo-acetamide |
| 107 | (3-Cyclobutyl-2-{4-[4-(4,6-dimethyl-pyridin-2-yl)-piperazin-1-yl]-phenylaminooxalyl}-pyrrol-1-yl)-acetic acid methyl ester |
| 108 | 2-(1,5-Dimethyl-3-phenyl-1H-pyrrol-2-yl)-N-{2-fluoro-4-[4-(2-methyl-allyl)-piperazin-1-yl]-phenyl}-2-oxo-acetamide |
| 109 | N-{2-Fluoro-4-[4-(2-methyl-allyl)-piperazin-1-yl]-phenyl}-2-[1-(2-methoxy-ethyl)-5-methyl-3-phenyl-1H-pyrrol-2-yl]-2-oxo-acetamide |
| 110 | N-[2-Fluoro-4-(4-isobutyl-piperazin-1-yl)-phenyl]-2-[1-(2-methoxy-ethyl)-5-methyl-3-phenyl-1H-pyrrol-2-yl]-2-oxo-acetamide |
| 111 | (2-{4-[4-(4,6-Dimethyl-pyridin-2-yl)-piperazin-1-yl]-2-fluoro-phenylaminooxalyl}-5-methyl-3-phenyl-pyrrol-1-yl)-acetic acid methyl ester |
| 112 | 2-(1,5-Dimethyl-3-phenyl-1H-pyrrol-2-yl)-N-{4-[4-(2,2-dimethyl-propyl)-piperazin-1-yl]-2-fluoro-phenyl}-2-oxo-acetamide |

-continued

| Example | Compound |
|---|---|
| 113 | N-{4-[4-(2,2-Dimethyl-propyl)-piperazin-1-yl]-2-fluoro-phenyl}-2-[1-(2-methoxy-ethyl)-5-methyl-3-phenyl-1H-pyrrol-2-yl]-2-oxo-acetamide |
| 114 | N-(2-Fluoro-4-piperidin-1-yl-phenyl)-2-[1-(2-methoxy-ethyl)-5-methyl-3-phenyl-1H-pyrrol-2-yl]-2-oxo-acetamide |
| 115 | 2-(1,5-Dimethyl-3-phenyl-1H-pyrrol-2-yl)-N-(3-fluoro-4-piperidin-1-yl-phenyl)-2-oxo-acetamide |
| 116 | 2-(1,5-Dimethyl-3-phenyl-1H-pyrrol-2-yl)-N-[3-fluoro-4-(4-pyridin-2-yl-piperazin-1-yl)-phenyl]-2-oxo-acetamide |
| 117 | N-(2-Fluoro-4-morpholin-4-yl-phenyl)-2-[1-(2-methoxy-ethyl)-5-methyl-3-phenyl-1H-pyrrol-2-yl]-2-oxo-acetamide |
| 118 | 2-(1,5-Dimethyl-3-phenyl-1H-pyrrol-2-yl)-N-[3-fluoro-4-(4-isobutyl-piperazin-1-yl)-phenyl]-2-oxo-acetamide |
| 119 | N-(3-Fluoro-4-piperdin-1-yl-phenyl)-2-[1-(2-methoxy-ethyl)-5-methyl-3-phenyl-1H-pyrrol-2-yl]-2-oxo-acetamide |
| 120 | 2-(1,5-Dimethyl-3-phenyl-1H-pyrrol-2-yl)-N-{4-[4-(5-morpholin-4-ylmethyl-pyridin-2-yl)-piperazin-1-yl]-phenyl}-2-oxo-acetamide |
| 121 | 2-[1-(2-Methoxy-ethyl)-4-phenyl-1H-pyrrol-2-yl]-2-oxo-N-propyl-acetamide |
| 122 | (2-{4-[4-(4,6-Dimethyl-pyridin-2-yl)-piperazin-1-yl]-phenylaminooxalyl}-4-phenyl-pyrrol-1-yl)-acetic acid methyl ester |
| 123 | N-{4-[4-(4,6-Dimethyl-pyridin-2-yl)-piperazin-1-yl]-2-fluoro-phenyl}-2-[1-(2-methoxy-ethyl)-5-methyl-3-phenyl-1H-pyrrol-2-yl]-2-oxo-acetamide |
| 124 | N-{4-[4-(4,6-Dimethyl-pyridin-2-yl)-piperizin-1-yl]-phenyl}-2-[1-methyl-3-phenyl-5-propyl-1H-pyrrol-2-yl]-2-oxo-acetamide |
| 125 | N-{4-[4-(4,6-Dimethyl-pyridin-2-yl)-piperazin-1-yl]-phenyl}-2-(5-ethyl-1-methoxymethyl-3-phenyl-1H-pyrrol-2-yl)-2-oxo-acetamide |
| 127 | 2-(1,5-Dimethyl-3-phenyl-1H-pyrrol-2-yl)-N-(5-fluoro-naphthalen-1-yl)-2-oxo-acetamide |
| 132 | N-{4-[4-(4,6-Dimethyl-pyridin-2-yl)-piperazin-1-yl]-phenyl}-2-(1-ethoxymethyl-5-methyl-3-phenyl-1H-pyrrol-2-yl)-2-oxo-acetamide |
| 133 | N-{4-[4-(4,6-Dimethyl-pyridin-2-yl)-piperazin-1-yl]-phenyl}-2-[5-methyl-1-(2-methylsulfanyl-ethyl)-3-phenyl-1H-pyrrol-2-yl]-2-oxo-acetamide |
| 134 | N-{4-[4-(4,6-Dimethyl-pyridin-2-yl)-piperazin-1-yl]-phenyl}-2-[5-methyl-1-(2-phenoxy-ethyl)-3-phenyl-1H-pyrrol-2-yl]-2-oxo-acetamide |
| 135 | 2-(1-Butoxymethyl-5-methyl-3-phenyl-1H-pyrrol-2-yl)-N-{4-[4-(4,6-dimethyl-pyridin-2-yl)-piperazin-1-yl]-phenyl}-2-oxo-acetamide |
| 136 | N-{4-[4-(4,6-Dimethyl-pyridin-2-yl)-piperazin-1-yl]-phenyl}-2-[1-(3-ethoxy-propyl)-5-methy-3-phenyl-1H-pyrrol-2-yl]-2-oxo-acetamide |
| 138 | N-{4-[4-(4,6-Dimethyl-pyridin-2-yl)-piperazin-1-yl]-phenyl}-2-[1-(2-methoxy-ethoxymethyl)-5-methyl-3-phenyl-1H-pyrrol-2-yl]-2-oxo-acetamide |
| 139 | N-{4-[4-(4,6-Dimethyl-pyridin-2-yl)-piperazin-1-yl]-phenyl}-2-(5-methyl-3-phenyl-1-propoxymethyl-1H-pyrrol-2-yl)-2-oxo-acetamide |
| 140 | N-{4-[4-(4,6-Dimethyl-pyridin-2-yl)-piperazin-1-yl]-phenyl}-2-[5-methyl-3-phenyl-1-(2-propoxy-ethyl)-1H-pyrrol-2-yl]-2-oxo-acetamide |
| 141 | N-{4-[4-(4,6-Dimethyl-pyridin-2-yl)-piperazin-1-yl]-phenyl}-2-[1-(4-methoxy-but-2-enyl)-5-methyl-3-phenyl-1H-pyrrol-2-yl]-2-oxo-acetamide |
| 142 | N-{4-[4-(4,6-Dimethyl-pyridin-2-yl)-piperazin-1-yl]-phenyl}-2-[1-(4-methoxy-butyl)-5-methy-3-phenyl-1H-pyrrol-2-yl]-2-oxo-acetamide |
| 143 | 2-(1,5-Dimethyl-3-phenyl-1H-pyrrol-2-yl)-2-oxo-N-(4-piperidin-1-yl-phenyl)-acetamide |
| 148 | 2-(1,5-Dimethyl-3-phenyl-1H-pyrrol-2-yl)-N-[3-fluoro-4-oxazole-2-yl-phenyl]-2-oxo-acetamide |
| 154 | 2-(1,5-Dimethyl-3-phenyl-1H-pyrrol-2-yl)-N-(4-morpholin-4-yl-phenyl)-2-oxo-acetamide |

Example 126

N-(3-Fluoro-4-morpholin-4-yl-phenyl)-2-[1-(2-methoxy-ethyl)-5-methyl-3-phenyl-1H-pyrrol-2-yl]-2-oxo-acetamide Oxalyl chloride (0.19 g, 1.53 mmol) was added to a solution of 1-(2-methoxy-ethyl)-2-methyl-4-phenyl-1H-pyrrole (0.30 g, 1.39 mmol) in chloroform (5 mL) at 0° C. and slowly warmed the ambient temperature to RT over 30 min. Completion of reaction and removal of excess oxalyl chloride in vacuo afforded the intermediate acid chloride, [1-(2-methoxy-ethyl)-5-methyl-3-phenyl-1H-pyrrol-2-yl]-oxo-acetyl chloride which was taken in chloroform (5 mL). This was then added to a solution of 3-fluoro-4-morpholin-4-yl-phenylamine (0.19 g, 0.97 mmol) in chloroform (5 mL) with triethyl amine (0.28 g, 2.78 mmol). The reaction was stirred for 30 min at ambient temperature and then diluted with water and extracted into chloroform. Combined organic extracts were washed with saturated bicarbonate solution, dried over anhydrous sodium sulfate and stirred over neutral alumina for 10 min. The mixture was filtered and concentrated in vacuo to afford N-(3-fluoro-4-morpholin-4-yl-phenyl)-2-[1-(2-methoxy-ethyl)-5-methyl-3-phenyl-1H-pyrrol-2-yl]-2-oxo-acetamide (0.26 g, 40%) as pale yellow solid.

The compounds set out below were prepared in a manner analogous to Example 126:

| Example | Compound |
|---|---|
| 128 | 2-(1,5-Dimethyl-3-phenyl-1H-pyrrol-2-yl)-N-(1-ethyl-4-fluoro-1H-indol-5-yl)-2-oxo-acetamide |
| 129 | N-{4-[4-(4,6-Dimethyl-pyridin-2-yl)-piperazin-1-yl]-phenyl}-2-[5-(2-methoxy-ethyl)-1-methyl-3-phenyl-1H-pyrrol-2-yl]-2-oxo-acetamide |
| 137 | N-{4-[4-(4,6-Dimethyl-pyridin-2-yl)-piperazin-1-yl]-phenyl}-2-(5-methyl-1-methylsulfanylmethyl-3-phenyl-1H-pyrrol-2-yl)-2-oxo-acetamide |
| 144 | N-[4-(4-Benzyl-piperazin-1-yl)-phenyl]-2-(1,5-dimethyl-3-phenyl-1H-pyrrol-2-yl)-2-oxo-acetamide |
| 145 | 2-(1,5-Dimethyl-3-phenyl-1H-pyrrol-2-yl)-N-[4-(4-isobutyryl-piperazin-1-yl)-phenyl]-2-oxo-acetamide |
| 146 | N-{4-[4-(4,6-Dimethyl-pyridin-2-yl)-piperazin-1-yl]-phenyl}-2-[5-methyl-1-(2-methyl-oxazol-4-ylmethyl)-3-phenyl-1H-pyrrol-2-yl]-2-oxo-acetamide |
| 147 | 2-(1,5-Dimethyl-3-phenyl-1H-pyrrol-2-yl)-N-(4-oxazol-2-yl-phenyl)-2-oxo-acetamide |
| 149 | 2-[1-(2-Methoxy-ethyl)-5-methyl-3-phenyl-1H-pyrrol-2-yl]-N-(4-oxazol-2-yl-phenyl)-2-oxo-acetamide |
| 150 | 2-(1,5-Dimethyl-3-phenyl-1H-pyrrol-2-yl)-N-{4-[4-(1,2-dimethyl-propyl)-piperazin-1-yl]-phenyl}-2-oxo-acetamide |
| 151 | 2-(1,5-Dimethyl-3-phenyl-1H-pyrrol-2-yl)-N-{4-[4-(2-methoxy-1-methyl-ethyl)-piperazin-1-yl]-phenyl}-2-oxo-acetamide |
| 152 | 2-(1,5-Dimethyl-3-phenyl-1H-pyrrol-2-yl)-N-{4-[4-(2-furan-2-yl-1-methyl-ethyl)-piperazin-1-yl]-phenyl}-2-oxo-acetamide |
| 153 | 2-(1,5-Dimethyl-3-phenyl-1H-pyrrol-2-yl)-2-oxo-N-[4-(5-piperdin-1-ylmethyl-oxazol-2-yl)-phenyl]-acetamide |

Example 64

N-{4-[4-(4,6-Dimethyl-pyridin-2-yl)-piperazin-1-yl]-phenyl}-2-[1-(2-hydroxy-ethyl)-5-methyl-3-phenyl-1H-pyrrol-2-yl]-2-oxo-acetamide Lithium hydroxide monohydrate (30 mg, 0.70 mmol) was added to a suspension of acetic acid 2-(2-{4-[4-(4,6-dimethyl-pyridin-2-yl)-piperazin-1-yl]-phenylaminooxalyl}-5-methyl-3-phenyl-pyrrol-1-yl)-ethyl ester (340 mg, 0.59 mmol) in methanol (10 mL) at room temperature and stirred for 60 min. The solvent was evaporated in vacuo and the resulting residue dissolved in water (20 mL). The solution was acidified with 1N acetic acid to adjust the pH to ~6 to 7 and the aqueous layer was extracted with ethyl acetate (2×25 mL). The combined organic layer was washed with water (2×30 mL), brine (2×30 mL), dried over anhydrous sodium sulphate and concentrated in vacuo to yield the crude compound. Purification by preparative TLC using 2.5% of methanol in chloroform as eluent afforded N-{4-[4-(4,6-dimethyl-pyridin-2-yl)-piperazin-1-yl]-phenyl}-2-[1-(2-hydroxy-ethyl)-5-methyl-3-phenyl-1H-pyrrol-2-yl]-2-oxo-acetamide (230 mg, 73%) as an orange solid.

Example 72

N-{4-[4-(4,6-Dimethyl-pyridin-2-yl)-piperazin-1-yl]-phenyl}-2-[1-(2-methoxy-ethyl)-3-thiophen-3-yl-1H-pyrrol-2-yl]-2-oxo-acetamide Diisopropylethylamine (0.40 mL, 2.17 mmol), (2-(7-Aza-1H-benzotriazole-1-yl)-1,1,3,3-tetramethyluronium hexafluorophosphate) (0.28 mg, 0.72 mmol) was added to a solution of [1-(2-methoxy-ethyl)-3-thiophen-3-yl-1H-pyrrol-2-yl]-oxo-acetic acid (200 mg, 0.72 mmol) in dry dichloromethane at room temperature and the reaction mixture stirred for 1 h. 4-[4-(4,6-Dimethyl-pyridin-2-yl)-piperazin-1-yl]-phenylamine (160 mg, 0.56 mmol) was added and the mixture was then heated in a sealed tube at 90° C. for 18 h. The reaction mixture was cooled to room temperature, washed with water and brine. The organic layer was dried over anhydrous sodium sulfate and evaporated under reduced pressure to give crude compound which was purified by preparative HPLC to afford N-{4-[4-(4,6-dimethyl-pyridin-2-yl)piperazin-1-yl]-phenyl}-2-[1-(2-methoxy-ethyl)-3-thiophen-3-yl-1H-pyrrol-2-yl]-2-oxo-acetamide (80 mg, 20%) as a solid.

The compounds set out below were prepared in a manner analogous to Example 72:

| Example | Compound |
|---|---|
| 130 | N-{4-[4-(4,6-Dimethyl-pyridin-2-yl)-piperazin-1-yl]-phenyl}-2-(5-methoxymethyl-1-methyl-3-phenyl-1H-pyrrol-2-yl)-2-oxo-acetamide |
| 131 | 2-(1,5-Bis-methoxymethyl-3-phenyl-1H-pyrrol-2-yl)-N-{4-[4-(4,6-dimethyl-pyridin-2-yl)-piperazine-1-yl]-phenyl}-2-oxo-acetamide |

Example 75

2-(1-Carbamoylmethyl-3-phenyl-1H-pyrrol-2-yl)-N-{4-[4-(4,6-dimethyl-pyridin-2-yl)-piperazin-1-yl]-phenyl}-2-oxo-acetamide (2-{4-[4-(4,6-Dimethyl-pyridin-2-yl)-piperazin-1-yl]-phenylaminooxalyl}-3-phenyl-pyrrol-1-yl)acetic ethyl acid ester (100 mg, 0.17 mmol) and methanolic ammonia (5 mL) were heated at 60° C. in a sealed tube for 2 h. On completion of the reaction the volatiles were removed in vacuo to give the crude compound, which was purified by preparative HPLC to afford 2-(1-carbamoylmethyl-3-phenyl-1H-pyrrol-2-yl)-N-{4-[4-(4,6-dimethyl-pyridin-2-yl)-piperazin-1-yl]-phenyl}-2-oxo-acetamide (70 mg, 74%) as a yellow powder.

The compound set out below was prepared in a manner analogous to Example 75:

| Example | Compound |
|---|---|
| 76 | N-{4-[4-(4,6-Dimethyl-pyridin-2-yl)-piperazin-1-yl]-phenyl}-2-(1-methylcarbamoylmethyl-3-phenyl-1H-pyrrol-2-yl)-2-oxo-acetamide |

| Example | NMR Data | MS Spectrum |
|---|---|---|
| 1 | $^1$H NMR (400 MHz, CDCl$_3$) δ 8.20 (s, 1H), 7.31-7.28 (m, 2H), 7.27-7.21 (m, 4H), 7.09 (d, 2H), 6.84 (d, 2H), 6.38 (s, 1H), 6.31 (s, 1H), 6.13 (s, 1H), 3.81 (s, 3H), 3.65 (t, 4H), 3.22 (t, 4H), 2.37 (s, 3H), 2.32 (s, 3H), 2.23 (s, 3H) | 508 (M + H) |
| 2 | $^1$H NMR (400 MHz, CDCl$_3$) δ 9.00 (s, 1H), 8.23 (dd, 1H), 7.53 (d, 2H), 7.47-7.45 (m, 3H), 7.31-7.29 (dd, 2H), 7.16 (t, 1H), 6.95 (d, 2H), 6.44 (s, 1H), 6.40 (s, 1H), 6.30 (s, 1H), 3.65 (t, 4H), 3.24 (t, 4H), 2.38 (s, 3H), 2.24 (s, 3H) | 480 (M + H) |
| 3 | $^1$H NMR (400 MHz, CDCl$_3$) δ 9.01 (s, 1H), 8.21 (d, 1H), 7.53-7.50 (m, 5H), 7.23-7.21 (m, 2H), 6.94 (d, 2H), 6.38 (s, 1H), 6.31 (s, 1H), 6.23 (d, 1H), 3.69 (s, 4H), 3.26 (s, 4H), 2.38 (s, 3H), 2.23 (s, 3H), 2.09 (s, 3H) | 494 (M + H) |
| 4 | $^1$H NMR (400 MHz, CDCl$_3$): δ 11.4 (broad s, 1H), 9.35 (broad s, 1H), 7.60 (d, 2H), 7.33 (broad s, 1H), 6.98 (d, 2H), 6.39 (s, 1H), 6.32 (s, 1H), 6.13 (m, 1H), 3.68 (t, 4H), 3.28 (t, 4H), 2.38 (s, 6H), 2.24 (s, 3H) | 418 (M + H) |
| 5 | $^1$H NMR (400 MHz, CDCl$_3$) δ 8.11 (s, 1H), 7.33-7.32 (m, 2H), 7.26-7.22 (m, 3H), 7.09 (d, 2H), 6.84 (d, 2H), 6.38 (s, 1H), 6.31 (s, 1H), 6.08 (s, 1H), 4.39 (t, 2H), 3.69 (s, 2H), 3.35 (t, 4H), 3.22 (t, 4H), 2.83 (t, 2H), 2.49 (s, 3H), 2.37 (s, 3H), 2.23 (s, 3H) | 549 (M + H) |
| 6 | $^1$H NMR (400 MHz, CDCl$_3$) δ 8.16 (s, 1H), 7.37 (d, 2H), 7.35-7.25 (m, ~3H, solvent overlap), 7.18 (d, 2H), 6.85 (d, 2H), 6.38 (s, 1H), 6.31 (s, 1H), 6.10 (s, 1H), 4.37 (qn, 2H), 3.66 (t, 4H), 3.23 (t, 4H), 2.92 (t, 2H), 2.59-2.52 (m, 2H), 2.38 (s, 3H), 2.23 (s, 3H) | 520 (M + H) |
| 7 | $^1$H NMR (400 MHz, CDCl$_3$) δ 8.13 (s, 1H), 7.33-7.24 (m, ~5H, solvent overlap), 7.11 (d, 2H), 6.84 (d, 2H), 6.39 (s, 1H), 6.31 (s, 1H), 6.10 (s, 1H), 4.91 (s, 2H), 4.37 (t, 2H), 4.06 (t, 2H), 3.66 (t, 4H), 3.23 (t, 4H), 2.37 (s, 3H), 2.23 (s, 3H) | 536 (M + H) |
| 8 | $^1$H NMR (400 MHz, CDCl$_3$) δ 8.26 (s, 1H), 7.31-7.29 (m, 2H), 7.26-7.21 (m, 3H), 7.09 (d, 2H), 6.85 (d, 2H), 6.41 (s, 1H), 6.33 (s, 1H), 6.10 (s, 1H), 3.68 (t, 4H), 3.24 (t, 4H), 2.47 (s, 3H), 2.40 (m, 1H), 2.39 (s, 3H), 2.25 (s, 3H), 1.60 (d, 6H) | 536 (M + H) |
| 9 | $^1$H NMR (400 MHz, CDCl$_3$) δ 8.06 (s, 1H), 7.32 (d, 2H), 7.24-7.21 (m, 3H), 7.06 (d, 2H), 6.82 (d, 2H), 6.38 (s, 1H), 6.31 (s, 1H), 6.13 (s, 1H), 4.38 (t, 2H), 3.73 (t, 2H), 3.65 (t, 4H), 3.32 (s, 3H), 3.22 (t, 4H), 2.38 (s, 3H), 2.37 (s, 3H), 2.23 (s, 3H) | 552 (M + H) |
| 10 | $^1$H NMR (400 MHz, CDCl$_3$): δ 8.19 (s, 1H), 7.30 (d, 2H), 7.24-7.20 (m, 3H), 7.14-7.10 (m, 2H), 6.71 (d, 1H), 6.35 (s, 1H), 6.25 (s, 1H), 6.13 (s, 1H), 3.97 (t, 2H), 3.82 (s, 3H), 3.71 (t, 4H), 3.53-3.50 (m, 6H), 2.56 (m, 4H), 2.51 (t, 2H), 2.45 (m, 4H), 2.35 (s, 3H), 2.33 (s, 3H), 2.21 (s, 3H), 1.95 (qn, 2H) | 665 (M + H) |
| 11 | $^1$H NMR (400 MHz, CDCl$_3$) δ 8.18 (s, 1H), 7.29-7.22 (m, ~5H, solvent overlap), 7.20 (d, 1H), 7.04 (dd, 1H), 6.92 (d, 1H), 6.38 (s, 1H), 6.31 (s, 1H), 6.14 (s, 1H), 3.82 (s, 3H), 3.67 (t, 4H), 3.09 (t, 4H), 2.37 (s, 3H), 2.33 (s, 3H), 2.23 (s, 3H) | 541 (M − H) |
| 12 | $^1$H NMR (400 MHz, CDCl$_3$) δ 8.40 (s, 1H), 7.45 (d, 2H), 7.20 (s, 1H), 6.93 (d, 2H), 6.48 (d, 1H), 6.39-6.37 (m, 2H), 6.32 (s, 1H), 6.20 (s, 1H), 3.77 (s, 3H), 3.67 (t, 4H), 3.26 (t, 4H), 2.38 (s, 3H), 2.30 (s, 3H), 2.23 (s, 3H) | 498 (M + H) |
| 13 | $^1$H NMR (400 MHz, CDCl$_3$) δ 8.25 (s, 1H), 7.29-7.26 (m, ~2H, solvent overlap), 7.22 (d, 1H), 6.98 (d, 1H), 6.93-6.88 (m, 3H), 6.39 (s, 1H), 6.32 (s, 1H), 6.17 (s, 1H), 3.78 (s, 3H), 3.66 (t, 4H), 3.24 (t, 4H), 2.38 (s, 3H), 2.31 (s, 3H), 2.23 (s, 3H) | 514 (M + H) |
| 14 | $^1$H NMR (400 MHz, CD$_3$OD) δ 7.53 (d, 2H), 7.03 (d, 2H), 6.48 (s, 1H), 6.44 (s, 1H), 6.04 (s, 1H), 3.80 (s, 3H), 3.63 (t, 4H), 3.26 (m, 4H), 3.15 (m, 1H), 2.33 (s, 3H), 2.27 (s, 3H), 2.24 (s, 3H), 1.15 (d, 6H) | 472 (M − H) |
| 15 | $^1$H NMR (400 MHz, CDCl$_3$) δ 8.43 (s, 1H), 7.57 (d, 2H), 6.99 (d, 2H), 6.40 (s, 1H), 6.33 (s, 1H), 6.00 (s, 1H), 3.98 (dd, 2H), 3.69-3.67 (m, 7H), 3.42 (t, 2H), 3.29 (m, 4H), 3.13 (m, 1H), 2.38 (s, 3H), 2.26 (s, 3H), 2.24 (s, 3H), 1.79-1.69 (m, 4H) | 516 (M + H) |
| 16 | $^1$H NMR (400 MHz, CDCl$_3$) δ 8.88 (broad s, 1H), 7.90 (d, 1H), 7.84 (d, 1H), 7.63 (d, 1H), 7.62-7.49 (m, 2H), 7.40-7.34 (m, 4H), 7.27-7.23 (m, ~3H, solvent overlap), 6.16 (s, 1H), 3.87 (s, 3H), 2.35 (s, 3H) | 369 (M + H) |

-continued

| Example | NMR Data | MS Spectrum |
|---|---|---|
| 17 | ¹H NMR (400 MHz, CDCl₃) δ 8.21 (s, 1H), 7.29 (m, 2H), 7.26-7.22 (m, 3H), 7.14-7.09 (m, 2H), 6.71 (d, 1H), 6.34 (s, 1H), 6.25 (s, 1H), 6.13 (s,1H), 4.03 (t, 2H), 3.81 (s, 3H), 3.53 (m, 6H), 2.72 (t, 2H), 2.56 (t, 4H), 2.36 (s, 3H), 2.33 (s, 6H), 2.32 (s, 3H), 2.21 (s, 3H) | 609 (M + H) |
| 18 | ¹H NMR (400 MHz, CDCl₃) δ 7.98 (s, 1H), 7.29-7.23 (m, 5H), 7.01 (d, 2H), 6.83 (d, 2H), 6.79 (s, 1H), 6.39 (s, 1H), 6.31 (s, 1H), 3.89 (s, 3H), 3.66 (t, 4H), 3.22 (t, 4H), 2.38 (s, 3H), 2.23 (s, 3H), 2.01 (s, 3H) | 508 (M + H) |
| 19 | ¹H NMR (400 MHz, CDCl₃) δ 8.18 (s, 1H), 7.30 (d, 2H), 7.24-7.20 (m, 3H), 7.13-7.10 (m, 2H), 6.71 (d, 1H), 6.34 (s, 1H), 6.25 (s, 1H), 6.13 (s, 1H), 3.96 (t, 2H), 3.81 (s, 3H), 3.53 (m, 6H), 2.57-2.40 (broad m, ~14H), 2.36 (s, 3H), 2.33 (s, 3H), 2.29 (s, 3H), 2.21 (s, 3H), 1.95 (qn, 2H) | 678 (M + H) |
| 20 | ¹H NMR (400 MHz, CDCl₃) δ 8.21 (s, 1H), 7.32-7.30 (m, 2H), 7.26-7.21 (m, 3H), 7.09 (d, 2H), 6.84 (d, 2H), 6.38 (s, 1H), 6.32 (s, 1H), 6.16 (s, 1H), 3.85 (s, 3H), 3.66 (t, 4H), 3.22 (t, 4H), 3.02 (m, 1H), 2.37 (s, 3H), 2.23 (s, 3H), 1.32 (d, 6H) | 536 (M + H) |
| 21 | ¹H NMR (400 MHz, CDCl₃) δ 8.64 (s, 1H), 7.49 (d, 1H), 7.30 (d, 2H), 7.21-7.19 (m, 3H), 6.92 (d, 1H), 6.70 (dd, 1H), 6.39 (s, 1H), 6.31 (s, 1H), 6.13 (s, 1H), 3.83 (s, 3H), 3.65 (t, 4H), 3.22 (t, 4H), 2.37 (s, 3H), 2.33 (s, 3H), 2.23 (s, 3H) | 540 (M − H) |
| 22 | ¹H NMR (400 MHz, CDCl₃): δ 8.26 (s, 1H), 7.30-7.22 (m, ~5H, solvent overlap), 7.05 (d, 1H), 6.84 (s, 1H), 6.72 (d, 1H), 6.38 (s, 1H), 6.32 (s, 1H), 6.14 (s, 1H), 3.81 (s, 3H), 3.65 (m, 4H), 3.60 (s, 1H), 2.94 (m, 4H), 2.37 (s, 3H), 2.33 (s, 3H), 2.21 (s,3H) | 524 (M + H) |
| 23 | ¹H NMR (400 MHz, CDCl₃) δ 8.17 (s, 1H), 7.31-7.26 (m, 5H), 6.98 (t, 1H), 6.81 (d, 1H), 6.55 (d, 1H), 6.13 (s, 1H), 4.55 (d, 2H), 3.81 (s, 3H), 3.03 (t, 2H), 2.34 (s, 3H) | 361 (M + H) |
| 24 | ¹H NMR (400 MHz, CDCl₃) δ 8.08 (s, 1H), 7.30-7.09 (m, ~5H, solvent overlap), 7.16 (d, 1H), 7.01 (d, 1H), 6.91 (d, 1H), 6.38 (s, 1H), 6.31 (s, 1H), 6.14 (s, 1H), 4.40 (t, 2H), 3.73 (t, 2H), 3.69 (m, 4H), 3.33 (s, 3H), 3.09 (m, 4H), 2.39 (s, 3H), 2.37 (s, 3H), 2.23 (s, 3H) | 586 (M + H) |
| 25 | ¹H NMR (400 MHz, CDCl₃) δ 8.25 (s, 1H), 7.55 (d, 2H), 6.98 (d, 2H), 6.39 (s, 1H), 6.32 (s, 1H), 5.98 (s, 1H), 4.31 (t, 2H), 3.69-3.64 (m, 6H), 3.29-3.24 (m, 8H), 2.38 (s, 3H), 2.30 (s, 3H), 2.24 (s, 3H), 1.18 (d, 6H) | 518 (M + H) |
| 26 | ¹H NMR (400 MHz, CDCl₃) δ 8.54 (d, 1H), 7.46 (d, 1H), 7.31 (d, 2H), 7.25-7.18 (m, 3H), 6.91 (d, 1H), 6.70 (dd, 1H), 6.39 (s, 1H), 6.31 (s, 1H), 6.13 (s, 1H), 4.41 (t, 2H), 3.75 (t, 2H), 3.65 (m, 4H), 3.33 (s, 3H), 3.22 (m, 4H), 2.39 (s, 3H), 2.37 (s, 3H), 2.23 (s, 3H) | 586 (M + H) |
| 27 | ¹H NMR (400 MHz, CDCl₃) δ 8.13 (s, 1H), 7.32 (d, 2H), 7.25-7.21 (m, 3H), 7.06 (d, 2H), 6.82 (d, 2H), 6.38 (s, 1H), 6.31 (s, 1H), 6.13 (s, 1H), 4.39 (t, 2H), 3.77 (t, 2H), 3.65 (t, 4H), 3.47 (q, 2H), 3.22 (t, 4H), 2.39 (s, 3H), 2.37 (s, 3H), 2.23 (s, 3H), 1.14 (t, 3H) | 564 (M − H) |
| 28 | ¹H NMR (400 MHz, CDCl₃) δ 8.15 (s, 1H), 7.31 (d, 2H), 7.24-7.21 (m, 3H), 7.07 (d, 2H), 6.83 (d, 2H), 6.38 (s, 1H), 6.31 (s, 1H), 6.12 (s, 1H), 4.32 (t, 2H), 3.65 (t, 4H), 3.41 (t, 2H), 3.35 (s, 3H), 3.22 (t, 4H), 2.37-2.36 (m, 6H), 2.36 (s, 3H), 2.04 (m, 2H) | 564 (M − H) |
| 29 | ¹H NMR (400 MHz, CDCl₃) δ 8.92 (m, 1H), 8.74 (broad s, 1H), 8.12 (d, 1H), 7.91 (d, 1H), 7.57 (t, 1H), 7.42-7.34 (m, 4H), 7.29-7.26 (m, 3H), 6.17 (s, 1H), 4.44 (t, 2H), 3.78 (t, 2H), 3.35 (s, 3H), 2.50 (s, 3H) | 412 (M − H) |
| 30 | ¹H NMR (400 MHz, CDCl₃) δ 9.24 (s, 1H), 8.78 (broad s, 1H), 8.56 (d, 1H), 7.75 (d, 1H), 7.62 (m, 2H), 7.46 (t, 1H), 7.36-7.34 (m, 2H), 7.26-7.23 (m, 3H), 6.17 (s, 1H), 4.44 (t, 2H), 3.79 (t, 2H), 3.35 (s, 3H), 2.24 (s, 3H) | 412 (M − H) |
| 31 | ¹H NMR (400 MHz, CDCl₃) δ 8.86 (d, 1H), 8.15-8.09 (dd, 2H), 7.49-7.44 (m, 2H), 7.38 (t, 1H), 7.31-7.26 (m, 3H), 7.05-7.03 (m, 3H), 6.13 (s, 1H), 3.90 (s, 3H), 2.35 (S, 3H) | 368 (M − H) |
| 32 | ¹H NMR (400 MHz, CDCl₃) δ 8.93 (d, 1H), 8.81 (broad s, 1H), 8.14 (d, 1H), 7.92 (d, 1H), 7.58 (t, 1H), 7.43-7.34 (m, 4H), 7.29-7.28 (m, 3H), 6.16 (s, 1H), 3.87 (s, 3H), 2.36 (s, 3H) | 370 (M + H) |
| 33 | ¹H NMR (400 MHz, CDCl₃) δ 8.42 (d, 1H), 7.26-7.22 (m, 3H), 7.21-7.19 (m, 4H), 7.12 (d, 2H), 6.15 (s, 1H), 3.83 (s, 3H), 2.34 (s, 3H) | 320 (M + H) |

-continued

| Example | NMR Data | MS Spectrum |
|---|---|---|
| 34 | ¹H NMR (400 MHz, CDCl₃) δ 8.14 (s, 1H), 7.32-7.21 (m, 5H), 7.07 (d, 2H), 6.83 (d, 2H), 6.38 (s, 1H), 6.31 (s, 1H), 6.12 (s, 1H), 4.26 (q, 2H), 3.65 (t, 4H), 3.22 (t, 4H), 2.37 (s, 3H), 2.36 (s, 3H), 2.33 (s, 3H), 1.41 (t, 3H) | 520 (M − H) |
| 35 | ¹H NMR (400 MHz, CDCl₃) δ 10.17 (s, 1H), 7.22 (d, 2H), 7.10-7.03 (m, 5H), 6.79 (d, 2H), 6.47 (s, 1H), 6.37 (s, 1H), 6.08 (s, 1H), 4.18 (t, 2H), 3.55 (m, 4H), 3.11 (m, 4H), 2.33 (s, 3H), 2.25 (s, 3H), 2.17 (s, 3H), 1.70 (q, 2H), 0.91 (t, 3H) | 534 (M − H) |
| 36 | ¹H NMR (400 MHz, CDCl₃) δ 8.14 (s, 1H), 7.30 (d, 2H), 7.26-7.20 (m, 3H), 7.07 (d, 2H), 6.83 (d, 2H), 6.38 (s, 1H), 6.31 (s, 1H), 6.12 (s, 1H), 4.19 (t, 2H), 3.65 (t, 4H), 3.22 (t, 4H), 2.37 (s, 3H), 2.35 (s, 3H), 2.23 (s, 3H), 1.17 (m, 2H), 1.43 (m, 2H), 0.98 (t, 3H) | 550 (M + H) |
| 37 | ¹H NMR (400 MHz, CDCl₃) δ 8.60 (s, 1H), 8.49 (s, 1H), 8.15 (s, 1H), 8.02 (d, 1H), 7.69 (d, 1H), 7.62 (t, 1H), 7.51 (t, 1H), 7.31 (d, 2H), 7.21-7.16 (m, 3H), 6.17 (s, 1H), 3.86 (s, 3H), 2.36 (s, 3H) | 370 (M + H) |
| 38 | ¹H NMR (400 MHz, CDCl₃) δ 8.20 (m, 2H), 7.50 (t, 1H), 7.31 (d, 2H), 7.23 (m, 3H), 7.10 (d, 2H), 6.84 (d, 2H), 6.70-6.64 (m, 2H), 6.13 (s, 1H), 3.82 (s, 3H), 3.68 (t, 4H), 3.23 (t, 4H), 2.33 (s, 3H) | 480 (M + H) |
| 39 | ¹H NMR (400 MHz, CDCl₃) δ 8.19 (s, 1H), 7.39 (t, 1H), 7.31 (d, 2H), 7.21-7.31 (m, 3H), 7.10 (d, 2H), 6.84 (d, 2H), 6.52-6.47 (dd, 2H), 6.13 (s, 1H), 3.82 (s, 3H), 3.67 (t, 4H), 3.23 (t, 4H), 2.41 (s, 3H), 2.33 (s, 3H) | 494 (M + H) |
| 40 | ¹H NMR (400 MHz, CDCl₃) δ 8.19 (s, 1H), 8.07 (d, 1H), 7.31 (d, 2H), 7.25-7.21 (m, 3H), 7.10 (d, 2H), 6.85 (d, 2H), 6.50 (d, 2H), 6.13 (s, 1H), 3.82 (s, 3H), 3.67 (t, 4H), 3.23 (t, 4H), 2.33 (s, 3H), 2.28 (s, 3H) | 494 (M + H) |
| 41a | ¹H NMR (400 MHz, CDCl₃) δ 8.26 (s, 1H), 7.31-7.29 (d, 2H), 7.24-7.21 (m, 2H), 7.11 (d, 2H), 6.84 (d, 2H), 6.38 (s, 1H), 6.31 (s, 1H), 6.09 (s, 1H), 4.39 (s, 3H), 3.65 (t, 4H), 3.22 (t, 4H), 2.81 (m, 2H), 2.37 (s, 3H), 2.31 (s, 3H), 1.85 (broad s, 4H), 1.74 (broad s, 2H) | 548 (M + H) |
| 41b | ¹H NMR (400 MHz, CDCl₃) δ 9.10 (s, 1H), 8.09 (s, 1H), 7.60 (d, 3H), 7.41-7.26 (m, H), 6.98 (d, 2H), 6.39 (s, 1H), 6.32 (s, 3H), 4.78 (broad s, 2H), 3.68 (t, 4H), 3.27 (t, 4H), 2.93 (m, 2H), 2.38 (s, 3H), 2.23 (s, 3H), 1.89-1.83 (m, 4H), 1.73 (m, 2H) | 548 (M + H) |
| 42 | ¹H NMR (400 MHz, CDCl₃) δ 9.38 (broad s, 1H), 8.98 (broad s, 1H), 8.57 (broad s, 1H), 7.64-7.51 (m, 4H), 7.35 (d, 2H), 7.24-7.19 (m, 3H), 6.17 (s, 1H), 4.45 (t, 2H), 3.78 (t, 2H), 3.35 (s, 3H), 3.41 (s, 3H) | 414 (M + H) |
| 43 | ¹H NMR (400 MHz, CDCl₃) δ 9.41 (s, 1H), 9.06 (s, 1H), 8.57 (d, 1H), 7.64-7.53 (m, 4H), 7.34-7.33 (m, 2H), 7.31-7.18 (m, 3H), 6.17 (s, 1H), 3.88 (s, 3H), 2.36 (s, 3H) | 368 (M − H) |
| 44 | ¹H NMR (400 MHz, CDCl₃) δ 8.45 (s, 1H), 7.56-7.68 (m, 4H), 7.44-7.34 (m, 2H), 7.32 (d, 2H), 7.24-7.15 (m, 4H), 6.15 (s, 1H), 3.84 (s, 3H), 2.34 (s, 3H) | 367 (M − H) |
| 45 | ¹H NMR (400 MHz, CDCl₃) δ 9.11 (s, 1H), 8.18 (s, 1H), 7.32 (d, 2H), 7.26-7.23 (merged with solvent, ~3H), 7.12 (d, 2H), 6.94 (d, 1H), 6.84 (d, 2H), 6.38 (s, 1H), 6.31 (s, 1H), 3.91 (s, 3H), 3.66 (t, 4H), 3.23 (t, 4H), 2.37 (s, 3H), 2.23 (s, 3H) | 494 (M + H) |
| 46 | ¹H NMR (400 MHz, CDCl₃) δ 9.10 (s, 1H), 8.38 (d, 1H), 7.62 (d, 2H), 7.55 (d, 2H), 7.36 (t, 2H), 7.31 (s, 1H), 7.25-7.22 (merged with solvent, ~1H), 7.00 (d, 2H), 6.40 (s, 1H), 6.32 (s, 1H), 4.05 (s, 3H), 3.69 (t, 4H), 3.29 (t, 4H), 2.38 (s, 3H), 2.24 (s, 3H) | 494 (M + H) |
| 47 | ¹H NMR (400 MHz, CDCl₃) δ 8.14 (s, 1H), 7.32 (d, 2H), 7.28-7.22 (m, 3H), 7.11-7.09 (m, 3H), 6.84 (d, 2H), 6.38 (s, 1H), 6.33-6.31 (m, 2H), 4.43 (t, 2H), 3.72 (t, 2H), 3.65 (t, 4H), 3.34 (s, 3H), 3.22 (t, 4H), 2.37 (s, 3H), 2.23 (s, 3H) | 538 (M + H) |
| 48 | ¹H NMR (400 MHz, CDCl₃) δ 8.15 (s, 1H), 7.36-7.29 (m, 6H), 7.27-7.23 (m, 3H), 7.06 (d, 4H), 6.82 (d, 2H), 6.38 (s, 1H), 6.30 (s, 1H), 6.20 (s, 1H), 5.51 (s, 1H), 3.64 (t, 4H), 3.21 (t, 4H), 2.37 (s, 3H), 2.26 (s, 3H), 2.23 (s, 3H) | 583 (M − H) |
| 49 | ¹H NMR (400 MHz, CDCl₃) δ 8.85 (s, 1H), 8.01 (d, 1H), 7.61 (d, 1H), 7.46 (t, 1H), 7.35-7.32 (m, 4H), 7.25-7.23 (m, 3H), 7.12 (d, 1H), 6.15 (s, 1H), 3.86 (s, 3H), 3.13 (broad s, 4H), 2.70 (broad s, 4H), 2.41 (s, 3H), 2.35 (s, 3H) | 468 (M + H) |
| 50 | ¹H NMR (400 MHz, CDCl₃) δ 11.93 (broad s, 1H), 9.42 (s, 1H), 7.61 (d, 2H), 7.55 (d, 2H), 7.42-7.32 (m, 3H), 6.98 (d, 2H), 6.39 (s, 1H), 6.32 (s, 1H), 6.21 (d, 1H), 3.68 (t, 4H), 3.29 (t, 4H), 2.41 (s, 3H), 2.38 (s, 3H), 2.24 (s, 3H) | 494 (M + H) |

-continued

| Example | NMR Data | MS Spectrum |
|---|---|---|
| 51 | $^1$H NMR (400 MHz, CDCl$_3$) δ 8.17 (s, 1H), 7.32-7.23 (m, 4H), 6.97 (d, 2H), 6.89 (d, 2H), 6.38 (s, 1H), 6.31 (s, 1H), 6.13 (s, 1H), 3.82 (s, 3H), 3.63 (t, 4H), 2.95 (t, 4H), 2.37 (s, 3H), 2.33 (s, 3H), 2.26 (s, 3H), 2.23 (s, 3H) | 522 (M + H) |
| 52 | $^1$H NMR (400 MHz, CDCl$_3$) δ 8.05 (s, 1H), 7.34-7.32 (m, 2H), 7.25-7.24 (m, 3H), 7.06 (d, 2H), 6.82 (d, 2H), 6.38 (s, 1H), 6.31 (s, 1H), 6.20 (s, 1H), 4.93 (s, 2H), 3.84 (s, 3H), 3.65 (t, 4H), 3.21 (t, 4H), 2.37 (s, 3H), 2.31 (s, 3H), 2.23 (s, 3H) | 566 (M + H) |
| 53 | $^1$H NMR (400 MHz, CDCl$_3$) δ 8.23 (s, 1H), 7.31 (d, 2H), 7.27-7.24 (m, 3H), 7.10 (d, 2H), 6.84 (d, 2H), 6.39 (s, 1H), 6.31 (s, 1H), 6.16 (s, 1H), 3.82 (s, 3H), 3.65 (t, 4H), 3.23 (t, 4H), 2.67 (q, 2H), 237 (s, 3H), 2.23 (s, 3H), 1.32 (t, 3H) | 522 (M + H) |
| 54 | $^1$H NMR (400 MHz, CDCl$_3$) δ 8.13 (s, 1H), 7.36-7.33 (m, 3H), 7.27-7.25 (m, 2H), 7.08 (d, 2H), 6.84 (d, 2H), 6.40 (s, 1H), 6.32 (s, 1H), 6.19 (s, 1H), 4.42 (t, 2H), 3.74 (t, 2H), 3.67 (t, 4H), 3.34 (s, 3H), 3.23 (t, 4H), 2.27 (m, 2H), 2.39 (s, 3H), 2.25 (s, 3H), 1.34 (t, 3H) | 566 (M + H) |
| 55 | $^1$H NMR (400 MHz, CDCl$_3$) δ 9.21 (s, 1H), 7.40 (m, 5H), 6.85 (d, 2H), 6.59 (d, 2H), 6.39 (s, 1H), 6.30 (s, 1H), 6.05 (d, 1H), 4.16 (q, 2H), 3.63 (m, 4H), 3.30 (m, 4H), 2.37 (s, 6H), 2.23 (s, 3H), 1.15 (t, 3H) | 566 (M + H) |
| 56 | $^1$H NMR (400 MHz, CDCl$_3$) δ 9.21 (s, 1H), 7.39 (s, 5H), 6.85 (d, 2H), 6.61 (d, 2H), 6.39 (s, 1H), 6.33 (s, 1H), 6.05 (s, 1H), 3.71 (s, 3H), 3.65 (t, 4H), 3.30 (t, 4H), 2.38 (s, 6H), 2.23 (s, 3H) | 552 (M + H) |
| 57 | $^1$H NMR (400 MHz, CDCl$_3$) δ 8.01 (s, 1H), 7.33-7.28 (m, 2H), 7.19-7.09 (m, 5H), 6.84 (d, 2H), 6.39 (s, 1H), 6.32 (s, 1H), 6.28 (d, 1H), 4.48 (t, 2H), 3.75 (t, 2H), 3.66 (t, 4H), 3.35 (s, 3H), 3.23 (t, 4H), 2.38 (s, 3H), 2.23 (s, 3H) | 572 (M + H) |
| 58 | $^1$H NMR (400 MHz, CDCl$_3$) δ 9.10 (s, 1H), 8.46 (d, 1H), 8.21 (d, 2H), 7.55-7.52 (m, 1H), 7.44 (dd, 1H), 7.30-7.27 (m, 1H), 7.21 (t, 1H), 7.09 (d, 2H), 6.41 (s, 1H), 6.34 (s, 1H), 4.64 (t, 2H), 3.74 (t, 2H), 3.70 (t, 4H), 3.34 (s, 3H), 3.30 (t, 4H), 2.39 (s, 3H), 2.25 (s, 3H) | 572 (M + H) |
| 59 | $^1$H NMR (400 MHz, CDCl$_3$) δ 8.20 (s, 1H), 7.26-7.23 (m, 4H), 7.15-7.12 (d, 2H), 7.08 (d, 1H), 6.88 (d, 2H), 6.39 (s, 1H), 6.31 (s, 1H), 6.29 (d, 1H), 4.42 (t, 2H), 3.71-7.65 (m, 6H), 3.33 (s, 3H), 3.26 (m, 4H), 2.37 (s, 3H), 2.24 (s, 3H) | 572 (M + H) |
| 60 | $^1$H NMR (400 MHz, CDCl$_3$) δ 8.22 (s, 1H), 7.32-7.30 (dd, 2H), 7.24-7.16 (m, 7H), 7.07-7.04 (m, 1H), 6.14 (s, 1H), 4.41-4.39 (t, 2H), 3.75-3.72 (t, 2H), 3.27 (s, 3H), 2.39 (s, 3H) | 363 (M + H) |
| 61 | $^1$H NMR (400 MHz, CDCl$_3$) δ 9.01 (s, 1H), 8.21 (dd, 1H), 7.57 (d, 2H), 7.03 (s, 1H), 6.97 (d, 2H), 6.39 (s, 1H), 6.35-6.32 (m, 2H), 5.04 (s, 2H), 3.80 (s, 3H), 3.68 (t, 4H), 3.27 (t, 4H), 2.38 (s, 3H), 2.23 (s, 3H) | 476 (M + H) |
| 62 | $^1$H NMR (400 MHz, CDCl$_3$) δ 8.18 (s, 1H), 7.32-7.30 (m, 3H), 7.28-7.26 (m, 2H), 7.09 (d, 2H), 6.84 (d, 2H), 6.38 (s, 1H), 6.31 (S, 1H), 6.20 (s, 1H), 5.60 (s, 2H), 3.65 (t, 4H), 3.40 (s, 3H), 3.22 (t, 4H), 2.42 (s, 3H), 2.37 (s, 3H), 2.23 (s, 3H) | 538 (M + H) |
| 63 | $^1$H NMR (400 MHz, CDCl$_3$) δ 8.27 (s, 1H), 7.36-7.34 (m, 2H), 7.30-7.26 (m, 3H), 7.17-7.14 (m, 3H), 6.86 (d, 2H), 6.41-6.39 (m, 2H), 6.32 (s, 1H), 5.57 (s, 2H), 3.66 (t, 4H), 3.34 (s, 3H), 3.23 (t, 4H), 2.38 (s, 3H), 2.24 (s, 3H) | 522 (M − H) |
| 64 | $^1$H NMR (400 MHz, CDCl$_3$) δ 8.14 (s, 1H), 7.30 (m, 2H), 7.26-7.24 (m, 3H), 7.02 (d, 2H), 6.83 (d, 2H), 6.74 (s, 1H), 6.39 (s, 1H), 6.30 (d, 1H), 6.17 (d, 1H), 4.37 (t, 2H), 4.00 (d, 2H), 3.64 (m, 4H), 3.22 (m, 4H), 2.39 (s, 3H), 2.37 (s, 3H), 2.23 (s, 3H) | 538 (M + H) |
| 65 | $^1$H NMR (400 MHz, CDCl$_3$) δ 8.21 (s, 1H), 7.30-7.28 (m, 2H), 7.26-7.22 (m, 3H), 7.05 (d, 2H), 6.82 (d, 2H), 6.39 (s, 1H), 6.31 (s, 1H), 6.24 (broad s, 1H), 6.16 (s, 1H), 4.37 (t, 2H), 3.66-3.58 (m, 6H), 3.23 (m 4H), 2.37 (s, 6H), 2.23 (s, 3H), 1.94 (s, 3H) | 579 (M + H) |
| 66 | $^1$H NMR (400 MHz, CDCl$_3$) δ 8.16 (s, 1H), 7.50 (d, 1H), 7.33-7.31 (m, 3H), 7.27-7.25 (m, 2H), 7.10-7.07 (m, 2H), 6.84 (d, 2H), 6.75 (s, 1H), 6.39-6.36 (m, 2H), 6.30 (m, 1H), 4.41 (t, 2H), 3.97 (t, 2H), 3.64 (m, 4H), 3.34-3.17 (m, 4H), 2.37 (s, 3H), 2.23 (s, 3H) | 524 (M + H) |
| 67 | $^1$H NMR (400 MHz, CDCl$_3$) δ 8.20 (s, 1H), 7.26-7.21 (m, 3H), 7.06 (d, 1H), 6.99 (d, 1H), 6.93-6.87 (m, 3H), 6.38 (s, 1H), 6.35 (d, 1H), 6.31 (s, 1H), 4.40 (t, 2H), 3.70-3.65 (m, 6H), 3.32 (s, 3H), 3.24 (t, 4H), 2.37 (s, 3H), 2.23 (s, 3H) | 544 (M + H) |

-continued

| Example | NMR Data | MS Spectrum |
|---|---|---|
| 68 | ¹H NMR (400 MHz, CDCl₃) δ 8.29 (s, 1H), 7.56 (d, 2H), 6.98 (t, 3H), 6.39 (s, 1H), 6.32 (s, 1H), 6.05 (d, 1H), 4.37 (t, 2H), 3.68 (m, 4H), 3.62 (t, 2H), 3.29 (s, 3H), 3.27 (m, 4H), 2.63 (d, 2H), 2.38 (s, 3H), 2.24 (s, 3H), 1.80 (m, 1H), 0.84 (d, 6H) | 518 (M + H) |
| 69 | ¹H NMR (400 MHz, CDCl₃) δ 8.03 (broad s, 1H), 7.34-7.31 (m, 2H), 7.25-7.23 (m, 3H), 7.06 (d, 2H), 6.83 (d, 2H), 6.38 (s, 1H), 6.31 (s, 1H), 6.19 (s, 1H), 4.92 (s, 2H), 4.30 (q, 2H), 3.65 (t, 4H), 3.21 (t, 4H), 2.37 (s, 3H), 2.31 (s, 3H), 2.23 (s, 3H), 1.33 (t, 3H) | 580 (M + H) |
| 70 | ¹H NMR (400 MHz, CDCl₃) δ 8.22 (broad s, 1H), 7.33 (s, 1H), 7.20-7.16 (m, 5H), 7.07 (d, 1H), 6.87 (d, 2H), 6.38 (s, 1H), 6.31 (d, 2H), 4.42 (t, 2H), 3.72-3.65 (m, 6H), 3.33 (s, 3H), 3.24 (t, 4H), 2.37 (s, 3H), 2.23 (s, 3H) | 572 (M + H) |
| 71 | ¹H NMR (400 MHz, CDCl₃) δ 9.07 (s, 1H), 8.44 (d, 1H), 7.61 (d, 2H), 7.55 (s, 1H), 7.44 (d, 2H), 7.29 (d, 1H), 7.19 (d, 1H), 6.99 (d, 1H), 6.39 (s, 1H), 6.32 (s, 1H), 4.59 (t, 2H), 3.72-3.67 (m, 6H), 3.33 (s, 3H), 3.29 (t, 4H), 2.38 (s, 3H), 2.24 (s, 3H) | 572 (M + H) |
| 72 | ¹H NMR (400 MHz, CDCl₃) δ 8.19 (s, 1H), 7.26 (q, 3H), 7.17 (d, 1H), 7.12 (d, 1H), 7.08 (d, 1H), 6.90 (s, 1H), 6.88 (s, 1H), 6.39 (s, 1H), 6.31 (t, 2H), 4.42 (t, 2H), 3.69 (m, 6H), 3.33 (s, 3H), 3.24 (t, 4H), 2.38 (s, 3H), 2.24 (s, 3H) | 544 (M + H) |
| 73 | ¹H NMR (400 MHz, CDCl₃) δ 8.05 (s, 1H), 7.35 (d, 2H), 7.29 (m, 3H), 7.07 (d, 2H), 6.99 (d, 1H), 6.83 (d, 2H), 6.39 (d, 2H), 6.31 (s, 1H), 4.94 (s, 2H), 4.28 (q, 2H), 3.65 (t, 4H), 3.22 (t, 4H), 2.37 (s, 3H), 2.23 (s, 3H), 1.32 (t, 3H) | 566 (M + H) |
| 74 | ¹H NMR (400 MHz, CDCl₃) δ 8.02 (s, 1H), 7.34 (m, 3H), 7.25 (m, 2H), 7.07 (d, 2H), 6.99 (d, 1H), 6.83 (d, 2H), 6.38 (d, 2H), 6.30 (s, 1H), 4.95 (s, 2H), 3.83 (s, 3H), 3.65 (m, 4H), 3.22 (m, 4H), 2.37 (s, 3H), 2.32 (s, 3H) | 552 (M + H) |
| 75 | ¹H NMR (400 MHz, CDCl₃) δ 8.24 (s, 1H), 7.33-7.25 (m, 5H), 7.07 (m, 3H), 6.83 (d, 2H), 6.43 (d, 1H), 6.39 (s, 1H), 6.31 (s, 1H), 6.03 (s, 1H), 5.63 (s, 1H), 4.88 (s, 2H), 3.65 (t, 4H), 3.22 (t, 4H), 2.38 (s, 3H), 2.23 (s, 3H) | 537 (M + H) |
| 76 | ¹H NMR (400 MHz, CDCl₃) δ 8.16 (s, 1H), 7.34-7.27 (m, 4H), 7.08 (m, 3H), 6.84 (d, 2H), 6.43 (d, 1H), 6.39 (s, 1H), 6.31 (s, 1H), 6.01 (s, 1H), 5.63 (s, 1H), 4.86 (s, 2H), 3.65 (t, 4H), 3.23 (t, 4H), 2.83 (d, 3H), 2.38 (s, 3H), 2.23 (s, 3H) | 549 (M − H) |
| 77 | ¹H NMR (400 MHz, CDCl₃) δ 8.06 (s, 1H), 7.23-7.32 (q, 2H), 7.23 (d, 2H), 7.05 (d, 2H), 6.83 (d, 2H), 6.39 (s, 1H), 6.31 (s, 1H), 6.19 (s, 1H), 5.15 (q, 1H), 4.89 (s, 2H), 3.65 (t, 4H), 3.21 (t, 4H), 2.37 (s, 3H), 2.31 (s, 3H), 2.23 (s, 3H), 1.30 (m, 7H) | 594 (M + H) |
| 78 | ¹H NMR (400 MHz, CDCl₃) δ 8.12 (broad s, 1H), 7.32 (d, 2H), 7.23 (m, 3H), 7.06 (d, 2H), 6.83 (d, 2H), 6.38 (s, 1H), 6.30 (s, 1H), 6.18 (s, 1H), 4.43 (m, 2H), 3.71 (m, 2H), 3.65 (m, 4H), 3.32 (s, 3H), 3.21 (m, 5H), 2.37 (s, 3H), 2.23 (s, 3H), 1.30 (d, 6H) | 578 (M − H) |
| 79 | ¹H NMR (400 MHz, CDCl₃) δ 8.86 (s, 1H), 7.76 (d, 1H), 7.70 (broad s, 1H), 7.64 (d, 1H), 7.48 (t, 1H), 7.60-7.40 (m, merged with solvent, 3H), 7.34-7.33 (m, 2H), 7.26-7.23 (m, 2H), 6.17 (s, 1H), 3.87 (s, 3H), 2.36 (s, 3H) | 368 (M − H) |
| 80 | ¹H NMR (400 MHz, CDCl₃) δ 8.27 (s, 1H), 7.40-7.35 (m, 3H), 7.31 (d, 2H), 7.22 (d, 2H), 6.89 (d, 2H), 6.39 (s, 1H), 6.31 (s, 1H), 6.14 (s, 1H), 3.67-3.63 (m, 6H), 3.35 (s, 3H), 3.24 (t, 4H), 3.11 (t, 2H), 2.37 (s, 3H), 2.23 (s, 3H), 2.08 (s, 3H) | 552 (M + H) |
| 81 | ¹H NMR (400 MHz, CDCl₃) δ 8.25 (broad s, 1H), 7.33-7.31 (m, 2H), 7.25-7.10 (m 7H), 7.10-7.07 (m, 2H), 6.33-6.32 (d, 1H), 4.46-4.42 (t, 2H), 3.74-3.70 (t, 2H), 3.34 (s, 3H) | 347 (M − H) |
| 82 | ¹H NMR (400 MHz, CDCl₃) δ 7.33-7.25 (m, 5H), 7.05 (d, 1H), 6.32 (broad s, 1H), 6.27-6.26 (d, 1H), 4.41-4.39 (t, 2H), 3.71-3.69 (t, 2H), 3.33 (s, 3H), 2.90-2.85 (q, 2H), 1.36-1.30 (q, 2H), 0.85-0.81 (t, 3H) | 315 (M + H) |
| 83 | ¹H NMR (400 MHz, CDCl₃) δ 8.34 (s, 1H), 7.56 (d, 2H), 6.98 (d, 3H), 6.39-6.32 (d, 2H), 6.16 (d, 1H), 4.34 (t, 2H), 3.69-3.62 (m, 6H), 3.33-3.27 (m, 8H), 2.38 (s, 3H), 2.24 (s, 3H), 1.20 (d, 6H) | 504 (M + H) |
| 84 | ¹H NMR (400 MHz, CDCl₃) δ 8.28 (s, 1H), 7.33 (d, 2H), 7.28-7.22 (m, 3H), 7.14 (d, 2H), 7.04 (d, 1H), 6.85 (d, 2H), 6.39 (s, 1H), 6.33-6.31 (m, 2H), 4.35 (t, 2H), 3.65 (t, 4H), 3.23 (t, 4H), 2.66 (t, 2H), 2.38 (s, 3H), 2.26 (s, 6H), 2.23 (s, 3H) | 551 (M + H) |

| Example | NMR Data | MS Spectrum |
|---|---|---|
| 85 | ¹H NMR (400 MHz, CDCl₃) δ 9.13 (s, 1H), 8.43 (d, 1H), 7.63 (d, 2H), 7.56 (d, 2H), 7.43-7.35 (m, 3H), 7.23 (m, 1H), 7.00 (d, 2H), 6.40 (s, 1H), 6.33 (s, 1H), 4.52 (t, 2H), 3.69 (t, 4H), 3.29 (t, 4H), 2.69 (t, 2H), 2.38 (s, 3H), 2.33 (s, 6H), 2.24 (s, 3H) | 551 (M + H) |
| 86 | ¹H NMR (400 MHz, CDCl₃) δ 8.17 (s, 1H), 7.31-7.29 (m, 2H), 7.26-7.21 (m, merged with solvent, ~3H), 7.08 (d, 2H), 6.83 (d, 2H), 6.38 (s, 1H), 6.31 (s, 1H), 6.13 (s, 1H), 4.32 (t, 2H), 3.65 (t, 4H), 3.22 (t, 4H), 2.65 (t, 2H), 2.37 (s, 6H), 2.31 (s, 6H), 2.23 (s, 3H) | 565 (M + H) |
| 87 | ¹H NMR (400 MHz, CDCl₃) δ 8.08 (s, 1H), 7.23-7.21 (m, 3H), 7.02-6.93 (m, 3H), 6.87 (d, 2H), 6.40 (d, 2H), 6.31 (s, 1H), 4.94 (s, 2H), 3.82 (s 3H), 3.66 (t, 4H), 3.24 (t, 4H), 2.37 (s, 3H), 2.23 (s, 3H) | 558 (M + H) |
| 88 | ¹H NMR (400 MHz, CDCl₃) δ 8.30 (s, 1H), 7.54 (d, 2H), 6.99-6.91 (m, 3H), 6.40-6.33 (d, 2H), 6.25 (d, 1H), 4.85 (s, 2H), 3.80 (s, 3H), 3.68 (t, 4H), 3.36 (m, 1H), 3.28 (t, 4H), 2.38 (s, 3H), 2.24 (s, 3H), 1.21 (d, 6H) | 518 (M + H) |
| 89 | ¹H NMR (400 MHz, CDCl₃) δ 9.05 (s, 1H), 8.01 (d, 1H), 7.58 (d, 2H), 6.97 (d, 2H), 6.83 (d, 1H), 6.39 (s, 1H), 6.32 (s, 1H), 4.99 (s, 2H), 3.80 (s, 3H), 3.68 (t, 4H), 3.27 (t, 4H), 2.67 (d, 2H), 2.41 (s, 3H), 2.35 (s, 3H), 1.81 (t, 1H), 0.92 (d, 6H) | 532 (M + H) |
| 90 | ¹H NMR (400 MHz, CDCl₃) δ 8.18 (s, 1H), 7.33-7.26 (m, 5H), 7.07 (d, 2H), 6.83 (d, 2H), 6.38 (s, 1H), 6.31 (s, 1H), 3.80 (s, 3H), 3.65 (t, 4H), 3.23 (t, 4H), 2.37 (s, 3H), 2.30 (s, 3H), 2.23 (s, 3H) | 526 (M + H) |
| 91 | ¹H NMR (400 MHz, CDCl₃) δ 8.58 (s, 1H), 8.17 (s, 1H), 7.63 (t, 1H), 7.36 (d, 2H), 7.32-7.22 (m, 3H), 7.18 (t, 1H), 7.05 (d, 2H), 6.92 (d, 1H), 6.82 (d, 2H), 6.39 (s, 1H), 6.24 (d, 2H), 5.61 (s, 2H), 3.62 (s, 4H), 3.21 (s, 4H), 2.38 (s, 3H), 2.36 (s, 3H), 2.22 (s, 3H) | 585 (M + H) |
| 92 | ¹H NMR (400 MHz, CDCl₃) δ 8.54 (s, 1H), 7.46 (d, 1H), 7.31 (d, 2H), 7.25-7.19 (m, 3H), 6.91-6.90 (d, 1H), 6.71-6.68 (dd, 1H), 6.39 (s, 1H), 6.30 (s, 1H), 6.13 (s, 1H), 4.40 (t, 2H), 3.75 (t, 2H), 3.65 (t, 4H), 3.32 (s, 3H), 3.22 (t, 4H), 2.38 (d, 6H), 2.23 (s, 3H) | 586 (M + H) |
| 93 | ¹H NMR (400 MHz, CDCl₃) δ 8.54 (d, 1H), 8.50 (s, 1H), 8.16 (s, 1H), 7.40-7.34 (m, 3H), 7.32-7.26 (m, 4H), 7.08 (d, 2H), 6.84 (d, 2H), 6.40 (s, 1H), 6.33 (s, 1H), 6.26 (s, 1H), 5.56 (s, 2H), 3.64 (m, 4H), 3.22 (m, 4H), 2.40 (s, 3H), 2.30 (s, 3H), 2.24 (s, 3H) | 585 (M + H) |
| 94 | ¹H NMR (400 MHz, CDCl₃) δ 8.08 (s, 1H), 7.35-7.24 (m, 5H), 7.05 (d, 2H), 6.82 (d, 2H), 6.39 (s, 1H), 6.31 (s, 1H), 4.36 (t, 2H), 3.73 (t, 2H), 3.65 (t, 4H), 3.33 (s, 3H), 3.22 (t, 4H), 2.36 (d, 6H), 2.23 (s, 3H) | 570 (M + H) |
| 95 | ¹H NMR (400 MHz, CDCl₃) δ 8.31 (s, 1H), 8.21 (s, 1H), 7.50-7.45 (m, 2H), 7.28-7.20 (m, 5H), 6.70-6.64 (m, 3H), 6.54 (d, 1H), 6.12 (s, 1H), 3.82 (s, 3H), 3.68 (t, 4H), 3.24 (t, 4H), 2.33 (s, 3H) | 496 (M − H) |
| 96 | ¹H NMR (400 MHz, CDCl₃) δ 8.21 (s, 2H), 7.52-7.42 (m, 2H), 7.30 (d, 2H), 7.25-7.20 (m, 3H), 6.70-6.67 (m, 3H), 6.64 (d, 1H), 6.13 (s, 1H), 4.40 (t, 2H), 3.74 (t, 2H), 3.67 (t, 4H), 3.33 (s, 3H), 3.23 (t, 4H), 2.38 (s, 3H) | 540 (M − H) |
| 97 | ¹H NMR (400 MHz, CDCl₃) δ 8.10 (s, 1H), 7.32-7.21 (m, 5H), 7.06 (d, 2H), 6.82 (d, 2H), 6.38 (s, 1H), 6.31 (s, 1H), 6.12 (s, 1H), 4.37 (t, 2H), 3.76 (t, 2H), 3.65 (t, 4H), 3.56-3.47 (m, 1H), 3.22 (t, 4H), 2.38 (d, 6H), 2.23 (s, 3H), 1.10 (d, 6H) | 580 (M + H) |
| 98 | ¹H NMR (400 MHz, CDCl₃) δ 8.50 (s, 1H), 7.48-7.46 (d, 1H), 7.34-7.32 (m, 2H), 7.25-7.19 (m, 3H), 6.90 (d, 1H), 6.71-6.68 (dd, 1H), 6.39 (s, 1H), 6.30 (s, 1H), 6.20 (s, 1H), 4.95 (s, 2H), 3.84 (s, 3H), 3.64 (t, 4H), 3.22 (t, 4H), 2.37 (s, 3H), 2.31 (s, 3H), 2.23 (s, 3H) | 600 (M + H) |
| 99 | ¹H NMR (400 MHz, CDCl₃) δ 8.03 (s, 1H), 7.90 (d, 1H), 7.35-7.21 (m, 6H), 6.20 (d, 1H), 6.12 (s, 1H), 3.82 (s, 3H), 3.40 (t, 4H), 2.33 (s, 3H), 2.00-1.97 (m, 4H) | 387 (M − H) |
| 100 | ¹H NMR (400 MHz, CDCl₃) δ 8.57 (broad s, 1H), 7.80-7.65 (m, 4H), 7.27 (t, 2H), 7.22-7.14 (m, 4H), 6.15 (s, 1H), 3.85 (s, 3H), 2.35 (s, 3H) | 403 (M + H) |
| 101 | ¹H NMR (400 MHz, CDCl₃) δ 8.32 (s, 1H), 7.46 (t, 1H), 7.29 (d, 2H), 7.25-7.16 (m, 3H), 6.60 (d, 1H), 6.49 (d, 1H), 6.13 (s, 1H), 3.83 (t, 4H), 3.82 (s, 3H), 3.08 (t, 4H), 2.33 (s, 3H) | 422 (M + H) |

| Example | NMR Data | MS Spectrum |
|---|---|---|
| 102 | ¹H NMR (400 MHz, CDCl₃) δ 8.56 (d, 2H), 8.12 (s, 1H), 7.36-7.34 (m, 2H), 7.29-7.25 (m, 3H), 7.05 (d, 2H), 6.96 (d, 2H), 6.82 (d, 2H), 6.38 (s, 1H), 6.30 (s, 1H), 6.27 (s, 1H), 5.50 (s, 2H), 3.64 (t, 4H), 3.21 (t, 4H), 2.37 (s, 3H), 2.25 (s, 3H), 2.22 (s, 3H) | 585 (M + H) |
| 103 | ¹H NMR (400 MHz, CDCl₃) δ 8.09 (s, 1H), 7.51 (s, 1H), 7.32 (q, 2H), 7.22 (t, 3H), 7.06 (d, 2H), 6.84 (d, 2H), 6.68 (d, 2H), 6.13 (s, 1H), 4.39 (t, 2H), 3.75-3.66 (m, 10H), 3.40 (broad s, 3H), 3.32 (s, 3H), 3.22 (t, 4H), 2.38 (s, 6H) | 623 (M + H) |
| 104 | ¹H NMR (400 MHz, CDCl₃) δ 8.27 (s, 1H), 7.58 (d, 2H), 7.01 (m, 3H), 6.10 (s, 1H), 6.33 (s, 1H), 6.22 (d, 1H), 4.35 (t, 2H), 3.84 (t, 1H), 3.70-3.63 (m, 6H), 3.30-3.27 (m, 6H), 2.38 (s, 3H), 2.31-2.26 (m, 2H), 2.24 (s, 3H), 2.11-2.02 (m, 2H), 1.94-1.76 (m, 3H) | 514 (M − H) |
| 105 | ¹H NMR (400 MHz, CDCl₃) δ 8.30 (s, 1H), 7.43 (t, 1H), 7.29 (d, 2H), 7.24-7.16 (m, 3H), 6.62-6.58 (d, 1H), 6.49 (d, 1H), 6.12 (s, 1H), 3.82 (s, 3H), 3.12 (t, 4H), 2.57 (t, 4H), 2.33 (s, 3H), 2.13 (s, 2H), 1.84-1.77 (m, 1H), 0.91 (d, 6H) | 477 (M + H) |
| 106 | ¹H NMR (400 MHz, CDCl₃) δ 8.28 (s, 1H), 7.41 (t, 1H), 7.29-7.18 (m, 5H), 6.62-6.58 (dd, 1H), 6.51-6.48 (d, 1H), 6.12 (s, 1H), 3.82 (s, 3H), 3.09 (t, 4H), 2.33 (s, 3H), 1.67-1.55 (m, 6H) | 420 (M + H) |
| 107 | ¹H NMR (400 MHz, CDCl₃) δ 8.22 (s, 1H), 7.55 (d, 2H), 6.98 (d, 2H), 6.39 (s, 1H), 6.32 (s, 2H), 4.95 (dd, 2H), 4.84 (s, 2H), 3.80 (s, 3H), 3.69-3.67 (m, 4H), 3.29-3.27 (m, 4H), 2.38 (s, 3H), 2.34-2.26 (m, 2H), 2.24 (s, 3H), 2.11-2.01 (m, 2H), 1.95-1.78 (m, 2H) | 530 (M + H) |
| 108 | ¹H NMR (400 MHz, CDCl₃) δ 8.28 (s, 1H), 7.44 (t, 1H), 7.29-7.26 (m, 5H), 6.62-6.58 (d, 1H), 6.50-6.48 (d, 1H), 6.12 (s, 1H), 4.89-4.87 (d, 2H), 3.82 (s, 3H), 3.12 (t, 4H), 2.90 (s, 2H), 2.50 (t, 4H), 2.32 (s, 3H), 1.75 (s, 3H) | 473 (M − H) |
| 109 | ¹H NMR (400 MHz, CDCl₃) δ 8.19 (s, 1H), 7.41 (t, 1H), 7.30 (d, 2H), 7.23-7.17 (m, 3H), 6.61-6.57 (dd, 1H), 6.49 (d, 1H), 6.12 (s, 1H), 4.88 (d, 2H), 4.40 (t, 2H), 3.74 (t, 2H), 3.32 (s, 3H), 3.12 (t, 4H), 2.90 (s, 2H), 2.50 (t, 4H), 2.38 (s, 3H), 1.76 (s, 3H) | 517 (M − H) |
| 110 | ¹H NMR (400 MHz, CDCl₃) δ 8.02 (broad s, 1H), 7.40 (t, 1H), 7.30 (d, 3H), 7.21 (d, 2H), 6.59 (d, 1H), 6.49 (d, 1H), 6.13 (s, 1H), 4.39 (s, 2H), 3.74 (s, 2H), 3.33 (s, 3H), 3.12 (s, 4H), 2.52 (s, 4H), 2.38 (s, 3H), 2.12 (s, 2H), 1.80 (m, 1H), 0.91 (d, 6H) | 521 (M + H) |
| 111 | ¹H NMR (400 MHz, CDCl₃) δ 8.19 (s, 1H), 7.46 (1, 1H), 7.32 (m, 2H), 7.23-7.20 (m, 3H), 6.64 (d, 1H), 6.54 (d, 1H), 6.39 (s, 1H), 6.30 (s, 1H), 6.20 (s, 1H), 4.94 (s, 2H), 3.84 (s, 3H), 3.64 (t, 4H), 3.22 (t, 4H), 2.37 (s, 3H), 2.31 (s, 3H), 2.23 (s, 3H) | 584 (M + H) |
| 112 | ¹H NMR (400 MHz, CDCl₃) δ 8.28 (s, 1H), 7.43 (t, 1H), 7.28 (d, 2H), 7.23-7.15 (m, 3H), 6.61-6.57 (dd, 1H), 6.48 (d, 1H), 6.12 (s, 1H), 3.82 (s, 3H), 3.09 (t, 4H), 2.64 (t, 4H), 2.32 (s, 3H), 2.10 (s, 2H), 0.88 (s, 9H) | 491 (M + H) |
| 113 | ¹H NMR (400 MHz, CDCl₃) δ 8.18 (s, 1H), 7.04 (t, 1H), 7.30 (d, 2H), 7.23-7.17 (m, 3H), 6.60-6.56 (q, 1H), 6.47 (d, 1H), 6.12 (s, 1H), 4.39 (t, 2H), 3.74 (t, 2H), 3.32 (s, 3H), 3.08 (t, 4H), 2.64 (t, 4H), 2.38 (s, 3H), 2.10 (s, 2H), 0.88 (s, 9H) | 535 (M + H) |
| 114 | ¹H NMR (400 MHz, CDCl₃) δ 8.18 (s, 1H), 7.38 (t, 3H), 7.30 (d, 2H), 7.22-7.15 (m, 3H), 6.59 (dd, 1H), 6.49 (d, 1H), 6.12 (s, 1H), 4.39 (t, 2H), 3.74 (t, 2H), 3.32 (s, 1H), 3.01-3.07 (m, 4H), 2.38 (s, 3H), 1.66-1.65 (m, 5H), 1.57 (m, 1H) | 464 (M + H) |
| 115 | ¹H NMR (400 MHz, CDCl₃) δ 8.20 (s, 1H), 7.27-7.20 (m, 5H), 6.95 (d, 1H), 6.83-6.78 (m, 2H), 6.13 (s, 1H), 3.81 (s, 3H), 2.95 (t, 4H), 2.33 (s, 3H), 1.73-1.69 (m, 4H), 1.56-1.55 (m, 2H) | 420 (M + H) |
| 116 | ¹H NMR (400 MHz, CDCl₃) δ 8.23-8.20 (m, 2H), 7.50 (t, 1H), 7.28-7.23 (m, 5H), 7.00 (d, 1H), 6.86-6.81 (m, 2H), 6.70-6.63 (m, 2H), 6.13 (s, 1H), 3.81 (s, 3H), 3.69 (t, 4H), 3.13 (t, 4H), 2.33 (s, 3H) | 496 (M − H) |
| 117 | ¹H NMR (400 MHz, CDCl₃) δ 8.21 (s, 1H), 7.44 (t, 1H), 7.30 (d, 2H), 7.23-7.17 (m, 3H), 6.59 (dd, 1H), 6.48 (d, 1H), 6.13 (s, 1H), 4.40 (t, 2H), 3.83-3.81 (m, 4H), 3.74 (t, 2H), 3.32 (s, 3H), 3.09-3.07 (m, 4H), 2.38 (s, 3H) | 466 (M + H) |
| 118 | ¹H NMR (400 MHz, CDCl₃) δ 8.19 (broad s, 1H), 7.28-7.22 (m, 5H), 6.96 (d, 1H), 6.81 (t, 2H), 6.13 (s, 1H), 3.81 (s, 3H), 3.04 (t, 4H), 2.55 (s, 4H), 2.33 (s, 3H), 2.13 (d, 2H), 1.83-1.77 (m, 1H), 0.91 (d, 6H) | 477 (M + H) |

| Example | NMR Data | MS Spectrum |
|---|---|---|
| 119 | ¹H NMR (400 MHz, CDCl$_3$) δ 8.08 (s, 1H), 7.29-7.28 (d, 2H), 7.23 (d, 3H), 6.93-6.90 (d, 1H), 6.80-6.78 (d, 2H), 6.13 (s, 1H), 4.39 (t, 2H), 3.72 (t, 2H), 3.32 (s, 3H), 2.94 (t, 4H), 2.38 (s, 3H), 1.71 (m, 4H), 1.54 (m, 2H). | 464 (M + H) |
| 120 | ¹H NMR (400 MHz, CDCl$_3$) δ 8.19 (s, 1H), 8.09 (d, 1H), 7.50 (t, 1H), 7.29 (d, 1H), 7.23 (t, 3H), 7.10 (d, 2H), 6.84 (d, 2H), 6.68 (d, 1H), 6.13 (s, 1H), 3.82 (s, 3H), 3.67 (t, 8H), 3.39 (s, 2H), 3.23 (t, 4H), 2.43 (s, 4H), 2.33 (s, 3H) | 579 (M + H) |
| 121 | ¹H NMR (400 MHz, CDCl$_3$) δ 8.33 (d, 1H), 7.55 (d, 2H), 7.41-7.40 (d, 1H), 7.35 (t, 3H), 7.24-7.20 (m, 1H), 4.55 (t, 2H), 3.68 (t, 2H), 3.3.6-3.31 (m, 5H), 1.63 (q, 2H), 0.98 (t, 3H) | 315 (M + H) |
| 122 | ¹H NMR (400 MHz, CDCl$_3$) δ 9.03 (s, 1H), 8.51 (s, 1H), 7.61-7.55 (m, 4H), 7.34 (m, 4H), 7.07 (d, 2H), 6.38 (d, 2H), 5.08 (s, 2H), 3.83 (s, 3H), 3.65 (m, 4H), 3.28 (m, 4H), 2.38 (s, 3H), 2.32 (s, 3H) | 552 (M + H) |
| 123 | ¹H NMR (400 MHz, CDCl$_3$) δ 8.21 (s, 1H), 7.44 (t, 1H), 7.30 (d, 2H), 7.25-7.18 (m, 3H), 6.64 (d, 1H), 6.54 (d, 1H), 6.39 (s, 1H), 6.30 (s, 1H), 6.13 (s, 1H), 4.40 (t, 2H), 3.74 (t, 2H), 3.65 (t, 4H), 3.33 (s, 3H), 3.22 (t, 4H), 2.38 (s, 3H), 2.37 (s, 3H), 2.23 (s, 3H) | 568 (M − H) |
| 124 | H NMR (400 MHz, CDCl$_3$) δ 8.12 (s, 1H), 7.31 (d, 2H), 7.25-7.20 (m, 3H), 7.10 (d, 2H), 6.84 (d, 2H), 6.38 (s, 1H), 6.30 (s, 1H), 6.14 (s, 1H), 3.82 (s, 3H), 3.65 (t, 4H), 3.22 (t, 4H), 2.61 (t, 2H), 2.37 (s, 3H), 2.23 (s, 3H), 1.75 (m, 2H), 1.06 (t, 3H) | 534 (M − H) |
| 125 | H NMR (400 MHz, CDCl$_3$) δ 8.19 (s, 1H), 7.32 (d, 2H), 7.29-7.21 (m, 3H, solvent overlap) 7.10-7.08 (d, 2H), 6.85-6.83 (d, 2H), 6.38 (s, 1H), 6.31 (s, 1H), 6.23 (s, 1H), 5.6 (s, 2H), 3.65 (t, 4H), 3.33 (s, 3H), 3.22 (t, 4H), 2.77 (q, 2H), 2.37 (s, 3H), 2.23 (s, 3H), 1.54 (t, 3H) | 552 (M + H) |
| 126 | ¹H NMR (400 MHz, CDCl$_3$) δ 8.12 (s, 1H), 7.30-7.21 (m, 5H), 6.95 (d, 1H), 6.80 (d, 2H), 6.13 (s, 1H), 4.41 (t, 2H), 3.84 (t, 4H), 3.72 (t, 2H), 3.32 (s, 3H), 3.01 (t, 4H), 2.38 (s, 3H | 464 (M − H) |
| 127 | H NMR (400 MHz, CDCl$_3$) δ 8.87 (s, 1H), 7.90 (d, 1H), 7.69 (d, 1H), 7.49-7.34 (m, 5H), 7.29-7.22 (m, 3H, solvent overlap), 7.18 (t, 1H), 6.16 (s, 1H), 3.86 (s, 3H), 2.36 (s, 3H) | 387 (M + H) |
| 128 | ¹H NMR (400 MHz, CDCl$_3$) δ 8.44 (s, 1H), 7.36-7.32 (m, 3H), 7.25-7.15 (m, 3H), 7.05 (d, 2H), 6.92 (d, 1H), 6.52 (d, 1H), 6.13 (s, 1H), 4.13-4.08 (q, 2H), 3.84 (s, 3H), 2.33 (s, 3H), 1.43 (t, 3H). | 404 (M + H) |
| 129 | ¹H NMR (400 MHz, CDCl$_3$) δ 8.20 (s, 1H), 7.31-7.29 (m, 2H), 7.25-7.20 (m, 3H), 7.09 (d, 2H), 6.83 (d, 2H), 6.38 (s, 1H), 6.31 (s, 1H), 6.18 (s, 1H), 3.83 (s, 3H), 3.69 (t, 2H), 3.65 (t, 4H), 3.39 (s, 3H), 3.22 (t, 4H), 2.93 (t, 2H), 2.37 (s, 3H), 2.23 (s, 3H). | 552 (M + H) |
| 130 | ¹H NMR (400 MHz, CDCl$_3$) δ 8.21 (s, 1H), 7.29 (m, 3H), 7.23 (m, 2H), 7.11 (d, 2H), 6.80 (d, 2H), 6.55 (s, 1H), 6.48 (s, 1H), 6.32 (s, 1H), 4.48 (s, 2H), 3.86 (t, 7H), 3.40 (s, 3H), 3.29 (t, 4H), 2.60 (s, 3H), 2.37 (s, 3H) | 536 (M − H) |
| 131 | ¹H NMR (400 MHz, CDCl$_3$) δ 8.26 (s, 1H), 7.33-7.26 (m, 5H), 7.14 (d, 2H), 6.85 (d, 2H), 6.39 (d, 2H), 6.31 (s, 1H), 5.66 (s, 2H), 4.57 (s, 2H), 3.65 (t, 4H), 3.41 (s, 3H), 3.31 (s, 3H), 3.23 (t, 4H), 2.37 (s, 3H), 2.23 (s, 3H) | 568 (M + H) |
| 132 | ¹H NMR (400 MHz, CDCl$_3$) δ 8.19 (s, 1H), 7.32-7.30 (m, 3H), 7.25-7.24 (m, 2H), 7.10 (d, 2H), 6.85 (d, 2H), 6.38 (s, 1H), 6.30 (s, 1H), 6.18 (s, 1H), 5.65 (s, 2H), 3.66-3.64 (m, 4H), 3.56-3.55 (q, 2H), 3.23-3.21 (m, 4H), 2.42 (s, 3H), 2.37 (s, 3H), 2.23 (s, 3H), 1.19 (t, 3H) | 552 (M + H) |
| 133 | ¹H NMR (400 MHz, CDCl$_3$) δ 8.08 (s, 1H), 7.31 (d, 3H), 7.22 (d, 2H), 7.06 (d, 2H), 6.82 (d, 2H), 6.38 (s, 1H), 6.30 (s, 1H), 6.15 (s, 1H), 4.40 (t, 2H), 3.65 (t, 4H), 3.22 (t, 4H), 2.89 (s, 2H), 2.39 (s, 3H), 2.37 (s, 3H), 2.23 (s, 3H), 2.17 (s, 3H) | 568 (M + H) |
| 134 | ¹H NMR (400 MHz, CDCl$_3$) δ 8.04 (s, 1H), 7.31-7.21 (m, 7H), 7.06-7.04 (d, 2H), 6.93 (t, 1H), 6.88-6.81 (dd, 4H), 6.38 (s, 1H), 6.30 (s, 1H), 6.14 (s, 1H), 4.60 (t, 2H), 4.39 (t, 2H), 3.65 (t, 4H), 3.21 (t, 4H), 2.47 (s, 3H), 2.37 (s, 3H), 2.23 (s, 3H) | 614 (M + H) |
| 135 | ¹H NMR (400 MHz, CDCl$_3$) δ 8.21 (s, 1H), 7.33-7.31 (m, 2H), 7.28-7.23 (m, 3H), 7.10 (d, 2H), 6.84 (d, 2H), 6.39 (s, 1H), 6.31 (s, 1H), 6.18 (s, 1H), 5.64 (s, 2H), 3.65 (t, 4H), 3.49 (t, 2H), 3.22 (t, 4H), 2.42 (s, 3H), 2.37 (s, 3H), 2.23 (s, 3H), 1.53 (q, 2H), 1.36-1.25 (m, 2H), 0.87 (t, 3H) | 580 (M + H) |

-continued

| Example | NMR Data | MS Spectrum |
|---|---|---|
| 136 | ¹H NMR (400 MHz, CDCl₃) δ 8.13 (s, 1H), 7.31-7.29 (m, 2H), 7.24-7.22 (m, 3H), 7.07 (d, 2H), 6.84 (d, 2H), 6.38 (s, 1H), 6.30 (s, 1H), 6.11 (s, 1H), 4.33 (t, 2H), 3.66-3.64 (m, 4H), 3.50-3.42 (m, 4H), 3.23-3.30 (m, 4H), 2.37 (s, 3H), 2.36 (s, 3H), 2.23 (s, 3H), 2.05-2.02 (m, 2H), 1.20 (t, 3H) | 580 (M + H) |
| 137 | ¹H NMR (400 MHz, CDCl₃) δ 8.17 (s, 1H), 7.32-7.22 (m, 5H), 7.09 (s, 2H), 6.84 (d, 2H), 6.38 (s, 1H), 6.31 (s, 1H), 6.18 (s, 1H), 5.41 (s, 2H), 3.65 (t, 4H), 3.22 (t, 4H), 2.42 (s, 3H), 2.37 (s, 3H), 2.23 (s, 3H), 2.13 (s, 3H) | 552 (M − H) |
| 138 | ¹H NMR (400 MHz, CDCl₃) δ 8.21 (s, 1H), 7.32-7.30 (q, 2H), 7.27-7.25 (m, 4H), 7.08 (d, 2H), 6.84 (d, 2H), 6.39 (s, 1H), 6.31 (s, 1H), 6.19 (s, 1H), 5.72 (s, 2H), 3.68-3.64 (m, 5H), 3.50 (t, 2H), 3.35 (s, 3H,) 3.22 (t, 4H), 2.44 (s, 3H), 2.37 (s, 3H), 2.23 (s, 3H) | 582 (M + H) |
| 139 | ¹H NMR (400 MHz, CDCl₃) δ 8.21 (s, 1H), 7.33-7.31 (m, 2H), 7.28-7.25 (m, 3H), 7.10 (d, 2H), 6.84 (d, 2H), 6.39 (s, 1H), 6.31 (s, 1H), 6.19 (s, 1H), 5.65 (s, 2H), 3.65 (t, 4H), 3.45 (t, 2H), 3.22 (t, 4H), 2.43 (s, 3H), 2.37 (s, 3H), 2.23 (s, 3H), 1.57 (m, 2H), 0.88 (t, 3H) | 566 (M + H) |
| 140 | ¹H NMR (400 MHz, CDCl₃) δ 8.12 (s, 1H), 7.32-7.25 (m, 5H), 7.06 (d, 2H), 6.83 (d, 2H), 6.39 (s, 1H), 6.31 (s, 1H), 6.13 (s, 1H), 4.39 (t, 2H), 3.77 (t, 2H), 3.64 (m, 4H), 3.36 (t, 2H), 3.22 (m, 4H), 2.40 (s, 3H), 2.37 (s, 3H), 2.23 (s, 3H), 1.57-1.51 (m, 2H), 0.87 (t, 3H) | 580 (M + H) |
| 141 | ¹H NMR (400 MHz, CDCl₃) δ 8.20 (s, 1H), 7.31-7.22 (m, 5H), 7.08 (d, 2H), 6.83 (d, 2H), 6.39 (s, 1H), 6.31 (s, 1H), 6.14 (s, 1H), 5.73-5.64 (m, 2H), 4.95 (d, 2H), 4.08 (d, 2H), 3.65 (m, 4H), 3.38 (s, 3H) 3.22 (m, 4H), 2.37 (s, 3H), 2.34 (s, 3H), 2.23 (s, 3H) | 578 (M + H) |
| 142 | ¹H NMR (400 MHz, CDCl₃) δ 8.14 (s, 1H), 7.31-7.21 (m, 5H), 7.06 (d, 2H), 6.83 (d, 2H), 6.39 (s, 1H), 6.31 (s, 1H), 6.12 (s, 1H), 4.22 (t, 2H), 3.65 (t, 4H), 3.42 (t, 2H), 3.34 (s, 3H), 3.22 (t, 4H), 2.38 (s, 3H), 2.35 (s, 3H), 2.23 (s, 3H), 1.87-1.83 (m, 2H), 1.70-1.65 (m, 2H). | 578 (M − H) |
| 143 | ¹H NMR (400 MHz, DMSO-d₆) δ 10.17 (s, 1H), 7.22 (m, 2H), 7.11 (m, 3H), 7.00 (d, 2H), 6.73 (d, 2H), 6.09 (s, 1H), 3.81 (s, 3H), 3.02 (s, 4H), 2.31 (s, 3H), 1.58-1.49 (m, 6H) | 400 (M − H) |
| 144 | ¹H NMR (400 MHz, CDCl₃) δ 8.20 (s, 1H), 7.35-7.20 (m, 10H), 7.06 (d, 2H), 6.77 (d, 2H), 6.12 (s, 1H), 3.80 (s, 3H), 3.56 (s, 2H), 3.13 (m, 4H), 2.59 (m, 4H), 2.32 (s, 3H) | 493 (M + H) |
| 145 | ¹H NMR (400 MHz, CDCl₃) δ 8.21 (s, 1H), 7.31-7.21 (m, 5H), 7.09 (d, 2H), 6.79 (d, 2H), 6.13 (s, 1H), 3.81 (s, 3H), 3.76 (t, 2H), 3.65 (t, 2H), 3.09 (t, 4H), 2.82 (septet, 1H), 2.33 (s, 3H), 1.15 (d, 6H). | 471 (M − H) |
| 146 | ¹H NMR (400 MHz, CDCl₃) δ 8.13 (s, 1H), 7.44 (s, 1H), 7.32-7.29 (m, 2H), 7.25-7.21 (m, 3H), 7.05 (d, 2H), 6.82 (d, 2H), 6.39 (s, 1H), 6.31 (s, 1H), 6.16 (s, 1H), 5.34 (s, 2H), 3.65 (m, 4H), 3.22 (m, 4H), 2.48 (s, 3H), 2.41 (s, 3H), 2.37 (s, 3H), 2.23 (s, 3H) | 587 (M − H) |
| 147 | ¹H NMR (400 MHz, CDCl₃) δ 8.44 (s, 1H), 7.91 (d, 2H), 7.68 (s, 1H), 7.31-7.28 (m, 4H), 7.26-7.21 (m, 4H), 6.15 (s, 1H), 3.83 (s, 3H), 2.34 (s, 3H) | 384 (M − H) |
| 148 | H NMR (400 MHz, CDCl₃) δ 8.44 (broad s, 1H), 7.90 (t, 1H), 7.73 (s, 1H), 7.28-7.20 (m, 7H), 7.01 (d, 1H), 6.15 (s, 1H), 3.83 (s, 3H), 2.34 (s, 3H) | 402 (M − H) |
| 149 | ¹H NMR (400 MHz, CDCl₃) δ 8.30 (s, 1H), 7.91 (d, 2H), 7.68 (s, 1H), 7.31-7.26 (m, 4H), 7.22-7.20 (m, 4H), 6.15 (s, 1H), 4.41 (t, 2H), 3.74 (t, 2H), 3.33 (s, 3H), 2.39 (s, 3H) | 428 (M − H) |
| 150 | ¹H NMR (400 MHz, CDCl₃) δ 8.18 (s, 1H), 7.31-7.18 (m, 5H), 7.06 (d, 2H), 6.78 (d, 2H), 6.12 (s, 1H), 3.81 (s, 3H), 3.15-3.08 (m, 4H), 2.73-2.68 (m, 2H), 2.55-2.52 (m, 2H), 2.32 (s, 3H), 2.17-2.14 (m, 1H), 1.72-1.70 (m, 1H), 0.95 (d, 6H), 0.88 (d, 3H) | 473 (M + H) |
| 151 | ¹H NMR (400 MHz, CDCl₃) δ 8.18 (s, 1H), 7.30-7.20 (m, 5H), 7.06 (d, 2H), 6.78 (d, 2H), 6.12 (s, 1H), 3.81 (s, 3H), 3.51-3.47 (m, 1H), 3.35-3.31 (m, 4H), 3.13 (t, 4H), 2.84-2.79 (m, 1H), 2.73 (t, 4H), 2.32 (s, 3H), 1.10 (d, 3H) | 475 (M + H) |
| 152 | ¹H NMR (400 MHz, CDCl₃) δ 8.17 (s, 1H), 7.30-7.22 (m, 6H), 7.06 (d, 2H), 6.78 (d, 2H), 6.28 (s, 1H), 6.12 (s, 1H), 6.04 (s, 1H), 3.81 (s, 3H), 3.13 (m, 4H), 2.98-2.94 (m, 2H), 2.72 (m, 4H), 2.60-2.54 (m, 1H), 2.32 (s, 3H), 1.04 (d, 3H) | 511 (M + H) |
| 153 | ¹H NMR (400 MHz, CDCl₃) δ 8.36 (s, 1H), 7.90 (d, 2H), 7.29-7.27 (m, 4H), 7.23-7.21 (m, 3H), 6.99 (s, 1H), 6.15 (s, 1H), 3.84 (s, 3H), 3.62 (s, 2H), 2.47 (m, 4H), 2.34 (s, 3H), 1.61 (m, 4H), 1.42 (m, 2H) | 481 (M − H) |

| Example | NMR Data | MS Spectrum |
|---|---|---|
| 154 | $^1$H NMR (400 MHz, CDCl$_3$) δ 8.18 (s, 1H), 7.30-7.28 (m, 2H), 7.24-7.20 (m, 3H), 7.09 (d, 2H), 6.77 (d, 2H), 6.12 (s, 1H), 3.83 (t, 4H), 3.81 (s, 3H), 3.08 (t, 4H), 2.32 (s, 3H). | 404 (M + H) |

Activity Example

Measurement of Minimum Inhibitory Concentrations (MICS)

Between 1 and 5 mgs of compound were accurately weighed out into a sterile Eppendorf tube. The compound was dissolved in DMSO to give a solution containing 5 mg/mL. Tubes were stored at −20° C. until required.

On the day of testing thawed solutions were vortex mixed to ensure homogeneity. 30 µL of solution was removed and added to 570 µL of sterile water in a separate sterile Eppendorf. The thoroughly mixed solution was used to prepare a series of doubling dilutions in water, in a deep well plate. Thirteen replicate plates were prepared using a Minitrak by aspirating 20 µL from each well into eleven clear polystyrene 96 well plates.

Spores of *Aspergillus* spp. (*Aspergillus fumigatus* [two strains], *Aspergillus terreus* [two strains], *Aspergillus niger* and *Aspergillus flavus*) were harvested from cultures grown on Sabarauds agar for 5 days, and resuspended in PBS/Tween 80 to approx 1×10$^7$ cfu/mL. Each organism suspension was diluted in YAG medium (1% glucose, 1% ammonium chloride and 0.5% yeast extract) to 0.5−2×10$^4$ cfu/mL. 80 µL of an organism suspension was added to each well of the plate containing drug dilutions.

This produced MIC plates with a drug range 50-0.05 mg/L and organism inocula of 1−2×10$^4$ cfu/mL for *Aspergillus* spp. All plates were incubated for 24 h at 35° C. Growth was assessed by monitoring the optical density at 485 nm for each well. The MIC of a compound is the lowest drug concentration that inhibits growth of an organism by >70% compared with a drug free control. MICs are recorded as mg/L. In cases where the MIC of an organism is >=0.05 mg/L the MIC is repeated using a concentration range of 0.5-0.0005 mg/L.

Assays were also performed in RPMI medium for both *Aspergillus* spp. (strains described above) and *Candida* spp. (*Candida albicans, Candida glabrata, Candida krusei, Candida parapsilosis* and *Candida tropicalis*). To perform MIC tests in this medium, dilutions of compounds are prepared in microtitre plates as described above. Fungal strains to be tested are grown and harvested in an identical manner to that described above, and each organism suspension was diluted in RPMI medium, containing 2% glucose and 0.135 M MOPS buffer (pH 7.0) to 0.5-2×10$^4$ cfu/mL, rather than in YAG medium. 80 µL of an organism suspension was added to each well of the plate containing drug dilutions.

This produced MIC plates with a drug range 50-0.05 mg/L and organism inocula of 1−2×10$^4$ cfu/mL. All plates were incubated for 24-48 h at 35° C. Growth was assessed by monitoring the optical density at 485 nm for each well. The MIC of a compound is the lowest drug concentration that inhibits growth of an organism by >80% compared with a drug free control.

The following organisms were tested: *Aspergillus flavus*, *Aspergillus fumigatus* AF293 and AF210, *Aspergillus niger*, *Aspergillus terreus* AT4 and AT49, *Candida albicans, Candida glabrata, Candida krusei, Candida parapsilosis* and *Candida tropicalis*.

Other fungi including *Absidia corymbifera; Acremonium* spp; *Alternaria alternata; Aspergillus nidulans; Aspergillus parasiticus; Bipolaris* spp; *Blastomyces dermatitidis; Blumeria graminis; Cladosporium cladosporoides; Cladosporium herbarium; Coccidioides immitis; Coccidioides posadasii; Colletotrichium trifolii; Curvularia lunata; Colletotrichium trifolii; Cryptococcus neoformans; Encephalitozoon cuniculi; Epicoccum nigrum; Epidermophyton floccosum; Exophiala* spp; *Exserohilum rostratum; Fusarium graminearium; Fusarium solani; Fusarium sporotrichoides; Histoplasma capsulatum; Leptosphaeria nodorum; Magnaporthe grisea; Microsporum canis; Mycosphaerella graminicola; Neurospora crassa; Paecilomyces lilanicus; Paecilomyces varioti; Penicillium chrysogenum; Phytophthora capsici; Phytophthora infestans; Plasmopara viticola; Pneumocystis jiroveci; Puccinia coronata; Puccinia graminis; Pyricularia oryzae; Pythium ultimum; Rhizomucor* sp.; *Rhizoctonia solani; Rhizomucor* spp.; *Rhizopus* spp.; *Scedosporium apiospermum; Scedosporium prolificans; Scopulariopsis brevicaulis; Trichophyton interdigitale; Trichophyton mentagrophytes; Trichophyton rubrum; Trichosporon asahii; Trichosporon beigelii*; and *Ustilago* maydis may also be used in the above assay. Fungi are cultured by standard methods known to those skilled in the art, and MICs determined as above.

*Aspergillus* MIC results in mg/L (YAG medium):

The following MIC results have been banded into grades. Thus, a grade of 1 represents an MIC of greater than 10 mg/L. A grade of 2 represents an MIC of from 1 to 10 mg/L. A grade of 3 represents an MIC of less than 1 mg/L.

| Example no. | A. flavus | A. fumigatus | A. fumigatus 210 | A. niger | A. terreus | A. terreus 49 |
|---|---|---|---|---|---|---|
| 1 | 3 | 3 | 3 | 3 | 3 | 3 |
| 2 | 3 | 2 | 2 | 1 | 3 | 3 |
| 3 | 2 | 1 | 2 | 1 | 3 | 3 |
| 4 | 2 | 2 | 2 | 2 | 1 | 2 |
| 5 | 2 | 3 | 3 | 2 | 3 | 3 |
| 6 | 3 | 3 | 3 | 3 | 3 | 3 |
| 7 | 3 | 3 | 3 | 3 | 3 | 3 |
| 8 | 2 | 3 | 3 | 3 | 2 | 2 |
| 9 | 3 | 3 | 3 | 3 | 3 | 3 |
| 10 | 2 | 1 | 1 | 1 | 1 | 2 |
| 11 | 3 | 3 | 3 | 3 | 3 | 3 |
| 12 | 3 | 3 | 3 | 3 | 3 | 3 |
| 13 | 3 | 3 | 3 | 3 | 3 | 3 |
| 14 | 3 | 3 | 3 | 3 | 3 | 3 |
| 15 | 3 | 3 | 3 | 3 | 3 | 3 |
| 16 | 3 | 3 | 3 | 3 | 3 | 3 |
| 17 | 2 | 2 | 2 | 2 | 2 | 2 |
| 18 | 3 | 3 | 3 | 1 | 3 | 3 |
| 19 | 2 | 1 | 1 | 1 | 1 | 2 |
| 20 | 1 | 1 | 3 | 1 | 3 | 3 |
| 21 | 3 | 3 | 3 | 3 | 3 | 3 |
| 22 | 3 | 3 | 3 | 3 | 3 | 3 |
| 23 | 3 | 3 | 2 | 3 | 3 | 3 |
| 24 | 3 | 3 | 3 | 3 | 3 | 3 |

| Example no. | A. flavus | A. fumigatus | A. fumigatus 210 | A. niger | A. terreus | A. terreus 49 |
|---|---|---|---|---|---|---|
| 25 | 2 | 3 | 3 | 2 | 2 | 2 |
| 26 | 1 | 3 | 3 | 3 | 3 | 3 |
| 27 | 1 | 3 | 3 | 2 | 2 | 2 |
| 28 | 2 | 3 | 3 | 3 | 3 | 3 |
| 29 | 1 | 1 | 1 | 1 | 1 | 1 |
| 30 | 2 | 2 | 2 | 1 | 2 | 2 |
| 31 | 3 | 2 | 2 | 2 | 3 | 3 |
| 32 | 3 | 2 | 2 | 2 | 3 | 3 |
| 33 | 1 | 1 | 1 | 1 | 1 | 2 |
| 34 | 3 | 3 | 3 | 3 | 3 | 3 |
| 35 | 3 | 3 | 3 | 3 | 3 | 3 |
| 36 | 3 | 3 | 3 | 3 | 3 | 3 |
| 37 | 3 | 3 | 3 | 3 | 3 | 3 |
| 38 | 3 | 3 | 3 | 3 | 3 | 3 |
| 39 | 3 | 3 | 3 | 3 | 3 | 3 |
| 40 | 3 | 3 | 3 | 3 | 3 | 3 |
| 41 a | 3 | 3 | 3 | 3 | 3 | 3 |
| 41 b | 1 | 2 | 2 | 1 | 1 | 1 |
| 42 | 1 | 2 | 2 | 1 | 1 | 1 |
| 43 | 3 | 2 | 2 | 1 | 2 | 2 |
| 44 | 3 | 3 | 3 | 3 | 3 | 3 |
| 45 | 3 | 3 | 3 | 3 | 3 | 3 |
| 46 | 3 | 2 | 3 | 1 | 1 | 3 |
| 47 | 3 | 3 | 3 | 2 | 2 | 3 |
| 48 | 1 | 2 | 3 | 1 | 1 | 1 |
| 49 | 3 | 2 | 2 | 1 | 1 | 3 |
| 50 | 3 | 3 | 3 | 3 | 3 | 3 |
| 51 | 3 | 3 | 3 | 3 | 3 | 3 |
| 52 | 3 | 3 | 3 | 3 | 3 | 3 |
| 53 | 3 | 3 | 3 | 3 | 3 | 3 |
| 54 | 2 | 3 | 3 | 2 | 2 | 3 |
| 55 | 1 | 2 | 2 | 1 | 1 | 2 |
| 56 | 1 | 2 | 2 | 2 | 2 | 2 |
| 57 | 2 | 3 | 3 | 2 | 2 | 3 |
| 58 | 2 | 2 | 2 | 1 | 2 | 2 |
| 59 | 1 | 2 | 2 | 1 | 2 | 2 |
| 60 | 1 | 2 | 2 | 2 | 2 | 2 |
| 61 | 1 | 1 | 2 | 1 | 1 | 1 |
| 62 | 3 | 3 | 3 | 3 | 3 | 3 |
| 63 | 3 | 3 | 3 | 2 | 3 | 3 |
| 64 | 3 | 3 | 3 | 3 | 3 | 3 |
| 65 | 1 | 1 | 1 | 1 | 1 | 1 |
| 66 | 2 | 3 | 2 | 1 | 2 | 3 |
| 67 | 3 | 3 | 3 | 2 | 3 | 3 |
| 68 | 1 | 2 | 1 | 1 | 2 | 2 |
| 69 | 2 | 3 | 3 | 3 | 3 | 3 |
| 70 | 2 | 3 | 3 | 1 | 3 | 3 |
| 71 | 1 | 1 | 1 | 1 | 1 | 2 |
| 72 | 2 | 3 | 3 | 3 | 3 | 3 |
| 73 | 1 | 3 | 3 | 3 | 1 | 2 |
| 74 | 1 | 3 | 3 | 3 | 2 | 2 |
| 75 | 1 | 1 | 1 | 1 | 1 | 1 |
| 76 | 1 | 2 | 2 | 1 | 1 | 1 |
| 77 | 1 | 3 | 3 | 2 | 2 | 2 |
| 78 | 1 | 1 | 1 | 1 | 1 | 2 |
| 79 | 3 | 2 | 2 | 2 | 3 | 3 |
| 80 | 1 | 1 | 1 | 1 | 1 | 1 |
| 81 | 1 | 1 | 1 | 1 | 1 | 1 |
| 82 | 1 | 2 | 2 | 1 | 2 | 2 |
| 83 | 1 | 2 | 2 | 1 | 2 | 2 |
| 84 | 1 | 1 | 1 | 1 | 1 | 1 |
| 85 | 1 | 1 | 1 | 2 | 1 | 1 |
| 86 | 2 | 1 | 1 | 1 | 1 | 1 |
| 87 | 1 | 3 | 3 | 3 | 2 | 3 |
| 88 | 1 | 3 | 3 | 2 | 2 | 1 |
| 89 | 1 | 3 | 3 | 2 | 2 | 2 |
| 90 | 3 | 3 | 3 | 3 | 3 | 3 |
| 91 | 1 | 2 | 2 | 1 | 1 | 2 |
| 92 | 3 | 3 | 3 | 3 | 3 | 3 |
| 93 | 2 | 3 | 3 | 3 | 2 | 2 |
| 94 | 2 | 2 | 2 | 2 | 3 | 3 |
| 95 | 3 | 3 | 3 | 3 | 3 | 3 |
| 96 | 3 | 3 | 3 | 3 | 3 | 3 |
| 97 | 2 | 2 | 3 | 2 | 2 | 2 |
| 98 | 1 | 3 | 3 | 3 | 3 | 3 |
| 99 | 3 | 2 | 3 | 2 | 3 | 3 |
| 100 | 3 | 3 | 2 | 3 | 3 | 3 |
| 101 | 3 | 3 | 3 | 3 | 3 | 3 |
| 102 | 1 | 2 | 1 | 1 | 1 | 1 |
| 103 | 1 | 3 | 3 | 1 | 2 | 2 |
| 104 | 1 | 2 | 2 | 1 | 2 | 2 |
| 105 | 3 | 3 | 3 | 3 | 3 | 3 |
| 106 | 3 | 3 | 3 | 3 | 3 | 3 |
| 107 | 1 | 3 | 3 | 1 | 1 | 1 |
| 108 | 3 | 3 | 3 | 3 | 3 | 3 |
| 109 | 3 | 3 | 3 | 3 | 3 | 3 |
| 110 | 2 | 3 | 3 | 3 | 3 | 2 |
| 111 | 2 | 3 | 3 | 3 | 3 | 3 |
| 112 | 3 | 3 | 3 | 3 | 3 | 3 |
| 113 | 3 | 3 | 3 | 3 | 3 | 3 |
| 114 | 3 | 3 | 3 | 3 | 3 | 3 |
| 115 | 3 | 3 | 3 | 3 | 3 | 3 |
| 116 | 3 | 3 | 3 | 3 | 3 | 3 |
| 117 | 3 | 3 | 2 | 3 | 3 | 3 |
| 118 | 3 | 3 | 3 | 3 | 3 | 3 |
| 119 | 2 | 3 | 3 | 3 | 3 | 3 |
| 120 | 3 | 3 | 3 | 3 | 3 | 3 |
| 121 | 1 | 1 | 2 | 1 | 2 | 2 |
| 122 | 1 | 3 | 2 | 2 | 1 | 1 |
| 123 | 3 | 3 | 3 | 3 | 3 | 3 |
| 124 | 3 | 3 | 3 | 3 | 3 | 3 |
| 125 | 3 | 3 | 3 | 3 | 3 | 3 |
| 126 | 2 | 3 | 3 | 2 | 3 | 3 |
| 127 | 3 | 1 | 2 | 3 | 3 | 3 |
| 128 | 3 | 3 | 3 | 3 | 3 | 3 |
| 129 | 3 | 3 | 3 | 3 | 3 | 3 |
| 130 | 3 | 3 | 3 | 3 | 3 | 3 |
| 131 | 2 | 2 | 2 | 2 | 2 | 2 |
| 132 | 3 | 3 | 3 | 3 | 3 | 3 |
| 133 | 2 | 3 | 3 | 3 | 3 | 3 |
| 134 | 2 | 2 | 1 | 1 | 2 | 2 |
| 135 | 1 | 3 | 2 | 2 | 2 | 1 |
| 136 | 3 | 3 | 3 | 3 | 2 | 3 |
| 137 | 3 | 3 | 3 | 3 | 3 | 3 |
| 138 | 3 | 3 | 3 | 3 | 3 | 3 |
| 139 | 2 | 3 | 3 | 3 | 2 | 3 |
| 140 | 2 | 2 | 3 | 2 | 2 | 2 |
| 141 | 2 | 3 | 3 | 2 | 2 | 2 |
| 142 | 3 | 3 | 3 | 3 | 3 | 3 |
| 143 | 3 | 3 | 3 | 3 | 3 | 3 |
| 144 | 3 | 3 | 3 | 3 | 3 | 3 |
| 145 | 3 | 3 | 3 | 3 | 3 | 3 |
| 146 | 2 | 3 | 3 | 2 | 2 | 2 |
| 147 | 3 | 3 | 3 | 3 | 3 | 3 |
| 148 | 3 | 3 | 3 | 3 | 3 | 3 |
| 149 | 3 | 3 | 3 | 3 | 3 | 3 |
| 150 | 3 | 3 | 3 | 3 | 3 | 3 |
| 151 | 3 | 3 | 3 | 3 | 3 | 3 |
| 152 | 3 | 3 | 3 | 3 | 3 | 3 |
| 153 | 3 | 3 | 2 | 3 | 2 | 3 |
| 154 | 3 | 3 | 3 | 3 | 3 | 3 |

*Aspergillus* MIC Results in mg/L (RPMI Medium):

The following MIC results have been banded into grades as defined above.

| Example no. | A. flavus | A. fumigatus | A. fumigatus 210 | A. niger | A. terreus | A. terreus 49 |
|---|---|---|---|---|---|---|
| 1 | 3 | 3 | 3 | 3 | 3 | 3 |
| 2 | 1 | 1 | 1 | 1 | 1 | 1 |
| 3 | 1 | 1 | 1 | 1 | 2 | 2 |
| 4 | 1 | 1 | 1 | 1 | 1 | 1 |
| 5 | 2 | 2 | 2 | 2 | 3 | 3 |
| 6 | 3 | 3 | 3 | 3 | 3 | 3 |
| 7 | 3 | 3 | 3 | 3 | 3 | 3 |
| 8 | 1 | 2 | 2 | 2 | 2 | 2 |
| 9 | 1 | 3 | 3 | 3 | 2 | 2 |
| 10 | 1 | 1 | 1 | 1 | 1 | 1 |

| Example no. | A. flavus | A. fumigatus | A. fumigatus 210 | A. niger | A. terreus | A. terreus 49 |
|---|---|---|---|---|---|---|
| 11 | 3 | 3 | 3 | 3 | 3 | 3 |
| 12 | 3 | 3 | 3 | 3 | 3 | 3 |
| 13 | 3 | 3 | 3 | 3 | 3 | 3 |
| 14 | 3 | 3 | 3 | 3 | 3 | 3 |
| 15 | 3 | 3 | 3 | 3 | 3 | 3 |
| 16 | 3 | 3 | 2 | 3 | 3 | 3 |
| 17 | 1 | 1 | 1 | 1 | 1 | 1 |
| 18 | 2 | 3 | 3 | 1 | 3 | 3 |
| 19 | 1 | 1 | 1 | 1 | 1 | 1 |
| 20 | 1 | 1 | 1 | 1 | 1 | 2 |
| 21 | 3 | 3 | 3 | 3 | 3 | 3 |
| 22 | 3 | 3 | 3 | 3 | 3 | 3 |
| 23 | 3 | 2 | 2 | 2 | 3 | 3 |
| 24 | 2 | 3 | 3 | 3 | 2 | 1 |
| 25 | 1 | 1 | 2 | 2 | 1 | 1 |
| 26 | 1 | 3 | 3 | 3 | 1 | 1 |
| 27 | 1 | 2 | 2 | 2 | 1 | 1 |
| 28 | 2 | 3 | 3 | 3 | 2 | 2 |
| 29 | 1 | 1 | 1 | 1 | 1 | 1 |
| 30 | 1 | 1 | 1 | 1 | 1 | 1 |
| 31 | 2 | 2 | 2 | 2 | 3 | 3 |
| 32 | 2 | 1 | 1 | 2 | 2 | 2 |
| 33 | 1 | 1 | 1 | 1 | 1 | 1 |
| 34 | 3 | 3 | 3 | 3 | 3 | 3 |
| 35 | 3 | 3 | 3 | 3 | 3 | 3 |
| 36 | 3 | 3 | 3 | 3 | 3 | 3 |
| 37 | 3 | 2 | 2 | 2 | 3 | 3 |
| 38 | 3 | 3 | 3 | 3 | 3 | 3 |
| 39 | 3 | 3 | 3 | 3 | 3 | 3 |
| 40 | 3 | 3 | 3 | 3 | 3 | 3 |
| 41 a | 1 | 2 | 1 | 1 | 2 | 3 |
| 41 b | 1 | 2 | 1 | 1 | 1 | 1 |
| 42 | 1 | 2 | 1 | 1 | 1 | 1 |
| 43 | 2 | 1 | 1 | 1 | 2 | 1 |
| 44 | 3 | 3 | 3 | 3 | 3 | 3 |
| 45 | 3 | 3 | 3 | 3 | 3 | 3 |
| 46 | 1 | 1 | 1 | 1 | 2 | 2 |
| 47 | 2 | 2 | 2 | 2 | 2 | 2 |
| 48 | 1 | 1 | 1 | 1 | 1 | 1 |
| 49 | 2 | 2 | 1 | 1 | 2 | 2 |
| 50 | 3 | 3 | 3 | 3 | 3 | 3 |
| 51 | 3 | 3 | 3 | 3 | 3 | 3 |
| 52 | 2 | 3 | 3 | 3 | 3 | 3 |
| 53 | 3 | 3 | 3 | 3 | 3 | 3 |
| 54 | 1 | 3 | 2 | 2 | 1 | 1 |
| 55 | 1 | 1 | 1 | 1 | 1 | 1 |
| 56 | 1 | 1 | 1 | 1 | 1 | 1 |
| 57 | 1 | 2 | 2 | 2 | 2 | 2 |
| 58 | 1 | 1 | 1 | 1 | 1 | 1 |
| 59 | 1 | 2 | 2 | 1 | 1 | 1 |
| 60 | 1 | 2 | 2 | 2 | 1 | 1 |
| 61 | 1 | 1 | 2 | 1 | 1 | 1 |
| 62 | 3 | 3 | 3 | 3 | 3 | 3 |
| 63 | 3 | 3 | 3 | 3 | 3 | 3 |
| 64 | 2 | 3 | 3 | 3 | 2 | 3 |
| 65 | 1 | 1 | 1 | 1 | 1 | 1 |
| 66 | 1 | 2 | 2 | 1 | 2 | 2 |
| 67 | 2 | 2 | 2 | 1 | 3 | 3 |
| 68 | 1 | 1 | 1 | 1 | 1 | 1 |
| 69 | 1 | 3 | 3 | 3 | 2 | 2 |
| 70 | 2 | 2 | 2 | 1 | 2 | 2 |
| 71 | 1 | 1 | 1 | 1 | 1 | 1 |
| 72 | 2 | 2 | 2 | 2 | 2 | 2 |
| 73 | 1 | 3 | 3 | 3 | 1 | 1 |
| 74 | 1 | 3 | 3 | 3 | 2 | 2 |
| 75 | 1 | 1 | 1 | 1 | 1 | 1 |
| 76 | 1 | 1 | 2 | 1 | 1 | 1 |
| 77 | 1 | 2 | 2 | 1 | 1 | 1 |
| 78 | 1 | 1 | 1 | 1 | 1 | 1 |
| 79 | 2 | 1 | 1 | 2 | 2 | 2 |
| 80 | 1 | 1 | 1 | 1 | 1 | 1 |
| 81 | 1 | 1 | 1 | 1 | 1 | 1 |
| 82 | 1 | 1 | 1 | 1 | 1 | 1 |
| 83 | 1 | 1 | 1 | 1 | 1 | 1 |
| 84 | 1 | 1 | 1 | 1 | 1 | 1 |
| 85 | 1 | 1 | 1 | 2 | 2 | 2 |
| 86 | 1 | 1 | 1 | 1 | 1 | 1 |
| 87 | 1 | 3 | 3 | 3 | 2 | 2 |
| 88 | 1 | 3 | 3 | 2 | 1 | 1 |
| 89 | 1 | 2 | 2 | 2 | 1 | 1 |
| 90 | 3 | 3 | 3 | 3 | 3 | 3 |
| 91 | 1 | 1 | 1 | 1 | 1 | 1 |
| 92 | 1 | 3 | 3 | 3 | 1 | 1 |
| 93 | 1 | 2 | 2 | 2 | 1 | 1 |
| 94 | 1 | 3 | 2 | 2 | 2 | 2 |
| 95 | 3 | 3 | 3 | 3 | 3 | 3 |
| 96 | 2 | 3 | 3 | 3 | 3 | 2 |
| 97 | 2 | 3 | 2 | 2 | 2 | 2 |
| 98 | 2 | 3 | 3 | 3 | 3 | 3 |
| 99 | 3 | 3 | 2 | 3 | 3 | 3 |
| 100 | 3 | 3 | 2 | 3 | 3 | 3 |
| 101 | 3 | 3 | 3 | 3 | 3 | 3 |
| 102 | 1 | 1 | 1 | 1 | 1 | 1 |
| 103 | 1 | 2 | 2 | 3 | 2 | 2 |
| 104 | 1 | 1 | 1 | 1 | 1 | 1 |
| 105 | 3 | 3 | 3 | 3 | 3 | 3 |
| 106 | 3 | 3 | 3 | 3 | 3 | 3 |
| 107 | 1 | 3 | 2 | 1 | 1 | 1 |
| 108 | 3 | 3 | 3 | 3 | 3 | 3 |
| 109 | 3 | 3 | 3 | 3 | 3 | 3 |
| 110 | 2 | 3 | 3 | 2 | 3 | 3 |
| 111 | 2 | 3 | 3 | 3 | 3 | 2 |
| 112 | 3 | 3 | 3 | 3 | 3 | 3 |
| 113 | 2 | 2 | 3 | 3 | 3 | 2 |
| 114 | 2 | 2 | 2 | 3 | 2 | 2 |
| 115 | 3 | 3 | 3 | 3 | 3 | 3 |
| 116 | 1 | 3 | 3 | 3 | 3 | 3 |
| 117 | 1 | 2 | 2 | 3 | 2 | 1 |
| 118 | 3 | 3 | 3 | 3 | 3 | 3 |
| 119 | 2 | 3 | 3 | 3 | 3 | 2 |
| 120 | 3 | 3 | 3 | 3 | 3 | 3 |
| 121 | 1 | 1 | 1 | 1 | 1 | 1 |
| 122 | 1 | 1 | 1 | 2 | 1 | 1 |
| 123 | 3 | 3 | 3 | 3 | 3 | 2 |
| 124 | 2 | 2 | 2 | 1 | 2 | 2 |
| 125 | 2 | 2 | 2 | 2 | 2 | 2 |
| 126 | 1 | 2 | 2 | 1 | 2 | 2 |
| 127 | 3 | 1 | 1 | 3 | 3 | 3 |
| 128 | 3 | 3 | 3 | 3 | 3 | 3 |
| 129 | 3 | 3 | 2 | 2 | 2 | 2 |
| 130 | 3 | 3 | 3 | 3 | 3 | 3 |
| 131 | 1 | 1 | 1 | 2 | 2 | 2 |
| 132 | 1 | 3 | 3 | 3 | 3 | 3 |
| 133 | 1 | 3 | 3 | 3 | 2 | 2 |
| 134 | 1 | 1 | 1 | 1 | 1 | 1 |
| 135 | 1 | 1 | 1 | 1 | 1 | 1 |
| 136 | 2 | 2 | 2 | 2 | 2 | 2 |
| 137 | 2 | 3 | 2 | 2 | 2 | 2 |
| 138 | 2 | 3 | 3 | 2 | 2 | 2 |
| 139 | 1 | 2 | 2 | 2 | 2 | 2 |
| 140 | 1 | 1 | 1 | 1 | 1 | 1 |
| 141 | 1 | 1 | 1 | 1 | 1 | 1 |
| 142 | 3 | 3 | 3 | 3 | 3 | 3 |
| 143 | 3 | 3 | 3 | 3 | 3 | 3 |
| 144 | 3 | 3 | 3 | 3 | 3 | 3 |
| 145 | 3 | 3 | 3 | 2 | 3 | 3 |
| 146 | 1 | 3 | 1 | 2 | 1 | 1 |
| 147 | 3 | 3 | 3 | 3 | 3 | 3 |
| 148 | 3 | 3 | 2 | 3 | 3 | 3 |
| 149 | 1 | 2 | 2 | 3 | 2 | 2 |
| 150 | 3 | 3 | 3 | 3 | 3 | 3 |
| 151 | 3 | 3 | 3 | 3 | 3 | 3 |
| 152 | 3 | 3 | 3 | 3 | 3 | 3 |
| 153 | 2 | 2 | 2 | 3 | 3 | 3 |
| 154 | 3 | 3 | 3 | 3 | 3 | 3 |

*Candida* MIC Results in mg/L (RPMI Medium):

The following MIC results have been banded into grades as defined above.

| Example no. | C. albicans | C. glabrata | C. krusei | C. parapsilosis | C. tropicalis |
|---|---|---|---|---|---|
| 9 | 2 | 3 | 3 | 3 | 2 |
| 13 | 3 | 3 | 3 | 3 | 3 |
| 47 | 2 | 3 | 2 | 2 | 2 |
| 52 | 2 | 3 | 3 | 2 | 2 |
| 57 | 2 | 3 | 3 | 2 | 2 |
| 59 | 3 | 3 | 2 | 3 | 3 |
| 60 | 3 | 3 | 3 | 3 | 2 |
| 63 | 2 | 3 | 3 | 3 | 3 |
| 68 | 3 | 3 | 2 | 3 | 3 |
| 69 | 2 | 3 | 2 | 3 | 3 |
| 70 | 2 | 3 | 2 | 3 | 2 |
| 72 | 3 | 3 | 2 | 3 | 3 |
| 73 | 2 | 3 | 2 | 2 | 3 |
| 74 | 2 | 3 | 2 | 3 | 3 |
| 76 | 3 | 3 | 3 | 3 | 3 |
| 81 | 3 | 3 | 3 | 3 | 3 |
| 84 | 3 | 3 | 3 | 3 | 3 |
| 85 | 2 | 2 | 2 | 2 | 2 |
| 86 | 3 | 3 | 3 | 3 | 3 |
| 87 | 2 | 3 | 2 | 3 | 3 |
| 88 | 2 | 3 | 3 | 3 | 3 |
| 89 | 2 | 3 | 3 | 3 | 3 |
| 103 | 3 | 3 | 3 | 3 | 3 |
| 104 | 2 | 3 | 2 | 3 | 3 |
| 109 | 3 | 3 | 3 | 3 | 2 |
| 113 | 3 | 3 | 3 | 3 | 3 |
| 114 | 3 | 3 | 3 | 3 | 3 |

In Vivo Testing Example 2-(1,5-Dimethyl-3-phenyl-1H-pyrrol-2-yl)-N-{4-[4-(4,6-dimethyl-pyridin-2-yl)-piperazin-1-yl]-phenyl}-2-oxo-acetamide has excellent activity in vitro against *Aspergillus* and other filamentous fungi and shows good oral bio-availability and tissue distribution. The efficacy of oral dosed 2-(1,5-Dimethyl-3-phenyl-1H-pyrrol-2-yl)-N-{4-[4-(4,6-dimethyl-pyridin-2-yl)-piperazin-1-yl]-phenyl}-2-oxo-acetamide has been tested in murine survival models of disseminated aspergillosis.

Methods: Temporary (TI) or persistently (PI) neutropenic CD-1 mouse models of disseminated *aspergillus* were used. 3 days post immunosuppression with cyclophosphamide (200 mg/kg ip) mice were infected IV with an $LD_{90}$ challenge of *A. fumigatus* A1163. Treatment commenced 5 h post infection and animals were treated for 9 days and observed for either 2 days or 7 days following cessation of treatment. In PI models animals had a further dose of cyclophosphamide one day after infection. 2-(1,5-Dimethyl-3-phenyl-1H-pyrrol-2-yl)-N-{4-[4-(4,6-dimethyl-pyridin-2-yl)-piperazin-1-yl]-phenyl}-2-oxo-acetamide was dosed orally as a suspension in HPMC/Tween 80 once or twice daily. Caspofungin dosed IP was used as a comparator.

Results: A dose dependent response was seen in the TI survival model with doses of 1.25 and 2.5 mg/kg per day showing little benefit, 5 mg/kg per day showing 80% survival, 10 mg/kg/day being highly effective (90% survival) and doses of 20, 30 and 40 mg/kg/day giving 100% survival. In a severe PI model 20 mg/kg BD gave 70% survival at day 12, untreated animals were all dead at day 7. A comparison of once and twice daily dosing in a TI model with prolonged observation showed that 10 mg/kg BD (80% survival at day 18) was superior to 20 mg/kg OD (70% survival at day 18).

Conclusions: 2-(1,5-Dimethyl-3-phenyl-1H-pyrrol-2-yl)-N-{4-[4-(4,6-dimethyl-pyridin-2-yl)-piperazin-1-yl]-phenyl}-2-oxo-acetamide demonstrated dose dependent survival improvement following a lethal *A. fumigatus* infection and efficacy in persistently neutropenic models and in models where animals were observed for 7 days following cessation of treatment. 2-(1,5-Dimethyl-3-phenyl-1H-pyrrol-2-yl)-N-{4-[4-(4,6-dimethyl-pyridin-2-yl)-piperazin-1-yl]-phenyl}-2-oxo-acetamide was at least as effective as CAS in these models.

Combination Therapy Example 1

Determination of Combined Effect of Two Antifungal Agents

In order to determine the combined effect of an antifungal pyrrole compound and a second antifungal agent as described above a checkerboard titration can be carried out. These are relatively simple tests to determine if an additive or synergistic effect between two compounds is present. The description which follows describes an exemplary checkerboard titration; the skilled person would readily identify which aspects of the method can be changed, for example using different organisms, different growth media, different concentrations of stock solutions and so forth.

In the checkerboard titration doubling dilutions of compound A (e.g. an antifungal pyrrole compound as defined earlier) are prepared in every row across a microtitre plate and doubling dilutions of compound B (e.g. a second antifungal agent as defined earlier) are prepared in every column down a microtitre plate. The activity of the two compounds in combination can be compared with the activity of each compound alone. In such experiments a narrow range of dilutions can be tested for each compound around the minimum inhibitory concentration (MIC).

As an example, a stock solution of compound A (e.g. 5 mg/ml) can be prepared in a suitable solvent such as DMSO. A stock solution of compound B (e.g. caspofungin) is also prepared (e.g. 2 mg/ml). The stock solution of compound A is diluted (e.g. at a concentration of 1:2000 in water) to 2.5 µg/ml. From this stock, aqueous solutions containing the following concentrations of compound A can be prepared: 0.9, 0.8, 0.7, 0.6, 0.5, 0.4, 0.3, 0.2, 0.1, 0.05, 0.025, 0.0125 µg/ml. 20 µl volumes of each stock solution can then be added to the first eleven wells in a column of a microtitre plate, with the remaining column being given 20 µl of water. Each row of the plate contains 20 µl of a series of dilutions of compound A and one free control well containing no antifungal agent.

The compound B stock solution can be diluted in water by adding 5.5 µl of stock solution to 10 ml water. From this stock aqueous dilutions of compound B containing the following concentrations can be prepared: 0.55, 0.45, 0.35, 0.25, 0.15, 0.05, 0.025 ug/ml. Each of these stocks can then be added to every row in the microtitre plate containing the compound A dilutions. The bottom row of the plate can be given 20 µl of water.

Thus each well contains 40 µl of liquid comprising 20 µl of compound A or water and 20 µl of compound B or water.

Spores of a relevant organism (e.g. *Aspergillus fumigatus* AF210) are harvested, for example from a 5-10 day old culture grown on a Sabourad agar plates. A suspension is made in PBS/Tween80 and the number of spores estimated using a spectrophotometer at A495 using a previously constructed calibration curve.

Appropriate growth media can be used, for example RPMI or YAG media. These can be prepared in line with the following example: 10.1 g of RPMI powder (Gibco) are added to a 1 L Duran bottle, along with 34.5 g MOPS buffer and 18 g Glucose. Approximately 500 ml of deionised water is added and the bottle placed on a magnetic stirrer to assist solution. When completely dissolved the solution is adjusted to pH 7.0 using 5N NaOH. The solution is then made up to 600 ml total volume using deionised water and then filter sterilised through a 0.2 μm membrane and stored at 4° C.

For the test the spores of the chosen organism are diluted in the relevant medium (e.g. RPMI) to give a concentration of 1–3×10$^4$ cfu/ml. The media is vortex mixed and the 60 μl of spore suspension is added to each well of the plate, to give a final spore concentration of 0.5–2.5×10$^4$ cfu/ml. The final concentrations of compound A and compound B in the medium is:

Compound A: 0.18, 0.16, 0.14, 0.12, 0.1, 0.08, 0.06, 0.04, 0.03, 0.02, 0.01 μg/ml Compound B: 0.11, 0.09, 0.07, 0.05, 0.03, 0.01, 0.005 μg/ml The plate is incubated in a moist chamber for 48 hrs and then examined for growth. The row containing dilutions of compound A without compound B provides the MIC of compound A. Similarly, the column which contains dilutions of compound B with no compound A provides the MIC of compound B.

To determine the combined effect of the compounds the Fractional inhibitory concentration FIC is determined, where FIC is defined as:

$$FIC = FIC_A + FIC_B = C_A^{comb}/MIC_A^{alone} + C_B^{comb}/MIC_B^{alone}$$

where $MIC_A^{alone}$ and $MIC_B^{alone}$ are the MICs of compounds A and B when acting alone and $C_A^{comb}$ and $C_B^{comb}$ are concentrations of compounds A and B at the isoeffective combinations, respectively. The interpretation of the FIC is as follows: a FIC value of 0.5 reveals synergy, a value of 1 to 4 reveals indifference, and a value of >4 represents antagonism.

In accordance with the description above, a study was carried out with *Aspergillus fumigatus* AF210 in RPMI media with 2-(1,5-Dimethyl-3-phenyl-1H-pyrrol-2-yl)-N-{4-[4-(4,6-dimethyl-pyridin-2-yl)-piperazin-1-yl]-phenyl}-2-oxo-acetamide (i.e. the compound of Example 1) as compound A and caspofungin as compound B. In this experiment an FIC of 0.67 was obtained.

Combination Therapy Example 2

Determination of Synergy Between Two Antifungal Compounds In Vivo

Antifungal drugs are often used in combination to treat systemic infections in ill patients. When drugs are used together in combination various interactions may occur, these actions may be synergistic, antagonistic or indifferent (also known as an additive effect). For patient care antagonistic combinations should be avoided as they may be associated with a worse outcome, synergistic effects are desirable however indifferent or additive combinations can be of benefit.

Interactions between two antifungal drugs can be studied in vitro using checkerboard synergy tests, or kill curve type studies, however it is also useful to be able to assess the interaction between a combination of drugs in in vivo models which are more realistic as the pharmacokinetics effects of each drug are taken into account.

There are several models that can be used to assess the efficacy of a combination of antifungal drugs, the models typically being tissue burden models or survival models.

In the first model groups of mice (typically 6-7 although larger groups can be used) are immunosuppressed with cyclophosphamide 200 mg/kg on day 1, on day 4 they are then infected with the infecting organism eg *Aspergilli*. or *Candida* spp. Infection may be through the lateral tail vein, intranasal, pulmonary or GI. The inoculum is sufficient to establish infection in different body organs. Four to 24 hours after infection animals are treated with each of the test drugs individually at appropriate doses and with both drugs in combination. Typical doses could be from 5 to 150 mg/kg of the pyrrole agent in combination with the approved dose of other marketed agents.

Different routes of administration may be used for the different drugs, and different frequencies of dosing may be appropriate for each drug. The animals are treated for up to 14 days and then remain untreated for 12-18 hr following the last dose of drug.

A group of animals which are infected but untreated are used as controls for comparison purposes. The animals are then humanely euthanized, and the kidneys are removed. Both kidneys from each mouse are pooled, weighed and then homogenised in 1 ml of PBS/Tween. The homogenate is then diluted in PBS and aliquots of the homogenates are plated onto Sabourauds agar and incubated for 24-48 hrs. Colonies are counted and the actual colony count per gram (cfu/gm) of tissue calculated taking into account dilution factors and tissue weight.

The cfu/gm of each mouse in each treatment group is plotted graphically. This allows comparison of the untreated animals with the treatment groups, and also a comparison of each drug used singly and in combination. Statistical analyses can be carried out on each treatment group compared with the control group and between the individual drugs and the combination of drugs.

Other in vivo studies that are used for assessing the efficacy of combinations in comparison with single drugs are survival studies. In these models groups of mice (typically 10 per group) are immunosuppressed with cyclophosphamide and infected with *A. fumigatus* in the same manner as the tissue burden study. Animals are treated with drug for 10 days using relevant dosages, routes and frequencies and then observed for 2-7 days after treatment has ceased. The number of mice surviving in each group is assessed on a daily basis. Infected but untreated animals serve as controls and usually succumb to infection and die by day 5-7. The efficacy of compounds is assessed by comparing survival rates at the end of the study. Although such studies are useful for comparing different single agents unless individual agents have poor survival rates then it will be difficult to identify additive or synergistic effects between two agents. More severe models can be employed to reduce the survival rates for single agents such as using a persistently neutropenic survival model, in which animals are given additional doses of immunosuppressive agents or delayed treatment models in which the first dose of drug is given 24 hrs or later following infection.

The models described previously are disseminated models of *A. fumigatus* infection in which infection is established in numerous body organs following intravenous injection of spores. Alternative models of infection for conducting synergy studies include survival studies using pulmonary models of infection. In such models *Aspergillus* spores are introduced into the lung either through inhalation of aerosols or spore suspensions. Infection develops in the lung, the most common site of infection in humans. These infections are perhaps a better mimic of human infection. Such infection models can be used to examine synergy between compounds. These models are typically severe as the animals are persistently immunosuppressed and untreated animals rapidly succumb to infection. Further modifications to these models can be made by delaying treatment and continuing observation of animals following cessation of treatment.

Synergy studies are carried out by comparing the effect of each individual drug and the drugs in combination. If drugs are highly potent and give good survival rates when used singly despite increasing the severity of the infection then a suitable approach is to lower the dose of each drug either by reducing the dose or dosing frequency. In this way survival rates below 50% may be achieved which will allow synergy to be demonstrated when both drugs are used in combination.

In another example of combination therapy, dosing of the novel pyrrole agent may allow the reduced dosing of other more toxic antifungal agents. This would result in a reduction of the toxic effects or drug-drug interaction profiles ordinarily seen with the established agent.

Examples of this would be with the azole class of antifungals where toxicities and drug interactions are well known. By using members of this class, specifically itraconazole, voriconazole and posaconazole, in combination with the novel pyrrole agent described, increased efficacy could be expected with reduced azole dosing and result in reduced toxicities.

The invention claimed is:

1. A pharmaceutical combination comprising a combination of a first antifungal agent which is a pyrrole derivative of formula (I) or a pharmaceutically acceptable salt thereof, with a second antifungal agent:

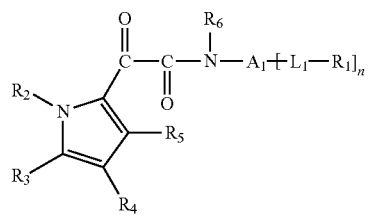

wherein:
R1 represents hydrogen, unsubstituted or substituted C1-C8 alkyl, C2-C8 alkenyl, C2-C8 alkynyl, —COR' or —SO$_2$(C1-C4 alkyl), or a group -A2, -L2-A2, -L3-A2, -A2-L3-A3 or -A4;
A1 represents a C3-C6 cycloalkyl or an unsubstituted or substituted C6-C10 aryl or 5- to 12-membered heterocyclyl group;
A2 and A3 are the same or different and represent C3-C6 cycloalkyl or an unsubstituted or substituted C6-C10 aryl or 5- to 12-membered heterocyclyl group;
A4 is an unsubstituted or substituted 5- to 12-membered heterocyclyl group wherein 1 or 2 ring carbon atoms are replaced with a group selected from >C(=O), >S(=O)$_2$, >C(=NOR7), >C=CH$_2$ or >C(—OCH$_2$CH$_2$O—), where R7 is hydrogen or a C1-C4 alkyl group;
L1 represents a bond, a C1-C6 alkylene group in which none, one, two or three —CH$_2$— groups are independently replaced by —O—, —S— or —NR'—, or a 5- to 12-membered heterocyclyl group;
L2 represents —NR'—, —O—, —CO—, —OCO, —OCONR'R"—, —CONR'R"— or —SO$_2$—;
L3 represents a bond or a C1-C4 alkylene group in which none, one or two —CH$_2$— groups are independently replaced by —O—, —S— or —NR'—;
n is 1 or 2;
R6 represents hydrogen or C1-C4 alkyl;
R5 represents an unsubstituted or substituted group selected from C6-C10 aryl, a 5- to 12-membered heterocyclyl group, C1-C8 alkyl and C3-C6 cycloalkyl, halogen or a group of formula —B1-B2 or —B3;
B1 represents an unsubstituted or substituted C6-C10 aryl group;
B2 represents an unsubstituted or substituted C6-C10 aryl or 5- to 12-membered heterocyclyl group;
B3 is an unsubstituted or substituted 5- to 12-membered heterocyclyl group where 1 or 2 ring carbon atoms are replaced with a group selected from >C(=O), >S(=O)$_2$, >C(=NOR11), >C=CH$_2$ or >C(—OCH$_2$CH$_2$O—), where R11 is hydrogen or a C1-C4 alkyl group;
R2 and R3 independently represent C6-C10 aryl, a 5- to 12-membered heterocyclyl group, C3-C6 cycloalkyl, hydrogen, halogen, C1-C8 alkyl, C2-C8 alkenyl, C2-C8 alkynyl, C3-C6 cycloalkyl, —OR', —SR', —SOR', —SO$_2$R', —SO$_2$NR'R", —SO$_3$H, —NR'R", —NR'COR', —CO$_2$R', —CONR'R", —COR', —OCOR', —CF$_3$, —NSO$_2$R' or —OCONR'R", or a group (C1-4) alkyl-A5, wherein none, one or two —CH$_2$— groups are independently replaced by —O—, —S— or —NR'— and wherein A5 represents C6-10 aryl or a 5- to 12-membered heterocyclyl group; or R2 and R3 together with the ring atoms to which they are bonded form a 5- to 7-membered, saturated or partially saturated ring containing a nitrogen atom from the adjacent pyrrole ring, and optionally one or two further heteroatoms selected from N, O and S, with the proviso that R2 and R3 do not form, together with the pyrrole ring to which they are bonded, a tetrahydroindolizine ring;
R4 represents hydrogen, halogen, C1-C8 alkyl, C2-C8 alkenyl, C2-C8 alkynyl, —OR', —CONR'R", —COR', —CN, —NO$_2$, —NR'R", CF$_3$, —Y—Z, C6-C10 aryl, or 5- to 12-membered heterocyclyl group, or a group of formula -Alk$^6$-L5-A12, where Alk$^6$ is a C1-C4 alkylene group, L5 is a group of formula —O—C(=O)—, —C(=O)— or —NR13-C(=O)— and R13 is hydrogen or C1-C4 alkyl, and A12 is an unsubstituted or substituted C6-C10 aryl or 5- to 12-membered heterocyclyl group;
Y represents C1-C8 alkylene, C2-C8 alkenylene or C2-C8 alkynylene;
Z represents halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$, —NSO$_2$R', —OCONR'R" or —CR'=NOR"; and
R' and R" independently represent hydrogen, C1-C8 alkyl, C2-C8 alkenyl or C2-C8 alkynyl;
wherein an alkyl, alkenyl, alkynyl, cycloalkyl, aryl or heterocyclyl group or moiety can be substituted or unsubstituted; and wherein:
a substituted alkyl, alkenyl or alkynyl group or moiety is a said alkyl, alkenyl or alkynyl group or moiety which is substituted with up to three substituents selected from halogen, hydroxy, amino, (C1-C4 alkyl)amino, di(C1-C4 alkyl)amino, C1-C4 alkoxy, —S(C1-C4 alkyl), —CO$_2$H, —CO$_2$(C1-C4 alkyl), phenyl, 5- or 6-membered heterocyclyl, CONR$^{b'}$R$^{b''}$ and NR$^{b'}$CO(C1-C4 alkyl) where R$^{b'}$ and R$^{b''}$ are the same or different and represent hydrogen or unsubstituted C1-C4 alkyl, wherein the substitutents on a substituted alkyl, alkenyl or alkynyl group or moiety are themselves unsubstituted or, the case of C1-C4 alkoxy substituents, may be further substituted with unsubstituted methoxy or ethoxy;

a substituted cycloalkyl group is a said cycloalkyl group which is substituted with up to three substituents selected from C1-C8 alkyl, C2-C8 alkenyl, C2-C8 alkynyl, Z and —Y—Z;

a substituted aryl or heterocyclyl group or moiety is a said aryl or heterocyclyl group or moiety which is substituted with up to three substituents selected from C1-C8 alkyl, C2-C8 alkenyl, C2-C8 alkynyl, Z and —Y—Z.

2. A combination according to claim 1, wherein the pyrrole derivative of formula (I) or pharmaceutically acceptable salt thereof and the second antifungal agent are formulated for simultaneous or successive administration.

3. A combination according to claim 1, wherein the second antifungal agent is selected from the group consisting of azoles, polyenes, purine nucleotide inhibitors, pyrimidine nucleotide inhibitors, mannan inhibitors, protein elongation factor inhibitors, echinocandins, allylamines, anti-HSP90 antibodies, bactericidal/permeability inducing protein products or polyoxins, or one of the compounds AN2690, AN2718 or icofungipen.

4. A combination according to claim 3, wherein the second antifungal agent is (i) an azole selected from clotrimazole, econazole, bifonazole, butoconazole, fenticonazole, fluconazole, isoconazole, itraconazole, ketoconazole, miconazole, oxiconazole, sertaconazole, sulconazole, tioconazole, isavuconazole, ravuconazole, posaconazole, terconazole and voriconazole; (ii) an echinocandin selected from anidulafungin, caspofungin and micafungin; (iii) an allylamine selected from terbinafine, butenafine, amorolfine and naftifine; (iv) a polyene selected from amphotericin B and nystatin; (v) a purine or pyrimidine nucleotide inhibitor which is flucytosine; (vi) a mannan inhibitor which is pradamicin; (vii) a protein elongation factor inhibitor selected from sordarin and analogues thereof; or (viii) a polyoxin which is nikkomycin Z.

5. A pharmaceutical composition comprising (i) a first antifungal agent which is a pyrrole derivative of formula (I) or a pharmaceutically acceptable salt thereof, (ii) a second antifungal agent, and (iii) a pharmaceutically acceptable carrier or diluent:

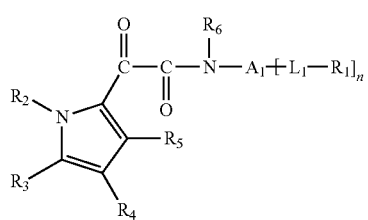

(I)

wherein:
R1 represents hydrogen, unsubstituted or substituted C1-C8 alkyl, C2-C8 alkenyl, C2-C8 alkynyl, —COR' or —SO$_2$(C1-C4 alkyl), or a group -A2, -L2-A2, -L3-A2, -A2-L3-A3 or -A4;

A1 represents a C3-C6 cycloalkyl or an unsubstituted or substituted C6-C10 aryl or 5- to 12-membered heterocyclyl group;

A2 and A3 are the same or different and represent C3-C6 cycloalkyl or an unsubstituted or substituted C6-C10 aryl or 5- to 12-membered heterocyclyl group;

A4 is an unsubstituted or substituted 5- to 12-membered heterocyclyl group wherein 1 or 2 ring carbon atoms are replaced with a group selected from >C(=O), >S(=O)$_2$, >C(=NOR7), >C=CH$_2$ or >C(—OCH$_2$CH$_2$O—), where R7 is hydrogen or a C1-C4 alkyl group;

L1 represents a bond, a C1-C6 alkylene group in which none, one, two or three —CH$_2$— groups are independently replaced by —O—, —S— or —NR'—, or a 5- to 12-membered heterocyclyl group;

L2 represents —NR'—, —O—, —CO—, —OCO—, —OCONR'R''—, —CONR'R''— or —SO$_2$—;

L3 represents a bond or a C1-C4 alkylene group in which none, one or two —CH$_2$— groups are independently replaced by —O—, —S— or —NR'—;

n is 1 or 2;

R6 represents hydrogen or C1-C4 alkyl;

R5 represents an unsubstituted or substituted group selected from C6-C10 aryl, a 5- to 12-membered heterocyclyl group, C1-C8 alkyl and C3-C6 cycloalkyl, halogen or a group of formula —B1-B2 or —B3;

B1 represents an unsubstituted or substituted C6-C10 aryl group;

B2 represents an unsubstituted or substituted C6-C10 aryl or 5- to 12-membered heterocyclyl group;

B3 is an unsubstituted or substituted 5- to 12-membered heterocyclyl group where 1 or 2 ring carbon atoms are replaced with a group selected from >C(=O), >S(=O)$_2$, >C(=NOR11), >C=CH$_2$ or >C(—OCH$_2$CH$_2$O—), where R11 is hydrogen or a C1-C4 alkyl group;

R2 and R3 independently represent C6-C10 aryl, a 5- to 12-membered heterocyclyl group, C3-C6 cycloalkyl, hydrogen, halogen, C1-C8 alkyl, C2-C8 alkenyl, C2-C8 alkynyl, C3-C6 cycloalkyl, —OR', —SR', —SOR', —SO$_2$R', —SO$_2$NR'R'', —SO$_3$H, —NR'R'', —NR'COR', —CO$_2$R', —CONR'R'', —COR', —OCOR', —CF$_3$, —NSO$_2$R' or —OCONR'R'', or a group (C1-4) alkyl-A5, wherein none, one or two —CH$_2$— groups are independently replaced by —O—, —S— or —NR'- and wherein A5 represents C$_{6-10}$ aryl or a 5- to 12-membered heterocyclyl group; or R2 and R3 together with the ring atoms to which they are bonded form a 5- to 7-membered, saturated or partially saturated ring containing a nitrogen atom from the adjacent pyrrole ring, and optionally one or two further heteroatoms selected from N, O and S, with the proviso that R2 and R3 do not form, together with the pyrrole ring to which they are bonded, tetrahydroindolizine ring;

R4 represents hydrogen, halogen, C1-C8 alkyl, C2-C8 alkenyl, C2-C8 alkynyl, —OR', —CONR'R'', —COR', —CN, —NO$_2$, —NR'R'', CF$_3$, —Y—Z, C6-C10 aryl, or 5- to 12-membered heterocyclyl group, or a group of formula -Alk$^6$-L5-A12, where Alk$^6$ is a C1-C4 alkylene group, L5 is a group of formula —O—C(=O)—, —C(=O)— or —NR13—C(=O)— and R13 is hydrogen or C1-C4 alkyl, and A12 is an unsubstituted or substituted C6-C10 aryl or 5- to 12-membered heterocyclyl group;

Y represents C1-C8 alkylene, C2-C8 alkenylene or C2-C8 alkynylene;

Z represents halogen, C3-C6 cycloalkyl, —OR', —SR', —SOR', —SO$_2$R', —SO$_2$NR'R'', —SO$_3$H, —NR'R'', —NR'COR', —NO$_2$, —CO$_2$R', —CONR'R'', —COR', —OCOR', —CN, —CF$_3$, —NSO$_2$R', —OCONR'R'' or —CR'=NOR''; and R' and R'' independently represent hydrogen, C1-C8 alkyl, C2-C8 alkenyl or C2-C8 alkynyl;

wherein an alkyl, alkenyl, alkynyl, cycloalkyl, aryl or heterocyclyl group or moiety can be substituted or unsubstituted; and wherein:

a substituted alkyl, alkenyl or alkynyl group or moiety is a said alkyl, alkenyl or alkynyl group or moiety which is substituted with up to three substituents selected from halogen, hydroxy, amino, (C1-C4 alkyl)amino, di(C1-C4 alkyl)amino, C1-C4 alkoxy, —S(C1-C4 alkyl), —CO$_2$H, —CO$_2$(C1-C4 alkyl), phenyl, 5- or 6-membered heterocyclyl, CONR$^{b'}$R$^{b''}$ and NR$^{b''}$CO(C1-C4 alkyl) where R$^{b'}$ and R$^{b''}$ are the same or different and represent hydrogen or unsubstituted C1-C4 alkyl, wherein the substitutents on a substituted alkyl, alkenyl or alkynyl group or moiety are themselves unsubstituted or, the case of C1-C4 alkoxy substituents, may be further substituted with unsubstituted methoxy or ethoxy;

a substituted cycloalkyl group is a said cycloalkyl group which is substituted with up to three substituents selected from C1-C8 alkyl, C2-C8 alkenyl, C2-C8 alkynyl, Z and —Y—Z;

a substituted aryl or heterocyclyl group or moiety is a said aryl or heterocyclyl group or moiety which is substituted with up to three substituents selected from C1-C8 alkyl, C2-C8 alkenyl, C2-C8 alkynyl, Z and —Y—Z.

6. A kit comprising, in admixture or in separate containers, a first antifungal agent which is a pyrrole derivative of formula (I) or a pharmaceutically acceptable salt thereof and a second antifungal agent:

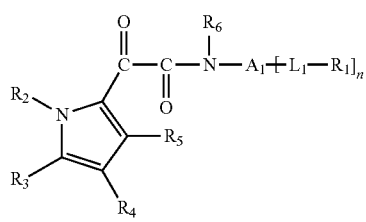

(I)

wherein:
R1 represents hydrogen, unsubstituted or substituted C1-C8 alkyl, C2-C8 alkenyl, C2-C8 alkynyl, —COR' or —SO$_2$(C1-C4 alkyl), or a group -A2, -L2-A2, -L3-A2, -A2-L3-A3 or -A4;

A1 represents a C3-C6 cycloalkyl or an unsubstituted or substituted C6-C10 aryl or 5- to 12-membered heterocyclyl group;

A2 and A3 are the same or different and represent C3-C6 cycloalkyl or an unsubstituted or substituted C6-C10 aryl or 5- to 12-membered heterocyclyl group;

A4 is an unsubstituted or substituted 5- to 12-membered heterocyclyl group wherein 1 or 2 ring carbon atoms are replaced with a group selected from >C(=O), >S(=O)$_2$, >C(=NOR7), >C=CH$_2$ or >C(—OCH$_2$CH$_2$O—), where R7 is hydrogen or a C1-C4 alkyl group;

L1 represents a bond, a C1-C6 alkylene group in which none, one, two or three —CH$_2$— groups are independently replaced by —O—, —S— or —NR'—, or a 5- to 12-membered heterocyclyl group;

L2 represents —NR'—, —O—, —CO—, —OCO—, —OCONR'R"—, —CONR'R"— or —SO$_2$—;

L3 represents a bond or a C1-C4 alkylene group in which none, one or two —CH$_2$— groups are independently replaced by —O—, —S— or —NR'—;

n is 1 or 2;

R6 represents hydrogen or C1-C4 alkyl;

R5 represents an unsubstituted or substituted group selected from C6-C10 aryl, a 5- to 12-membered heterocyclyl group, C1-C8 alkyl and C3-C6 cycloalkyl, halogen or a group of formula —B1-B2 or —B3;

B1 represents an unsubstituted or substituted C6-C10 aryl group;

B2 represents an unsubstituted or substituted C6-C10 aryl or 5- to 12-membered heterocyclyl group;

B3 is an unsubstituted or substituted 5- to 12-membered heterocyclyl group where 1 or 2 ring carbon atoms are replaced with a group selected from >C(=O), >S(=O)$_2$, >C(=NOR11), >C=CH$_2$ or >C(—OCH$_2$CH$_2$O—), where R11 is hydrogen or a C1-C4 alkyl group;

R2 and R3 independently represent C6-C10 aryl, a 5- to 12-membered heterocyclyl group, C3-C6 cycloalkyl, hydrogen, halogen, C1-C8 alkyl, C2-C8 alkenyl, C2-C8 alkynyl, C3-C6 cycloalkyl, —OR', —SR', —SOR', —SO$_2$R', —SO$_2$NR'R", —SO$_3$H, —NR'R", —NR'COR', —CO$_2$R', —CONR'R", —COR', —OCOR', —CF$_3$, —NSO$_2$R' or —OCONR'R", or a group (C1-4) alkyl-A5, wherein none, one or two —CH$_2$— groups are independently replaced by —O—, —S— or —NR'— and wherein A5 represents C6-10 aryl or a 5- to 12-membered heterocyclyl group; or R2 and R3 together with the ring atoms to which they are bonded form a 5- to 7-membered, saturated or partially saturated ring containing a nitrogen atom from the adjacent pyrrole ring, and optionally one or two further heteroatoms selected from N, O and S, with the proviso that R2 and R3 do not form, together with the pyrrole ring to which they are bonded, a tetrahydroindolizine ring;

R4 represents hydrogen, halogen, C1-C8 alkyl, C2-C8 alkenyl, C2-C8 alkynyl, —OR', —CONR'R", —COR', —CN, —NO$_2$, —NR'R", CF$_3$, —Y—Z, C6-C10 aryl, or 5- to 12-membered heterocyclyl group, or a group of formula -Alk$^6$-L5-A12, where Alk$^6$ is a C1-C4 alkylene group, L5 is a group of formula —O—C(=O)—, —C(=O)— or —NR13—C(=O)— and R13 is hydrogen or C1-C4 alkyl, and A12 is an unsubstituted or substituted C6-C10 aryl or 5- to 12-membered heterocyclyl group;

Y represents C1-C8 alkylene, C2-C8 alkenylene or C2-C8 alkynylene;

Z represents halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$, —NSO$_2$R', —OCONR'R" or —CR'=NOR"; and R' and R" independently represent hydrogen, C1-C8 alkyl, C2-C8 alkenyl or C2-C8 alkynyl;

wherein an alkyl, alkenyl, alkynyl, cycloalkyl, aryl or heterocyclyl group or moiety can be substituted or unsubstituted; and wherein:

a substituted alkyl, alkenyl or alkynyl group or moiety is a said alkyl, alkenyl or alkynyl group or moiety which is substituted with up to three substituents selected from halogen, hydroxy, amino, (C1-C4 alkyl)amino, di(C1-C4 alkyl)amino, C1-C4 alkoxy, —S(C1-C4 alkyl), —CO$_2$H, —CO$_2$(C1-C4 alkyl), phenyl, 5- or 6-membered heterocyclyl, CONR$^{b'}$R$^{b''}$ and NR$^{b''}$CO(C1-C4 alkyl) where R$^{b'}$ and R$^{b''}$ are the same or different and represent hydrogen or unsubstituted C1-C4 alkyl, wherein the substitutents on a substituted alkyl, alkenyl or alkynyl group or moiety are themselves unsubstituted or, the case of C1-C4 alkoxy substituents, may be further substituted with unsubstituted methoxy or ethoxy;

a substituted cycloalkyl group is a said cycloalkyl group which is substituted with up to three substituents selected from C1-C8 alkyl, C2-C8 alkenyl, C2-C8 alkynyl, Z and —Y—Z;

a substituted aryl or heterocyclyl group or moiety is a said aryl or heterocyclyl group or moiety which is substituted with up to three substituents selected from C1-C8 alkyl, C2-C8 alkenyl, C2-C8 alkynyl, Z and —Y—Z.

7. A compound which is a pyrrole derivative of formula (I) or a pharmaceutically or agriculturally acceptable salt thereof:

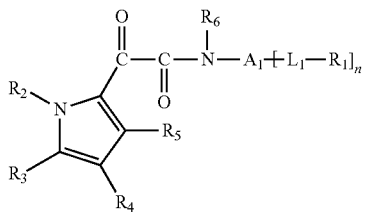

(I)

wherein R1 represents hydrogen, unsubstituted or substituted C1-C8 alkyl, C2-C8 alkenyl, C2-C8 alkynyl, —COR' or —SO$_2$(C1-C4 alkyl), or a group -A2, -L2-A2, -L3-A2, -A2-L3-A3 or -A4;

A2 and A3 are the same or different and represent C3-C6 cycloalkyl or an unsubstituted or substituted C6-C10 aryl or 5- to 12-membered heterocyclyl group;

A4 is an unsubstituted or substituted 5- to 12-membered heterocyclyl group wherein 1 or 2 ring carbon atoms are replaced with a group selected from >C(=O), >S(=O)$_2$, >C(=NOR7), >C=CH$_2$ or >C(OCH$_2$CH$_2$O), where R7 is hydrogen or a C1-C4 alkyl group;

L1 represents a bond, a C1-C6 alkylene group in which none, one, two or three —CH$_2$— groups are independently replaced by —O—, —S— or —NR'—, or a 5- to 12-membered heterocyclyl group;

L2 represents —NR'—, —O—, —CO—, —OCO—, —OCONR'R"—, —CONR'R"— or —SO$_2$—;

L3 represents a bond or a C1-C4 alkylene group in which none, one or two —CH$_2$— groups are independently replaced by —O—, —S— or —NR'—;

n is 1 or 2;

R5 represents an unsubstituted or substituted group selected from C6-C10 aryl, a 5- to 12-membered heterocyclyl group, C1-C8 alkyl and C3-C6 cycloalkyl, halogen or a group of formula B1 B2 or —B3;

B1 represents an unsubstituted or substituted C6-C10 aryl group;

B2 represents an unsubstituted or substituted C6-C10 aryl or 5- to 12-membered heterocyclyl group;

B3 is an unsubstituted or substituted 5- to 12-membered heterocyclyl group where 1 or 2 ring carbon atoms are replaced with a group selected from >C(=O), >S(=O)$_2$, >C(=NOR11), >C=CH$_2$ or >C(OCH$_2$CH$_2$O), where R11 is hydrogen or a C1-C4 alkyl group;

R3 represents C6-C10 aryl, a 5- to 12-membered heterocyclyl group, C3-C6 cycloalkyl, hydrogen, halogen, C1-C8 alkyl, C2-C8 alkenyl, C2-C8 alkynyl, C3-C6 cycloalkyl, —OR', —SR', —SOR', —SO$_2$R', —SO$_2$NR'R", —SO$_3$H, —NR'R", —NR'COR', —CO$_2$R', —CONR'R", —COR', —OCOR', —CF$_3$, —NSO$_2$R' or —OCONR'R", or a group (C1-4) alkyl-A5, wherein none, one or two —CH$_2$— groups are independently replaced by —O—, —S— or —NR'— and wherein A5 represents C6-10 aryl or a 5- to 12-membered heterocyclyl group;

A1 is a C3-C6 cycloalkyl or an unsubstituted or substituted C6-C10 aryl, 5- or 6-membered heterocyclyl or 8- to 10-membered bicyclic heterocyclyl group;

R6 represents hydrogen;

R2 represents C6-C10 aryl, a 5- to 12-membered heterocyclyl group other than benzothiophene, unsubstituted C3-C6 cycloalkyl, hydrogen, halogen, C1-C8 alkyl, C2-C8 alkenyl, C2-C8 alkynyl, C3-C6 cycloalkyl, —OR', —SR', —SOR', —SO$_2$R', —SO$_2$NR'R", —SO$_3$H, —NR'R", —NR'COR', —CO$_2$R', —CONR'R", —COR', —OCOR', —CF$_3$, —NSO$_2$R' or —OCONR'R", or a group (C1-4) alkyl-A5, wherein none, one or two —CH$_2$— groups are independently replaced by —O—, —S— or —NR'— and wherein A5 represents C6-10 aryl or a 5- to 12-membered heterocyclyl group; or R2 together with R3 and the ring atoms to which they are bonded form a 5- to 7-membered, saturated or partially saturated ring containing a nitrogen atom from the adjacent pyrrole ring, and optionally one or two further heteroatoms selected from N, O and S, with the proviso that R2 and R3 do not form, together with the pyrrole ring to which they are bonded, a tetrahydroindolizine ring;

wherein when R2 represents aryl or heterocyclyl it is unsubstituted or substituted with one or more unsubstituted substituents selected from halogen, —NR$^{a'}$R$^{a'''}$, —CO$_2$R$^{a'}$, —CONR$^{a'}$R$^{a'''}$, —OCONR$^{a'}$R$^{a'''}$, —OCOR$^{a'}$, —COCF$_3$ and hydroxyl, or C1-C6 alkyl or C1-C4 alkoxy which are unsubstituted or substituted with a hydroxyl or unsubstituted C1-C4 alkoxy group; wherein R$^{a'}$ and R$^{a'''}$ are independently selected from hydrogen, unsubstituted C1-C4 alkyl and C1-C4 alkyl substituted with a hydroxyl or unsubstituted C1-C4 alkoxy group R4 represents hydrogen, halogen, C1-C8 alkyl, C2-C8 alkenyl, C2-C8 alkynyl, —OR', —CONR'R", —CN, —NO$_2$, —NR'R", CF$_3$, —Y—Z, C6-C10 aryl, or 5- to 12-membered heterocyclyl group, or a group of formula -Alk$^6$-L5-A12, where Alk$^6$ is a C1-C4 alkylene group, L5 is a group of formula —O—C(=O)—, —C(=O)— or —NR13—C(=O)— and R13 is hydrogen or C1-C4 alkyl, and A12 is an unsubstituted or substituted C6-C10 aryl or 5- to 12-membered heterocyclyl group;

Y represents C1-C8 alkylene, C2-C8 alkenylene or C2-C8 alkynylene;

Z represents halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$, —NSO$_2$R', —OCONR'R" or —CR'=NOR"; and R' and R" independently represent hydrogen, C1-C8 alkyl, C2-C8 alkenyl or C2-C8 alkynyl;

wherein an alkyl, alkenyl, alkynyl, cycloalkyl, aryl or heterocyclyl group or moiety can be substituted or unsubstituted; and wherein:

a substituted alkyl, alkenyl or alkynyl group or moiety is a said alkyl, alkenyl or alkynyl group or moiety which is substituted with up to three substituents selected from halogen, hydroxy, amino, (C1-C4 alkyl)amino, di(C1-C4 alkyl)amino, C1-C4 alkoxy, —S(C1-C4 alkyl), —CO₂H, —CO₂(C1-C4 alkyl), phenyl, 5- or 6-membered heterocyclyl, CONR$^{b'}$R$^{b''}$ and NR$^{b''}$CO(C1-C4 alkyl) where R$^{b'}$ and R$^{b''}$ are the same or different and represent hydrogen or unsubstituted C1-C4 alkyl, wherein the substitutents on a substituted alkyl, alkenyl or alkynyl group or moiety are themselves unsubstituted or, the case of C1-C4 alkoxy substituents, may be further substituted with unsubstituted methoxy or ethoxy;

a substituted cycloalkyl group is a said cycloalkyl group which is substituted with up to three substituents selected from C1-C8 alkyl, C2-C8 alkenyl, C2-C8 alkynyl, Z and —Y—Z;

a substituted aryl or heterocyclyl group or moiety on A1 to A5, A12, R3, the ring formed by R2 and R3, R4, R5, L1, or B1 to B3, is a said aryl or heterocyclyl group or moiety which is substituted with up to three substituents selected from C1-C8 alkyl, C2-C8 alkenyl, C2-C8 alkynyl, Z and —Y—Z.

8. A compound according to claim 7, wherein R2 represents phenyl, hydrogen, —COO(C1-C4 alkyl), halogen, unsubstituted C3-C6 cycloalkyl, or a C1-C4 alkyl, C2-C4 alkenyl or C1-C4 alkoxy group which is unsubstituted or substituted with —SMe, —SEt, hydroxyl, di(C1-C4 alkyl)amino, —COO(C1-C4 alkyl), —CONR'R", —NR'CO(C1-C4 alkyl), unsubstituted C1-C4 alkoxy or C1-C4 alkoxy substituted with —OMe or —OEt, where R' and R" are the same or different and represent hydrogen or unsubstituted C1-C4 alkyl; or R2 represents a group (C1-C4) alkyl-A5, wherein none or one —CH₂— groups are independently replaced by —O—, —S— or —NR'— and wherein A5 represents phenyl, pyridinyl or oxazolyl.

9. A compound which is a pyrrole derivative of formula (IB) or a pharmaceutically or agriculturally acceptable salt thereof:

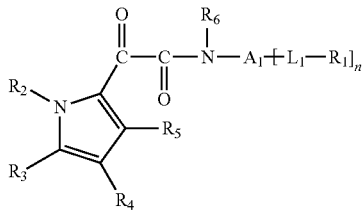

(IB)

wherein:
R1 represents hydrogen, unsubstituted or substituted C1-C8 alkyl, C2-C8 alkenyl, C2-C8 alkynyl, —COR' or —SO₂(C1-C4 alkyl), or a group -A2, -L2-A2, -L3-A2, -A2-L3-A3 or -A4;

A1 represents a C3-C6 cycloalkyl or an unsubstituted or substituted C6-C10 aryl or 5- to 12-membered heterocyclyl group;

A2 and A3 are the same or different and represent C3-C6 cycloalkyl or an unsubstituted or substituted C6-C10 aryl or 5- to 12-membered heterocyclyl group;

A4 is an unsubstituted or substituted 5- to 12-membered heterocyclyl group wherein 1 or 2 ring carbon atoms are replaced with a group selected from >C(=O), >S(=O)₂, >C(=NOR7), >C=CH₂ or >C(—OCH₂CH₂O—), where R7 is hydrogen or a C1-C4 alkyl group;

L1 represents a bond, a C1-C6 alkylene group in which none, one, two or three —CH₂— groups are independently replaced by —O—, —S— or —NR'—, or a 5- to 12-membered heterocyclyl group;

L2 represents —NR'—, —O—, —CO—, —OCO—, —OCONR'R"—, —CONR'R" or —SO₂—;

L3 represents a bond or a C1-C4 alkylene group in which none, one or two —CH₂— groups are independently replaced by —O—, —S— or —NR'—;

n is 1 or 2;

R⁶ represents hydrogen or C1-C4 alkyl;

R5 represents an unsubstituted or substituted group selected from C6-C10 aryl, a 5- to 12-membered heterocyclyl group, C1-C8 alkyl and C3-C6 cycloalkyl, halogen or a group of formula —B1-B2 or —B3;

B1 represents an unsubstituted or substituted C6-C10 aryl group;

B2 represents an unsubstituted or substituted C6-C10 aryl or 5- to 12-membered heterocyclyl group;

B3 is an unsubstituted or substituted 5- to 12-membered heterocyclyl group where 1 or 2 ring carbon atoms are replaced with a group selected from >C(=O), >S(=O)₂, >C(=NOR11), >C=CH₂ or >C(—OCH₂CH₂O—), where R11 is hydrogen or a C1-C4 alkyl group;

R² is a group of formula -Alk₁-X—R$^{a'}$, wherein Alk₁ is an unsubstituted or substituted C1-C6 alkylene group, X is a group —O—, —S—, NR$^{a''}$—, —CO₂—, —CONR$^{a''}$—, —OCO—, —OCONR$^{a''}$— or —SO₂—, and R$^{a'}$ and R$^{a''}$ are independently selected from hydrogen and unsubstituted or substituted C1-C4 alkyl;

R³ represents C6-C10 aryl, a 5- to 12-membered heterocyclyl group, C3-C6 cycloalkyl, hydrogen, halogen, C1-C8 alkyl, C2-C8 alkenyl, C2-C8 alkynyl, C3-C6 cycloalkyl, —OR', —SR', —SOR', —SOX, —SO₂NR'R", —SO₃H, —NR'R", —NR'COR', —CO₂R', —CONR'R", —COR', —OCOR', —CF₃, —NSO₂R' or —OCONR'R", or a group (C1-4) alkyl-A5, wherein none, one or two —CH₂— groups are independently replaced by —O—, —S— or —NR'— and wherein A5 represents C6-10 aryl or a 5- to 12-membered heterocyclyl group;

R4 represents hydrogen, halogen, C1-C8 alkyl, C2-C8 alkenyl, C2-C8 alkynyl, —OR', —CONR'R", —COR', —CN, —NO₂, —NR'R", CF₃, —Y—Z, C6-C10 aryl, or 5- to 12-membered heterocyclyl group, or a group of formula -Alk⁶-L5-A12, where Alk⁶ is a C1-C4 alkylene group, L5 is a group of formula —O—C(=O)—, —C(=O)— or —NR13—C(=O)— and R13 is hydrogen or C1-C4 alkyl, and A12 is an unsubstituted or substituted C6-C10 aryl or 5- to 12-membered heterocyclyl group;

Y represents C1-C8 alkylene, C2-C8 alkenylene or C2-C8 alkynylene;

Z represents halogen, C3-C6 cycloalkyl, —OR', —SR', —SOR', —SO₂R', —SO₂NR'R", —SO₃H, —NR'R", —NR'COR', —NO₂, —CO₂R', —CONR'R", —COR', —OCOR', —CN, —CF₃, —NSO₂R', —OCONR'R" or —CR'=NOR"; and R' and R" independently represent hydrogen, C1-C8 alkyl, C2-C8 alkenyl or C2-C8 alkynyl;

wherein an alkyl, alkenyl, alkynyl, cycloalkyl, aryl or heterocyclyl group or moiety can be substituted or unsubstituted; and wherein:

a substituted alkyl, alkenyl or alkynyl group or moiety is a said alkyl, alkenyl or alkynyl group or moiety which is substituted with up to three substituents selected from halogen, hydroxy, amino, (C1-C4 alkyl)amino, di(C1-C4 alkyl)amino, C1-C4 alkoxy, —S(C1-C4 alkyl), —CO₂H, —CO₂(C1-C4 alkyl), phenyl, 5- or 6-membered heterocyclyl, CONR$^{b'}$R$^{b''}$ and NR$^{b''}$CO(C1-C4 alkyl) where R$^{b'}$ and R$^{b''}$ are the same or different and represent hydrogen or unsubstituted C1-C4 alkyl, wherein the substitutents on a substituted alkyl, alkenyl or alkynyl group or moiety are themselves unsubstituted or, the case of C1-C4 alkoxy substituents, may be further substituted with unsubstituted methoxy or ethoxy;

a substituted cycloalkyl group is a said cycloalkyl group which is substituted with up to three substituents selected from C1-C8 alkyl, C2-C8 alkenyl, C2-C8 alkynyl, Z and —Y—Z;

a substituted aryl or heterocyclyl group or moiety is a said aryl or heterocyclyl group or moiety which is substituted with up to three substituents selected from C1-C8 alkyl, C2-C8 alkenyl, C2-C8 alkynyl, Z and —Y—Z;

wherein the compound is not 3-[2-(4-fluoro-phenylaminooxalyl)-pyrrol-1-yl]-propionic acid or 3-{2-[2-(3,4-Dimethoxy-phenyl)-ethylaminooxalyl]-pyrrol-1-yl}-propionic acid.

10. A composition comprising a compound or pharmaceutically acceptable salt as defined in claim 7 and a pharmaceutically acceptable carrier or diluent, or comprising a compound or agriculturally acceptable salt as defined in claim 7 and an agriculturally acceptable carrier or diluent.

11. A compound according to claim 7, wherein L1 represents a bond, a 5- to 7-membered heterocyclyl group or a C1-C6 alkylene group wherein none, one or two —CH2— groups are independently replaced by —O— or —NR'—, wherein R' is hydrogen, unsubstituted C1-C4 alkyl or C1-C4 alkyl substituted with an unsubstituted C1-C4 alkoxy group; and A1 represents a phenyl, napthyl, a 5- or 6-membered heterocyclyl group or an 8-10-membered bicyclic heterocyclyl group.

12. A compound according to claim 7, wherein n is 1; R1 is hydrogen, an unsubstituted group selected from C1-6 alkyl, C2-C6 alkenyl, C2-C6 alkynyl, —CO(C1-C4 alkyl) and —SO2(C1-C4 alkyl), or a group -A2, -L2-A2, -L3-A2, -A2-L3-A3 or A4; A2 and A3 are the same or different and represent phenyl or a 5- or 6-membered heterocyclic group; and L3 represents a bond or a C1-C4 alkylene group in which none, one or two —CH2— moieties are independently replaced with —O— or —NR'—, wherein R' represents hydrogen or unsubstituted C1-C4 alkyl.

13. A compound according to claim 7, wherein R5 is phenyl, a monocyclic 5- to 8-membered heterocyclyl ring, an unsubstituted C3-C6 cycloalkyl group, an unsubstituted C1-C8 alkyl or a C1-C8 alkyl substituted with a C1-C4 alkoxy group.

14. A compound which is a pyrrole derivative of formula (IA) or a pharmaceutically acceptable salt thereof:

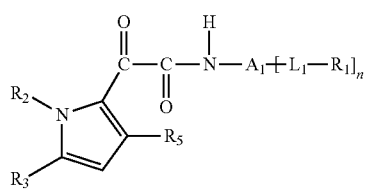

(IA)

wherein:

A1 represents phenyl, naphthyl, pyridyl, piperidinyl, benzofuranyl, isoquinolinyl or quinolinyl, each of which may be unsubstituted or substituted with one or more substituents selected from unsubstituted C1-C4 alkyl, C1-C4 alkyl substituted with an unsubstituted C1-C4 alkoxy group, unsubstituted C1-C4 alkoxy, —CO₂H and halogen, or from a group of formula —(C1-C2 alkyl)-O—(C1-C4 alkyl)-NR'R" where R' and R" are the same or different and represent hydrogen or C1-C4 alkyl, or R' and R", together with the nitrogen atom to which they are bonded, form a piperazinyl or morpholinyl group which is unsubstituted or substituted with 1 or 2 C1-C4 alkyl groups;

n represents one or two;

L1 represents a bond, a saturated 5- to 7-membered heterocyclyl group containing one or two nitrogen atoms, or an unsubstituted C1-C6 alkylene group wherein none, one or two —CH₂— groups are independently replaced with —O— or —NR'—, wherein R' is hydrogen, unsubstituted C1-C4 alkyl or C1-C4 alkyl substituted with an unsubstituted C1-C4 alkoxy group, and wherein the heterocyclyl group is unsubstituted or substituted with an unsubstituted group selected from C1-C4 alkyl, C1-C4 alkoxy, hydroxy and halogen;

when L1 is a bond, R1 represents hydrogen, -A2, —SO₂-A2, A2-L3-A3 or A4; and when L1 is other than a bond, R1 represents hydrogen or an unsubstituted group selected from C1-C6 alkyl, C2-C6 alkenyl, C2-C6 alkynyl and —SO₂(C1-C4 alkyl), or a group -A2, —SO₂-A2, -L3-A2 or -A2-L3-A3;

A2 and A3 independently represent phenyl or a 5- or 6-membered heterocyclyl group, wherein A2 and A3 are unsubstituted or substituted with one, two or three substituents selected from the unsubstituted substituents halogen, —COCF₃, —OCONR'R" and —NR'R", and from C1-C4 alkyl and C1-C4 alkoxy groups which are unsubstituted or substituted with —OH, —OMe, —OEt or —O(C1-C4 alkyl)-O(C1-C2 alkyl), wherein R' and R" are independently selected from hydrogen, unsubstituted C1-C4 alkyl and C1-C4 alkyl substituted with a hydroxyl or unsubstituted C1-C4 alkoxy group;

L3 represents a bond or unsubstituted methylene or ethylene;

A4 represents unsubstituted dioxothiomorpholinyl, methoxyiminopiperidinyl, methoxyiminopyrrolidinyl, methylenepiperidinyl, dioxoazaspirodecyl or oxadihydropyrazolyl;

R5 represents unsubstituted or substituted phenyl, unsubstituted C3-C6 cycloalkyl, unsubstituted or substituted pyridinyl or piperidinyl, or unsubstituted thiophenyl, furanyl or tetrahydropyranyl, the substituents being selected from halogen, unsubstituted C1-C4 alkyl, unsubstituted C1-C4 alkoxy or R5 is a C1-C8 alkyl group substituted with a C1-C4 alkoxy group; and either (i) R2 represents unsubstituted phenyl, hydrogen, halogen, unsubstituted C1-C4 alkoxy, unsubstituted C2-C4 alkenyl, unsubstituted C1-C4 alkyl, or C1-C4 alkyl or C2-C4 alkenyl substituted with —OMe, —OEt, —OPr, —OBu, —OCH₂CH₂OMe, —SMe, hydroxy, di(C1-C4 alkyl)amino, —COO(C1-C4 alkyl), —CONR'R" or —NR'CO(C1-C4 alkyl) where R' and R" are the same or different and represent hydrogen or unsubstituted C1-C4 alkyl; or R2 represents a group (C1-C4) alkyl-A5, wherein none or one —CH₂— groups are independently replaced by —O— and wherein A5 represents phenyl, pyridinyl or oxazolyl, each of which is unsubstituted or substituted with one or two substituents selected from halogen, C1-C4 alkyl and C1-C4 alkoxy; and R3 represents hydrogen, halogen, unsubstituted phenyl, unsubstituted C1-C4 alkoxy, unsubstituted C1-C4 alkyl, or C1-C4 alkyl substituted with —OMe or —OEt; or (ii) R2 and R3 together with the ring atoms to which they are bonded form a substituted or unsubstituted saturated or partially saturated 5- or 6-membered ring containing a nitrogen atom from the adjacent pyrrole ring and none or one further heteroatom selected from N and O, with the proviso that R2 and R3 do not form, together with the pyrrole ring to which they are bound, a tetrahydroindolizine ring, the substituents being selected from unsubstituted C1-C4 alkyl and unsubstituted C1-C4 alkoxy groups.

15. A compound according to claim 14, wherein A1 represents phenyl, which may be unsubstituted or substituted with one or more substituents selected from unsubstituted C1-C4 alkyl, C1-C4 alkyl substituted with an unsubstituted C1-C4 alkoxy group, unsubstituted C1-C4 alkoxy, —CO$_2$H and halogen;

n represents one;

L1 represents an unsubstituted, saturated 5- to 7-membered heterocyclyl group containing two nitrogen atoms, the heterocycle being attached to A1 and to R1 via a nitrogen atom;

R1 represents unsubstituted C1-C6 alkyl, unsubstituted C2-C6 alkenyl, or a group -A2, —CH$_2$-A2 or -A2-CH$_2$-A3;

A2 and A3 independently represent phenyl or a 5- or 6-membered heterocyclyl group, wherein A2 and A3 are unsubstituted or substituted with one, two or three substituents selected from the unsubstituted substituents halogen, —COCF$_3$, —OCONR'R" and —NR'R", and from C1-C4 alkyl and C1-C4 alkoxy groups which are unsubstituted or substituted with —OH, —OMe, —OEt or —O(C1-C4 alkyl)-O(C1-C2 alkyl), wherein R' and R" are independently selected from hydrogen, unsubstituted C1-C4 alkyl and C1-C4 alkyl substituted with a hydroxyl or unsubstituted C1-C4 alkoxy group;

R5 represents unsubstituted phenyl;

R2 represents hydrogen, or C1-C4 alkyl or C2-C4 alkenyl, each of which may be unsubstituted or substituted with —OMe, —OEt, —OPr, —OBu, —OCH$_2$CH$_2$OMe, —SMe, hydroxy, di(C1-C4 alkyl)amino, —COO(C1-C4 alkyl), —CONR'R" or —NR'CO(C1-C4 alkyl) where R' and R" are the same or different and represent hydrogen or unsubstituted C1-C4 alkyl; or R2 represents a group (C1-C4) alkyl-A5, wherein none or one —CH$_2$— groups are independently replaced by —O— and wherein A5 represents phenyl, pyridinyl or oxazolyl, each of which is unsubstituted or substituted with one or two substituents selected from halogen, C1-C4 alkyl and C1-C4 alkoxy; and R3 represents hydrogen or C1-C4 alkyl which is unsubstituted or substituted with —OMe or —OEt.

16. A compound according to claim 15, wherein A1 is unsubstituted phenyl and L1 is piperazinyl.

17. A compound according to claim 7, wherein the pyrrole derivative is 2-(1,5-Dimethyl-3-phenyl-1H-pyrrol-2-yl)-N-{4-[4-(4,6-dimethyl-pyridin-2-yl)-piperazin-1-yl]-phenyl}-2-oxo-acetamide, N-{4-[4-(4,6-Dimethyl-pyridin-2-yl)-piperazin-1-yl]-phenyl}-2-oxo-2-(1-phenyl-1H-pyrrol-2-yl)-acetamide, N-{4-[4-(4,6-Dimethyl-pyridin-2-yl)-piperazin-1-yl]-phenyl}-2-(5-methyl-1-phenyl-1H-pyrrol-2-yl)-2-oxo-acetamide, N-{4-[4-(4,6-Dimethyl-pyridin-2-yl)-piperazin-1-yl]-phenyl}-2-(5-methyl-1H-pyrrol-2-yl)-2-oxo-acetamide, N-{4-[4-(4,6-Dimethyl-pyridin-2-yl)-piperazin-1-yl]-phenyl}-2-(2-methyl-7-phenyl-1,2,3,4-tetrahydro-pyrrolo[1,2-a]pyrazin-6-yl)-2-oxo-acetamide, N-{4-[4-(4,6-Dimethyl-pyridin-2-yl)-piperazin-1-yl]-phenyl}-2-oxo-2-(2-phenyl-6,7-dihydro-5H-pyrrolizin-3-yl)-acetamide, N-{4-[4-(4,6-Dimethyl-pyridin-2-yl)-piperazin-1-yl]-phenyl}-2-oxo-2-(7-phenyl-3,4-dihydro-1H-pyrrolo[2,1-c][1,4]oxazin-6-yl)-acetamide, N-{4-[4-(4,6-Dimethyl-pyridin-2-yl)-piperazin-1-yl]-phenyl}-2-(1-isopropyl-5-methyl-3-phenyl-1H-pyrrol-2-yl)-2-oxo-acetamide, N-{4-[4-(4,6-Dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide, 2-(1,5-Dimethyl-3-phenyl-1H-pyrrol-2-yl)-N-[4-[4-(4,6-dimethyl-pyridin-2-yl)-piperazin-1-yl]-3-(3-morpholin-4-yl-propoxymethyl)-phenyl]-2-oxo-acetamide, N-{3-Chloro-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide, N-{4-[4-(4,6-Dimethyl-pyridin-2-yl)-piperazin-1-yl]-phenyl}-2-(3-furan-2-yl-1,5-dimethyl-1H-pyrrol-2-yl)-2-oxo-acetamide, N-{4-[4-(4,6-Dimethyl-pyridin-2-yl)-piperazin-1-yl]-phenyl}-2-(1,5-dimethyl-3-thiophen-2-yl-1H-pyrrol-2-yl)-2-oxo-acetamide, N-{4-[4-(4,6-Dimethyl-pyridin-2-yl)-piperazin-1-yl]-phenyl}-2-(3-isopropyl-1,5-dimethyl-1H-pyrrol-2-yl)-2-oxo-acetamide, N-{4-[4-(4,6-Dimethyl-pyridin-2-yl)-piperazin-1-yl]-phenyl}-2-[1,5-dimethyl-3-(tetrahydro-pyran-4-yl)-1H-pyrrol-2-yl]-2-oxo-acetamide, 2-(1,5-Dimethyl-3-phenyl-1H-pyrrol-2-yl)-N-naphthalen-1-yl-2-oxo-acetamide, N-{3-(2-Dimethylamino-ethoxymethyl)-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide, 2-(1,4-Dimethyl-3-phenyl-1H-pyrrol-2-yl)-N-{4-[4-(4,6-dimethyl-pyridin-2-yl)-piperazin-1-yl]-phenyl}-2-oxo-acetamide, 2-(1,5-Dimethyl-3-phenyl-1H-pyrrol-2-yl)-N-{4-[4-(4,6-dimethyl-pyridin-2-yl)-piperazin-1-yl]-3-[3-(4-methyl-piperazin-1-yl)-propoxymethyl]-phenyl}-2-oxo-acetamide, N-{4-[4-(4,6-Dimethyl-pyridin-2-yl)-piperazin-1-yl]-phenyl}-2-(5-isopropyl-1-methyl-3-phenyl-1H-pyrrol-2-yl)-2-oxo-acetamide, N-{2-Chloro-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide, 2-(1,5-Dimethyl-3-phenyl-1H-pyrrol-2-yl)-N-{4-[4-(4,6-dimethyl-pyridin-2-yl)-piperazin-1-yl]-3-hydroxy-phenyl}-2-oxo-acetamide, N-(2,3-Dihydro-benzofuran-4-yl)-2-(1,5-dimethyl-3-phenyl-1H-pyrrol-2-yl)-2-oxo-acetamide, N-{3-Chloro-4-[4-(4,6-dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide, N-{4-[4-(4,6-Dimethyl-pyridin-2-yl)-piperazin-1-yl]-phenyl}-2-[3-isopropyl-1-(2-methoxy-ethyl)-5-methyl-1H-pyrrol-2-yl]-2-oxo-acetamide, N-{2-Chloro-4-[4-(4,6-dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide, N-{4-[4-(4,6-Dimethyl-pyridin-2-yl)-piperazin-1-yl]-phenyl}-2-[1-(2-ethoxy-ethyl)-5-methyl-3-phenyl-1H-pyrrol-2-yl]-2-oxo-acetamide, N-{4-[4-(4,6-Dimethyl-pyridin-2-yl)-piperazin-1-yl]-phenyl}-2-[1-(3-methoxy-propyl)-5-methyl-3-phenyl-1H-pyrrol-2-yl]-2-oxo-acetamide, 2-[1-(2-Methoxy-ethyl)-5-methyl-3-phenyl-1H-pyrrol-2-yl]-2-oxo-N-quinolin-5-yl-acetamide, N-Isoquinolin-5-yl-2-[1-(2-methoxy-ethyl)-5-methyl-3-phenyl-1H-pyrrol-2-yl]-2-oxo-acetamide, 2-(1,5-Dimethyl-3-phenyl-1H-pyrrol-2-yl)-2-oxo-N-quinolin-8-yl-acetamide, 2-(1,5-Dimethyl-3-phenyl-1H-pyrrol-2-yl)-2-oxo-N-quinolin-5-yl-acetamide, 2-(1,5-Dimethyl-3-phenyl-1H-pyrrol-2-yl)-2-oxo-N-pyridin-4-yl-acetamide, N-{4-[4-(4,6-Dimethyl-pyridin-2-yl)-piperazin-1-yl]-phenyl}-2-(1-ethyl-5-methyl-3-phenyl-1H-pyrrol-2-yl)-2-oxo-acetamide, N-{4-[4-(4,6-Dimethyl-pyridin-2-yl)-piperazin-1-yl]-phenyl}-2-(5-methyl-3-phenyl-1-propyl-1H-pyrrol-2-yl)-2-oxo-acetamide, 2-(1-Butyl-5-methyl-3-phenyl-1H-pyrrol-2-yl)-N-{4-[4-(4,6-dimethyl-pyridin-2-yl)-piperazin-1-yl]-phenyl}-2-oxo-acetamide, 2-(1,5-Dimethyl-3-phenyl-1H-pyrrol-2-yl)-2-oxo-N-quinolin-3-yl-acetamide, 2-(1,5-Dimethyl-3-phenyl-1H-pyrrol-2-yl)-2-oxo-N-[4-(4-pyridin-2-yl-piperazin-1-yl)-phenyl]-acetamide, 2-(1,5-Dimethyl-3-phenyl-1H-pyrrol-2-yl)-N-{4-[4-(6-methyl-pyridin-2-yl)-piperazin-1-yl]-phenyl}-2-oxo-acetamide, 2-(1,5-Dimethyl-3-phenyl-1H-pyrrol-2-yl)-N-{4-[4-(4-methyl-pyridin-2-yl)-piperazin-1-yl]-phenyl}-2-oxo-acetamide, N-{4-[4-(4,6-Dimethyl-pyridin-2-yl)-piperazin-1-yl]-phenyl}-2-oxo-2-(2-phenyl-6,7,8,9-tetrahydro-5H-pyrrolo[1,2-a]azepin-3-yl)-acetamide, N-{4-[4-(4,6-Dimethyl-pyridin-2-yl)-piperazin-1-yl]-phenyl}-2-oxo-2-(1-phenyl-6,7,8,9-tetrahydro-5H-pyrrolo[1,2-a]azepin-3-yl)-acetamide, N-Isoquinolin-8-yl-2-[1-(2-methoxy-ethyl)-5-methyl-3-phenyl-1H-pyrrol-2-yl]-2-oxo-acetamide, 2-(1,5-Dimethyl-3-phenyl-1H-pyrrol-2-yl)-N-isoquinolin-8-yl-2-oxo-acetamide, 2-(1,5-Dimethyl-3-phenyl-1H-pyrrol-2-yl)-N-naphthalen-2-yl-2-oxo-acetamide, N-{4-[4-(4,6-Dimethyl-pyridin-2-yl)-piperazin-1-yl]-phenyl}-2-(1-methyl-3-phenyl-1H-pyrrol-2-yl)-2-oxo-acetamide, N-{4-[4-(4,6-Dimethyl-pyridin-2-yl)-piperazin-1-yl]-phenyl}-2-(1-methyl-4-phenyl-1H-pyrrol-2-yl)-2-oxo-acetamide, N-{4-[4-(4,6-Dimethyl-pyridin-2-yl)-piperazin-1-yl]-phenyl}-2-[1-(2-methoxy-ethyl)-3-phenyl-1H-pyrrol-2-yl]-2-oxo-acetamide, 2-(1-Benzyl-5-methyl-3-phenyl-1H-pyrrol-2-yl)-N-{4-[4-(4,6-dimethyl-pyridin-2-yl)-piperazin-1-yl]-phenyl}-2-oxo-acetamide, 2-(1,5-Dimethyl-3-phenyl-1H-pyrrol-2-yl)-N-[5-(4-methyl-piperazin-1-yl)-naphthalen-1-yl]-2-oxo-acetamide, N-{4-[4-(4,6-Dimethyl-pyridin-2-yl)-piperazin-1-yl]-phenyl}-2-(5-methyl-3-phenyl-1H-pyrrol-2-yl)-2-oxo-acetamide, 2-(1,5-Dimethyl-3-phenyl-1H-pyrrol-2-yl)-N-{4-[4-(4,6-dimethyl-pyridin-2-yl)-piperazin-1-yl]-3-methyl-phenyl}-2-oxo-acetamide, (2-{4-[4-(4,6-Dimethyl-pyridin-2-yl)-piperazin-1-yl]-phenylaminooxalyl}-5-methyl-3-phenyl-pyrrol-1-yl)-acetic acid methyl ester, N-{4-[4-(4,6-Dimethyl-pyridin-2-yl)-piperazin-1-yl]-phenyl}-2-(5-ethyl-1-methyl-3-phenyl-1H-pyrrol-2-yl)-2-oxo-acetamide, N-{4-[4-(4,6-Dimethyl-pyridin-2-yl)-piperazin-1-yl]-phenyl}-2-[5-ethyl-1-(2-methoxy-ethyl)-3-phenyl-1H-pyrrol-2-yl]-2-oxo-acetamide, 2-{4-[4-(4,6-Dimethyl-pyridin-2-yl)-piperazin-1-yl]-phenylaminooxalyl}-5-methyl-3-phenyl-pyrrole-1-carboxylic acid ethyl ester, 2-{4-[4-(4,6-Dimethyl-pyridin-2-yl)-piperazin-1-yl]-phenylaminooxalyl}-5-methyl-3-phenyl-pyrrole-1-carboxylic acid methyl ester, 2-[3-(2-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide, 2-[4-(2-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide, 2-[3-(4-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide, 2-[1-(2-Methoxy-ethyl)-5-methyl-3-phenyl-1H-pyrrol-2-yl]-2-oxo-N-phenyl-1-acetamide, (2-{4-[4-(4,6-dimethyl-pyridin-2-yl)-piperazin-1-yl]-phenylaminooxalyl}-pyrrol-1-yl)-acetic acid methyl ester, N-{4-[4-(4,6-Dimethyl-pyridin-2-yl)-piperazin-1-yl]-phenyl}-2-(1-methoxymethyl-5-methyl-3-phenyl-1H-pyrrol-2-yl)-2-oxo-acetamide, N-{4-[4-(4,6-Dimethyl-pyridin-2-yl)-piperazin-1-yl]-phenyl}-2-(1-methoxymethyl-3-phenyl-1H-pyrrol-2-yl)-2-oxo-acetamide, N-{4-[4-(4,6-Dimethyl-pyridin-2-yl)-piperazin-1-yl]-phenyl}-2-[1-(2-hydroxy-ethyl)-5-methyl-3-phenyl-1H-pyrrol-2-yl]-2-oxo-acetamide, 2-[1-(2-Acetylamino-ethyl)-5-methyl-3-phenyl-1H-pyrrol-2-yl]-N-{4-[4-(4,6-dimethyl-pyridin-2-yl)-piperazin-1-yl]-phenyl}-2-oxo-acetamide, N-{4-[4-(4,6-Dimethyl-pyridin-2-yl)-piperazin-1-yl]-phenyl}-2-[1-(2-hydroxy-ethyl)-3-phenyl-1H-pyrrol-2-yl]-2-oxo-acetamide, N-{4-[4-(4,6-Dimethyl-pyridin-2-yl)-piperazine-1-yl]-phenyl}-2[1-(2-methoxy-ethyl)-3-thiophen-2-yl-1H-pyrol-2-yl]-2-oxo-acetamide, N-{4-[4-(4,6-Dimethyl-pyridin-2-yl)piperazin-1-yl]-phenyl}-2-[3-isobutyl-1-(2-methoxy-ethyl)-1H-pyrrol-2-yl]-2-oxo-acetamide, 2-{4-[4-(4,6-Dimethyl-pyridin-2-yl)-piperazin-1-yl]-phenylaminooxalyl}-5-methyl-3-phenyl-pyrrol-1-yl)-acetic acid ethyl ester, 2-[3-(3-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide, 2-[4-(3-Chloro-phenyl)-1-(2-methoxy-ethyl)-1H-pyrrol-2-yl]-N-{4-[4-(4,6-dimethyl-pyridin-2-yl)-piperazin-1-yl]-phenyl}-2-oxo-acetamide, N-{4-[4-(4,6-Dimethyl-pyridin-2-yl)-piperazine-1-yl]-phenyl}-2[1-(2-methoxy-ethyl)-3-thiophen-3-yl-1H-pyrol-2-yl]-2-oxo-acetamide,
(2-{4-[4-(4,6-Dimethylpyridine-2-yl)-piperazin-1-yl]-phenylaminooxalyl}-3-phenyl pyrrol-1-yl)acetic acid ester,
(2-{4-[4-(4,6-Dimethyl-pyridin-2-yl)-piperazin-1-yl]-phenylaminooxalyl}-3-phenyl-pyrrol-1-yl)-acetic acid methyl ester,
2-(1-Carbamoylmethyl-3-phenyl-1H-pyrrol-2-yl)-N-{4-[4-(4,6-dimethyl-pyridin-2-yl)-piperazin-1-yl]-phenyl}-2-oxo-acetamide,
N-{4-[4-(4,6-Dimethyl-pyridin-2-yl)-piperazin-1-yl]-phenyl}-2-(1-methyl carbamoylmethyl-3-phenyl-1-H-pyrrol-2-yl)-2-oxo-acetamide,
2-{4-[4-(4,6-Dimethyl-pyridin-2-yl)-piperazin-1-yl]-phenylaminooxalyl}-5-methyl-3-phenyl-pyrrol-1-yl)acetic acid isopropyl ester,
N-{4-[4-(4,6-Dimethyl-pyridin-2-yl)-piperazin-1-yl]-phenyl}-2-[5-isopropyl-1-(2-methoxy-ethyl)-3-phenyl-1H-pyrrol-2-yl]-2-oxo-acetamide,
2-(1,5-Dimethyl-3-phenyl-1H-pyrrol-2-yl)-N-2-oxo-quinolin-5-yl-acetamide,
N-{4-[4-(4,6-Dimethyl-pyridin-2-yl)-piperazin-1-yl]-phenyl}-2-[3-(2-methoxy-ethyl)-5-methyl-1-phenyl-1H-pyrrol-2-yl]-2-oxo-acetamide,
2-[1-(2-Methoxy-ethyl)-3-phenyl-1H-pyrrol-2-yl]-2-oxo-N-phenyl-1-acetamide,
2-[1-(2-Methoxy-ethyl)-3-phenyl-1H-pyrrol-2-yl]-2-oxo-N-propyl-acetamide,
N-{4-[4-(4,6-Dimethyl-pyridin-2-yl)-piperazin-1-yl]-phenyl}-2-[3-isopropyl-1-(2-methoxy-ethyl)-1H-pyrrol-2-yl]-2-oxo acetamide,
2-[1-(2-Dimethylamino-ethyl)-3-phenyl-1H-pyrrol-2-yl]-N-{4-[4-(4,6-dimethyl-pyridin-2-yl)-piperazin-1-yl]-phenyl}-2-oxo-acetamide,
2-[1-(2-Dimethylamino-ethyl)-4-phenyl-1H-pyrrol-2-yl]-N-{4-[4-(4,6-dimethyl-pyridin-2-yl)-piperazin-1-yl]-phenyl}-2-oxo-acetamide,
2-[1-(2-Dimethylamino-ethyl)-5-methyl-3-phenyl-1H-pyrrol-2-yl]-N-{4-[4-(4,6-dimethyl-pyridin-2-yl)-piperazin-1-yl]-phenyl}-2-oxo-acetamide,
(2-{4-[4-(4,6-Dimethyl-pyridin-2-yl)-piperazin-1-yl]-phenylaminooxalyl}-3-thiophen-2-yl-pyrrol-1-yl)-acetic acid methyl ester,
(2-{4-[4-(4,6-Dimethyl-pyridin-2-yl)-piperazin-1-yl]-phenylaminooxalyl}-[3-isopropyl-pyrrol-1-yl)-acetic acid methyl ester,
(2-{4-[4-(4,6-Dimethylpyridine-2-yl)piperazine-1-yl]-phenylaminooxalyl}-3-isobutyl-pyrrol-1-yl)-acetic acid methyl ester,
N-{4-[4-(4,6-Dimethyl-pyridin-2-yl)-piperazin-1-yl]-phenyl}-2-(4-fluoro-1,5-dimethyl-3-phenyl-1H-pyrrol-2-yl)-2-oxo-acetamide,
N-{4-[4-(4,6-Dimethyl-pyridin-2-yl)-piperazin-1-yl]-phenyl}-2-(5-methyl-3-phenyl-1pyridin-2-ylmethyl-1H-pyrrol-2-yl)-2-oxo-acetamide,
N-{2-Chloro-4-[4-(4,6-dimethyl-pyridin-2-yl)-piperazin-1-yl]-phenyl}-2-[1-(2-methoxy-ethyl)-5-methyl-3-phenyl-1H-pyrrol-2-yl]-2-oxo-acetamide,
N-{4-[4-(4,6-Dimethyl-pyridin-2-yl)-piperazin-1-yl]-phenyl}-2-(5-methyl-3-phenyl-1-pyridin-3-ylmethyl-1H-pyrrol-2-yl)-2-oxo-acetamide,
N-{4-[4-(4,6-Dimethyl-pyridin-2-yl)-piperazin-1-yl]-phenyl}-2-[4-fluoro-1-(2-methoxy-ethyl)-5-methyl-3-phenyl-1H-pyrrol-2-yl]-2-oxo-acetamide,
2-(1,5-Dimethyl-3-phenyl-1H-pyrrol-2-yl)-N-[2-fluoro-4-(4-pyridin-2-yl-piperazin-1-yl)-phenyl]-2-oxo-acetamide,
N-[2-Fluoro-4-(4-pyridin-2-yl-piperazin-1-yl)-phenyl]-2-[1-(2-methoxy-ethyl-)-5-methyl-3-phenyl-1H-pyrrol-2-yl]-2-oxo-acetamide,
N-{4-[4-(4,6-Dimethyl-pyridin-2-yl)-piperazin-1-yl]-phenyl}-2-[1-(2-isopropoxy-ethyl)-5-methyl-3-phenyl-1H-pyrrol-2-yl]-2-oxo-acetamide,
(2-{2-Chloro-4-[4-(4,6-dimethyl-pyridin-2-yl)-piperazin-1-yl]-phenylaminooxalyl}-5-methyl-3-phenyl-pyrrol-1-yl)-acetic acid methyl ester,
2-(1,5-Dimethyl-3-phenyl-1H-pyrrol-2-yl)-2-oxo-N-(6-pyrrolidin-1-yl-pyridin-3-yl)-acetamide,
2-(1,5-Dimethyl-3-phenyl-1H-pyrrol-2-yl)-N-(2-fluoro-4-oxazole-2-yl-phenyl)-2-oxo-acetamide,
2-(1,5-Dimethyl-3-phenyl-1H-pyrrol-2-yl)-N-(2-fluoro-4-morpholin-4-yl-phenyl)-2-oxo-acetamide,
N-{4-[4-(4,6-Dimethyl-pyridin-2-yl)-piperazin-1-yl]-phenyl}-2-(5-methyl-3-phenyl-1-pyridin-4-ylmethyl-1H-pyrrol-2-yl)-2-oxo-acetamide,
2-[1-(2-Methoxy-ethyl)-5-methyl-3-phenyl-1H-pyrrrol-2-yl]-N-{4-[4-(5-morpholin-4-ylmethyl-pyridin-2-yl)-piperazin-1-yl]-phenyl}-2-oxo-acetamide,
2-[3-Cyclobutyl-1-(2-methoxy-ethyl)-1H-pyrrol-2-yl]-N-{4-[4-(4,6-Dimethyl-pyridin-2-yl)-piperizin-1-yl]-phenyl}-2-oxo-acetamide,
2-(1,5-Dimethyl-3-phenyl-1H-pyrrol-2-yl)-N-[2-fluoro-4-(4-isobutyl-piperazin-1-yl)-phenyl]-2-oxoacetamide,
2-(1,5-Dimethyl-3-phenyl-1H-pyrrol-2-yl)-N-(2-fluoro-4-piperidin-1-yl-phenyl)-2-oxo-acetamide,
(3-Cyclobutyl-2-{4-[4-(4,6-dimethyl-pyridin-2-yl)-piperazin-1-yl-]-phenylaminooxalyl}-pyrrol-1-yl)-acetic acid methyl ester,
2-(1,5-Dimethyl-3-phenyl-1H-pyrrol-2-yl)-N-{2-fluoro-4-[4-(2-methyl-allyl)-piperazin-1-yl]-phenyl}-2-oxo-acetamide,
N-{2-Fluoro-4-[4-(2-methyl-allyl)-piperazin-1-yl]-phenyl}-2-[1-(2-methoxy-ethyl)-5-methyl-3-phenyl-1H-pyrrol-2-yl]-2-oxo-acetamide,
N-[2-Fluoro-5-(4-isobutyl-piperazine-1-yl)-phenyl]-2-[1-(2-methoxy-ethyl)-5-methyl-3-phenyl-1H-pyrrol-2-yl]-2-oxo-acetamide,
(2-{4-[4-(4,6-Dimethyl-pyridin-2-yl)-piperazin-1-yl]-2-fluoro-phenylaminooxylyl}-5-methyl-3-phenyl-pyrrol-1-yl)-acetic acid methyl ester,
2-(1,5-Dimethyl-3-phenyl-1H-pyrrol-2-yl)-N-{4-[4-(2,2-dimethyl-propyl)-piperazin-1-yl]-2-fluoro-phenyl}-2-oxo-acetamide,
N-{4-[4-(2,2-Dimethyl-propyl)-piperazin-1-yl]-2-fluoro-phenyl}-2-[1-(2-methoxy-ethyl)-5-methyl-3-phenyl-1H-pyrrol-2-yl]-2-oxo-acetamide,
N-(2-Fluoro-4-piperidin-1-yl-phenyl)-2-[1-(2-methoxy-ethyl)-5-methyl-3-phenyl-1H-pyrrol-2-yl]-2-oxo-acetamide,
2-(1,5-Dimethyl-3-phenyl-1H-pyrrol-2-yl)-N-(3-fluoro-4-piperidin-1-yl-phenyl)-2-oxo-acetamide,
2-(1,5-Dimethyl-3-phenyl-1H-pyrrol-2-yl)-N-[3-fluoro-4-(4-pyridin-2-yl-piperazin-1-yl)-phenyl]-2-oxo-acetamide,
N-(2-Fluoro-4-morpholin-4-yl-phenyl)-2-[1-(2-methoxy-ethyl)-5-methyl-3-phenyl-1H-pyrrol-2-yl]-2-oxo-acetamide,
2-(1,5-Dimethyl-3-phenyl-1H-pyrrol-2-yl)-N-[3-fluoro-4-(4-isobutyl-piperazin-1-yl)-phenyl]-2-oxo-acetamide, N-(3-Fluoro-4-piperidin-1-yl-phenyl)-2-[1-(2-methoxy-ethyl)-5-methyl-3-phenyl-1H-pyrrol-2-yl]-2-oxo-acetamide, 2-(1,5-Dimethyl-3-phenyl-1H-pyrrol-2-yl)-N-{4-[4-(5-morpholin-4-ylmethyl-pyridin-2-yl)-piperazin-1-yl]-phenyl}-2-oxo-acetamide, 2-[1-(2-Methoxy-ethyl)-4-phenyl-1H-pyrrol-2-yl]-2-oxo-N-propyl-acetamide, (2-{4-[4-(4,6-Dimethyl-pyridin-2-yl)-piperazin-1-yl]-phenylaminooxalyl}-4-phenyl-pyrrol-1-yl)-acetic acid methyl ester, N-{4-[4-(4,6-Dimethyl-pyridin-2-yl)-piperazin-1-yl]-2-fluoro-phenyl}-2-[1-(2-methoxy-ethyl)-5-methyl-3-phenyl-1H-pyrrol-2-yl]-2-oxo-acetamide, N-{4-[4-(4,6-Dimethyl-pyridin-2-yl)-piperizin-1-yl]-phenyl}-2-[1-methyl-3-phenyl-5-propyl-1H-pyrrol-2-yl)-2-oxo-acetamide, N-{4-[4-(4,6-Dimethyl-pyridin-2-yl)-piperazin-1-yl]-phenyl}-2-(5-ethyl-1-methoxymethyl-3-phenyl-1H-pyrrol-2-yl)-2-oxo-acetamide, N-(3-Fluoro-4-morpholin-4-yl-phenyl)-2-[1-(2-methoxy-ethyl)-5-methyl-3-phenyl-1H-pyrrol-2-yl]-2-oxo-acetamide, 2-(1,5-Dimethyl-3-phenyl-1H-pyrrol-2-yl)-N-(5-fluoro-naphthalen-1-yl)-2-oxo-acetamide, 2-(1,5-Dimethyl-3-phenyl-1H-pyrrol-2-yl)-N-(1-ethyl-4-fluoro-1H-indol-5-yl)-2-oxo-acetamide, N-{4-[4-(4,6-Dimethyl-pyridin-2-yl)-piperazin-1-yl]-phenyl}-2-[5-(2-methoxy-ethyl)-1-methyl-3-phenyl-1H-pyrrol-2-yl]-2-oxo-acetamide, N-{4-[4-(4,6-Dimethyl-pyridin-2-yl)-piperazin-1-yl]-phenyl}-2-(5-methoxymethyl-1-methyl-3-phenyl-1H-pyrrol-2-yl)-2-oxo-acetamide, 2-(1,5-Bis-methoxymethyl-3-phenyl-1H-pyrrol-2-yl)-N-{4-[4-(4,6-dimethyl-pyridin-2-yl)-piperazine-1-yl]-phenyl}-2-oxo-acetamide, N-{4-[4-(4,6-Dimethyl-pyridin-2-yl)-piperazin-1-yl]-phenyl}-2-(1-ethoxymethyl-5-methyl-3-phenyl-1H-pyrrol-2-yl)-2-oxo-acetamide, N-{4-[4-(4,6-Dimethyl-pyridin-2-yl)-piperazin-1-yl]-phenyl}-2-[5-methyl-1-(2-methylsulfanyl-ethyl)-3-phenyl-1H-pyrrol-2-yl]-2-oxo-acetamide, N-{4-[4-(4,6-Dimethyl-pyridin-2-yl)-piperazin-1-yl]-phenyl}-2-[5-methyl-1-(2-phenoxy-ethyl)-3-phenyl-1H-pyrrol-2-yl]-2-oxo-acetamide, 2-(1-Butoxymethyl-5-methyl-3-phenyl-1H-pyrrol-2-yl)-N-{4-[4-(4,6-dimethyl-pyridin-2-yl)-piperazin-1-yl]-phenyl}-2-oxo-acetamide, N-{4-[4-(4,6-Dimethyl-pyridin-2-yl)-piperazin-1-yl]-phenyl}-2-[1-(3-ethoxy-propyl)-5-methyl-3-phenyl-1H-pyrrol-2-yl]-2-oxo-acetamide, N-{4-[4-(4,6-Dimethyl-pyridin-2-yl)-piperazin-1-yl]-phenyl}-2-(5-methyl-1-methylsulfanylmethyl-3-phenyl-1H-pyrrol-2-yl)-2-oxo-acetamide, N-{4-[4-(4,6-Dimethyl-pyridin-2-yl)-piperazin-1-yl]-phenyl}-2-[1-(2-methoxy-ethoxymethyl)-5-methyl-3-phenyl-1H-pyrrol-2-yl]-2-oxo-acetamide, N-{4-[4-(4,6-Dimethyl-pyridin-2-yl)-piperazin-1-yl]-phenyl}-2-(5-methyl-3-phenyl-1-propoxymethyl-1H-pyrrol-2-yl)-2-oxo-acetamide, N-{4-[4-(4,6-Dimethyl-pyridin-2-yl)-piperazin-1-yl]-phenyl}-2-[5-methyl-3-phenyl-1-(2-propoxy-ethyl)-1H-pyrrol-2-yl]-2-oxo-acetamide, N-{4-[4-(4,6-Dimethyl-pyridin-2-yl)-piperazin-1-yl]-phenyl}-2-[1-(4-methoxy-but-2-enyl)-5-methyl-3-phenyl-1H-pyrrol-2-yl]-2-oxo-acetamide, N-{4-[4-(4,6-Dimethyl-pyridin-2-yl)-piperazin-1-yl]-phenyl}-2-[1-(4-methoxy-butyl)-5-methyl-3-phenyl-1H-pyrrol-2-yl]-2-oxo-acetamide, 2-(1,5-Dimethyl-3-phenyl-1H-pyrrol-2-yl)-2-oxo-N-(4-piperidin-1-yl-phenyl)-acetamide, N-[4-(4-Benzyl-piperazin-1-yl)-phenyl]-2-(1,5-dimethyl-3-phenyl-1H-pyrrol-2-yl)-2-oxo-acetamide, 2-(1,5-Dimethyl-3-phenyl-1H-pyrrol-2-yl)-N-[4-(4-isobutyryl-piperazin-1-yl)-phenyl]-2-oxo-acetamide, N-{4-[4-(4,6-Dimethyl-pyridin-2-yl)-piperazin-1-yl]-phenyl}-2-[5-methyl-1-(2-methyl-oxazol-4-ylmethyl)-3-phenyl-1H-pyrrol-2-yl]-2-oxo-acetamide 2-(1,5-Dimethyl-3-phenyl-1H-pyrrol-2-yl)-N-(4-oxazol-2-yl-phenyl)-2-oxo-acetamide, 2-(1,5-Dimethyl-3-phenyl-1H-pyrrol-2-yl)-N-[3-fluoro-4-oxazole-2-yl-phenyl)-2-oxo-acetamide, 2-[1-(2-Methoxy-ethyl)-5-methyl-3-phenyl-1H-pyrrol-2-yl]-N-(4-oxazol-2-yl-phenyl)-2-oxo-acetamide, 2-(1,5-Dimethyl-3-phenyl-1H-pyrrol-2-yl)-N-{4-[4-(1,2-dimethyl-propyl)-piperazin-1-yl]-phenyl}-2-oxo-acetamide, 2-(1,5-Dimethyl-3-phenyl-1H-pyrrol-2-yl)-N-{4-[4-(2-methoxy-1-methyl-ethyl)-piperazin-1-yl]-phenyl}-2-oxo-acetamide, 2-(1,5-Dimethyl-3-phenyl-1H-pyrrol-2-yl)-N-{4-[4-(2-furan-2-yl-1-methyl-ethyl)-piperazin-1-yl]-phenyl}-2-oxo-acetamide, 2-(1,5-Dimethyl-3-phenyl-1H-pyrrol-2-yl)-2-oxo-N-[4-(5-piperidin-1-ylmethyl-oxazol-2-yl)-phenyl]-acetamide, or 2-(1,5-Dimethyl-3-phenyl-1H-pyrrol-2-yl)-N-(4-morpholin-4-yl-phenyl)-2-oxo-acetamide;

or a pharmaceutically acceptable salt thereof.

* * * * *